US009605064B2

(12) United States Patent
Okun et al.

(10) Patent No.: US 9,605,064 B2
(45) Date of Patent: Mar. 28, 2017

(54) METHODS AND COMPOSITIONS FOR TREATMENT OF SKIN DISORDERS

(75) Inventors: Martin M. Okun, Libertyville, IL (US); Rebecca S. Hoffman, Wilmette, IL (US); Jonathan Barker, London (GB)

(73) Assignee: AbbVie Biotechnology Ltd, Hamilton (BM)

( * ) Notice: Subject to any disclaimer, the term of this patent is extended or adjusted under 35 U.S.C. 154(b) by 34 days.

(21) Appl. No.: 12/859,181

(22) Filed: Aug. 18, 2010

(65) Prior Publication Data

US 2011/0171227 A1 Jul. 14, 2011

Related U.S. Application Data

(63) Continuation of application No. 12/646,891, filed on Dec. 23, 2009, now abandoned, and a continuation-in-part of application No. 12/402,408, filed on Mar. 11, 2009, now abandoned, which is a continuation-in-part of application No. 12/352,503, filed on Jan. 12, 2009, now abandoned, said application No. 12/352,503 is a continuation of application No. 12/130,831, filed on May 30, 2008, now abandoned, said application No. 12/402,408 is a continuation of application No. 11/880,433, filed on Jul. 20, 2007, now abandoned, which is a continuation-in-part of application No. 11/786,445, filed on Apr. 10, 2007, now abandoned.

(60) Provisional application No. 61/140,606, filed on Dec. 23, 2008, provisional application No. 61/183,446, filed on Jun. 2, 2009, provisional application No. 60/932,914, filed on Jun. 1, 2007, provisional application No. 61/011,538, filed on Jan. 17, 2008, provisional application No. 61/024,122, filed on Jan. 28, 2008, provisional application No. 61/128,498, filed on May 22, 2008, provisional application No. 60/790,909, filed on Apr. 10, 2006, provisional application No. 60/809,770, filed on May 30, 2006, provisional application No. 60/815,489, filed on Jun. 20, 2006, provisional application No. 60/817,891, filed on Jun. 29, 2006, provisional application No. 60/840,122, filed on Aug. 25, 2006, provisional application No. 60/899,262, filed on Feb. 2, 2007, provisional application No. 60/909,683, filed on Apr. 2, 2007, provisional application No. 60/849,671, filed on Oct. 4, 2006, provisional application No. 60/832,370, filed on Jul. 20, 2006, provisional application No. 60/851,830, filed on Oct. 12, 2006, provisional application No. 60/857,352, filed on Nov. 6, 2006.

(51) Int. Cl.
*A61K 39/395* (2006.01)
*A61K 39/00* (2006.01)
*C07K 16/24* (2006.01)

(52) U.S. Cl.
CPC ...... *C07K 16/241* (2013.01); *A61K 2039/545* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 5,231,024 A | 7/1993 | Moeller et al. | |
| 5,654,407 A | 8/1997 | Boyle et al. | |
| 5,656,272 A | 8/1997 | Le et al. | |
| 5,705,389 A | 1/1998 | Braham et al. | |
| 5,795,967 A | 8/1998 | Aggarwal et al. | |
| 5,859,205 A | 1/1999 | Adair et al. | |
| 5,877,293 A | 3/1999 | Adair et al. | |
| 5,888,511 A | 3/1999 | Skurkovich et al. | |
| 5,929,212 A | 7/1999 | Jolliffe et al. | |
| 5,958,953 A | 9/1999 | Marfat | |
| 5,994,510 A | 11/1999 | Adair et al. | |
| 6,090,382 A * | 7/2000 | Salfeld et al. | ............. 424/133.1 |
| 6,177,077 B1 | 1/2001 | Tobinick | |
| 6,214,870 B1 | 4/2001 | McClure et al. | |
| 6,235,281 B1 | 5/2001 | Stenzel et al. | |
| 6,258,562 B1 | 7/2001 | Salfeld et al. | |
| 6,270,766 B1 | 8/2001 | Feldman et al. | |

(Continued)

FOREIGN PATENT DOCUMENTS

CA 2803741 A1 1/2004
EP 0101681 3/1984
(Continued)

OTHER PUBLICATIONS http://www.mayoclinic.com/health/psoriatic-arthritis/DS00476, accessed Jan. 4, 2012.*
Chew et al. 2004. Br. J Dermatology 151:492-496.*
Paul, Fundamental Immunology, 3rd Edition, 1993, pp. 292-295, under the heading "Fv Structure and Diversity in Three Dimensions".*
Rudikoff et al Proc. Natl. Acad. Sci. USA, 79(6):1979-1983, Mar. 1982.*
Brocq et al. 2004. Jnl of Joint Bone Spine 71:601-603.*
Van et al. 2008, Arch Dermatol. 144:804-806.*
Saini et al 2005. Current Pharm Design 11:273-280.*
www.rheumatology.org/practice/clinical/patients/medications/anti_tnf.pdf, downloaded Jan. 10, 2013.*
(Continued)

Primary Examiner — Shulamith H Shafer
(74) Attorney, Agent, or Firm — Foley Hoag LLP

(57) ABSTRACT

The invention provides methods and compositions for the treatment of a skin disorder associated with detrimental TNFα activity, such as psoriasis. The invention includes methods for treating a skin disorder associated with detrimental TNFα activity, such as psoriasis, in a subject who has failed or lost response to prior biologic therapy, such as prior administration of etanercept. The invention further provides methods for determining the efficacy of a human TNFα antibody, or antigen-binding portion thereof, for the treatment of a skin disorder associated with detrimental TNFα activity, such as psoriasis.

12 Claims, 13 Drawing Sheets

(56) References Cited

U.S. PATENT DOCUMENTS

| | | |
|---|---|---|
| 6,372,715 B1 | 4/2002 | Kaltwasser et al. |
| 6,379,666 B1 | 4/2002 | Tobinick |
| 6,419,944 B2 | 7/2002 | Tobinick |
| 6,423,321 B2 | 7/2002 | Tobinick |
| 6,448,380 B2 | 9/2002 | Rathjen et al. |
| 6,451,983 B2 | 9/2002 | Rathjen et al. |
| 6,498,237 B2 | 12/2002 | Rathjen et al. |
| 6,509,015 B1 | 1/2003 | Salfeld et al. |
| 6,537,549 B2 | 3/2003 | Tobinick |
| 6,593,458 B1 | 7/2003 | Rathjen et al. |
| 6,747,002 B2 | 6/2004 | Cheung et al. |
| 7,012,135 B2 | 3/2006 | Athwal et al. |
| 7,070,775 B2 | 7/2006 | Le et al. |
| 7,153,507 B2 | 12/2006 | van de Winkel et al. |
| 7,192,584 B2 | 3/2007 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,276,478 B2 | 10/2007 | Sivakumar et al. |
| 7,438,907 B2 | 10/2008 | Schuurman et al. |
| 7,521,206 B2 | 4/2009 | Heavner et al. |
| 7,541,031 B2 | 6/2009 | Salfeld et al. |
| 7,588,761 B2 | 9/2009 | Salfeld et al. |
| 7,691,378 B2 | 4/2010 | Heavner et al. |
| 7,833,525 B2 | 11/2010 | Shenoy et al. |
| 7,863,426 B2 | 1/2011 | Wan et al. |
| 7,879,328 B2 | 2/2011 | Ruben et al. |
| 7,919,264 B2 | 4/2011 | Maksymowych et al. |
| 8,034,906 B2 | 10/2011 | Borhani et al. |
| 8,092,998 B2 | 1/2012 | Stuhlmuller et al. |
| 8,093,045 B2 | 1/2012 | Pla et al. |
| 8,168,760 B2 | 5/2012 | Borhani et al. |
| 8,187,836 B2 | 5/2012 | Hsieh |
| 8,197,813 B2 | 6/2012 | Salfeld et al. |
| 8,206,714 B2 | 6/2012 | Salfeld et al. |
| 8,216,583 B2 | 7/2012 | Kruase et al. |
| 8,231,876 B2 | 7/2012 | Wan et al. |
| 8,372,400 B2 | 2/2013 | Salfeld et al. |
| 8,420,081 B2 | 4/2013 | Fraunhofer et al. |
| 8,715,664 B2 * | 5/2014 | Hoffman .............. C07K 16/241 424/142.1 |
| 8,747,854 B2 * | 6/2014 | Okun .................. C07K 16/244 424/130.1 |
| 8,753,633 B2 * | 6/2014 | Salfeld ................ C07K 16/241 424/130.1 |
| 8,808,700 B1 | 8/2014 | Hoffman et al. |
| 8,889,136 B2 * | 11/2014 | Hoffman et al. .......... 424/145.1 |
| 8,906,373 B2 | 12/2014 | Banerjee et al. |
| 8,926,975 B2 * | 1/2015 | Wong .................. C07K 16/241 424/142.1 |
| 8,986,693 B1 | 3/2015 | Hoffman et al. |
| 9,067,992 B2 * | 6/2015 | Hoffman .............. C07K 16/241 |
| 9,085,620 B1 * | 7/2015 | Hoffman .............. C07K 16/241 |
| 9,090,689 B1 * | 7/2015 | Hoffman .............. C07K 16/241 |
| 9,284,370 B1 * | 3/2016 | Medich ................ C07K 16/241 |
| 2001/0021380 A1 | 9/2001 | Pluenneke |
| 2003/0012786 A1 | 1/2003 | Teoh et al. |
| 2003/0161828 A1 | 8/2003 | Abdelghany et al. |
| 2003/0206898 A1 | 11/2003 | Fischkoff et al. |
| 2003/0219438 A1 | 11/2003 | Salfeld et al. |
| 2003/0235585 A1 | 12/2003 | Fischkoff et al. |
| 2004/0009166 A1 | 1/2004 | Filpula et al. |
| 2004/0009172 A1 | 1/2004 | Fischkoff et al. |
| 2004/0033228 A1 | 2/2004 | Krause et al. |
| 2004/0038874 A1 | 2/2004 | Omoigui |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0166111 A1 | 8/2004 | Kaymakcalan et al. |
| 2004/0219142 A1 | 11/2004 | Banerjee et al. |
| 2005/0249735 A1 | 11/2005 | Le et al. |
| 2006/0009385 A1 | 1/2006 | Hoffman et al. |
| 2006/0018907 A1 | 1/2006 | Le et al. |
| 2006/0083741 A1 | 4/2006 | Hoffman et al. |
| 2006/0153846 A1 | 7/2006 | Krause et al. |
| 2006/0246073 A1 | 11/2006 | Knight et al. |
| 2007/0041905 A1 | 2/2007 | Hoffman et al. |
| 2007/0071747 A1 | 3/2007 | Hoffman et al. |
| 2007/0081996 A1 | 4/2007 | Hoffman et al. |
| 2007/0196373 A1 | 8/2007 | Le et al. |
| 2007/0202104 A1 | 8/2007 | Banerjee et al. |
| 2007/0298040 A1 | 12/2007 | Le et al. |
| 2008/0025976 A1 | 1/2008 | Le et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0227136 A1 | 9/2008 | Pla et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0068172 A1 | 3/2009 | Kaymkcalan et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0155205 A1 | 6/2009 | Salfeld et al. |
| 2009/0202557 A1 | 8/2009 | Argiriadi et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040630 A1 | 2/2010 | Elden et al. |
| 2010/0160894 A1 | 6/2010 | Julian et al. |
| 2010/0278822 A1 | 11/2010 | Fraunhofer et al. |
| 2011/0002935 A1 | 1/2011 | Wan et al. |
| 2011/0054414 A1 | 3/2011 | Shang et al. |
| 2011/0171227 A1 | 7/2011 | Okun et al. |
| 2011/0300151 A1 | 12/2011 | Okun et al. |
| 2012/0014956 A1 | 1/2012 | Kupper et al. |
| 2012/0039900 A1 | 2/2012 | Stuhlmuller et al. |
| 2012/0077213 A1 | 3/2012 | Pla et al. |
| 2012/0107783 A1 | 5/2012 | Julian et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0219564 A1 | 8/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0282262 A1 | 11/2012 | Okun et al. |
| 2012/0282270 A1 | 11/2012 | Krause et al. |
| 2013/0004507 A1 | 1/2013 | Fischkoff et al. |
| 2013/0028903 A1 | 1/2013 | Wan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0243786 A1 | 9/2013 | Banerjee et al. |
| 2013/0330356 A1 | 12/2013 | Salfeld et al. |
| 2014/0248215 A1 * | 9/2014 | Hoffman ............ A61K 49/0004 424/9.2 |
| 2014/0286939 A1 * | 9/2014 | Banerjee .............. C07K 16/241 424/133.1 |
| 2014/0286940 A1 * | 9/2014 | Banerjee .............. C07K 16/241 424/133.1 |
| 2014/0286941 A1 * | 9/2014 | Banerjee .............. C07K 16/241 424/133.1 |
| 2015/0050216 A1 * | 2/2015 | Willian ................ C07K 16/241 424/9.2 |
| 2015/0056212 A1 * | 2/2015 | Kupper ................ C07K 16/241 424/142.1 |

(56) References Cited

U.S. PATENT DOCUMENTS

| | | | |
|---|---|---|---|
| 2015/0064194 A1* | 3/2015 | Kupper | C07K 16/241 424/142.1 |
| 2015/0064195 A1* | 3/2015 | Kupper | C07K 16/241 424/142.1 |
| 2015/0147335 A1* | 5/2015 | Okun | C07K 16/244 424/142.1 |
| 2015/0368335 A1* | 12/2015 | Banerjee | C07K 16/241 424/158.1 |
| 2016/0176957 A1 | 6/2016 | Hoffman et al. | |
| 2016/0200809 A1 | 7/2016 | Willian et al. | |

FOREIGN PATENT DOCUMENTS

| | | |
|---|---|---|
| EP | 0186833 | 7/1986 |
| EP | 0212489 | 3/1987 |
| EP | 0 230 574 A2 | 8/1987 |
| EP | 0351789 | 1/1990 |
| EP | 0366043 | 5/1990 |
| EP | 0 374 510 A1 | 6/1990 |
| EP | 0 377 823 A2 | 7/1990 |
| EP | 0 453 898 A2 | 10/1991 |
| EP | 0492448 | 7/1992 |
| EP | 260 610 | 9/1993 |
| EP | 0 585 705 A1 | 3/1994 |
| EP | 0614984 | 9/1994 |
| EP | 0659766 | 6/1995 |
| EP | 1 232 753 A1 | 8/2002 |
| EP | 1944322 A2 | 7/2008 |
| JP | 11127882 | 5/1999 |
| JP | 2001-302542 | 10/2001 |
| WO | WO-91/02078 | 2/1991 |
| WO | WO-91/03553 A1 | 3/1991 |
| WO | WO-91/0405 A1 | 4/1991 |
| WO | WO-91/09967 A1 | 7/1991 |
| WO | WO-92/11383 | 7/1992 |
| WO | WO-92/16221 A1 | 10/1992 |
| WO | WO-92/16553 | 10/1992 |
| WO | WO-92/17583 A1 | 10/1992 |
| WO | WO-93/06213 | 4/1993 |
| WO | WO-93/11793 | 6/1993 |
| WO | WO-93/19751 A1 | 10/1993 |
| WO | WO-94/29347 | 12/1994 |
| WO | WO-95/23813 | 9/1995 |
| WO | WO-96/33204 A1 | 10/1996 |
| WO | WO-97/29131 | 8/1997 |
| WO | WO-98/04281 A1 | 2/1998 |
| WO | WO-98/05357 | 2/1998 |
| WO | WO-98/22460 | 5/1998 |
| WO | WO-98/46642 A1 | 10/1998 |
| WO | WO-00/62790 A2 | 10/2000 |
| WO | WO-01/00229 | 1/2001 |
| WO | WO-01/37874 | 5/2001 |
| WO | WO-01/43773 A1 | 6/2001 |
| WO | WO-01/62272 | 8/2001 |
| WO | WO-01/94585 | 12/2001 |
| WO | WO-02/012502 | 2/2002 |
| WO | WO-02/072636 A2 | 9/2002 |
| WO | WO-02/096461 | 12/2002 |
| WO | WO-02/100330 | 12/2002 |
| WO | WO-03/016468 A2 | 2/2003 |
| WO | WO-2004/016286 A2 | 2/2004 |
| WO | WO-2004/037205 A2 | 5/2004 |
| WO | WO-2004/082635 A2 | 9/2004 |
| WO | WO-2004/092448 | 10/2004 |
| WO | WO-2006/041970 | 4/2006 |
| WO | WO-2005/110452 | 8/2006 |

OTHER PUBLICATIONS

Asadullah et al., "A high prevalence of cytomegalovirus in patients with moderate to severe chronic plaque psoriasis: an association with systemic tumour necrosis factor a over expression," Br. J. Dermatol., 141 (1):94-102 (1999).

Badia et al., British Journal of Dermatology 141 :698-702,1999.

Casset et al., "A peptide mimetic of an anti-CD4 monoclonal antibody by rational design," Biochem. Biophys. Res. Comm., 397:198-205 (2003).

Chaudhari et al., "Efficacy and safety of infliximab monotherapy for plaque-type psoriasis: a randomized trial," Lancet, 357(9271):1842-1847 (2001).

Chen et al., "Adalimumab efficacy and safety in patients with moderate to severe chronic plaque psoriasis: preliminary findings from a 12-week dose-ranging trial," Supplement to the J. Am. Acad. of Dermatol., 50(3), Abstract P2 (2004).

Chew et al., "Successful treatment of severe psoriasis and psoriatic arthritis with adalimumab," Br. J. Dermatol., 151(2):492-496 (2004).

Davison et al., "Etanercept for severe arthritis and psoriatic arthritis; observations on combination therapy," Br. J. Dermatol., 147:831-832 (2002).

Elewski et al., "Infliximab for the treatment of severe pustular psoriasis," Am. Acad. Dermatol., 47(5):796-797 (2002).

Finlay et al., Clinical and Experimentl Dermatology 19:210-216, 1994.

Gordon et al., "Definitions of measures of effect duration for psoriasis treatments," Archives of Dermatology, 141(1):82-84 (2005).

Gordon et al. "Adalimumab efficacy and safety in patients with moderate to severe chronic plaque psoriasis: preliminary findings from a 12-week dose-ranging trail," Poster presented at the American Academy of Dermatology 62nd Annual Meeting, Washington, DC, Feb. 6, 2004.

Gottlieb et al., "The National Psoriasis Foundation Psoriasis Score System Versus the Psoriasis Area Severity Index and Physician's Global Assessment: A Comparison," Journal of Drugs in Dermatology, 3:260-266 (2003).

Iyer et al., "Etanercept for severe psoriasis and psoriatic arthritis: observations on combination therapy," Br. J. Dermatol., 146(1):118-121 (2002).

Kamarashev et al., "Generalised Pustular Psoriasis Induced by Cyclosporin a Withdrawal Responding to the Tumour Necrosis Factor Alpha Inhibitor Etanercept," Dermatology, 205(2):213-216 (2002).

Keystone E. et al., "The Fully Human Anti-TNF Monoclonal Antibody Adalimumab (D2E7), Dose Ranging Study: The 24-Week Clinical Results in Patients With Active RA on Methotrexate Therapy (The ARMADA Trial)," Presented at the Annual Meeting of the European League Against Rheumatoid Arthritis (EULAR), Prague, Czech Republic (2001).

Kirby et al., "Successful treatment of severe recalcitrant psoriasis with combination infliximab and methotrexate," Clinical and Experimental. Dermatol., 26:27-29 (2001).

Koo et al., "Update on the mechanisms and efficacy of biological therapies for psoriasis," Journal of Dermatological Science, 38(2):75-87 (2005).

MacCallum et al., "Antibody-antigen Interactions: Contact Analysis and Binding Site Topography," J. Mol. Biol., 262:732-745 (1996).

Mackiewicz et al., "Dual effects caspase-1, interleukin-1β, tumour necrosis factor-α and nerve growth factor receptor in inflammatory myopathies," Clinical Exp. Rheumatol., 21(1):41-48 (2003).

Mang et al., "Response to severe psoriasis to infliximab," Dermatology, 204:156-157 (2002).

Marzella et al., "Briefing Document: Biologic License Application STN BL 125036/0 for alefacept for treatment of chronic plaque psoriasis," pp. 1-111 (2002).

Mease et al., "Etanercept in the treatment of psoriatic arthritis and psoriasis: a randomised trial," Lancet, 356(9227):385-390 (2000).

Moretti et al., "New insights in the pathogenesis of vitiligo: Imbalance of epidermal cytokines at sites of lesions," Pigment Cell Research, 15(2):81-92 (2002).

Moretti et al., "Vitiligo and Epidermal Microenvironment: Possible Involvement of Keratinnocyte-Derived Cytokines," Arch. Dermatol., 138(2):2734 (2002).

Murota et al., "Disruption of tumor necrosis receptor P55 impairs collagen turnover in experimentally induced sclerodermic skin fibroblasts," Arthritis Rheum., 48(4):1117-1125 (2003).

(56) References Cited

OTHER PUBLICATIONS

Neuner et al., "Cytokine Release by Peripheral Blood Mononuclear Cells is Affected by 8-Methoxypsoralen Plus UV-A," *Photochem. Photobiol.*, 59(2):182-188 (1994).

Newland et al., "Rapid response to infliximab in severe pustular psoriasis Zumbusch type," *Int. Journal of Dermatology*, 41(7):449-452 (2002).

O'Quinn and Miller, "The effectiveness tumor necrosis factor α antibody (Infliximab) in treating recalcitrant psoriasis," *Arch. Dermatol.*, 138(5):646-648 (2002).

Ogilvie et al., "Treatment of psoriatic arthritis with antitumour necrosis factor-α antibody clears skin lesions of psoriasis resistant to treatment with methotrexate," *Brit. J. Dermatol.*, 144:587-589 (2001).

Oh et al., "Treatment with anti-tumour necrosis factor α (TNF-α) monoclonal antibody dramatically decreases the clinical activity of psoriasis lesions," *J. Am. Acad. Dermatol.*, 42(5):829-830 (2000).

Patel and Gordon, "Adalimumab: efficacy and safety in psoriasis and rheumatoid arthritis," *Dermatologic Therapy*, 17(5):427-431 (2004).

Paul, *Fundamental Immunology*, 3rd Ed., pp. 242, 292-295, under the heading "Fv Structure and Diversity in Three Dimensions" (1993).

Reuss-Borst et al., "Sweet's syndrome associated with myelodysplasia: possible role of cytokines in thepathogenesis of the disease," *British Journal of Haematolgy*, 84(2) :356-358 (1993).

Rudikoff et al., Proc Natl Acad Sci USA 1982 vol. 79 p. 1979.

Russell-Jones et al., "High-dose of interferon and the U.K. guidelines for cutaneous melanoma," *British Journal of Dermatology*, 147(4) :832-834 (2002).

Saini et al., "Advances in therapy for psoriasis: an overview of nifliximab, etanercept, efalizumab, alefacept, adalimumab, tazarotene, and pimecrolimus," *Current Pharmaceutical Design* 11(2):273-280 (2005).

Schopf et al., "Treatment of psoriasis with the chimeric monoclonal antibody against tumor necrosis factor α, infliximab," *Journal American Academy of Dermatology*, 46(6):886-891 (2002).

Shikiar et al., Health and Quality of Life Outcomes 1 :53, 2003.

Siadden et al., "Extensive plaque psoriasis successfully treated with adalimumab (Humira)," *The British Journal of Dermatology*, 152(5):1091-1092 (2005).

Smith et al. 2005. Brit J. Dermatology. 153:486-497.

Takematsu et al., "Absence of tumor necrosis factor α in suction blister fluids and stratum corneum from patients with psoriasis," *Arch. Dermatology Research*, 281(6):398-400 (1989).

Tutuncu et al., "Anti-TNF therapy for other inflammatory conditions," *Clinical Experimental Rheumatology*, 20(6)(suppl 28):S146-S151 (2002).

Website http://www.mayoclinic.com/health/psoriatic-arthritisIDSO04 76, accessed Jan. 4, 2012.

Winterfield et al., "Psoriasis treatment: current and emerging directed therapies," *Annals of the Rheumatic Diseases*, 64(suppl 2):1187-1190 (2005).

"Active Pharmaceutical Ingredient Watch," Chemical Market Reporter, 11 (Mar. 2003).

"Annual Updates 2003: Dematologic Drugs," Drugs of the Future 28(2):175-209 (2003).

[online] Statement on a Nonproprietary Name Adopted by the USAN Council: Adalimumab, [retrieved on May 19, 2011] Retrieved from: www.ama-assn.org/resources/doc/usan/adalimumab.doc, p. 1.

Abbott Laboratories, Earnings Conference Call transcript (Apr. 9, 2002).

Abbott Laboratories, Earnings Conference Call transcript (Jul. 11, 2002).

Aboulafia, "Etanercept for the treatment of human immunodeficiency virus-associated D psoriatic arthritis," Mayo Clinic Proceedings, 75(10):1093-1098 (2000).

Abraham et al., "Efficacy and Safety of Monoclonal Antibody to Human Tumor Necrosis Factor a in Patients with Sepsis Syndrome," *JAMA*, 273(12): 934-941 (1995).

Abraham et al., "Why immunomodulatory therapies have not worked in sepsis," *Intensive Care Med*, 25:556-566 (1999).

Adalimumab Product Approval Information—Licensing Action Dec. 31, 2002: Statistical Review.

Advisory Committee Briefing Document Humira (Adalimumab), Abbott Laboratories, Briefing document dated Feb. 4, 2003.

Alexander et al., "Elevated Levels of Proinflammatory Cytokines in The Semen of Patients With Chronic Prostatitis/Chronic Pelvic Pain Syndrome," *Urology*, 52:744 (1998).

Alonso et al., "Psoriatic Arthritis (PA): A Clinical, Immunological and Radiological Study of 180 Patients," *Br. J. Rheumatol*, 30:245-260 (1991).

Antoni et al., "Infliximab for psoriasis and psoriatic arthritis," *Clin. Exp. Rheum.*, 20:S122-S125 (2002).

Antoni et al., "Open-label study of infliximab treatment for psoriatic arthritis: clinical and C2 magnetic resonance imaging measurements of reduction of inflammation," *Arthritis & Rheumatism*, 47(5):506-512 (2002).

Antoni et al., "Successful treatment of severe psoriatic arthritis with infliximab," *Arthr. Rheum.* 42(Suppl.):5371 (Abstract #1801) (1999).

Antoni, C., et al., "Successful Treatment of Psoriatic Arthritis with Infliximab in a MRI Controlled Study," Abstract OP 6.1, *J. of Rheumatology*, 27 (Supp. 59):24 (2000).

Asadullah, "Novel immunotherapies for psoriasis," 23(1):47-53 (2002).

Asakawa et al., "Effects of Cernitin Pollen-Extract (Cernilton) on Inflammatory Cytokines in Sex-Hormone Induced Nonbacterial Prostatitis Rats," *Hinyokika Kiyo*, 47:459-465 (2001).

Asli et al., "Inhibition of tumor necrosis factor alpha and ankylosing spondylitis," N Engl J Med, 348(4):359-61 (2003).

Awni et al., "Steady-State Pharmacokinetics (PK) of Adalimumab (Humira1M, Abbott) Following 40 mg Subcutaneous (sc) Injection Every Other Week (eow) in Rheumatoid Arthritis (RA) Patients with and without Methotrexate (MTX) Background Therapy," *Arthritis Rheum*, 48(9):5140 (2003).

Baeten et al., "Immunomodulatory effects of anti-tumor necrosis factor alpha therapy on synovium in spondylarthropathy: histologic findings in eight patients from an open-label pilot study," *Arthritis & Rheumatism*, 44(1):186-195 (2001).

Bain et al., "Adalimumab," *Nat. Rev. Drug Disc.*, 2(9):693-694 (2003).

Bang et al., "Adalimumab: a review of its use in rheumatoid arthritis," *BioDrugs*, 18(2):121-139 (2004).

Bansback et al., "Cost effectiveness of adalimumab in the treatment of patients with moderate to severe rheumatoid arthritis in Sweden," *Annals of the Rheumatic Diseases*, 64(7):995-1002 (2005).

Bansback et al., "The Cost Effectiveness of Adalimumab (Humira™, Abbott) in the Treatment of Patients with Moderate to Severe Rheumatoid Arthritis (RA)," *Arthritis Rheum*, 48(9):S611 (2003).

Barbuto et al., "Production of Neutralizing Antibodies to Tumor Necrosis Factor by Human Tumor-Infiltrating B Lymphocytes," Proc. Am. Assoc. Cancer Res, 34(487) Abstr. 2904 (1993).

Barrera et al., "Drug survival, efficacy and toxicity of monotherapy with a fully human anti-tumour necrosis factor-a antibody compared with methotrexate in long-standing rheumatoid arthritis," *Rheumatology*, 41:430-439 (2002).

Barrera et al., "Effect of a Fully Human Anti-TNFa Monoclonal Antibody on the Local and Systemic Expression of TNFa and IL-113," *Arthritis Rheum*, 42(9):S75 (1999).

Barrera et al., "Effects of treatment with a fully human anti-tumour necrosis factor a monoclonal antibody on the local and systemic homeostasis of interleukin 1 and TNFa in patients with rheumatoid arthritis," *Ann. Rheum Dis.*, 60:660-669 (2001).

Bathon et al., "A Comparison of Etanercept and Methotrexate in Patients with early Rheumatoid Arthritis," *N Engl J Med.*, 343(22):1586-93 (2000).

(56) References Cited

OTHER PUBLICATIONS

Baugh et al., "Mechanisms for modulating TNFa in immune and inflammatory disease," Current Opinion in Drug Discovery & Development, 4(5):635-650 (2001).
Beers et al., "Inflammatory Bowel Diseases," The Merck Manual of Diagnosis and Therapy, 17(31):302-313 (1999).
Beers et al., "Juvenile rheumatoid arthritis," The Merck Manual of Diagnosis and Therapy, 17(270):2402-2403 (1999).
Bendtzen et al., "Auto-antibodies to IL-1a and TNFa in Normal Individuals and in Infectious and Immunoinflammatory Disorders," The Physiological and Pathological Effects of Cytokines, 447-452 (1990).
Bennett, A.N. et al., "Adalimumab in clinical practice. Outcome in 70 rheumatoid arthritis patients, including comparison of patients with and without previous anti-TNF exposure," Rheumatology, 44:1026-1031 (2005).
Bhalero et al, "The genetics of psoriasis: a complex disorder of the skin and immune system," Human Molecular Genetics 7(10):1537-1545 (1998).
Billiau et al., "Infliximab for systemic onset juvenile idiopathic arthritis: experience in 3 children," Journal of Rheumatology, 29(5):1111-1114 (2002).
Biotech Week, "Cambridge Antibody Technology; Cambridge Antibody reports interim results on several trials" (Jun. 19, 2002).
Bodmer et al., "Preclinical review of anti-tumor necrosis factor monoclonal antibodies," Critical Care Medicine, 21(10):S441-S446 (1993).
Boeger et al., "Treatment of ankylosing spondylitis with infliximab," Ann Rheum Dis., 60(12):1159-1160 (2001).
Boekstegers et al., "Repeated administration of a F(ab')2 fragment of an anti-tumor necrosis factor alpha monoclonal antibody in patients with severe sepsis: effects on the cardiovascular system and cytokine levels," Shock, 1(4):237-245 (1994).
Bombardier et al., "Pattern of DMARD use in a North American Cohort of Patients with Early Rheumatoid Arthritis (RA) (SONORA)," Arthritis Rheum, 46(9):5344 (2002).
Borigini et al., "Innovative Treatment Approaches for rheumatoid arthritis. Combination Therapy," Bailliere's Clinical Rheumatology, 9(4):689-710 (1995).
Boyle et al., "A Novel Monoclonal Human IgM Autoantibody which Binds Recombinant Human and Mouse Tumor Necrosis Factor-a," Cell. Immunol, 152:556-68 (1993).
Boyle et al., "The B5 Monoclonal Human Autoantibody Binds to Cell Surface TNFa on Human Lymphoid Cells and Cell Lines and Appears to Recognize a Novel Epitope," Cell. Immunol., 152:569-81 (1993).
Brandt et al., "Successful short term treatment of severe undifferentiated spondyloarthropathy with the anti-tumor necrosis factor-alpha monoclonal antibody infliximab," J Rheumatol, 29(1):118-122 (2002).
Brandt et al., "Successful treatment of active ankylosing spondylitis with the anti-tumor necrosis factor alpha monoclonal antibody infliximab," Arthritis Rheum, 43(6):1346-1352 (2000).
Brandt et al., "'Experimentelle Therapie" bei entzündlichen Wirbelsäulenerkrankungen," Morbus Bechterew Journal, 1:81 (2000).
Braun et al., "Anti-TNFalpha: a new dimension in the pharmacotherapy of the spondyloarthropathies!?" Ann Rheum Dis, 59(6):404-6 (2000).
Braun et al., "Anti-tumour necrosis factor alpha therapy for ankylosing spondylitis: international experience," Ann Rheum Dis, 61(3):iii51-iii60 (2002).
Braun et al., "Biologic therapies in the spondyloarthritis: new opportunities, new challenges," Curr Opin Rheumatol, 15(4):394-407 (2003).
Braun et al., "International ASAS consensus statement for the use of anti-tumour necrosis factor agents in patients with ankylosing spondylitis," Ann Rheum Dis, 62(9):817-24 (2003).

Braun et al., "New treatment options in spondyloarthropathies: increasing evidence for significant efficacy of anti-tumor necrosis factor therapy," Curr Opin Rheumatol, 13(4):245-9 (2001).
Braun et al., "Novel approaches in the treatment of ankylosing spondylitis and other spondyloarthritides," Expert Opin Investig Drugs, 12(7):1097-109 (2003).
Braun et al., "Role of Novel Biological Therapies in Psoriatic Arthritis," BioDrugs 17(3):187-199 (2003).
Braun et al., "Therapy of ankylosing spondylitis and other spondyloarthritides: established medical; treatment anti-TNF-a therapy and other novel approaches," Arthritis Research, 4:307-321 (2002).
Braun et al., "Treatment of active ankylosing spondylitis with infliximab: a randomized controlled multicentre trial," Lancet, 659(9313):1187-93 (2002).
Breban et al., "Efficacy of infliximab in refractory ankylosing spondylitis: results of a six-month open-label study," Rheumatology, 41(11):1280-1285 (2002).
Breedveld et al., "Sustained Efficacy Over 4 Years with Adalimumab in Patients with Active Rheumatoid Arthritis," Ann. Rheum. Dis, 62(1):169 (2003).
Breedveld et al., "Sustained Efficacy over 5 Years with Adalimumab (Humira®) in Patients with Active Rheumatoid Arthritis," Arthritis Rheum, 48(9):S118 (2003).
Breedveld et al., "The Fully Human Anti-TNF Antibody Adalimumab (D2E7) in Combination with Methotrexate (MTX) in the Treatment of Active Rheumatoid Arthritis: Results of a 2-Year Study," EULAR, Prague, Czech Republic (2001).
Breedveld et al., "The Long-term Efficacy and Safety of Adalimumab (D2E7), the Fully Human Anti-TNF Monoclonal Antibody, in Combination with Methotrexate in the Treatment of Rheumatoid Arthritis: Results of a 2-Year Study," JCR, 8(3):546 (2002).
Brekke et al., "Therapeutic Antibodies for Human Diseases at the Dawn of the Twenty-first Century," Nat Rev Drug Discov., 2(3):240 (2003).
Brisby et al., "Proinflammatory cytokines in cerebrospinal fluid and serum in patients with disc herniation and sciatica", Eur Spine J., 11:62-66 (2002).
Burmester et al., "Effect of Dose Interruptions on the Efficacy and Safety of Adalimumab in Patients with RA," Ann. Rheum. Dis., 62(1):192 (2003).
Burmester et al., "Long-Term Efficacy and Safety of Adalimumab (D2E7) Monotherapy in Patients With DMARD-Refractory Rheumatoid Arthritis—Results From a 2-Year Study," Arthritis Rheum, 46(9):S537 (2002).
Burmester et al., "Sustained Efficacy of Adalimumab Monotherapy for More than Four Years in DMARD-Refractory RA," Ann. Rheum. Dis., 62(1):192-3 (2003).
Callen et al., "Adalimumab effectively controlled recalcitrant generalized pustular psoriasis in an adolescent," J. Dermatol. Treat. 16:350-352 (2005).
Canadian Coordinating Office for Health Technology Assessment, "Emerging Drug List: Adalimumab and Rheumatoid Arthritis," No. 42, available at https://www.cadth.ca/media/pdf/108_No42_adalimumab_edrug_e.pdf (2003).
Carlin et al., "A 50% reduction in the psoriasis area and severity index (PASI.50) is a clinically significant endpoint in the assessment of psoriasis," Journal of the American Academy of Dermatology, 50(6): 859-866 (2003).
Case, "Old and New Drugs Used in Rheumatoid Arthritis: A Historical Perspective," American Journal of Therapeutics, 8:163-179 (2001).
Cauza et al., "Treatment of psoriatic arthritis and psoriasis vulgaris with the tumor necrosis factor inhibitor infliximab," Rheumatol Int. 22:227-232 (2002).
Cavagna et al., "Infliximab in the treatment of adult Still's disease refractory to conventional therapy," Clin Exp Rheumatol, 19(3):329-332 (2001).
Cella, "Validation of the Functional Assessment of Chronic Illness Therapy-Fatigue (FACITF) in the Safety Trial of Adalimumab (D2E7) in Rheumatoid Arthritis (STAR)," Arthritis Rheum, 46(9):S115 (Abst 208) (2002).

(56) References Cited

OTHER PUBLICATIONS

Challener, Cynthia, "Biotechnology drugs offer fertile ground for API producers," Chemical Market Reporter 260(13):FR3-FR12 (2001).
Chartash et al., "Adalimumab Improves Fatigue in Patients with Active Rheumatoid Arthritis," Ann. Rheum. Dis., 62(1):349 (2003).
Cherouvim et al., "Infliximab Therapy for Patients With Active and Refractory Spondyloarthropathies at the Dose of 3 mg/kg," J. Clin. Rheumatol., 10:162-168 (2004).
Chikanza, "Juvenile rheumatoid arthritis: therapeutic perspectives," Pediatric Drugs 4(5):335-348 (2002).
Chow et al., "Effect of monoclonal antibody on human tumor necrosis factor (TNF MAb) on NFa, IL-113. and IL-6 levels in patients with sepsis syndrome," Clinical Research, 42(2): 299A (1994).
Clinical Trial NCT00645814, "Multicenter Study of the Safety and Efficacy of Adalimumab in Subjects With Moderate to Severe Chronic Plaque Psoriasis," (clinicaltrials.gov/ct2/show/NCT00645814, 2008), 2 pages (2003).
Clinical Trial NCT00645814, "Multicenter Study of the Safety and Efficacy of Adalimumab in Subjects With Moderate to Severe Chronic Plaque Psoriasis," (clinicaltrials.gov/ct2/show/NCT00645814, 2008), 2 pages (2003) (Tabular View).
Clinical Trial NCT00645905, "Study of Two Dosing Schedules of Adalimumab in Subjects With Moderate to Severe Chronic Plaque Psoriasis," (clinicaltrials.gov/ct2/show/NCT00645905, accessed on Oct. 29, 2015), 3 pages (2003).
Clinical Trial NCT00645905, "Study of Two Dosing Schedules of Adalimumab in Subjects With Moderate to Severe Chronic Plaque Psoriasis," (clinicaltrials.gov/ct2/show/NCT00645905, accessed on Oct. 29, 2015), 3 pages (2003) (Tabular View).
Clinical Trial NCT00646178, "Study of the Safety and Efficacy of Adalimumab in Subjects With Moderate to Severely Active Psoriatic Arthritis Subjects with Inadequate Response to Diesease Modifying Anti-Rheumatic Drug Therapy," (clinicaltrials.gov/ct2/show/NCT00646178, accessed on Oct. 29, 2015), 3 pages (2008).
Clinical Trial NCT00646178, "Study of the Safety and Efficacy of Adalimumab in Subjects With Moderate to Severely Active Psoriatic Arthritis Subjects with Inadequate Response to Diesease Modifying Anti-Rheumatic Drug Therapy," (clinicaltrials.gov/ct2/show/NCT00646178, accessed on Oct. 29, 2015), 3 pages (2008) (Tabular View).
Clinical Trial NCT00646191, "Study of the Safety and Efficacy of Adalimumab in Subjects With Moderate to Severe Chronic Plaque Psoriasis," (clinicaltrials.gov/ct2/show/NCT00646191, accessed on Oct. 24, 2014), 3 pages (2008).
Clinical Trial NCT00646191, "Study of the Safety and Efficacy of Adalimumab in Subjects With Moderate to Severe Chronic Plaque Psoriasis," (clinicaltrials.gov/ct2/show/NCT00646191, accessed on Oct. 24, 2014), 3 pages (2008) (Tabular View).
Clinical Trial NCT00646386, "Study of the Safety and Efficacy of the Human Anti-TNF Monoclonal Antibody Adalimumab in Subjects With Moderately to Severely Active Psoriatic Arthritis," (clinicaltrials.gov/show/NCT00646386, accessed on Aug. 1, 2013), 3 pages (2003).
Clinical Trial NCT00646386, "Study of the Safety and Efficacy of the Human Anti-TNF Monoclonal Antibody Adalimumab in Subjects With Moderately to Severely Active Psoriatic Arthritis," (clinicaltrials.gov/show/NCT00646386, accessed on Aug. 1, 2013), 3 pages (2003) (Tabular View).
Cohen et al., "Intersept: An international, multicenter, placebo-controlled trial of monoclonal antibody to human tumor necrosis factor-a in patients with sepsis," Crit Care Med., 24(9):1431-1440 (1996).
Colman, "Effects of amino acid sequence changes on antibody-antigen interactions," Research in Immunology, 145(1):33-36 (1994).
Commission Decision of Sep. 8, 2003 granting marketing authorization for Humira® Adalimumab.

Corluy, "Clinical Response Compared to DAS28 and ACR-Response Criteria in Rheumatoid Arthritis Patients on Infliximab," EULAR, abstract (2002).
Costello, "A New Era in Rheumatoid Arthritis Treament," Wisconsin Medical Journal 102(7):2933 (2003).
Cox et al., "A directory of human germ-line V segments reveals a strong bias in their usage," Eur. J. Immunol., 24(2):827-36 (1994).
Cush, "Infliximab (Remicade) Approved for Use in Rheumatoid Arthritis," American College of Rheum, (2000).
Dayer et al., "Anti-TNF-alpha therapy for ankylosing spondylitis-a specific or nonspecific treatment?" n. Engl J Med, 346(18):1399-400 (2002).
De Keyser et al., "Anti-TNF-alpha therapy in ankylosing spondylitis," Cytokine, 33:294-298 (2006).
den Broeder et al., "A Single Dose, Placebo Controlled Study of the Fully Human Anti-Tumor Necrosis Factor-a Antibody Adalimumab (D2E7) in Patients with Rheumatoid Arthritis," the Journal of Rheumatology, 29(11): 2288-2298 (2002).
den Broeder et al., "Long term anti-tumour necrosis factor a monotherapy in rheumatoid arthritis: effect on radiological course and prognostic value of markers of cartilage turnover and endothelial activation," Ann. Rheum. Dis., 61:311-318 (2002).
den Broeder et al., "The Effect of D2E7, a new human anti-TNFa monoclonal antibody, on the oxidative burst of PMN in patients with RA," Arthritis and Rheumatism, 41(9):557 (1998).
Department of Surgery, University of Toronto, Annual Report (1998-1999) found online at http://www.surQ.med.utoronto.ca/AnnRep/AR98 99/index.html.
Dermatology and Psychosomatics 4(2): 100-102 (2003).
Dermatology and Psychosomatics 4(2): 100-102 (2003)—English translation.
Dermatology and Psychosomatics 4(2): 100-102 (2003)—Information on the publication date.
Dernis et al., "Infliximab in spondylarthropathy-Influence on bone density," Clin Exp Rheumatol, 20(6 Suppl 28):S185-6 (2002).
Deutsche Apothekerzeitung, 14:1574-1575 (2003).
D'Haens et al., "Etanercept in Treatment of Active Refractory Crohn's Disease: A Single-Center Pilot Trial," J. Am. Gastroenterol, 118:2564-2568 (2001).
DiSepio et al., "Novel approaches for the treatment of psoriasis," Drug Discovery Today, 4:222-231 (1999).
Doring et al., "Identification and Characterization of a TNFa Antagonist Derived From a Monoclonal Antibody," Mol. Immunol., 31:1059-1067 (1994).
Dubin et al., "Biologics for psoriasis," Nature Reviews, 2:855-856 (2003).
Eckelbecker, Lisa, "Cranking out doses," Worcester, Mass. Telegram & Gazette, page E1 (Jan. 3, 2003).
Eckelbecker, Lisa, "D2E7 Placed Before FDA; Approval Sought for Local Drug," Worcester, Mass. Telegram & Gazette, page E1 (Apr. 10, 2002).
Egan et al., "A randomized, single-blind, pharmacokinetic and dose response study of subcutaneous methotrexate, 15 and 25 MG/week, for refractory ulcerative colitis and Crohn's Disease," Gastroenterology, 114(4):G3978 (1998).
Eisermann et al., "Tumor necrosis factor in peritoneal fluid of women undergoing laparoscopic surgery," Fertility and Sterility, 50:573 (1988).
Elkayam et al., "From wheels to feet: a dramatic response of severe chronic psoriatic arthritis to etanercept," Ann. Rheumatic Diseases, 59:839 (2000).
Elliott et al., "Suppression of fever and the acute-phase response in a patient with juvenile chronic arthritis treated with monoclonal antibody to tumour necrosis factor-alpha (cA2)," British Journal of Rheumatology, 36(5): 589-593 (1997).
Elliott et al., "Treatment of rheumatoid arthritis with chimeric monoclonal antibodies to tumor necrosis factor a," Arthritis & Rheumatism, 36(12):1681-90 (1993).
Emerald BioSystems Wizard I & II Instructions [online], Jan. 22, 2001 [retrieved Jan. 6, 2015]. Retrieved from Internet Archive wayback machine: <https://web.archive.org/web/20010122011100/http://www.emeraldbiostructures.com/wiz_instructions.htm>, 4 pages.

(56) References Cited

OTHER PUBLICATIONS

Emerald BioSystems Wizard II Formulations [online], Dec. 17, 2000 [retrieved Jan. 6, 2015]. Retrieved from Internet Archive wayback machine: <https://web.archive.org/web/20001217030900/http://www.emeraldbiostructures.com/wiz2_for mulations.htm>, 3 pages.

Emery et al., "Changes in PRO-MMP-1 in Relation to Standard Measures of Disease Activity Over a 6 Month Treatment Period with Adalimumab (D2E7) in Rheumatoid Arthritis," Arthritis & Rheumatism, 44(9):S215 (2001).

Emery et al., "Improvement in HAQ Disability in Rheumatoid Arthritis (RA) with Adalimumab (Humira™) Based on Duration of Disease," Arthritis Rheum, 48(9):5313 (2003).

Enbrel (etanercept) Label, 2007.

Enbrel (etanercept) Physician Package Insert, Jun. 5, 2003.

Enbrel® (etanercept) Nov. 1998 Label.

Enhanced Online News, "Competition for early-line biologic use among psoriasis patients intensifies as Humira continues to gain ground on Enbrel," BusinessWire, Web, Oct. 5, 2011.

Ettehadi et al., "Elevated tumor necrosis factor-alpha (TNF-a) biological activity in psoriatic skin lesions," Clin. Exp. Immunol, 96:146-151 (1994).

Evaluate Group, "Abbott Laboratories' Investigational Fully Human Anti-TNF Therapy, D2E7 (Adalimumab), Shows Promise in Reducing the Signs and Symptoms of Rheumatoid Arthritis," Evaluate Group (Nov. 12, 2001) (http://www.evaluategroup.com/Universal/View.aspx?type=Story&id=14334) [accessed on Nov. 2, 2015].

EvaluatePharma press release, "Abbott Laboratories Announces Positive Results of Phase II Humira® (Adalimunab) Study in Psoriasis," archive of press release dated Feb. 9, 2004.

Examination Report in EP 07 150 442.7 mailed Oct. 18, 2011.

Extract from British National Formulary, Mar. 2003.

Extract from European SmPC for Humira (Jun. 24, 2016).

Extract from European SmPC for Remicade (Oct. 4, 2005).

Fachinformation Humira® 40 mg/mL.

FDA approval of Humira (adalimumab): Prescribing information for Humira (adalimumab), Abbott Laboratories, North Chicago, IL, USA, Dec. 20, 2002, pp. 1-16.

FE Investigate, "ABT announces positive result," archive of Abbott Laboratories press release dated Feb. 9, 2004.

Feldmann et al., "Anti-TNFa Therapy of Rheumatoid Arthritis: What Have We Learned," Annu. Rev. Immunol., 19:163-196 (2001).

Figini et al., "In Vitro Assembly of Repertoires of Antibody Chains on the Surface of Phage by Renaturation," J. Mol. Biol., 239:68-78 (1994).

Fleischmann et al., "Developing a new generation of TNF-alpha antagonists for the treatment of rheumatoid arthritis," Molecular Interventions, 3(6):310-318 (2003).

Flendrie et al., "Survival during treatment with tumor necrosis factor blocking agents in rheumatoid arthritis," Ann. Rheum. Dis., 62(2): ii30-ii33 (2003).

Fomsgaard et al., "Auto-antibodies to Tumour Necrosis Factor a in Healthy Humans and Patients with Inflammatory Diseases and Gram-Negative Bacterial Infections," Scand. J. Immunol, 30:219-23 (1989).

Foote et al., "Antibody Framework Residues Affecting the Conformation of the Hypervariable Loops," J. Mol. Biol., 224:487-499 (1992).

Foster et al., "Secondary glaucoma in patients with juvenile rheumatoid arthritis-associated iridocyclitis," Acta Opthalamol. Scand, 78(5):576-579 (2000).

Fox et al., "Sjogren's Syndrome," Arthritis and Rheumatism, 29:577-85 (1986).

Furst et al., "Updated consensus statement on biological agents, specifically tumour necrosis factor a (TNFa) blocking agents and interleukin-1 receptor antagonist (IL-1ra), for the treatment of rheumatic diseases," Ann Rheum Dis., 63(2): ii2-ii12 (2004).

Furst et al., "Adalimumab, a Fully Human Anti-Tumor Necrosis Factor-a Monoclonal Antibody, and Concomitant Standard Antirheumatic Therapy for the Treatment of Rheumatoid Arthritis: Results of STAR (Safety Trial of Adalimumab in Rheumatoid Arthritis)," The Journal of Rheumatology, 30(12):2563-2571 (2003).

Furst et al., "Improvement of the Individual ACR Components in ACR20 Responders in an Adalimumab (Humira™) RA Clinical Trial," Arthritis Rheum, 48(9):5106 (2003).

Furst et al., "Safety and Efficacy of Adalimumab (D2E7), a Fully Human Anti-TNF-a Monoclonal Antibody, Given in Combination with Standard Antirheumatic Therapy: Safety Trial of Adalimumab in Rheumatoid Arthritis," Arthritis Rheum., 46(9):5572 (2002).

Furst et al., "TNF Blockade by the Fully Human Monoclonal Antibody Adalimumab (D2E7), in the Armada Trial Results in Decreases in Serum Matrix Metalloproteinase (MMP) Levels Along with Impressive Clinical Improvement in Refractory RA Patients," Arthritis Rheum., 44(9):5215 (2001).

Genetic Engineering & Biotechnology News, "Top 20 Best-Selling Drugs of 2012," Mar. 5, 2013.

Genovese et al., "Adalimumab efficacy in patients with psoriatic arthritis who failed prior DMARD therapy," Ann Rheum Dis., 64(3):313 (2005).

Genovese et al., "Safety and efficacy of adalimumab in treatment of patients with psoriatic arthritis who had failed DMARD therapy," J Rheumatol, 34:1040-1050 (2007).

Genovese et al., "Treatment of Rheumatoid Arthritis with Etanercept," Rheum Dis Clin N Am., 30(2):311-28, vi-vii (2004).

Gerloni et al., "Infliximab in the treatment of persistently active refractory juvenile idiopathic (chronic) arthritis: A short-term pilot study," Arthritis & Rheumatism 43(9): S256, abstract #1139 (2000).

Giannini et al., "Preliminary definition of improvement in juvenile arthritis," Arthritis & Rheumatism, 40:1202 (1997).

Gibaldi, Biopharmaceutics and Clinical Pharmacokinetics, 4th ed. at 12-13 (1991).

Gibaldi, M. & Perrier, D., Pharmacokinetics, 2d ed. (1982).

Goldenberg, "Pharmaceutical-Approval Update," P&T 28(4):254-258 (2003).

Goldenberg, M.M., "Trastuzumab, a recombinant DNA-derived humanized monoclonal antibody, a novel agent for the treatment of metastatic breast cancer," Clinical Therapeutics, 21(2):309-318 (1999).

Gordon et al., "Clinical Response to Adalimumab Treatment in Patients with Moderate to Severe psoriasis: Double-Blind, Randomized Controlled Trial and Open-Label Extension Study," J. Am. Acad. Derm., 55(1):598-606 (2006).

Gorman et al., "Treatment of ankylosing spondylitis by inhibition of tumor necrosis factor alpha," N Engl J Med., 346(18):1349-56 (2002).

Goto et al., "Adalimumab," Medline AC NLM12510366 (2002).

Goto et al., "Adalimumab," Nippon Rinsho (Japanese Journal of Clinical Medicine ), 60(12): 2384-2389 (2002).

Gottlieb, "Efficacy of etanercept (Enbrel R) in patients with psoriasis," Abstract EULAR (2002).

Gottlieb, "Pharmacodynamic and pharmacokinetic response to anti-tumor necrosis factor-α monoclonal antibody (infliximab) treatment of moderate to severe psoriasis vulgaris," 48(1):68-75 (2003).

Gottlieb, A., "Infliximab for psoriasis," J. Am. Acad. Dermatol. 49(2):S112-117 (2003).

Gottlieb, A., et al., "Infliximab monotherapy provides rapid and sustained benefit for plaquetype psoriasis," J. Am. Acad. Dermatol., 48(6):829-835 (2003).

Granneman et al., "Pharmacokinetic/Pharmacodynamic (PKIPD) Relationships of Adalimumab (Humira™, Abbott) in Rheumatoid Arthritis (RA) Patients during Phase II/III Clinical Trials," Arthritis. Rheum., 48(9):5140 (2003).

Griffiths et al., "Human anti-self antibodies with high specificity from phage display libraries," The EMBO J., 12(2):725-34 (1993).

Grom et al., "Patterns of Expression of Tumor Necrosis Factor a, Tumor Necrosis Factor a, and Their Receptors in Synovia of Patients with Juvenile Rheumatoid Arthritis and Juvenile Spondylarthropathy," Arthritis & Rheumatism, 39(10):1703-1710 (1996).

(56) References Cited

OTHER PUBLICATIONS

Guidance for Industry E6 Good Clinical Practice: Consolidated Guidance, The International Conference on Harmonisation of Technical Requirements for Registration of Pharmaceuticals for Human Use (ICH), (1996).
Halme, "Release of tumor necrosis factor-a by human peritoneal macrophages in vivo and in vitro," Am J Obstet Gynecol, 161:1718 (1989).
Harris et al., "Expression of proinflammatory Genes During Estrogen-Induced Inflammation of the Rat Prostate," Prostate, 44:19-25 (2000).
Hawkins et al., "Selection of Phage Antibodies by Binding Affinity Mimicking Affinity Maturation," J. Mol. Biol., 226:889-896 (1992).
Herceptin® (trastuzumab) Label (Sep. 1998).
Highlights of Humira Prescribing Information, Abbott Laboratories, North Chicago, IL, USA, pp. 1-70, updated Mar. 2011.
Highlights of Humira Prescribing Information, Abbott Laboratories, North Chicago, IL, USA, pp. 1-53, updated Mar. 2009.
Hitt, E, "Adalimumab effective for psoriasis," Medscape, Feb. 10, 2004.
Holler et al., "Modulation of Acute Graft-Versus-Host Disease After Allogeneic Bone Marrow Transplantation by Tumor Necrosis Factor a (TNFa) Release in the Course of Pretransplant Conditioning: Role of Conditioning Regimens and Prophylactic Application of a Monoclonal Antibody Neutralizing Human TNFa (MAK 195F)," Blood, 86(3):890-899 (1995).
Holliger et al., "Engineered antibody fragments and the rise of single domains," Nature Biotechnology, 23(9): 1126-1136 (2005).
Holt et al., "Domain Antibodies: Proteins for Therapy," Trends in Biotech, 21(11): 484-490 (2003).
Honkanen et al., "Infliximab Treatment in the refractory chronic uveitis of juvenile idiopathic arthritis (JRA)," Arthritis & Rheumatism, 44:277-390, (2001) abstract #1438.
Hoogenboom et al., "Converting rodent into human antibodies by guided selection," Antibody Engineering, 8:169-185 (1996).
Horneff et al., "TNF-alpha antagonists for the treatment of juvenile-onset spondyloarthritides," Clin Exp Rheumatol, 20(6 Supp 28):S137-42 (2002).
Humira (Adalimumab) European Medicines Agency (EMA) Label (Sep. 12, 2008).
Humira (adalimumab) Package Insert. Dec. 20, 2002. Retrieved from the Internet Dec. 11, 2009; <http://www.fda.gov/cder/foi/label/2002/adalabb1231 021b.pdf>; p. 1-3, 6.
Humira (adalimumab) Patient Information Label (Dec. 2002).
Humira (adalimumab). Data Sheet [online]. Abbott Laboratories, Dec. 20, 2002 [retrieved on Jun. 7, 2013]. Retrieved from the Internet: URL: www.fda.gov/downloads/Drugs/DevelopmentApprovalProcess/HowDrugsareDevelopedandApproved/ApprovalApplications/TherapeuticBiologicApplications/ucm092762.pdf.
Humira, Highlights of Prescribing Information, Abbott Laboratories, North Chicago, IL, USA, pp. 1-56, Nov. 2009.
Humira FDA approval letter for Adalimumab for the treatment of RA, Dec. 31, 2002.
Humira FDA approval letter for PsA, Oct. 3, 2005.
Humira Prescribing Information, Abbott Laboratories, North Chicago, IL, USA, pp. 1-13, Jan. 2003.
Humira Prescribing Information, Abbott Laboratories, North Chicago, IL, USA, pp. 1-33, Sep. 27, 2005.
Humira Prescribing Information, Abbott Laboratories, North Chicago, IL, USA, pp. 1-24, Jul. 30, 2004.
Humira product monograph (May 2013).
Huse et al., "Generation of a large combinatorial library of the immunoglobulin repertoire in phage lambda," Science, 246:1275-81 (1989).
Immunex Press Release, "First Therapy Approved for Treatment of psoriatic Arthritis," http://www.psoriasis-netz.de/medikamente/etanercept/pm-enbrel.html Jan. (2002).
International Preliminary Examination Report for PCT/US2003/022566 (WO 04/009776).

Jacobi et al., "Therapeutic application of TNF-alpha inhibitors infliximab and etanercept in inflammatory skin disorders," JDDG 1:259-272 (2003).
Janeway, "The protein products of MHC class I and class II genes are highly polymorphic," Immunobiology (3rd Edition) 4:24-4:30 (1997).
Janeway, "The structure of a typical antibody molecule," Immunobiology, 5 (2001).
Jespers et al., "Guiding the Selection of Human Antibodies from Phage Display Repertoires to a Single Epitope of an Antigen," Bio/Technology, 12:899-903 (1994).
Kaiser et al., "Efficacy of infliximab (Remicade) in the treatment of spondyloarthropathies two case reports," Joint Bone Spine, 68(6):525-7 (2001).
Kalden et al., "Emerging role of anti-tumor necrosis factor therapy in rheumatic diseases," Arthritis Research, 4(2): S34-40 (2002).
Kameda et al., "Treatment of Chronic Inflammatory Diseases by Targeting TNF," Journal of Clinical and Experimental Medicine, 208(5):336-342 (2004).
Kanakoudi-Tsakalidou et al., "Influenza vaccination in children with chronic rheumatic diseases and long-term immunosuppressive therapy," Clinical and Experimental Rheumatology, 19:589-594 (2001).
Katsanos, et al., "Axillary hidradenitis suppurativa successfully treated with infliximab in a Crohn's disease patient," AJG 97:2155-2156 (2002).
Kavanaugh et al., "Adalimumab treatment with and without methotrexate in patients with moderate to severe psoriatic arthritis: results from ADEPT," Ann Rheum Dis., 64(3):325 [FRI0227] (2005).
Kavanaugh et al., "Immune Response is Not Affected by Adalimumab Therapy," Ann. Rheum. Dis., 62(1): 169 (2003).
Kavanaugh et al., "The Armada Trial: 12-Month Efficacy and Safety of Combination Therapy with Adalimumab (D2E7), the First Fully Human Anti-TNF Monoclonal Antibody, and Methotrexate (MTX) in Patients with Active Rheumatoid Arthritis," Ann. Rheum. Dis., 61(1):S168 (2002).
Kavanaugh et al., "Treatment with Adalimumab (D2E7) does not Affect Normal Immune Responsiveness," Arthritis Rheum., 46(9):S132 (2002).
Kaymakcalan et al., "Comparison of Adalimumab (D2E7), Infliximab, and Etanercept in the Prevention of Polyarthritis in the Transgenic Murine Model of Rheumatoid Arthritis," Arthritis Rheum., 46(9):5304 (2002).
Kaymakcalan et al., "Murine Model for Assessing Adalimumab, Inflixmab, and Etanercept to Prevent Polyarthritis," Ann. Rheum. Dis., 62(1):136-7 (2003).
Keffer et al., "Transgenic Mice 1 Expressing Human Tumour Necrosis Factor: A Predictive Genetic Model of Arthritis," EMBO (European Molecular Biology Organization) Journal, 10(13):4025-4031 (1991).
Kempeni, "Preliminary Results of early clinical trials with the fully human anti-TNFα monoclonal antibody D2E7," Ann. Rheum. Dis., 58(1):170-172 (1999).
Kempeni, "Update on D2E7: a fully human anti-tumour necrosis factor a monoclonal antibody," Ann. Rheum. Dis., 59(1):144-145 (2000).
Keystone et al, "Radiographic, clinical and functional outcomes with adalimumab (a human anti-TNF monoclonal antibody) in the treatment of patients with active rheumatoid arthritis on concomitant methotrexate therapy: A randomized, placebo-controlled, 52-week trial," Arthritis Rheum;50(5):1400-1411 (2004).
Keystone et al., "Adalimumab Inhibits the Progression of Structural Joint Damage in Patients with Active RA," Ann. Rheum. Dis., 62(1):64-65 (2003).
Keystone et al., "Efficacy and Safety of Adalimumab (D2E7), the Fully Human Anti-TNF Monoclonal Antibody, in MTX Partial Responders: Results of the 24-week ARMADA Trial," JCR: Journal of Clinical Rheumatology, 8(3):569 (2002).
Keystone et al., "Subgroup Analysis of Radiographic Progression in RA Patients with Moderate Disease Treated with Adalimumab (Humira®)," Ann. Rheum. Dis., 62(1):169 (2003).

(56) References Cited

OTHER PUBLICATIONS

Keystone et al., "Sustained Radiographic Inhibition with Adalimumab (HUMIRA®) over 2 years in Patients with Long Standing Rheumatoid Arthritis (RA), " Arthritis Rheum., 48(9):S315 (2003).
Keystone et al., "The Armada Trial: A Double-Blind Placebo Controlled Trial of the Fully Human Anti-TNF Monoclonal Antibody, Adalimumab (D2E7), in Patients with Active RA on Methotrexate (MTX)," Arthritis & Rheumatism, 44(9):5213 (2001).
Keystone, E., et al., "Radiographic Inhibition of Structural Damage Sustained in Patients with Long-standing Rheumatoid Arthritis Following 3 Years of Treatment with Adalimumab (Humira®) Plus Methotrexate," Abstract 370, Arthritis & Rheumatism, 50 (Suppl. 9):S189 (2004).
Keystone, E., et al., "Subgroup Analysis of Radiographic Progression in RA Patients with Moderate Disease Treated With Adalimumab (Humira®)," Abstract FRI0064, Ann. Rheum. Dis., 63 (2004).
Keystone, et al., "Response to Adalimumab in Patients with Early Versus Late Rheumatoid Arthritis (RA)," Ann. Rheum. Dis., 62(1):170 (2003).
Kietz et al., "Clinical response to etanercept in polyarticular course juvenile rheumatoid arthritis," J. Rheumatology, 28(2):360-362 (2001).
Kimball et al., "Approved Adalimumab Dosing Regimen Associated With Greater Efficacy and Lower Cost per Responder Compared With 40-mg Every Other Week Dosing Without Initial 80-mg Dose: Analysis of Outcomes From Adalimumab Psoriasis Clinical Trial Database," 20th Congress of the Eur. Acad. Dermatol. Venereol. (Oct. 20-24, 2011) Lisbon, Portugal (FC01.8) (2013).
Klippel et al., "A. Epidemiology, Pathology, and Pathogenesis," Primer on Rheumatic Diseases, 11:155 (1997).
Klippel et al., "A. Juvenile Rheumatoid Arthritis and Juvenile Spondyloarthropathies," Primer on Rheumatic Diseases, 11:393 (1997).
Klippel, et al., "Juvenile Idiopathic Arthritis C. Treatment and Assessment," Primer on Rheumatic Diseases, 13:154-162 (2008).
Koski et al., "Tumor necrosis factor-alpha and receptors for it in labial salivary glands in Sjogren's syndrome," Clin Exp Rheumatol., 19:131 (2001).
Kraetsch et al., "Successful treatment of a small cohort of patients with adult onset of Still's disease with infliximab: first experiences," Annals of the Rheumatic Diseases, 60(3):iii55-iii57 (2001).
Krause, Carey, "Abbott bets on adalimumab in biologics RA market," Chemical Market Reporter, 261(25):12 (Jun. 24, 2002).
Kremer, "Rational Use of New and Existing Disease-Modifying Agents in Rheumatoid Arthritis," Ann. Intern. Med., 134:695-706 (2001).
Kress, Scheldon, "Clinical Review: Abbott, Biologic Licensing Application STN 125057, Adalimumab—For Use in the Treatment of Rheumatoid Arthritis," Center for Biologics Evaluation and Research, available at http://www.fda.gov/ohrms/dockets/ac/03/briefing/3930B1_01_C--HUMIRA.Med.Review.pdf (2002).
Krueger et al, "Involved and Uninvolved Skin from Psoriatic Subjects: Are they equally Diseased" J Clin Invest 68:1548-1557 (1981).
Kurschat et al., "Treatment of psoriatic arthritis with etanercept," JAM Acad Dermatology, 44(6): 1052 (2001).
Kyle et al., "Guideline for anti-TNF-alpha therapy in psoriatic arthritis," Rheumatol., 44(3):390-7 (2005).
Lahdenne et al., "Infliximab or etanercept in the treatment of children with refractory juvenile idiopathic arthritis: an open label study," Ann. Rhem. Dis., 62(3):245-247 (2003).
Lahdenne et al., "Infliximab vs Etanercept in the treatment of severe juvenile chronic arthritis," Arthritis & Rheumatism, 43(1): S381 abstract #1888 (2001).
Langely et al., "Long-term safety and efficacy of adalimumab in the treatment of moderate to severe chronic plaque psoriasis," J of the Am Academy of Dermatology, 52(3):P8 (2005).
Langley et al., "Benefit-risk assessment of tumour necrosis factor antagonists in the treatment of psoriasis," Br. J. Dermatol., 162(6):1349-58 (2010).
Lerner et al., "Antibodies without immunization," Science, 258:1313-14 (1992).
Letter dated Dec. 31, 2002 CEBR (FDA) to Abbott Laboratories.
Leusch et al., "Failure to demonstrate TNFa-specific autoantibodies in human sera by Elisa and Western blot," J. Immunol Methods, 139:145-47 (1991).
Lewis et al., "Use of alanine scanning mutagenesis to improve the affinity of an anti gp120 (HIV) antibody," J. Cell. Biochem., 18D:215 (1994).
LexisNexis—PR Newswire Assoc., Abbott Laboratories Initiates Clinical Trials to Explore Use of Humira® (adalimumab) in Psoriasis and Psoriatic Arthritis, Press Release by Abbott Laboratories (Mar. 3, 2003).
Li et al., "The TNF-alpha transgenic mouse model of inflammatory arthritis," Springer Seminars in Immunopathology, 25(1):19-33 (2003).
Lipsky et al., "Infliximab and Methotrexate in the Treatment of Rheumatoid Arthritis," The New England Journal of Medicine, 343(22):1594-1602 (2000).
Lipsy, "Etanercept and its implications for managed care," Am J of Managed Care, 8(6):S194-S200 (2002).
Inpharma newsletter, "Adalimumab has achieved significant reductions in disease activity in patients with moderate-to-severe chronic plaque psoriasis,"1424(1): 6, Feb. 14, 2004.
Lorenz et al., "Perspectives for TNF-alpha-targeting therapies," Arthritis Research, 4(3):S17-S24 (2002).
Lorenz et al., "Technology evaluation: Adalimumab, Abbott Laboratories," Current Opinions in Molecular Therapeutics, 4(2): 185-190 (2002).
Low et al., "Mimicking Somatic Hypermutation: Affinity Maturation of Antibodies Displayed on Bacteriophage Using a Bacterial Mutator Strain," J. Mol. Biol., 260:359-368 (1996).
Low, thesis extract, Cambridge University (1996).
MacDonald et al., "Tumor necrosis factor-alpha and interferon-gamma production measured at the single cell level in normal and inflamed human intestine," Clin. Exp. Immunol., 81:301-305 (1990).
Machold et al., "Adalimumab—a new TNF-a antibody for treatment of inflammatory joint disease," Expert Opin. Biol. Ther., 3(2):351-360 (2003).
Mader et al., "Does injectable gold retard radiologic evidence of joint damage in psoriatic arthritis?" Clin. Invest. Med., 18(2):139-143 (1995) [abstract].
Maini et al., "How does infliximab work in rheumatoid arthritis?" Arthrit. Res, 4(2):S22-S28 (2002).
Maini et al., "Infliximab (chimeric anti-tumour necrosis factor a monoclonal antibody) versus placebo in rheumatoid arthritis patients receiving concomitant methotrexate: a randomised phase III trial," The Lancet, 354:1932-39 (1999).
Maksymowych et al., "Canadian Rheumatology Association Consensus on the use of anti-tumor necrosis factor-alpha directed therapies in the treatment of spondyloarthritis," J Rheumatol, 30(6):1356-63 (2003).
Maksymowych., "Update on the treatment of ankylosing spondylitis," Therapeutics and Clinical Risk Management, 3(6):1125-33 (2007).
Mang et al., "TNF-alpha Antagonisten in der Therapie der Psoriasis Nutzen and Risiken," Z. Hautkr 77:548-550 (2002).
Mangge et al., "Serum cytokines in juvenile rheumatoid arthritis," Arthritis Rheum. 8:211 (1995).
Mangge et al., "Therapeutic experience with infliximab in a patient with polyarticular juvenile idiopathic arthritis and uveitis," Rheumatol Int., 5:258-261 (2003).
Marks et al., "By-Passing Immunization: Building High Affinity Human Antibodies by Chain Shuffling," Nature Biotechnology, 10:779-783 (1992).
Marks et al., "By-passing immunization: Human antibodies from V-gene libraries displayed on phage," J. Mol. Biol., 222:581-97 (1991).

(56) References Cited

OTHER PUBLICATIONS

Martinez et al., "Hidradenitis Suppurativa and Crohn's disease: Response to Treatment with Infliximab," Inflammatory Bowel Diseases, 7(4):323-326 (2001).
Marzi et al., "Effect of anti-tumor necrosis factor a on leukocyte adhesion in the liver after hemorrhagic shock: An intravital microscopic study in the rat," Shock, 3(1): 27-33 (1995).
Marzo-Ortega et al., "Infliximab is Effective in the Treatment of Resistant Psoriatic Arthritis and Skin Psoriasis: A Clinical and MRI Study," Rheumatology, 41(2):5 (2002).
Marzo-Ortega et al., "Inhibition of tumor necrosis factor alpha and ankylosing spondylitis," N Engl J Med., 348(4):359-61 (2003).
Massarotti et al., "Treatment Patterns in Early-onset Rheumatoid Arthritis (RA): Results from the Sonora Study," Ann. Rheum. Dis., 61(1):S93 (2002).
Mazumdar et al., "Golimumab," mAbs, 1:442-431 (2009).
McClure et al., "Comparative tolerability of systemic treatments for plaque-type psoriasis," Drug Safety, 25(13):913-27 (2002).
Mease et al., "Adalimumab for the treatment of patients with moderately to severely active psoriatic arthritis: results of a double-blind, randomized, placebo-controlled trial," Arthritis and Rheumatism, 52(10):3279-3289 (2005).
Mease et al., "Adalimumab therapy in patients with psoriatic arthritis: 24-week results of a phase III study," Arthritis & Rheumatism, 50(12):4097 (2004).
Mease et al., "Etanercept Treatment of Psoriatic Arthritis," Arthritis & Rheumatism, 50(7):2264-2272 (2004).
Mease et al., "Psoriatic Arthritis Treatment: Biological Response Modifiers," Annals of the Rheumatic Diseases, 64(2):ii78-ii82 (2005).
Mease et al., "Quality-of-life issues in psoriasis and psoriatic arthritis: Outcome measures and therapies from a dermatological perspective", J. Amer. Acad. Dermatol. 54:685-704 (2006).
Mease, "Adalimumab: an anti-TNF agent for the treatment of psoriatic arthritis," Expert Opin. Biol. Ther., 5(11):1491-1504 (2005).
Mease, "Cytokine blockers in psoriatic arthritis," Ann Rheum Dis, 60:iii37-iii40 (2001).
Mease, "Etanercept: A new era in the treatment of psoriatic arthritis," Am J of Managed Care, 8(6):S181-5193 (2002).
Mease, "Tumour necrosis factor (TNF) in psoriatic arthritis: pathophysiology and treatment with TNF inhibitors," Ann Rheum Dis., 61:298-304 (2002).
Mease, J et al., "Application and modification of minimal disease activity measures for patients with Psoriatic Arthritis Treated with Adalimumab: subanalyses of Adept," J. Rheumatology, 40:647-652 (2013).
Mease, P., et al., "24-Week Efficacy and Safety Results From the Adalimumab Effectiveness in Psoriatic Arthritis Trial (Adept)," Rheumatology, 44:OP5 (2005).
Mease, P., et al., "Clinical Efficacy and Safety of Adalimumab for Psoriatic Arthritis: 48-Week Results of Adept," Abstract 500, Arthritis & Rheumatism, 52(9) (Suppl.):S215 (2005).
Mease, P., et al., "Enbrel® (Etanercept) in Patients with Psoriatic Arthritis and Psoriasis," Abstract 1835, Arthritis Rheum., 42 (suppl.):S377 (1999).
Mease, P., et al., "Inhibition of Joint Destruction in PsA with Adalimumab: 48-Week Results of Adept," Abstract 1699, Arthritis & Rheumatism, 52(9) (Suppl.):S631 (2005).
Medynski, "Phage Display: All Dressed Up and Ready to Role," Bio/Technology, 12:1134-1136 (1994).
Menter A, "Anti-TNF Therapies for Psoriasis," Japanese Journal of Clinical Immunology, 27(4):236 (2004).
Menter et al., "Adalimumab efficacy and safety results in patients with moderate to severe chronic plaque psoriasis with and without psoriatic arthritis," J Am Academy of Dermatology, 52(3):P174 (2005).
Mishra et al., "Histone deacetylase inhibitors modulate renal disease in the MRL-Ipr/lpr mouse," J Clin Invest., 111(4):539-552 (2003).

Moller et al., "Monoclonal antibodies to human tumor necrosis factor a: in vitro and vivo application," Cytokine, 2(3):162-69 (1990).
Mordovtsev et al, "Morphology of Skin Microvasculature in Psoriasis," 11(1): 33-42 (1989).
Mori et al., "Peritoneal fluid interleukin-1/b and tumor necrosis factor in patients with benign gynecologic disease," Am J Reprod Immunol, 26:62 (1991).
Mosteller, RD "Simplified Calculation of Body-Surface Area," N Engl J Med 317(17):1098 (1987).
Mrowietz, "Definition of treatment goals for moderate to severe psoriasis: a European consensus," Arch. Dermatol. Res. 303(1):1-10 (2011).
Mullan et al., "Disease-modifying anti-rheumatic drug therapy and structural damage in early rheumatoid arthritis," Clinical and Experimental Rheumatology, 21(31):S158-164 (2003).
Mussi et al., "Serum TNF-alpha levels correlate with disease severity and are reduced by effective therapy in plaque-type psoriasis," J Bil Reul Homeost Agents, 11(3):115-8 (1997).
Nadler et al., "11-1 Band TNF-a in prostatic secretions are indicators in the evaluation of men with chronic prostatitis," Journal Urology, 164:214 (2000).
Nash et al., "Psoriatic arthritis therapy: NSAIDS and traditional DMARDs," Ann Rheum Dis 64(2):ii74-ii77 (2005).
News release, "Abbott Laboratories Initiates Clinical Trials to Explore Use of Humira® (adalimumab) in Psoriasis and Psoriatic Arthritis," Mar. 3, 2003.
Nickoloff et al., "Cellular Localization of Interleukin-8 and Its Inducer, Tumor Necrosis Factor-alpha in Psoriasis," Am. J. Pathology 138(1):129-140 (1991).
Nilsson, "Antibody engineering," Current Opinion in Structural Biology, 5:450-456 (1995).
Oh et al., "The potential angiogenic role of macrophages in the formation of choroidal neovascular membranes," Invest Ophthalmol Visual Sci, 40:1891 (1999).
Orhan et al., "Seminal plasma cytokine levels in the diagnosis of chronic pelvic pain syndrome," Int J Urol, 8:495 (2001).
Osbourn et al., "From rodent reagents to human therapeutics using antibody guided selection," Methods, 36:61-68 (2005).
Overton et al., "Peritoneal fluid cytokines and the relationship with endometrosis and pain," Hum Reprod, 11:380 (1996).
Ozaktay et al., "Dorsal root sensitivity to interleukin-1 beta, interleukin-6 and tumor necrosis factor in rats," Eur Spine Journal, 11:467 (2002).
Partsch et al., "Highly increased levels of tumor necrosis factor-alpha and other proinflammatory cytokines in psoriatic arthritis synovial fluid," J. Rheumatol., 24(3):518-23 (1997).
Partsch et al., "T cell derived cytokines derived in psoriatic arthritis synovial fluids," Annals Rheumatoid Disease, 57:691 (1998).
Patentee's Submission in EP07150442.7 to the EPO dated Apr. 15, 2013.
Patentee's Submission in EP07150442.7 to the EPO dated Apr. 30, 2012.
Patentee's Submission in EP07150442.7 to the EPO dated Jun. 30, 2011.
Paul et al., "Assessment of patients with spondyloarthropathies for treatment with tumour necrosis factor alpha blockade," Rheumatol, 44:17-23 (2005).
Paulus et al., "Relative contributions of the components of the American College of Rheumatology 20% criteria for improvement to responder status in patients with early seropositive rheumatoid arthritis," Arthritis & Rheumatism; 43(12): 2743-2750 (2000).
Peterson, "American College of Rheumatology New Orleans Oct. 25-29, 2002," Trends-in-Medicine, 1-12 (2002).
Pham et al., "Initiation of biological agents in patients with ankylosing spondylitis: results of a Delphi study by the ASAS Group," Ann Rheum Dis., 62(9):812-6 (2003).
Physician's Desk Reference, "Trexall," 57:833-836 (2003).
Pigman et al, "Sialic Acid in Normal and Arthritic Human Synovial Fluids," Arthritis & Rheumatism 1(2):151-166 (1958).
Pincus et al., "Combination Therapy with Multiple Disease-Modifying Antirheumatic Drugs in Rheumatoid Arthritis: A Preventive Strategy," Ann. Intern. Med., 131:768-774 (1999).

(56) References Cited

OTHER PUBLICATIONS

Pincus, T., et al., "Evidence from clinical trials and long-term observational studies that disease-modifying anti-rheumatic drugs slow radiographic progression in rheumatoid arthritis: updating a 1983 review," Rheumatology, 41:1346-1356 (2002).
PR Newswire, "Abbott Laboratories' D2E7—the next generation anti-TNF—shows promise in rheumatoid arthritis patients," Pr Newswire (Jun. 15, 2001) (http://www.prnewswire.co.uk/news-releases/abbott-laboratories-d2e7---the-next-generation-anti-tnf-shows-promise-in-rheumatoid%ADarthritis-patients-154493225. html) [accessed on Nov. 4, 2015].
PR Newswire, "First Phase III data for Abbott Laboratories' D2E7 (Adalimumab) support promise in rheumatoid arthritis (RA)," PR Newswire (Jun. 14, 2002) (http://www.prnewswire.co.uk/news-releases/first-phase-iii-data-for-abbott-laboratories-d2e7-adalimumab-support-promise-in-rheumatoid-arthritis-ra-154758845.html) [accessed on Nov. 2, 2015].
PR Newswire, "Abbott Laboratories Announces Positive Results of Phase II Humira® (adalimumab) Study in Psoriasis" (Feb. 9, 2004).
PR Newswire, "Cambridge Antibody Technology Interim Results for the Six Months Ended Mar. 31, 2002" (May 20, 2002).
Prahalad et al., "Etanercept in the treatment of macrophage activation syndrome," J. Rhematol., 28:2120-2124 (2001).
Prescribing Information for Humira (adalimumab) Injection, Solution for Subcutaneous use Initial U.S. Approval: 2002 (Updated Mar. 2009).
Product Monograph for Humira adalimumab (#00148) CAS Registry Number:331731-18-1, Abbott Laboratories, Jul. 10, 2012: 1-93.
Proudfoot, S. & Collett, J., "Dosage regimens" in Pharmaceutics: The Science of Dosage Form Design, 2d ed. (Aulton, M.E., ed.), Chapter 19 at 275-288 (2001).
Pucino, Jr. et al., "Use of biologics in rheumatoid arthritis: Where are we going?" Am. J. Health-Syst. Phann., 63(18 Suppl 4):519-41 (2006).
Queen et al., "A humanized antibody that binds to the interleukin 2 receptor," Proc. Natl. Acad. Sci. USA, 86:10029-10033 (1989).
Queiro-Silva et al., "A polyarticular onset predicts erosive and deforming disease in psoriatic arthritis," Ann. Rheum. Dis., 62:68-70 (2003).
R&D Focus Drug News, "Adalimumab Cambridge Antibody Technology clinical data" (Jul. 2, 2001) ("R&D Focus (2001)").
Rader et al., "A phage display approach to rapid antibody humanization: Designed combinatorial V gene libraries," Proc Natl. Acad Sci USA, 95:8910-8915 (1998).
Rau et al., "2.5-Year Treatment Results with Adalimumab (D2E7), the First Fully Human Anti-TNF Monoclonal Antibody, in Combination with Methotrexate in Active Rheumatoid Arthritis," Ann. Rheum. Dis., 61(1):555 (2002).
Rau et al., "Adalimumab Inhibits Radiographic Disease Progression in Long-Standing, Rapidly Progressive Rheumatoid Arthritis," Ann. Rheum. Dis., 62(1):191 (2003).
Rau et al., "Combination therapy with the human anti-Tnf antibody D2E7 and methotrexate in active chronic polyarthritis," Z. Rheumatol., 58(1): 1/35, F20 (1999).
Rau et al., "Effect and compatibility of repeated intravenous doses of the human anti-TNF antibody D2E7 in patients with chronic polyarthritis," Z. Rheumatol., 58(1):1/41, P12 (1999).
Rau et al., "Erfahrungen mit D2E7," Akt. Rheumatol., 25:83-88 (2000).
Rau et al., "Long-term efficacy and tolerability of multiple I.V. doses of the fully human Anti-TNF-Antibody D2E7 in patients with Rheumatoid Arthritis," Arthritis & Rheumatism, 41(137):S55 (1998).
Rau et al., "Long-term Treatment with the Fully Human Anti-TNF-Antibody D2E7 Slows Radiographic Disease Progression in Rheumatoid Arthritis," Arthritis and Rheumatism, 42(9):S400 (1999).
Rau et al., "Low dose prednilsolone therapy (LDPT) retards radiographically detectable destruction in early rheumatoid arthritis—Preliminary results of a multicenter, randomized, parallel, double blind study," Z. Rheumatol., 59(2)II/90-II/96 (2000).
Rau et al., "Treatment with Adalimumab (D2E7), the Fully Human Anti-TNF Monoclonal Antibody, Slows Radiographic Disease Progression in Rheumatoid Arthritis: Results of a 12-Month Study," J. Clin. Rheum., 8:S78 (2002).
Rau, "Adalimumab (a fully human anti-tumour necrosis factor a monoclonal antibody) in the treatment of active rheumatoid arthritis: the initial results of five trials," Ann. Rheum. Dis., 61(2)ii70-ii73 (2002).
Rau, "Experiments with D2E7," Z. Rheumatol., 58(1):1-21, S51 (1999).
Raychadhuri et al., "Psoriasis Risk Factors: Role of Lifestyle Practices," CUTIS 66 (5):348-352 (2000).
Reilly et al., "Use of genetic knockouts to modulate disease expression in a murine model of lupus, MRUipr mice," Immunologic Research, 25(2):143-153 (2002).
Reimold, "TNF alpha as therapeutic target: New drugs, more applications," Current Drug Targets-Inflammation and Allergy, 1:377-392 (2002).
Reimold, "New indications for treatment of chronic inflammation by TNF-alpha blockade," Am J Med Sci., 325(2):75-92 (2003).
Reinhart et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," Crit. Care. Med., 24(5):733-742 (1996).
Remicade (Infliximab) Drug Information: Uses, Side Effects, Drug Interactions and Warnings http://www.rxlist.com/remicadedrug. htm.
Remicade (infliximab) product information Feb. 1, 2002, retrieved from http://www.drugbank.ca/system/fda_labels/DB00065. pdf?1265922797.
Remicade (infliximab) Product Label (Jun. 2002).
Remicadetm (infliximab) Aug. 1998 Label.
Remicadetm (infliximab) Nov. 10, 1999 Approval Letter.
Results of adalimumab phase II clinical trial M02-529.
Revenga, F., et al., "Treatment of recalcitrant psoriasis with infliximab," Actas Dermo-Sifiliograficas, 95.1:44-50 (2004).
Revicki et al., "Treatment with Adalimumab (D2E7), a Fully Human Anti-TNF Monoclonal Antibody, Improves Physical Function, Vitality, and Mental Health While Reducing Bodily Pain in Patients with Active Rheumatoid Arthritis (RA)," Arthritis Rheum., 46(9):5537 (2002).
Ricardo, "Clinical benefits in patients with psoriasis after Efalizumab therapy: Clinical trial versus practice," CUTIS 74:193-200 (2004).
Riechmann et al., "Phage Display and Selection of a Site-Directed Randomized Single-Chain Antibody Fv Fragment for Its Affinity Improvement," Biochemistry, 32:8848-8855 (1993).
Rinehart-Kim et al., "Alterations in the Gene Expression Profile of Mcf-7 Breast Tumor Cells in Response to c-Jun," Int. J. Cancer, 88:180-190 (2000).
Ritchlin et al., "Patterns of cytokine productions in psoriatic synovium," J. Rheumatol, 25:1544 (1998).
Roberts et al., "Tumour necrosis factor inhibitors: risks and benefits in patients with rheumatoid arthritis," Int. Med. J., 34:687-693 (2004).
Rosenberg, Daniel, "Abbott sees new uses for rheumatoid arthritis drug [D2E7]," FirstWord Pharma (Sep. 9, 2002).
Rowland, M. & Tozer, T., Clinical Pharmacokinetics: Concepts and Applications, 3d ed., (1995).
Ruperto, "48-Week Data From the Study of Adalimumab in Children With Juvenile Rheumatoid Arthritis (JRA)," Ann. Rheum. Dis., 65(2):56 (2006).
Sakai et al., "Prognostic factor analysis for plaque psoriasis," J Invest Dermatol 121 (1):JID Abstracts, p. 58, abstract (0345).
Salfeld et al., "Generation of Fully Human Anti-TNF Antibody D2E7," Arthritis Rheum., 41(9):S57 (1998).
Sandborn et al., "CDP571, a humanised monoclonal antibody to tumour necrosis factor α, for moderate to severe Crohn's disease: a randomized, double blind, placebo controlled trial," Gut, 53:1485-1491 (2004).

(56) References Cited

OTHER PUBLICATIONS

Sandborn et al., "Etanercept for Active Crohn's Disease: A Randomized, Double-blind, Placebo-Controlled Trial," Gastroenterol, 121:1088-1094 (2001).
Sandborn et al., "Infliximab in the Treatment of Crohn's Disease: A User's Guide for Clinicians," The American Journal of Gastroenterology, 97(12):2962-2972 (2002).
Sandborn et al., "An engineered human antibody to TNF (CDP571) for active Crohn's disease: a randomized double-blind placebo-controlled trial," Gastroenterology, 120:1330-1338 (2001).
Sandborn, "Antitumor necrosis factor for inflammatory bowel disease: A Review of agents, pharmacology, clinical results, and safety," Inflamm. Bowel Disease, 5(2):199-233 (1999).
Santora et al., "Characterization of Noncovalent Complexes of Recombinant Human Monoclonal Antibody and Antigen Using Carbon Exchange, Size Exclusion Chromatography,and BIAcore," Analytical Biochemistry, 299(2):119-129 (2001).
Santora et al., "Characterization of Recombinant Human Monoclonal Tissue Necrosis Factor-a Antibody Using Cation-Exchange HPLC and Capillary Isoelectric Focusing," Analytical Biochemistry, 275:98-108 (1999).
Schattenkirchner et al, "Efficacy and Tolerability of Weekly Subcutaneous Injections of the Fully Human Anti-TNF-Antibody D2E7 in Patients with Rheumatoid Arthritis—Results of a Phase I Study," Arthritis and Rheumatism, 41(9):557 (1998).
Schattenkirchner et al., "Long-term Use of the Fully Human Anti-TNF Antibody Adalimumab (D2E7) in DMARD-refractory Rheumatoid Arthritis," EULAR, Prague, Czech Republic, Jun. (2001).
Schattenkirchner et al., "Long-term Use of the Fully Human Anti-TNF Antibody D2E7 in Combination with Methotrexate in Active Rheumatoid Arthritis," EULAR 43(9) (suppl.) S228 (2000).
Schattenkirchner et al., "Phase 1 study on the effectiveness and compatibility of weekly subcutaneous injections of the human anti-TNF antibody D2E7 in chronic polyarthritis," Z.Rheumatol., 58(1):1-42, P14 (1999).
Scheinfeld, "Adalimumab (Humira): A Review," J. Drugs Dermatol, 2:375-377 (2003).
Schiff et al., "A Randomized, Controlled, Safety Trial of Adalimumab (D2E7), a Fully Human Anti-TNF Monoclonal Antibody, Given to RA Patients in Combination with Standard Rheumatologic Care: The STAR (Safety Trial of Adalimumab in Rheumatoid Arthritis) Trial," Ann. Rheum. Dis., 61(1):5169 (2002).
Schiff et al., "Efficacy of Adalimumab Measured by the Disease Activity Score 28 (DAS28) and EULAR Response Criteria," Ann. Rheum. Dis., 62(1):170 (2003).
Schiff et al., "Malignancies in Rheumatoid Arthritis (RA) Clinical Trials with Adalimumab (Humira)," Arthritis Rheum., 48(9):5700 (2003).
Schiff et al., "Rates of Infection in Adalimumab Rheumatoid Arthritis Clinical Trials," Ann. Rheum. Dis., 62(1):184 (2003).
Schiff et al., "Sustained Efficacy of Adalimumab (Humira™) Plus Methotrexate in Rheumatoid Arthritis (RA) Patients," Arthritis Rheum., 48(9):S314 (Poster 740) (2003).
Schnarr et al., "Anti-tumour necrosis factor (TNF)-alpha therapy in undifferentiated spondyloarthropathy," Clin Exp Rheumatol, 20(6 Supp 28):S126-9 (2002).
Schneider, D., et al, "Safety, pharmacokinetics and biological activity of enlimomab (anti-ICAM-1 antibody): an open-label, dose escalation study in patients hospitalized for acute stroke," European Neurology, 40:78-83 (1998).
Shealy et al., "Anti-TNF-alpha antibody allows healing of joint damage in polyarthritis transgenic mice," Arthritis Research, Current Science, 4(5):R7 (2002).
Shealy et al., "Characterization of golimumab, a human monoclonal antibody specific for human tumor necrosis factor alpha," mAbs, 2(4):1-12 (2010).
Shikiar et al., "The validity and responsiveness of three quality of life measures in the assessment of psoriasis patients: results of a phase II study," Health and Quality of Life Outcomes 4:71 (2006).
Shvidel et al., "Cytokine release by activated T-cells in large granular lymphocytic leukemia associated with autoimmune disorders," Hematol J., 3:32 (2002).
Sibilia, "Combination therapy for rheumatoid arthritis," Ann. Med. Interne., 153(1):41-52 (2002).
Siegel et al., "Evidence of Effects of a TNF Blocking Agent in ACR20 Non-Responders," Arthritis Rheum., 48(9):S127 (2003).
Sieper et al., "New treatment options in ankylosing spondylitis: a role for anti-TNFalpha therapy," Ann Rheum Dis., 60(3):iii58-61 (2001).
Sieper, J. & Braun, J., "Anti-TNF agents for the treatment of spondyloarthropathies," Expert Opinion on Emerging Drugs, 7(2):235-246 (2002) ("Sieper (2002)").
Silicon Investor blog, "Abbott Laboratories announces positive results of Phase II Humira® (adalimumab) study in psoriasis," reproduction of Abbott Laboratories press release at entry 457 of 625, dated Feb. 9, 2004.
Simon et al., "Studies on efficacy in psoriasis and psoriatic arthritis initiated," Dermatol. Psychosom., 4:100-102 (2003).
Slatko, "Contender to the crown," MedAdNews, 29(7):1-3 (2010).
Smith, "Ibuprofen in psoriatic arthritis," Arthritis Rheum., 23(8):961-962 (1980).
Smolen et al., "A Comparison of the SDAI and DAS28 as Measures of Response in Adalimumab (Humira™) Clinical Trials in Rheumatoid Arthritis (RA)," Arthritis Rheum., 48(9):S107 (2003).
Smolen et al., "Objectives and Strategies for Rheumatoid Arthritis Therapy: Yesterday vs. Today," Drugs of Today, 39(B):3-8 (2003).
Spencer-Green, "Etanercept (Enbrel): update on therapeutic use," Ann Rheum Dis., 59(1):i46-i49 (2000).
St. Clair, "Infliximab treatment for rheumatic disease: clinical and radiological efficacy," Ann Rheum Dis, 61(2):ii67-ii69 (2002).
Steiner, et al, "Cytokine production by synovial T cells in rheumatoid arthritis," Rheumatology 38:202-213 (1999).
Stockinger, "CD147," http://mpr.nci.nhi.gov (1999).
Stokes et al., "Potential of tumor necrosis factor neutralization strategies in Rheumatologlc disorders other than rheumatoid arthritis," Semin Arthritis Rheum., 33(1):1-18 (2003).
Stone et al., "Clinical and imaging correlates of response to treatment with infliximab in patients with ankylosing spondylitis," J Rheumatol., 28(7):1605-14 (2001).
Strand et al., "Adalimumab Improves Health-related Quality of Life in Rheumatoid Arthritis Patients," Ann. Rheum. Dis., 62(1):356 (2003).
Strand et al., "Improvement in Health-related Quality of Life, Health Utility, and Fatigue in Patients with Active Rheumatoid Arthritis (RA) on Adalimumab (Humira™, Abbott) Therapy," Arthritis Rheum., 48(9):5402 (2003).
Strand et al., "Treatment with Adalimumab (D2E7), a Fully Human Anti-TNF Monoclonal Antibody, Improves Physical Function and Health Related Quality of Life (HRQOL) in Patients with Active Rheumatoid Arthritis (RA)," Ann. Rheum. Dis., 61(1):S175 (2002).
Studnicka-Benke et al., "Tumor necrosis factor alpha and its soluble receptors parallel clinical disease and autoimmune activity in systemic lupus erythematosus," Br J Rheumatol., 35:1067 (1996).
Sun et al., "Bowel necrosis induced by tumor necrosis factor in rats is mediated by platelet-activating factor," J. Clin. Invest., 81:1328-1331 (1988).
Sun et al., "Individually Distinct Ig Homology Domains in PECAM-1 Regulate Homophilic Binding and Modulate Receptor Affinity," J. Biol. Chem., 271:11090-11098 (1996).
Takahashi, "Current Situation and Future View of Antibody Therapy for Inflammatory Diseases," Journal of Clinical and Experimental Medicine, 211(7):99746-751 (2004).
Taketani et al., "Comparison of cytokine levels and embryo toxicity in peritoneal fluid in infertile women with untreated or treated endometrosis," Am J Obstet. Gynecol., 167:265 (1992).
Taylor, "Anti-tumor necrosis factor therapies," Current Opinion in Rheumatology, 13:164-169 (2001).
Third Party Observations against EP07150442.7, filed Oct. 29, 2014.
Thomas, Taber's Cyclopedic Medical Dictionary, 13:118-119 (1977).

(56) References Cited

OTHER PUBLICATIONS

Thompson et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," J. Mol. Biol., 256:77-88 (1996).
Thomson, "Abbott seeks U.S. and E.U. approval for D2E7 in rheumatoid arthritis," Reuters Drug News, Apr. 10, 2002, Retrieved from https://integrity.thomsonpharma.coml/integrity/xmlxsl/pk_ref_list.xml_show_ficha_ref?p_ref id=662437.
Thorp, "Tumour necrosis factor induction of ELAM-1 and ICAM-1 on human umbilical vein endothelial cells—analysis of tumour necrosis factor-receptor interactions," Cytokine, 4(4):313 (1992).
Tomlinson et al., "The Repertoire of Human Germline VH Sequences Reveals about Fifty Groups of VH Segments with Different Hypervariable Loops," J. Mol. Biol., 227:776-798 (1992).
Tomlinson et al., "The structural repertoire of the human VK domain," The EMBO Journal, 14(18):4628-4638 (1995).
Tracey et al., "Shock and tissue injury induced by recombinant human cachectin," Science, 234:470-474 (1986).
Tracey et al., "Tumor Necrosis Factor: A Pleiotropic Cytokine and Therapeutic Target," Annu. Rev. Med., 45:491-503 (1994).
Tsutsumimoto et al., "TNF-a and IL-1 B Suppress N-Cadherin Expression in MC3T3-E1 Cells," J Bone Miner Res., 14:1751 (1999).
Tugwell et al., "Adalimumab Improves Utility and Quality-adjusted Life Days in Rheumatoid Arthritis," Ann. Rheum. Dis., 62(1):107-8 (2003).
Tugwell et al., "Relationship Between ACR Response and HRQL in Adalimumab Clinical Trials," Ann. Rheum. Dis., 62(1):536 (2003).
Tyring et al., "Efficacy and Safety of Humira Every-Other-Week Dosing: Pooled Clinical Trial Experience," Abstract, Presented at the 21st World Congress of Dermatology, Buenos Aires, Argentina, Sep. 30-Oct. 5, 2007.
Ueda et al., "Two Mouse Monoclonal Antibodies Detecting Two Different Epitopes of an Activated Lymphocyte Antigen on Adult T-Cell Leukemia Cells," Cancer Res. 45:1314-1319 (1985).
UK High Court decision of *Actavis* v. *Eli Lilly* (Oct. 14, 2015) EWHC 3294 (pat).
Vajdos et al., "Comprehensive Functional Maps of the Antigen-binding Site of an Anti-ErbB2 Antibody Obtained with Shotgun Scanning Mutagenesis," J. Mol. Biol., 320:415-428 (2002).
Van Assche, "Anti-TNF agents in Crohn's Disease," Expert Opin. Investig. Drugs., 9(1):103-11 (2000).
Van de Putte et al., "Adalimumab (D2E7) Monotherapy in the Treatment of Patients with Severely Active Rheumatoid Arthritis (RA)," Arthritis Rheum., 46(9):5171 (2002).
Van de Putte et al., "A placebo-controlled phase 1 study of the human anti-TNP-antibody D2E7 in patients with active chronic polyarthritis," Z. Rheumatol., 58(1):1-34, F19 (1999).
Van de Putte et al., "A Single Dose Placebo Controlled Phase I Study of the Fully Human Anti-TNF Antibody D2E7 in Patients with Rheumatoid Arthritis," Arthritis Rheum., 41:S57 (1998).
Van De Putte et al., "Adalimumab (D2E7), the Fully Human Anti-TNF Monoclonal Antibody, in the Treatment of Patients with Rheumatoid Arthritis Who Failed Previous DMARD Therapy: Efficacy and Safety Results from a 6-Month Phase III Study," JCR, 8(3):589 (2002).
Van de Putte et al., "Adalimumab, " TNFa-Inhibition in the Treatment of Rheumatoid Arthritis, 71-93 (2003).
Van de Putte et al., "Efficacy and Safety of Adalimumab (D2E7), the First Fully Human Anti-TNF Monoclonal Antibody, in Patients with Rheumatoid Arthritis Who Failed Previous DMARD Therapy: 6-Month Results from a Phase III Study," Ann. Rheum. Dis., 61(1):5168 (2002).
Van de Putte et al., "Efficacy and safety of adalimumab as monotherapy in patients with rheumatoid arthritis for whom previous disease modifying antirheumatic drug treatment has failed," Ann. Rheum Dis., 63:508-516 (2004).

Van de Putte et al., "Efficacy and safety of the fully human anti-tumour necrosis factor a monoclonal antibody adalimumab (D2E7) in DMARD refractory patients with rheumatoid arthritis: a 12 week, phase II study," Ann. Rheum. Dis., 62:1168-1177 (2003).
Van de Putte et al., "Efficacy of the Fully Human anti-TNF Antibody D2E7 in Rheumatoid Arthritis," Arthritis & Rheumatism, 42(1977):5400 (1999).
Van de Putte et al., "One Year Efficacy Results of the Fully Human Anti-TNF Antibody D2E7 in Rheumatoid Arthritis," Arthritis Rheum., 43(9):5269 (2000).
Van de Putte et al., "Sustained 5-Year Efficacy of Adalimumab (Humira) Monotherapy in DMARD-Refractory rheumatoid arthritis (RA)," Arthritis Rheum., 48(9):5314 (2003).
Van den Bosch et al., "Crohn's disease associated with spondyloarthropathy: effect of TNF-alpha blockade with infliximab on articular symptoms," Lancet. 356(9244):1821-2 (2000).
Van den Bosch et al., "Effects of a loading dose regimen of three infusions of chimeric monoclonal antibody to tumour necrosis factor a (infliximab) in spondyloarthropathy: an open pilot study," Annal. Rheum. Dis. 59:428-433 (2000).
van der Heijde, D., et al., "Psoriatic arthritis imaging: a review of scoring methods," Ann. Rheum. Dis., 64 (Suppl. II):ii61-ii64 (2005).
van der Poll et al., "Effect of postponed treatment with an anti-tumour necrosis factor (TNF) F(ab')2 fragment on endotoxin-induced cytokine and neutrophil responses in chimpanzees," Clin. Exp. Immunol., 100:21-25 (1995).
van Riel et al., "Long-Term Treatment with Adalimumab (D2E7) Using Background Methotrexate in Active Rheumatoid Arthritis: Results of a 3 Year Study," Arthritis Rheum., 46(9):S534 (2002).
van Riel, "A Comparison of CRP and ESR to Measure the DAS28 in Adalimumab Clinical Trials," Ann Rheum Dis., 62:169-70 (2003).
Vasilli, "The pathophysiology of tumor necrosis factors", Annu. Rev. Immunol., 10:411-452 (1992).
Vaughan et al., "Human antibodies by design," Nature Biotechnology, 16:535-539 (1998).
Velagapudi et al., "Pharmacokinetics of Adalimumab (D2E7), a Fully Human Anti-TNF-a Monoclonal Antibody, Following a Single Intravenous Injection in Rheumatoid Arthritis Patient Treated with Methotrexate," Arthritis Rheum., 46(9):5133 (2002).
Velagapudi, et al., "Effect of Methotrexate (MTX) Coadministration on the Pharmacokinetics (PK) of Adalimumab (Humira™, Abbott) Following a Single Intravenous (iv) Injection," Arthritis Rheum., 48(9):5141 (2003).
Venn et al., "Elevated synovial fluid levels of interleukin-6 and tumor necrosis factor associated with early experimental canine osteoarthritis," Arthritis Rheum., 36:819-826 (1993).
Victor et al., "TNF-alpha and apoptosis: implications for the pathogenesis and treatment of psoriasis," J Drugs Dermatol, 1(3):264-75 (2002).
Vitali et al., "Preliminary criteria for the classification of sjogren's syndrome," Arthritis Rheum, 36:3407 (1993).
Wailoo et al., "Modeling the cost effectiveness of etanercept, adalimumab and anakinra compared to infliximab in the treatment of patients with rheumatoid arthritis in the medicare program," Agency for Healthcare Research and Quality, 1-74 (2006).
Wakefield et al., "The role of cytokines in the pathogenesis of inflammatory eye disease," Cytokine, 4:1 (1992).
Ward et al., "Binding activities of a repertoire of single immunoglobulin variable domains secreted from *Escherichia coli*," Nature, 341:544-546 (1989).
Website http://www.mayoclinic.com/health/psoriatic-arthritis/ DS004 76, accessed Jan. 4, 2012.
Weinblatt et al., "Adalimumab, a Fully Human Anti-Tumor Necrosis Factor a Monoclonal Antibody, for the Treatment of Rheumatoid Arthritis in Patients Taking Concomitant Methotrexate," Arthritis & Rheumatism, 48(1):35-45 (2003).
Weinblatt et al., "The Armada Trial: Efficacy and Safety of Adalimumab in Patients with Active RA at 24 Months," Ann. Rheum. Dis., 62(1):98 (2003).
Weinblatt et al., "The Armada Trial: Sustained Efficacy After Dose Reduction of Concomitant Methotrexate and/or Corticosteroids in

(56) References Cited

OTHER PUBLICATIONS

Patients With Rheumatoid Arthritis Treated With Adalimumab (Humira®)," 2005 EULAR Annual Meeting, Jun. 8-11, 2005, Vienna, Austria.
Weinblatt et al., "The Armada Trial: Sustained Improvement and Tolerability in Long-Term Follow-Up of Patients Treated with Adalimumab (Humira™)," Arthritis Rheum., 48(9):S314 (2003).
Weinstein et al., Therapy of Moderate-to-Severe Psoriasis 2nd Ed, pp. 1-21 (2003).
Weisman et al., "A Dose Escalation Study Designed to Demonstrate the Safety, Tolerability and Efficacy of the Fully Human Anti-TNF Antibody, D2E7, Given in Combination with Methotrexate," Arthritis Rheum., 43(9):S391 (2000).
Weisman et al., "Efficacy, Pharmacokinetic, and Safety Assessment of Adalimumab, a Fully Human Anti-Tumor Necrosis Factor-Alpha Monoclonal Antibody, in Adults with Rheumatoid Arthritis Receiving Concomitant Methotrexate: A Pilot Study," Clinical Therapeutics, 25(6): 1700-1721 (2003).
Weisman et al., 'The Importance of Pain and the Impact of Adalimumab on Pain in RA Patients, Ann. Rheum. Dis., 62(1):351 (2003).
Wellborne et al., "Adalimumab (D2E7), a Fully Human Anti-TNF-a Monoclonal Antibody, Improved Health-Related Quality of Life in Patients with Active Rheumatoid Arthritis Despite Concomitant Methotrexate Therapy," Arthritis Rheum., 46(9):S518 (2002).
Wells et al., "Incidence of Injection-Site Reactions Associated with Adalimumab (D2E7) Give Subcutaneously for at Least 6 Months: A Retrospective Analysis of 4 Phase II/III Clinical Trials," Arthritis Rheum., 46(9):S171 (2002).
Wells et al., "Injection-site Reactions in Adalimumab Rheumatoid Arthritis (RA) Pivotal Clinical Trials," Ann. Rheum. Dis., 62(1):411 (2003).
Westacott et al., "Tumor necrosis factor-a receptor expression on chondrocytes isolated from human articular cartilage," J. Rheumatology, 21:1710 (1994).
Wiendl et al., "Therapeutic Approaches in Multiple Sclerosis, Lessons from Failed and Interrupted Treatment Trials," Biodrugs, 16(3):183-200 (2002).
Williams et al., "Anti-tumor necrosis factor ameliorates joint disease in murine collagen-induced arthritis," Proc Natl Acad Sci USA, 89:9784 (1992).
Winter et al., "Humanized antibodies," Immunology Today, 14(6):243-246 (1993).
Winter et al., "Making Antibodies by Phage Display Technology," Annu. Rev. Immunol., 12:433-455 (1994).
Wollina et al., "Treatment of recalcitrant psoriatic arthritis with anti-tumor necrosis factor-alpha antibody," J. Eur. Acad. Dermatology and Venereology, 16(2):127-129 (2002).
Woon et al., "Kinetics of cytokine production in experimental autoimmune anterior uveitis (EAAU)," Current Eye Research, 17:955 (1998).
World Health Organization Informed Consent Form Template, available from http://www.who.int/rpc/research_ethics/informed_consent/en/.
World Medical Association Declaration of Helsinki (2002).
Yakeuchi et al., "Anti-TNF Therapy in Rheumor Arthritis," Japanese Journal of Clinical Immunology, 27(1):7-15 (2004).
Yamauchi et al., "Adalimubab in the Management of Hidradenitis Suppurativa," J Am Acad. Deam., AB41:P504 (2007).
Yazici et al., "A preliminary study of etanercept in the treatment of severe, resistant psoriatic arthritis," Clinical and Experimental Rheumatology, 18:732-734 (2000).
Yazici, et al., "Etanercept in the treatment of severe, resistant psoriatic arthritis: Continued efficacy and changing patterns of use after two years," Clin Exp Rheumatol. Jan.-Feb. 2002;20(1):115.
Zabraniecki et al., "TNF alpha inhibition in psoriatic arthritis: cause for hope," Joint Bone Spine Mar.;68(2):106-8 (2001).
Zhou et al., "Pharmacokinetics and Safety of Golimumab, a Fully Human Anti-TNF-a Monoclonal Antibody, in Subjects With Rheumatoid Arthritis," J. Clin. Pharmacol., 47:383-396, 2007.
Zou et al., "Immunological basis for the use of Tnf-alpha-blocking agents in ankylosing spondylitis and immunological changes during treatment," Clin Exp Rheumatol. Nov.-Dec.•20(6 Suppl 2S):S34-7 (2002).
U.S. Appl. No. 14/278,646, filed May 15, 2014, Issued.

\* cited by examiner

Figure 3. Study Design

Figure 5. Study Design

Figure 7. Study Design

Figure 8. Study design of Example 12

Figure 10. Mean Percentage PASI Improvement Through Week 60

```
SEQUENCE LISTING

<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: D2E7 light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: D2E7 heavy chain variable region

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
```

```
<212> TYPE: PRT
<213> ORGANISM: Artificial Sequence
<220> FEATURE:
<223> OTHER INFORMATION: D2E7 light chain variable region CDR3
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: D2E7 heavy chain variable region CDR3
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: D2E7 light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: D2E7 heavy chain variable region CDR1

<400> SEQUENCE: 8
```

Asp Tyr Ala Met His
1               5

<210> SEQ ID NO 9
<211> LENGTH: 107
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Leu Ser Ala Ser Ile Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
            35                  40                  45

Ser Ala Ile Thr Trp Asn Ser Gly His Ile Asp Tyr Ala Asp Ser Val
    50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

```
Gln Lys Tyr Asn Ser Ala Pro Tyr Ala
  1               5

<210> SEQ ID NO 12
<211> LENGTH: 9
<212> TYPE: PRT
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
  1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
  1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
  1               5

<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
  1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
  1               5

<210> SEQ ID NO 17
<211> LENGTH: 9
<212> TYPE: PRT
<213> ORGANISM: Artificial Sequence
<220> FEATURE:
<223> OTHER INFORMATION: L0E5 light chain variable region CDR3

<400> SEQUENCE: 17

Gln Lys Tyr Asn Ser Ala Pro Tyr Tyr
```

```
1               5
```

<210> SEQ ID NO 18
<211> LENGTH: 9
<212> TYPE: PRT
<213> ORGANISM: Artificial Sequence
<220> FEATURE:
<223> OTHER INFORMATION: VLLOG7 light chain variable region CDR3

<400> SEQUENCE: 18

```
Gln Lys Tyr Asn Ser Ala Pro Tyr Asn
1               5
```

<210> SEQ ID NO 19
<211> LENGTH: 9
<212> TYPE: PRT
<213> ORGANISM: Artificial Sequence
<220> FEATURE:
<223> OTHER INFORMATION: VLLOG9 light chain variable region CDR3

<400> SEQUENCE: 19

```
Gln Lys Tyr Thr Ser Ala Pro Tyr Thr
1               5
```

<210> SEQ ID NO 20
<211> LENGTH: 9
<212> TYPE: PRT
<213> ORGANISM: Artificial Sequence
<220> FEATURE:
<223> OTHER INFORMATION: VLLOH1 light chain variable region CDR3

<400> SEQUENCE: 20

```
Gln Lys Tyr Asn Arg Ala Pro Tyr Asn
1               5
```

<210> SEQ ID NO 21
<211> LENGTH: 9
<212> TYPE: PRT
<213> ORGANISM: Artificial Sequence
<220> FEATURE:
<223> OTHER INFORMATION: VLLOH10 light chain variable region CDR3

<400> SEQUENCE: 21

```
Gln Lys Tyr Asn Ser Ala Ala Tyr Ser
1               5
```

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

```
Gln Gln Tyr Asn Ser Ala Pro Asp Thr
1               5
```

<210> SEQ ID NO 23
<211> LENGTH: 9
<212> TYPE: PRT
<213> ORGANISM: Artificial Sequence
<220> FEATURE:
<223> OTHER INFORMATION: VL1C1 light chain variable region CDR3

<400> SEQUENCE: 23

```
Gln Lys Tyr Asn Ser Asp Pro Tyr Thr
1               5
```

```
<210> SEQ ID NO 24
<211> LENGTH: 9
<212> TYPE: PRT
<213> ORGANISM: Artificial Sequence
<220> FEATURE:
<223> OTHER INFORMATION: VL0.1F4 light chain variable region CDR3

<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
1               5

<210> SEQ ID NO 26
<211> LENGTH: 9
<212> TYPE: PRT
<213> ORGANISM: Artificial Sequence
<220> FEATURE:
<223> OTHER INFORMATION: LOE7.A light chain variable region CDR3

<400> SEQUENCE: 26

Gln Arg Tyr Asn Arg Ala Pro Tyr Ala
1               5

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
1               5                   10
```

```
<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
1               5                   10
```

```
<210> SEQ ID NO 36
<211> LENGTH: 321
<212> TYPE: DNA
<213> ORGANISM: Artificial Sequence
<220> FEATURE:
<223> OTHER INFORMATION: D2E7 light chain variable region

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                                321

<210> SEQ ID NO 37
<211> LENGTH: 363
<212> TYPE: DNA
<213> ORGANISM: Artificial Sequence
<220> FEATURE:
<223> OTHER INFORMATION: D2E7 heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tggagggccg attcaccatc tccagagaca acgccaagaa ctccctgtat     240
ctgcaaatga acagtctgag agctgaggat acggccgtat attactgtgc gaaagtctcg     300
taccttagca ccgcgtcctc ccttgactat tggggccaag gtaccctggt caccgtctcg     360
agt                                                                    363
```

METHODS AND COMPOSITIONS FOR TREATMENT OF SKIN DISORDERS

RELATED APPLICATIONS

This application is a continuation of U.S. application Ser. No. 12/646,891, filed Dec. 23, 2009, which is continuation-in-part of U.S. application Ser. No. 12/352,503, filed Jan. 12, 2009, and U.S. application Ser. No. 12/402,408, filed Mar. 11, 2009. U.S. application Ser. No. 12/646,891 claims the benefit of priority to U.S. Provisional Application No. 61/140,606, filed Dec. 23, 2008, and U.S. Provisional Application No. 61/183,446, filed Jun. 2, 2009. U.S. application Ser. No. 12/352,503 is a continuation of U.S. application Ser. No. 12/130,831, filed on May 30, 2008, which claims the benefit of priority to U.S. Provisional Application No. 60/932,914 filed on Jun. 1, 2007; U.S. Provisional Application No. 61/011,538, filed Jan. 17, 2008; U.S. Provisional Application No. 61/024,122, filed Jan. 28, 2008; and U.S. Provisional Application No. 61/128,498, filed May 22, 2008. U.S. application Ser. No. 12/402,408 is a continuation of U.S. application Ser. No. 11/880,433, filed on Jul. 20, 2007, which is a continuation in part of U.S. application Ser. No. 11/786,445, filed Apr. 10, 2007. U.S. application Ser. No. 11/786,445 claims the benefit of priority to U.S. Provisional Application No. 60/790,909 filed on Apr. 10, 2006; U.S. Provisional Application No. 60/809,770 filed on May 30, 2006; U.S. Provisional Application No. 60/815,489 filed on Jun. 20, 2006; U.S. Provisional Application No. 60/817,891 filed on Jun. 29, 2006; U.S. Provisional Application No. 60/840,122 filed on Aug. 25, 2006; U.S. Provisional Application No. 60/899,262 filed on Feb. 2, 2007; and U.S. Provisional Application No. 60/909,683 filed on Apr. 2, 2007. U.S. application Ser. No. 11/880,433 also claims priority to U.S. Provisional Application No. 60/849,671, filed on Oct. 4, 2006; U.S. Provisional Application No. 60/832,370, filed on Jul. 20, 2006; U.S. Provisional Application No. 60/851,830, filed on Oct. 12, 2006; and U.S. Provisional Application No. 60/857,352, filed on Nov. 6, 2006. The contents of all the above-mentioned priority applications are hereby incorporated by reference in their entirety.

BACKGROUND OF THE INVENTION

Psoriasis is a chronic, immune-mediated disease affecting 1-3% of the population worldwide (Jacobson and Kimball, Epidemiology: Psoriasis In: Psoriasis and Psoriatic Arthritis (Eds: Gordon K B, Ruderman E M). Springer-Verlag Berlin Heidelberg, Germany; 2005:47-56), with the greatest disease prevalence occurring in North America and Europe (Krueger and Duvic, *J. Invest. Dermatol*, 102:145-185, 1994). The most common form of psoriasis is plaque-type psoriasis, present in 65-86% of patients and characterized by the presence of thick, scaly plaques. Based on the National Psoriasis Foundation's definitions of moderate to severe psoriasis, the prevalence of moderate to severe psoriasis in the United States is estimated at 0.31% of persons age 18 or older (Stem et al., *J. Investig. Dermatol. Symp. Proc.* 9:136-139, 2004). Patients with psoriasis report reduction in physical functioning and mental functioning comparable to that observed in patients with cancer, arthritis, hypertension, heart disease, diabetes, and depression (Rapp et al., *J. Am. Acad. Dermatol.* 41(3Pt1):401-407, 1999). In a US survey of the impact of psoriasis on quality of life, respondents reported difficulties in the workplace, difficulties socializing with family members and friends, exclusion from public facilities, difficulties in getting a job, and contemplation of suicide (Krueger et al., *Arch. Dermatol.*, 137:280-284, 2001).

Traditionally, treatment for psoriasis has included medications that suppress the growth of skin cells. Treatment approaches for psoriasis often include creams and ointments, oral medications, and phototherapy.

In recent years, biologic response modifiers that inhibit certain cytokines have become a potential new avenue of treatment for psoriasis patients. For example, tumor necrosis factor (TNF) is a cytokine involved in inflammatory response and scientific evidence suggests it plays a fundamental role in the pathogenesis of psoriasis (Kreuger et al. (2004) *Arch Dermatol* 140:218; Kupper (2003) *N Engl J Med* 349:1987). The advent of targeted biologic therapies has made a significant impact on the treatment options for psoriasis, including moderate to severe psoriasis. In the United Kingdom, for example, the National Institute for Health and Clinical Excellence (NICE) recommends etanercept, a human recombinant TNF receptor fusion protein, for patients with moderate to severe psoriasis who have failed conventional therapies. Etanercept is not, however, effective in every patient. Thus, there remains a need for more effective treatment options in patients suffering from psoriasis.

SUMMARY OF THE INVENTION

There remains a need for an effective and safe treatment option for patients suffering from skin disorders in which TNFα activity is detrimental, such as psoriasis and psoriasis related disorders, who have failed or lost responsiveness to an initial treatment, such as treatment with a biologic therapy. Treatment of psoriasis with systemic therapy, such as methotrexate or cyclosporine, or biologic therapy, such as efalizumab, can be limited by lack of efficacy or precluded by side effects. Other types of therapy, for example ultraviolet light therapy, is often inconvenient. The instant invention provides improved methods and compositions for treating skin disorders in which TNFα activity is detrimental, such as psoriasis and psoriasis related disorders, in non-responders.

In one aspect, the invention provides a method for treating a skin disorder in which TNFα activity is detrimental, e.g., psoriasis, in a subject who has failed to respond to or has lost responsiveness to a biologic therapy, comprising administering to a subject in need thereof a human TNFα antibody, or antigen binding portion thereof, such that treatment occurs.

The invention also provides a method of treating a subject who has failed or has become intolerant to phototherapy or systemic therapy, e.g., etanercept or methotrexate, comprising administering to a subject in need thereof a human TNFα antibody, or antigen binding portion thereof, such that treatment occurs.

In one embodiment, the biologic therapy is etanercept. In one embodiment, the patient received entanercept therapy following a failure to respond to conventional psoriasis therapy.

In one embodiment, the subject failed to achieve a PASI 50 response rate after treatment with the biologic therapy. In certain embodiments, the subject failed to achieve a PASI 50 response rate after treatment with the biologic therapy, for example, for at least 6 weeks, at least 8 weeks, or at least 12 weeks.

In one embodiment, the subject who has failed prior therapy has a PASI of ≥10. In one embodiment, the subject who has failed prior therapy has a PASI≥10 and/or a DLQI>10.

In one embodiment, the a human TNFα antibody, or antigen binding portion thereof, is administered using a multiple dose regimen comprising at least one induction dose and at least one treatment dose. In one embodiment, the induction dose ranges from about 80 to about 160 mg. In one embodiment, the treatment does ranges from about 40 to about 80 mg. In another embodiment, the human TNFα antibody, or antigen binding portion thereof, is administered subcutaneously. In another embodiment, the treatment dose is administered one week following the induction dose. In yet another embodiment the treatment or induction dose is a fixed dose.

In another aspect, the invention provides a method of determining the efficacy of a TNFα inhibitor, e.g., human TNFα antibody, or antigen-binding portion thereof, for treating psoriasis in a subject who has failed to respond or has lost responsiveness to a biologic therapy comprising, determining the PASI, e.g., PASI50, of a subject or patient population who failed to respond to or lost responsiveness to a biologic therapy and who were administered the human TNFα antibody, or antigen-binding portion thereof, wherein a statistically significant improvement in the PASI of the patient population indicates that the TNFα inhibitor, e.g., human TNFα antibody, or antigen-binding portion thereof, is an effective for treating psoriasis in the subject. In one embodiment, the biologic therapy is etanercept.

In one embodiment, the human TNFα antibody, or antigen-binding portion is a human antibody, or antigen-binding portion thereof, that dissociates from human TNFα with a Kd of $1\times10^{-8}$M or less and a Koff rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. In one embodiment, the TNFα antibody, or antigen-binding portion thereof, is a human antibody, or antigen-binding portion thereof, having the following characteristics: dissociates from human TNFα with a Koff rate constant of $1\times10^{-3}$ s$^{-1}$ or less, as determined by surface plasmon resonance; has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 8 and/or 9; and has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12. In one embodiment, the TNFα antibody, or antigen-binding portion thereof, is a human TNFα antibody, or antigen-binding portion thereof, comprising a light chain variable region (LCVR) comprising the amino acid sequence of SEQ ID NO: 1 and a heavy chain variable region (HCVR) comprising the amino acid sequence of SEQ ID NO: 2.

In another embodiment, the human TNFα antibody, or antigen binding fragment thereof, is adalimumab, or an antigen binding portion thereof. In one embodiment, the human TNFα antibody, or antigen binding fragment thereof, is golimumab.

The invention also provides improved methods of treatment, including methods of improving disease reduction in patients having psoriasis and improvements in quality of life the psoriasis patients. The invention provides a method of improving a DLQI score of a subject having psoriasis from a large/extremely large score to a no or small impact score comprising administering a TNFα inhibitor, e.g., human TNFα antibody, or antigen-binding portion thereof, to the subject, such that the DLQI score improves from the large/extremely large score to the no or small impact score. The invention also provides a method of decreasing a Physician's Global Assessment (PGA) score of a subject having psoriasis by at least about 2 points comprising administering a TNFα inhibitor, e.g., human TNFα antibody, or antigen-binding portion thereof, to the subject, such that the PGA score is decreased by at least about 2 points. The invention also includes a method of improving a Psoriasis Area and Severity Index (PASI) score of a subject having psoriasis by at least about 8 points comprising administering a TNFα inhibitor, e.g., human TNFα antibody, or antigen-binding portion thereof, to the subject, such that the PASI score is improved by at least about 8 points.

The invention provides a method for treating certain subpopulations of patients, including, for example, those who have failed prior therapy or have had a subtherapeutic response. The invention includes a method of treating a subtherapeutic response to an original dose of a TNFα inhibitor, e.g., a human TNFα antibody, or an antigen-binding portion thereof, in a subject having psoriasis comprising administering the TNFα inhibitor to the subject at an increased dosing rate which is about twice as frequent as the original dosing rate. In one embodiment, the increased dosing rate is weekly. In one embodiment, the subtherapeutic response is defined as less than a PASI 50 response determined between baseline (week 0) and a time period following baseline. In one embodiment, the response is determined between baseline and at least about 24 weeks following baseline.

The invention further includes a method of achieving a PASI 100 and an improvement in the quality of life in a subject having psoriasis comprising administering a TNFα inhibitor, e.g., human TNFα antibody, or antigen-binding portion thereof, to the subject such that a PAS100 score and DLQI score of 0 or 1 is achieved.

In one aspect, the invention provides a method of achieving a clinical response in psoriasis in a subject comprising administering an effective amount of a TNFα inhibitor, e.g., a human TNFα antibody, or antigen-binding portion thereof, to the subject such that a clinical response in psoriasis is achieved, wherein the effective TNFα inhibitor was previously identified as achieving a PASI 75 response in at least about 77% of a patient population having psoriasis.

In one aspect, the invention provides a method of decreasing a DLQI score of a subject having psoriasis by at least about 10 points comprising administering a TNFα inhibitor, e.g., a human TNFα antibody to the subject, such that the DLQI score is decreased by at least about 10 points.

In one aspect, the invention provides a method of decreasing a DLQI score of a subject having psoriasis from a large/extremely large score to a no or small impact score comprising administering a TNFα inhibitor, e.g., human TNFα antibody to the subject, such that the DLQI score is decreased from the large/extremely large score to the no or small impact score.

In another aspect, the invention provides a method of decreasing a DLQI score of a subject having psoriasis by at least about 10 points comprising administering a TNFα inhibitor, e.g., a human TNFα antibody to the subject, such that the DLQI score is decreased by at least about 10 points.

In one aspect, the invention provides a method of decreasing a PASI score of a subject having psoriasis by at least about 8 points comprising administering a TNFα inhibitor, e.g., a human TNFα antibody to the subject, such that the PASI score is decreased by at least about 8 points.

In one aspect, the invention provides a method of decreasing a PGA score of a subject having psoriasis by at least about 2 points comprising administering a TNFα inhibitor, e.g., a human TNFα antibody to the subject, such that the PGA score is decreased by at least about 2 points.

In one embodiment, the TNFα inhibitor, e.g., human TNFα antibody, or antigen-binding portion thereof, is administered to the subject on a multiple variable dosing regimen.

In one embodiment, the TNFα inhibitor, e.g., human TNFα antibody, or antigen-binding portion thereof, is administered to the subject on a biweekly dosing regimen, including at a dose of about 40 mg.

In yet another embodiment, the TNFα inhibitor, e.g., a human TNFα antibody, or antigen-binding portion thereof, is administered to the subject via subcutaneous administration.

In another aspect, the invention further provides a method of treating psoriasis in a subject comprising administering an initial loading dose of a TNFα inhibitor, e.g., a human TNFα antibody or antigen-binding portion thereof, to the subject at week 0, administering a second dose, e.g., maintenance or treatment dose, of the TNFα inhibitor, to the subject, wherein the second dose is about half the dose amount of the loading dose.

In one embodiment, the initial dose is given in its entirety on one day or is divided over 2 days. In one embodiment, the second dose, e.g., maintenance or treatment dose, is administered to the subject about one week after the first dose on a biweekly dosing regimen.

The invention also provides a means for determining the efficacy of a TNFα inhibitor, e.g., a human TNFα antibody or antigen-binding portion thereof, for the treatment of psoriasis. The invention includes a method for determining the efficacy of a TNFα inhibitor, e.g., human TNFα antibody, or an antigen-binding portion thereof, for improving the functional limitations of a subject having psoriasis comprising determining an improvement in a DLQI score from a patient population who was administered the TNFα inhibitor, wherein a DLQI score of no or small impact in at least about 67% of the patient population indicates that the TNFα inhibitor is an effective TNFα inhibitor for improving the functional limitations of a subject having psoriasis. In one embodiment, the subject has a baseline PASI score greater than or equal to 10 and a baseline DLQI score greater than about 10

The invention further provides a method of determining the efficacy of a TNFα inhibitor, e.g., a human TNFα antibody, or an antigen-binding portion thereof, for treating psoriasis in a subject comprising determining a Psoriasis Area Severity Index (PASI) 75 response of a patient population having psoriasis who was administered the TNFα inhibitor wherein a PASI 75 response achieved in at least about 62% of the patient population indicates that the TNFα inhibitor is an effective TNFα inhibitor for the treatment of psoriasis in a subject. In one embodiment, a PASI 75 response is achieved in at least about 70% of the patient population indicates that the TNFα inhibitor is an effective human TNFα antibody, or antigen-binding portion thereof, for the treatment of psoriasis in a subject. In another embodiment, a PASI 75 response is achieved in at least about 75% of the patient population indicates that the TNFα inhibitor is an effective human TNFα antibody, or antigen-binding portion thereof, for the treatment of psoriasis in a subject. In still another embodiment, a PASI 75 response is achieved in at least about 80% of the patient population indicates that the TNFα inhibitor is an effective TNFα inhibitor for the treatment of psoriasis in a subject.

The invention also includes a method of determining the efficacy of a TNFα inhibitor, e.g., human TNFα antibody, or an antigen-binding portion thereof, for treating psoriasis in a subject comprising determining a Psoriasis Area Severity Index (PASI) 90 response of a patient population having psoriasis who was administered the TNFα inhibitor, wherein a PASI 90 response achieved in at least about 48% of the patient population indicates that the TNFα inhibitor, is an effective TNFα inhibitor for treating psoriasis in a subject. In one embodiment, a PASI 90 response achieved in at least about 52% of the patient population indicates that the TNFα inhibitor is an effective TNFα inhibitor, e.g., human TNFα antibody, or antigen-binding portion thereof, for treating psoriasis in a subject. In another embodiment, a PASI 90 response is achieved in at least about 61% of the patient population indicates that the TNFα inhibitor is an effective TNFα inhibitor for treating psoriasis in a subject.

The invention also provides a method of treating psoriasis in a subject comprising administering an effective amount of a TNFα inhibitor, e.g., human TNFα antibody, or antigen-binding portion thereof, to the subject, wherein the effective amount of the TNFα inhibitor was previously identified as achieving a PASI 90 response in at least about 48% of a patient population having psoriasis.

The invention includes a method of determining the efficacy of a TNFα inhibitor, e.g., a human TNFα antibody, or antigen-binding portion thereof, for treating psoriasis in a subject comprising determining a Psoriasis Area Severity Index (PASI) 100 response of a patient population having psoriasis and who was administered the TNFα inhibitor wherein a PASI 100 response is achieved in at least about 11% of the patient population indicates that the TNFα inhibitor is an effective TNFα inhibitor for treating psoriasis in a subject. In one embodiment, a PASI 100 response is achieved in at least about 20% of the patient population indicates that the TNFα inhibitor is an effective TNFα inhibitor for treating psoriasis in a subject. In another embodiment, a PASI 100 response is achieved in at least about 22% of the patient population indicates that the TNFα inhibitor is an effective TNFα inhibitor for treating psoriasis in a subject.

The invention further provides a method of determining the efficacy of a TNFα inhibitor, e.g., human TNFα antibody, or antigen-binding portion thereof, to treat psoriasis in a subject comprising determining a Physician's Global Assessment (PGA) score of a patient population having psoriasis who was administered the TNFα inhibitor, wherein a PGA score of "clear" or "almost clear" in at least about 27% of the patient population indicates that the TNFα inhibitor is an effective TNFα inhibitor for treating psoriasis in a subject. In one embodiment, a PGA score of "clear" or "almost clear" in at least about 48% of the patient population indicates that the TNFα inhibitor is an effective TNFα inhibitor for treating psoriasis in a subject. In another embodiment, a PGA score of "clear" or "almost clear" in at least about 65% of the patient population indicates that the TNFα inhibitor is an effective TNFα inhibitor for treating psoriasis in a subject.

The invention includes a method for determining the efficacy of a TNFα inhibitor, e.g., human TNFα antibody, or antigen-binding portion thereof, for improving the functional limitations of human subjects having moderate to severe psoriasis comprising administering the TNFα inhibitor to a preselected patient population having moderate to severe psoriasis; and determining the efficacy of the TNFα inhibitor sing a baseline Dermatology Life Quality Index (DLQI) score from the patient population and a DLQI score from a time period following administration of the TNFα inhibitor, herein a DLQI score of no or small impact in at least about 83% of the patient population indicates that TNFα inhibitor is efficacious for improving the functional limitations of human subjects having moderate to psoriasis.

The efficacy of a TNFα inhibitor, e.g., human TNFα antibody, or antigen-binding portion thereof, for treating psoriasis in a patient population, e.g., PASI 75 response (also referred to herein as a PASI/PASI75 score), may be evaluated by determining the percentage of the patient population for whom the TNFα inhibitor has been effective for treating psoriasis.

The invention also includes a method for determining the efficacy of a TNFα inhibitor, e.g., human TNFα antibody, or antigen-binding portion thereof, for treatment of psoriasis in a subject having a PASI of ≥10 and a DLQI>10 comprising determining the efficacy of the TNFα inhibitor in a patient population having a PASI of ≥10 and a DLQI>10, using a baseline PASI score of the patient population before administration of the TNFα inhibitor and a PASI score following administration of the TNFα inhibitor, wherein a PASI75 response in at least about 44% of the patient population following administration of the TNFα inhibitor indicates that the TNFα inhibitor is efficacious for treatment of psoriasis in a subject having a PASI≥10 and a DLQI>10.

The invention further provides a method for determining the efficacy of a TNFα inhibitor, e.g., human TNFα antibody, or antigen-binding portion thereof, for treatment of psoriasis in a subject having a PASI of ≥10 and a DLQI>10 comprising determining the efficacy of the TNFα inhibitor in a patient population having a PASI of ≥10 and a DLQI>10, using a baseline PGA score of the patient population before administration of the TNFα inhibitor and a PGA score following administration of the TNFα inhibitor, wherein a PGA score of "clear" or "almost clear" in at least about 33% of the patient population following administration of the TNFα inhibitor indicates that the TNFα inhibitor is efficacious for treatment of psoriasis in a subject having a PASI≥10 and a DLQI>10.

The invention describes a method for determining the efficacy of a TNFα inhibitor, e.g., human TNFα antibody, or antigen-binding portion thereof, for treatment of psoriasis in a subject having a PASI of ≥10 and a DLQI>10 comprising determining the efficacy of the TNFα inhibitor in a patient population having a PASI of ≥10 and a DLQI>10, using a baseline DLQI score of the patient population before administration of the TNFα inhibitor and a DLQI score following administration of the TNFα inhibitor, wherein a decrease in the DLQI score of at least about 12 indicates that the TNFα inhibitor is efficacious for treatment of psoriasis in a subject having a PASI≥10 and a DLQI>10.

The invention further provides a method for determining the efficacy of a TNFα inhibitor, e.g., human TNFα antibody, or antigen-binding portion thereof, for improving the general health of human subjects having moderate to severe psoriasis comprising administering the TNFα inhibitor to a preselected patient population having moderate to severe chronic plaque psoriasis; and determining the efficacy of the TNFα inhibitor using a baseline SF-36 (Short Form 36 Health Survey) score from the patient population and an SF-36 score from a time period following administration of the TNFα inhibitor, wherein an improvement in the SF-36 score indicates that TNFα inhibitor is efficacious for improving the functional limitations of human subjects having moderate to severe psoriasis. The change in the SF-36 score may be selected from any of the eight domains of the SF-36 instrument, including physical function, physical role limitations, vitality, general health perceptions, bodily pain, social function, emotional role limitations, and mental health. In one embodiment, an improvement of at least 16 in the bodily pain domain indicates that the TNFα inhibitor is efficacious for treatment of moderate to severe chronic plaque psoriasis. The invention further provides a method of improving an SF-36 score of a patient having moderate to severe chronic plaque psoriasis comprising administering to the patient a TNFα inhibitor.

In one embodiment, the invention provides a method of determining the efficacy of a TNFα inhibitor, e.g., human TNFα antibody, or antigen-binding portion thereof, for treating psoriasis in a subject comprising determining a Psoriasis Area Severity Index (PASI) score of a patient population having psoriasis and who was administered the TNFα inhibitor, wherein a PASI 75 response is achieved in at least about 32% of the patient population indicates that the TNFα inhibitor is an effective TNFα inhibitor for the treatment of psoriasis in a subject. In one embodiment, the method further comprises administering the effective TNFα inhibitor to a subject to treat psoriasis. The invention provides a method of treating psoriasis in a subject comprising administering an effective amount of a TNFα inhibitor to the subject such that treatment of psoriasis is maintained, wherein the effective human TNFα antibody was previously identified as achieving a PASI 75 response in at least about 32% of a patient population having psoriasis.

In one embodiment, the invention provides a method of treating psoriasis in a subject comprising administering an effective amount of a TNFα inhibitor, e.g., a human TNFα antibody to the subject such that psoriasis is treated, wherein the effective TNFα inhibitor was previously identified as achieving a PASI 75 response in at least about 32% of a patient population having psoriasis.

In one embodiment, a PASI 75 response is achieved in at least about 32% of the patient population indicates that the TNFα inhibitor, e.g., a human TNFα antibody is an effective TNFα inhibitor for the treatment of psoriasis in a subject. In one embodiment, a PASI 75 response is achieved in at least about 40% of the patient population indicates that the TNFα inhibitor is an effective TNFα inhibitor for the treatment of psoriasis in a subject. In one embodiment, a PASI 75 response is achieved in at least about 50% of the patient population indicates that the TNFα inhibitor is an effective TNFα inhibitor for the treatment of psoriasis in a subject. In one embodiment, a PASI 75 response is achieved in at least about 60% of the patient population indicates that the TNFα inhibitor is an effective TNFα inhibitor for the treatment of psoriasis in a subject. In one embodiment, a PASI 75 response is achieved in at least about 70% of the patient population indicates that the TNFα inhibitor is an effective human TNFα antibody for the treatment of psoriasis in a subject.

Numbers intermediate to the above recited percentages, e.g., 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, and 89%, as well as all other numbers recited herein, are also intended to be part of this invention. Ranges of values using a combination of any of the above recited values as upper and/or lower limits are intended to be included in the scope of the invention. For example, in one embodiment a PASI 75 response score of in at least between 32% and 90% of the patient population indicates that the TNFα inhibitor is an effective TNFα inhibitor for the treatment of psoriasis in a subject.

In one embodiment the invention provides a method of determining the efficacy of a TNFα inhibitor for achieving a clinical response in psoriasis in a subject comprising determining a PASI 90 response of a patient population having psoriasis and who was administered the human TNFα antibody, wherein a PASI 90 response is achieved in at least about 24% of the patient population indicates that the human TNFα antibody is an effective human TNFα antibody for achieving a clinical response in psoriasis in a subject.

In one embodiment, the invention provides a method for achieving a clinical response in psoriasis in a subject comprising administering an effective amount of a TNFα inhibitor, e.g., a human TNFα antibody, or antigen binding portion thereof, to the subject such that a clinical response in psoriasis is achieved, wherein the effective amount of the TNFα inhibitor was previously identified as achieving a PASI 90 response in at least about 24% of a patient population having psoriasis and a baseline PASI<10.

In one embodiment, a PASI 90 response is achieved in at least about 25% of the patient population indicates that the TNFα inhibito, e.g., human TNFα antibody is an effective TNFα inhibitor for achieving a clinical response in psoriasis in a subject. In one embodiment, a PASI 90 response is achieved in at least about 30% of the patient population indicates that the TNFα inhibitor is an effective TNFα inhibitor for achieving a clinical response in psoriasis in a subject. In one embodiment, a PASI 90 response is achieved in at least about 40% of the patient population indicates that the TNFα inhibitor is an effective TNFα inhibitor for achieving a clinical response in psoriasis in a subject. In one embodiment, a PASI 90 response is achieved in at least about 50% of the patient population indicates that the TNFα inhibitor is an effective TNFα inhibitor for achieving a clinical response in psoriasis in a subject. In one embodiment, a PASI 90 response is achieved in at least about 60% of the patient population indicates that the TNFα inhibitor is an effective TNFα inhibitor for achieving a clinical response in psoriasis in a subject. In one embodiment, a PASI 90 response is achieved in at least about 62% of the patient population indicates that the TNFα inhibitor is an effective TNFα inhibitor for achieving a clinical response in psoriasis in a subject.

Numbers intermediate to the above recited percentages, e.g., 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, and 61%, as well as all other numbers recited herein, are also intended to be part of this invention. Ranges of values using a combination of any of the above recited values as upper and/or lower limits are intended to be included in the scope of the invention. For example, in one embodiment a PASI 90 response score of in at least between 24% and 62% of the patient population indicates that the TNFα inhibitor is an effective TNFα inhibitor for the treatment of psoriasis in a subject.

In one embodiment the invention provides a method of determining the efficacy of a TNFα inhibitor, e.g., human TNFα antibody, or antigen binding portion thereof, for achieving a clinical response in psoriasis in a subject comprising determining a PASI 100 response of a patient population having psoriasis and who was administered the TNFα inhibitor, wherein a PASI 100 response is achieved in at least about 11% of the patient population indicates that the TNFα inhibitor is an effective TNFα inhibitor for achieving a clinical response in psoriasis in a subject.

In one embodiment, a PASI 100 response is achieved in at least about 15% of the patient population indicates that the TNFα inhibitor, e.g., a human TNFα antibody, is an effective TNFα inhibitor for achieving a clinical response in psoriasis in a subject. In one embodiment, a PASI 100 response is achieved in at least about 20% of the patient population indicates that the TNFα inhibitor is an effective TNFα inhibitor for achieving a clinical response in psoriasis in a subject. In one embodiment, a PASI 100 response is achieved in at least about 25% of the patient population indicates that the TNFα inhibitor is an effective TNFα inhibitor for achieving a clinical response in psoriasis in a subject. In one embodiment, a PASI 100 response is achieved in at least about 30% of the patient population indicates that the TNFα inhibitor is an effective TNFα inhibitor for achieving a clinical response in psoriasis in a subject. In one embodiment, a PASI 100 response is achieved in at least about 35% of the patient population indicates that the TNFα inhibitor is an effective TNFα inhibitor for achieving a clinical response in psoriasis in a subject.

Numbers intermediate to the above recited percentages, e.g., 15%, 16%, 17%, 18%, 19%, 20%, 21%, 22%, 23%, 24%, 25%, 26%, 27%, 28%, 29%, 30%, 31%, 32%, 33%, and 34% as well as all other numbers recited herein, are also intended to be part of this invention. Ranges of values using a combination of any of the above recited values as upper and/or lower limits are intended to be included in the scope of the invention. For example, in one embodiment a PASI 100 response score of in at least between 15% and 35% of the patient population indicates that the TNFα inhibitor is an effective TNFα inhibitor for the treatment of psoriasis in a subject.

In one embodiment the invention provides a method of determining the efficacy of a TNFα inhibitor, e.g., a human TNFα antibody, for achieving a clinical response in psoriasis in a subject comprising determining a Physician's Global Assessment (PGA) score of a patient population having psoriasis who was administered the TNFα inhibitor, wherein a PGA score of "clear" or "almost clear" in at least about 45% of the patient population indicates that the TNFα inhibitor is an effective TNFα inhibitor for treating psoriasis in a subject.

In one embodiment, the invention provides a method of treating psoriasis in a subject comprising administering an effective amount of a TNFα inhibitor, e.g., a human TNFα antibody, to the subject, wherein the effective TNFα inhibitor was previously identified as maintaining a PGA score of "clear" or "almost clear" in at least about 48% of a patient population having psoriasis.

In one embodiment, a PGA score of "clear" or "almost clear" in at least about 45% of a patient population having psoriasis indicates that the TNFα inhibitor, e.g., a human TNFα antibody, is an effective TNFα inhibitor for treating psoriasis in a subject. In one embodiment, a PGA score of "clear" or "almost clear" in at least about 65% of a patient population having psoriasis indicates that the TNFα inhibitor is an effective TNFα inhibitor for treating psoriasis in a subject.

Numbers intermediate to the above recited percentages, e.g., 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, and 75%, as well as all other numbers recited herein, are also intended to be part of this invention. Ranges of values using a combination of any of the above recited values as upper and/or lower limits are intended to be included in the scope of the invention. For example, in one embodiment a PGA score of "clear" or "almost clear" in at least between 45% and 76% of the patient population indicates that the TNFα inhibitor, e.g., a human TNFα antibody, is an effective TNFα inhibitor for the treatment of psoriasis in a subject.

The invention also includes further comprises administering an effective TNFα inhibitor, e.g., human TNFα antibody, or antigen-binding portion thereof, to a subject or patient population having psoriasis.

In one embodiment, the TNFα inhibitor, e.g., human TNFα antibody, or antigen-binding portion thereof, was administered to the patient population or subject on a biweekly dosing regimen.

In still another embodiment, the TNFα inhibitor, e.g., a human TNFα antibody, is administered in a multiple variable dose regimen. In one embodiment, the multiple variable dose regimen comprises an induction dose which is at least double the treatment or maintenance dose. In another embodiment, the TNFα inhibitor is administered biweekly to the patient population or subject. In one embodiment, the induction dose comprises about 80 mg. In one embodiment, the treatment dose comprises about 40 mg.

In one embodiment, the TNFα inhibitor, e.g., human TNFα antibody, or antigen-binding portion thereof, was administered to the patient population or subject at a dose of about 40 mg on a biweekly dosing regimen.

In another embodiment, the TNFα inhibitor, e.g., human TNFα antibody, or antigen-binding portion thereof, was administered to the patient population or subject via subcutaneous administration.

The invention also provides an article of manufacture comprising a TNFα inhibitor, e.g., human TNFα antibody, or antigen-binding portion thereof, and a label or package insert, wherein the label or package insert indicates that aminosalicylates, corticosteroids, and/or an immunomodulatory agent, e.g., 6-mercaptopurine and azathioprine, may be continued during treatment with the TNFα inhibitor, e.g., human TNFα antibody, or antigen-binding portion thereof, for psoriasis.

The invention includes an article of manufacture comprising a TNFα inhibitor, e.g., human TNFα antibody, or antigen-binding portion thereof, and a label or package insert indicating that a history of systemic or biologic therapy does not adversely effect efficacy of the TNFα inhibitor, e.g., human TNFα antibody or antigen-binding portion thereof, in patients for the treatment of psoriasis and/or that administration of the TNFα inhibitor is safe in patients with a history of systemic or biologic therapy.

The invention further provides an article of manufacture comprising a TNFα inhibitor, e.g., human TNFα antibody, or antigen-binding portion thereof, and a label or package insert indicating that use of TNF blockers has been associated with reactivation of hepatitis B virus (HBV) in patients who are chronic carriers of the virus.

The invention provides an article of manufacture comprising: a TNFα inhibitor, e.g., human TNFα antibody, or antigen-binding portion thereof, and a label or package insert contained within the packaging material indicating that an adverse event which has been reported in the use of the TNFα inhibitor, e.g., human TNFα antibody is angioneurotic edema.

The invention also includes an article of manufacture comprising a TNFα inhibitor, e.g., human TNFα antibody, or antigen-binding portion thereof, and a label or package insert indicating that the TNFα inhibitor, e.g., human TNFα antibody, or antigen-binding portion thereof, may be used as a first line treatment for the treatment of psoriasis.

Also included in the invention is an article of manufacture comprising a TNFα inhibitor, e.g., human TNFα antibody, or antigen-binding portion thereof, and a label or package insert indicating that the TNFα inhibitor, e.g., human TNFα antibody, or antigen-binding portion thereof, may be used for the treatment of psoriasis without methotrexate.

Further included in the invention is an article of manufacture comprising a TNFα inhibitor, e.g., human TNFα antibody, or antigen-binding portion thereof, and a label or package insert indicating that the TNFα inhibitor, e.g., human TNFα antibody, or antigen-binding portion thereof, was found to be more effective than methotrexate as a first line treatment and/or that the TNFα inhibitor, e.g., human TNFα antibody, or antigen-binding portion thereof, has significantly superior efficacy for the treatment of moderate to severe psoriasis versus methotrexate.

The invention includes a package comprising a TNFα inhibitor, e.g., human TNFα antibody, or antigen-binding portion thereof, and instructions for administering the TNFα inhibitor to a human subject for the treatment of adults with psoriasis, e.g., moderate to severe psoriasis, who have had an inadequate response to conventional therapy. The invention also includes a package comprising a TNFα inhibitor, e.g., human TNFα antibody, or antigen-binding portion thereof, wherein the package contains, on the label and in a position which is visible to a subject, including a prospective purchaser, a printed statement which informs a subject, including a prospective purchaser, that the TNFα inhibitor is indicated for the treatment of adults with moderate to severe psoriasis who have had an inadequate response to conventional therapy.

The invention further provides a package comprising a TNFα inhibitor, e.g., human TNFα antibody, or antigen-binding portion thereof, wherein the package contains, on the label and in a position which is visible to a subject, including a prospective purchaser, a printed statement which informs a subject, including a prospective purchaser, that the recommended dose of the TNFα inhibitor for patients with psoriasis is 40 mg TNFα inhibitor administered every other week as a single dose via subcutaneous injection.

The invention also provides a package comprising a TNFα inhibitor, e.g., human TNFα antibody, or antigen-binding portion thereof, wherein the package contains, on the label and in a position which is visible to a subject, including a prospective purchaser, a printed statement which informs prospective purchasers that the TNFα inhibitor has been shown to have an uncommon undesirable effect in clinical studies. Examples of such effects are provided in the examples section described herein.

The invention provides an article of manufacture comprising: a packaging material; a TNFα inhibitor, e.g., human TNFα antibody, or antigen-binding portion thereof, and a label or package insert contained within the packaging material indicating that a history of systemic or biologic therapy does not adversely effect efficacy of the TNFα inhibitor in patients.

In one aspect, the invention provides an article of manufacture comprising a TNFα inhibitor, e.g., human TNFα antibody and a package insert, wherein the package insert indicates the recommended TNFα inhibitor, e.g., human TNFα antibody, dose regimen for adult patients with psoriasis is 80 mg at week 0, 80 mg at week 1, followed by 40 mg every other week beginning at week 3.

In one aspect, the invention provides an article of manufacture comprising a TNFα inhibitor, e.g., human TNFα antibody and a package insert, wherein the package insert indicates the recommended TNFα inhibitor, e.g., human TNFα antibody, dose regimen for adult patients with psoriasis is 80 mg at week 0, 40 mg at week 1, followed by 40 mg every other week beginning at week 3.

In one aspect, the invention provides an article of manufacture which comprising adalimumab and a package insert, wherein the package insert indicates that the adalimumab may be used to treat psoriasis in patients who have had an inadequate response to conventional therapy and/or who have lost response to or are intolerant to infliximab.

In one aspect, the invention provides an article of manufacture comprising: a) a packaging material; b) a human TNFα antibody, and c) a label or package insert contained within the packaging material indicating that the human TNFα antibody may be used as a first line treatment for the treatment of psoriasis.

In one aspect, the invention provides an article of manufacture comprising: a) a packaging material; b) a human TNFα antibody, and c) a label or package insert contained within the packaging material indicating that the human TNFα antibody may be used for the treatment of psoriasis without methotrexate.

In another aspect, the invention provides an article of manufacture comprising:

a) a packaging material; b) a human TNFα antibody, and c) a label or package insert contained within the packaging material indicating that the human TNFα antibody was found to be more effective than methotrexate as a first line treatment and/or that the human TNFα antibody has significantly superior efficacy for the treatment of moderate to severe psoriasis versus methotrexate.

In one embodiment, the TNFα inhibitor is selected from the group consisting of an anti-TNFα antibody, or an antigen-binding portion thereof, a TNF fusion protein, or a recombinant TNF binding protein.

In one embodiment, the TNF fusion protein is etanercept.

In one embodiment, the TNFα antibody, or antigen-binding portion thereof, is selected from the group consisting of a chimeric antibody, a humanized antibody, and a multivalent antibody.

In one embodiment of the invention, the TNFα antibody, or antigen-binding portion thereof, is a human antibody.

In another embodiment, the TNFα antibody, or antigen-binding portion thereof, is an isolated human antibody that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less.

In one embodiment of the invention, the TNFα antibody is an isolated human antibody, or antigen-binding portion thereof, with the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment of the invention, the TNFα antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2.

In one embodiment, the TNFα antibody, or antigen-binding portion thereof, is adalimumab.

In one embodiment, the TNFα antibody, or antigen-binding portion thereof, is a 40 mg dose.

In another embodiment, the TNFα antibody, or antigen-binding portion thereof, is administered subcutaneously.

The another embodiment of the invention, the anti-TNFα antibody, or antigen-binding portion thereof, is infliximab or golimumab.

In one embodiment, the psoriasis is moderate to severe psoriasis. In another embodiment, the moderate to severe psoriasis is moderate to severe chronic plaque psoriasis.

In one embodiment, the TNFα inhibitor is administered weekly to the patient population or subject having psoriasis. In another embodiment, TNFα inhibitor is administered biweekly to the patient population or subject having psoriasis.

In one embodiment, the multiple variable dose regimen comprises an induction dose which is at least double the treatment dose. In one embodiment, the induction dose comprises about 80 mg. In one embodiment, the treatment dose comprises about 40 mg.

In one embodiment, the patient population or subject also has psoriatic arthritis.

In one embodiment, the patient population or subject has a PASI score, e.g., a baseline score, of ≥10 and a DLQI score e.g., a baseline score, >10.

DETAILED DESCRIPTION OF THE INVENTION

I. Definitions

Figure 1:
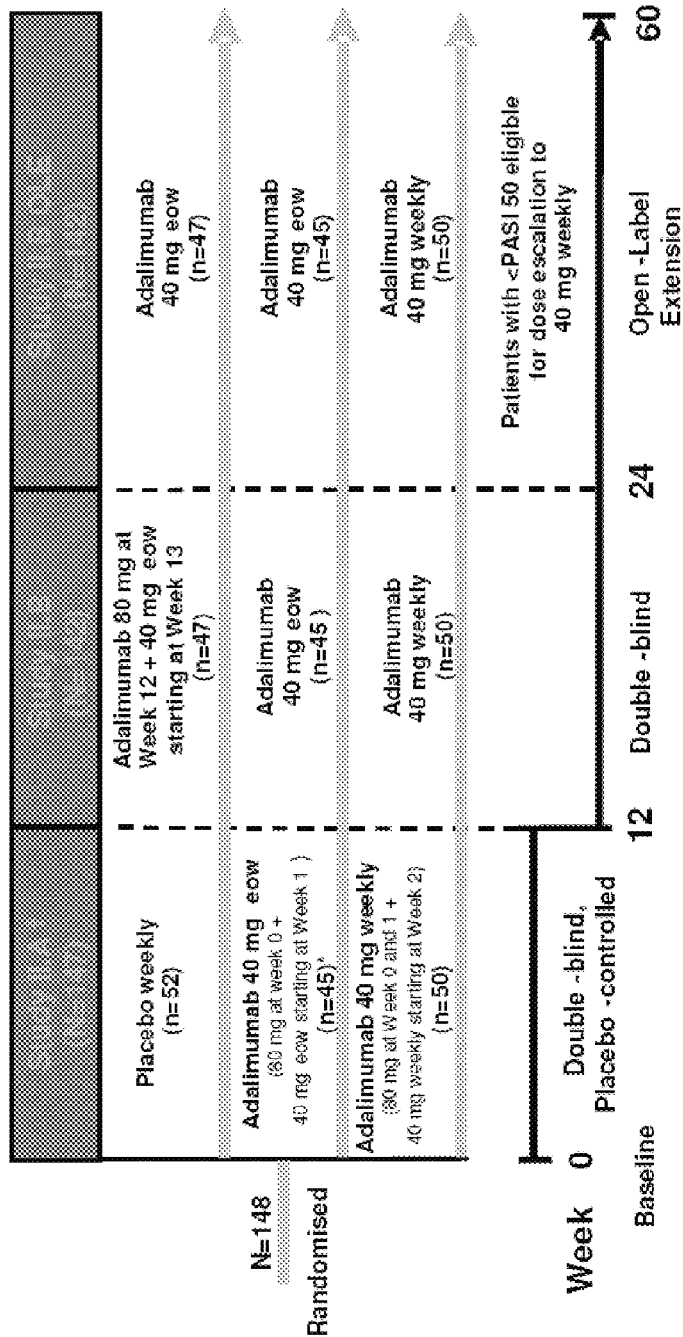
FIG. 1 shows the study design from Phase II clinical trial.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338: 225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" includes agents which interfere with TNFα activity. The term also includes each of the anti-TNFα human antibodies and antibody portions described herein as well as those described in U.S. Pat. Nos. 6,090,382; 6,258,562; 6,509,015, and in U.S. patent application Ser. Nos. 09/801,185 and 10/302,356. In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502 and U.S. Pat. No. 7,521,206 and U.S. Pat. No. 7,250,165, incorporated by reference herein), and adalimumab (HUMIRA® Abbott Laboratories, a human anti-TNF mAb, described in U.S. Pat. No. 6,090,382 as D2E7, incorporated by reference herein). Additional TNFα antibodies which may be used in the invention are described in U.S. Pat. Nos. 6,593,458; 6,498,237; 6,451,983; and 6,448,380, each of which is incorporated by reference herein. In another embodiment, the TNFα inhibitor is a TNF fusion protein, e.g., etanercept (Enbrel®, Amgen; described in WO 91/03553 and WO 09/406,476, incorporated by reference herein). In another embodiment, the TNFα inhibitor is a recombinant TNF binding protein (r-TBP-I) (Serono).

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "antigen-binding portion" or "antigen-binding fragment" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Binding fragments include Fab, Fab', F(ab')$_2$, Fabc, Fv, single chains, and single-chain antibodies. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Chimeric antibodies" refers to antibodies wherein one portion of each of the amino acid sequences of heavy and light chains is homologous to corresponding sequences in antibodies derived from a particular species or belonging to a particular class, while the remaining segment of the chains is homologous to corresponding sequences from another species. In one embodiment, the invention features a chimeric antibody or antigen-binding fragment, in which the variable regions of both light and heavy chains mimics the variable regions of antibodies derived from one species of mammals, while the constant portions are homologous to the sequences in antibodies derived from another species. In a preferred embodiment of the invention, chimeric antibodies are made by grafting CDRs from a mouse antibody onto the framework regions of a human antibody.

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or immunogenicity.

The term "multivalent antibody" refers to an antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" or "dual specific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060, Queen et al., *Proc. Natl. Acad. Sci. USA* 86:10029-10033 (1989), U.S. Pat. No. 5,530,101, U.S. Pat. No. 5,585,089, U.S. Pat. No. 5,693,761, U.S. Pat. No. 5,693,762, Selick et al., WO 90/07861, and Winter, U.S. Pat. No. 5,225,539.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "biologic therapy" refers to a protein-based therapy. In one embodiment, the biologic therapy is a TNFR: Fc fusion protein, such as etanercept.

The term "dose," as used herein, refers to an amount of TNFα inhibitor which is administered to a subject.

The term "dosing", as used herein, refers to the administration of a substance (e.g., an anti-TNFα antibody) to achieve a therapeutic objective (e.g., treatment of psoriasis).

A "dosing regimen" describes a treatment schedule for a TNFα inhibitor, e.g., a treatment schedule over a prolonged period of time and/or throughout the course of treatment, e.g. administering a first dose of a TNFα inhibitor at week 0 followed by a second dose of a TNFα inhibitor on a biweekly dosing regimen.

The term "fixed dosing regimen" refers to a dosing regimen which relies on a fixed dose amount of an agent for the treatment of a disorder. In a preferred embodiment, the fixed dosing regimen includes administering a fixed dose amount of a TNFα inhibitor, such as a human TNFα antibody, for the treatment of a skin disorder associated with detrimental TNFα activity, such as psoriasis. A fixed dose refers to a pre-determined amount of an agent, e.g., 20 mg, 21 mg, 22 mg, 23 mg, 24 mg, 25 mg, 40 mg, 45 mg, 50 mg, 80 mg, 90 mg, 100 mg, etc. In one embodiment, a fixed dosing regimen includes a dosing regimen where a TNFα inhibitor is administered to a subject as a fixed dose consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc., beginning at the initial dose. As used herein, a dose amount referred to by an amount in mg, e.g., 40 mg, is equivalent to a fixed dose. A fixed dose is not dependent on the weight of a subject.

The term "multiple-variable dose" includes different doses of a TNFα inhibitor which are administered to a subject for therapeutic treatment. "Multiple-variable dose regimen" or "multiple-variable dose therapy" describes a treatment schedule which is based on administering different amounts of TNFα inhibitor at various time points throughout the course of treatment. Multiple-variable dose regimens are described in PCT application no. PCT/US05/12007 and US 20060009385, which is incorporated by reference herein.

The term "maintenance therapy" or "maintenance dosing regime" refers to a treatment schedule for a subject or patient diagnosed with a disorder/disease, e.g., psoriasis, to enable them to maintain their health in a given state, e.g, remission. Generally, the first goal of treatment of psoriasis is to induce remission in the subject in need thereof. The next challenge is to keep the subject in remission. Maintenance doses may be used in a maintenance therapy for maintaining remission in a subject who has achieved remission of a disease or who has reached a state of the disease which is advantageous, e.g. reduction in symptoms. In one embodiment, a maintenance therapy of the invention is used for a subject or patient diagnosed with a disorder/disease, e.g., psoriasis to enable them to maintain their health in a state which is completely free of symptoms associated with the disease. In one embodiment, a maintenance therapy of the invention is used for a subject or patient diagnosed with a disorder/disease, e.g., psoriasis, to enable them to maintain their health in a state which is substantially free of symptoms associated with the disease. In one embodiment, a maintenance therapy of the invention is used for a subject or patient diagnosed with a disorder/disease, e.g., psoriasis, to enable them to maintain their health in a state where there is a significant reduction in symptoms associated with the disease.

The term "induction dose" or "loading dose," used interchangeably herein, refers to the first dose of TNFα inhibitor which is initially used to induce remission of psoriasis. Often, the loading dose is larger in comparison to the subsequent maintenance or treatment dose. The induction dose can be a single dose or, alternatively, a set of doses. In one embodiment, an induction dose is subsequently followed by administration of smaller doses of TNFα inhibitor, e.g., the treatment or maintenance dose. The induction dose is administered during the induction or loading phase of therapy. In one embodiment of the invention, the induction dose is at least twice the given amount of the treatment dose. In one embodiment of the invention, the induction dose is 80 mg.

The term "treatment phase" or "maintenance phase", as used herein, refers to a period of treatment comprising administration of a TNFα inhibitor to a subject in order to maintain a desired therapeutic effect, i.e., maintaining remission of psoriasis.

The term "maintenance dose" or "treatment dose" is the amount of TNFα inhibitor taken by a subject to maintain or continue a desired therapeutic effect. A maintenance dose can be a single dose or, alternatively, a set of doses. A maintenance dose is administered during the treatment or maintenance phase of therapy. In one embodiment, a maintenance dose(s) is smaller than the induction dose(s). In one embodiment, multiple maintenance doses can be equal to each other when administered in succession. In one embodiment, the invention provides a maintenance dose of 40 mg of a human TNFa antibody, or antigen-binding portion thereof, e.g., adalimumab, administered subcutaneously to a subject who is in remission, every other week, or biweekly. In one embodiment, the maintenance dose is administered every other week beginning at week 1 of treatment.

The terms "biweekly dosing regimen", "biweekly dosing", and "biweekly administration", as used herein, refer to the time course of administering a substance (e.g., an anti-TNFα antibody) to a subject to achieve a therapeutic objective, e.g, throughout the course of treatment. The biweekly dosing regimen is not intended to include a weekly dosing regimen. Preferably, the substance is administered every 9-19 days, more preferably, every 11-17 days, even more preferably, every 13-15 days, and most preferably, every 14 days. In one embodiment, the biweekly dosing regimen is initiated in a subject at week 0 of treatment. In another embodiment, a maintenance dose is administered on a biweekly dosing regimen. In one embodiment, both the loading and maintenance doses are administered according to a biweekly dosing regimen. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing methods are also described in US 20030235585, incorporated by reference herein.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-TNFα antibody and another drug. The other drug(s) may be administered concomitant with, prior to, or following the administration of an anti-TNFα antibody.

The term "treatment," as used within the context of the present invention, is meant to include therapeutic treatment, as well as prophylactic or suppressive measures, for the treatment of psoriasis. For example, the term treatment may include administration of a TNFα inhibitor prior to or following the onset of psoriasis thereby preventing or removing signs of the disease or disorder. As another example, administration of a TNFα inhibitor after clinical manifestation of psoriasis to combat the symptoms and/or complications and disorders associated with psoriasis comprises "treatment" of the disease. Further, administration of the agent after onset and after clinical symptoms and/or complications have developed where administration affects clinical parameters of the disease or disorder and perhaps amelioration of the disease, comprises "treatment" of the psoriasis. In one embodiment, treatment of psoriasis in a subject comprises inducing and maintaining remission of psoriasis in a subject. In another embodiment, treatment of psoriasis in a subject comprises maintaining remission of psoriasis in a subject.

Those "in need of treatment" include mammals, such as humans, already having psoriasis, including those in which the disease or disorder is to be prevented.

Various aspects of the invention are described in further detail herein.

The invention provides improved uses and compositions for treating psoriasis disease with a TNFα inhibitor, e.g., a human TNFα antibody, or an antigen-binding portion thereof. Compositions and articles of manufacture, including kits, relating to the methods and uses for treating psoriasis are also contemplated as part of the invention.

II. TNF Inhibitors

A TNFα inhibitor which is used in the methods and compositions of the invention includes any agent which interferes with TNFα activity. In a preferred embodiment, the TNFα inhibitor can neutralize TNFα activity, particularly detrimental TNFα activity which is associated with psoriasis, and related complications and symptoms.

In one embodiment, the TNFα inhibitor used in the invention is an TNFα antibody (also referred to herein as a TNFα antibody), or an antigen-binding fragment thereof, including chimeric, humanized, and human antibodies. Examples of TNFα antibodies which may be used in the invention include, but not limited to, infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498, 237; 6,451,983; and 6,448,380, each of which is incorporated by reference herein.

Other examples of TNFα inhibitors which may be used in the methods and compositions of the invention include etanercept (Enbrel, described in WO 91/03553 and WO 09/406,476), soluble TNF receptor Type I, a pegylated soluble TNF receptor Type I (PEGs TNF-R1), p55TNFR1gG (Lenercept), and recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

In one embodiment, the invention features methods and compositions for treating or determining the efficacy of a TNFα inhibitor for the treatment of a skin disorder in which TNFα activity is detrimental, e.g., psoriasis, wherein the TNFα antibody is an isolated human antibody, or antigen-binding portion thereof, that binds to human TNFα with high affinity and a low off rate, and also has a high neutralizing capacity. Preferably, the human antibodies used in the invention are recombinant, neutralizing human anti-hTNFα antibodies. The most preferred recombinant, neutralizing antibody of the invention is referred to herein as D2E7, also referred to as HUMIRA® or adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/HUMIRA®) have been described in Salfeld et al., U.S. Pat. Nos. 6,090,382, 6,258,562, and 6,509,015, which are each incorporated by reference herein. The methods of the invention may also be performed using chimeric and humanized murine anti-hTNFα antibodies which have undergone clinical testing for treatment of rheumatoid arthritis (see e.g., Elliott, M. J., et al. (1994) Lancet 344: 1125-1127; Elliot, M. J., et al. (1994) Lancet 344:1105-1110; Rankin, E. C., et al. (1995) Br. J. Rheumatol. 34:334-342).

In certain embodiments, the TNFα inhibitor used in the invention are D2E7 antibodies and antibody portions, D2E7-related antibodies and antibody portions, or other human antibodies and antibody portions with equivalent properties to D2E7, such as high affinity binding to hTNFα with low dissociation kinetics and high neutralizing capacity. In one embodiment, the invention provides treatment with an isolated human antibody, or an antigen-binding portion thereof, that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. More preferably, the isolated human antibody, or antigen-binding portion thereof, dissociates from human TNFα with a $K_{off}$ of $5\times10^{-4}$ s$^{-1}$ or less, or even more preferably, with a $K_{off}$ of $1\times10^{-4}$ s$^{-1}$ or less. More preferably, the isolated human antibody, or antigen-binding portion thereof, neutralizes human TNFα cytotoxicity in a standard in vitro L929 assay with an IC$_{50}$ of $1\times10^{-8}$ M or less, even more preferably with an IC$_{50}$ of $1\times10^{-9}$ M or less and still more preferably with an IC$_{50}$ of $1\times10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to treating psoriasis by administering human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the antibody or antigen-binding portion thereof preferably contains the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5\times10^{-4}$ s$^{-1}$ or less. Even more preferably, the antibody, or antigen-binding portion thereof, dissociates from human TNFα with a $K_{off}$ of $1\times10^{-4}$ s$^{-1}$ or less.

In yet another embodiment, the antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the V$_\kappa$I human germline family, more preferably from the A20 human germline Vk gene and most preferably from the D2E7 VL framework sequences shown in FIGS. 1A and 1B of U.S. Pat. No. 6,090,382. The framework regions for VH preferably are from the V$_H$3 human germline family, more preferably from the DP-31 human germline VH gene and most preferably from the D2E7 VH framework sequences shown in FIGS. 2A and 2B of U.S. Pat. No. 6,090,382.

Accordingly, in another embodiment, the antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention includes uses of an isolated human antibody, or an antigen-binding portions thereof, containing D2E7-related VL and VH CDR3 domains. For example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the methods and compositions of the invention may be modified for improved treatment of psoriasis. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat psoriasis by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion used in the methods of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, used in the methods and compositions of the invention, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express antibodies, such as adalimumab (D2E7) or an adalimumab (D2E7)-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Moreover, it should be noted that if the "germline" sequences obtained by PCR amplification encode amino acid differences in the framework regions from the true germline configuration (i.e., differences in the amplified sequence as compared to the true germline sequence, for example as a result of somatic mutation), it may be desirable to change these amino acid differences back to the true germline sequences (i.e., "backmutation" of framework residues to the germline configuration).

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of the foregoing, nucleic acid, vector and host cell compositions that can be used for recombinant expression of the antibodies and antibody portions used in the invention include nucleic acids, and vectors comprising said nucleic acids, comprising the human TNFα antibody adalimumab (D2E7). The nucleotide sequence encoding the D2E7 light chain variable region is shown in SEQ ID NO: 36. The CDR1 domain of the LCVR encompasses nucleotides 70-102, the CDR2 domain encompasses nucleotides 148-168 and the CDR3 domain encompasses nucleotides 265-291. The nucleotide sequence encoding the D2E7 heavy chain variable region is shown in SEQ ID NO: 37. The CDR1 domain of the HCVR encompasses nucleotides 91-105, the CDR2 domain encompasses nucleotides 148-198 and the CDR3 domain encompasses nucleotides 295-330. It will be appreciated by the skilled artisan that nucleotide sequences encoding D2E7-related antibodies, or portions thereof (e.g., a CDR domain, such as a CDR3 domain), can be derived from the nucleotide sequences encoding the D2E7 LCVR and HCVR using the genetic code and standard molecular biology techniques.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-65; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human neutralizing antibodies with high affinity and a low off rate constant for hTNFα are described in U.S. Pat. Nos. 6,090,382, 6,258,562, and 6,509,015, each of which is incorporated by reference herein.

Antibodies, antibody-portions, and other TNFα inhibitors for use in the methods of the invention, can be incorporated into pharmaceutical compositions suitable for administration to a subject. Typically, the pharmaceutical composition comprises an antibody, antibody portion, or other TNFα inhibitor, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods and compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In a preferred embodiment, the antibody or other TNFα inhibitor is administered by intravenous infusion or injection. In another preferred embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, the invention includes pharmaceutical compositions comprising an effective TNFα inhibitor and a pharmaceutically acceptable carrier, wherein the effective TNFα inhibitor may be used to treat psoriasis.

In one embodiment, the antibody or antibody portion for use in the methods of the invention is incorporated into a pharmaceutical formulation as described in PCT/IB03/04502 and U.S. Appln. No. 20040033228, incorporated by reference herein. This formulation includes a concentration 50 mg/ml of the antibody D2E7 (adalimumab), wherein one pre-filled syringe contains 40 mg of antibody for subcutaneous injection.

The antibodies, antibody-portions, and other TNFα inhibitors of the present invention can be administered by a variety of methods known in the art, although for many therapeutic applications, the preferred route/mode of administration is parenteral, e.g., subcutaneous injection. In another embodiment, administration is via intravenous injection or infusion.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Dekker, Inc., New York, 1978.

In one embodiment, the TNFα antibodies and inhibitors used in the invention are delivered to a subject subcutaneously. In one embodiment, the subject administers the TNFα inhibitor, including, but not limited to, TNFα antibody, or antigen-binding portion thereof, to himself/herself.

The TNFα antibodies and inhibitors used in the invention may also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. Appln. No. 20040033228, incorporated by reference herein, are used to treat rheumatoid arthritis using the treatment methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion for use in the methods of the invention is coformulated with and/or coadministered with one or more additional therapeutic agents, including a TNFα inhibitor or antagonist. For example, an anti-hTNFα antibody or antibody portion of the invention may be coformulated and/or coadministered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Additional description regarding methods and uses of the invention comprising administration of a TNFα inhibitor are described in Part III of this specification.

The invention also pertains to packaged pharmaceutical compositions or kits for administering the anti-TNF antibodies of the invention for the treatment of Psoriasis. In one embodiment of the invention, the kit comprises a TNFα inhibitor, such as an antibody and instructions for administration of the TNFα inhibitor for treatment of Psoriasis. The instructions may describe how, e.g., subcutaneously, and when, e.g., at week 0, week 2, week 4, etc., the different doses of TNFα inhibitor shall be administered to a subject for treatment.

Another aspect of the invention pertains to kits containing a pharmaceutical composition comprising a TNFα inhibitor, such as an antibody, and a pharmaceutically acceptable carrier and one or more pharmaceutical compositions each comprising an additional therapeutic agent useful for treating psoriasis, and a pharmaceutically acceptable carrier. Alternatively, the kit comprises a single pharmaceutical composition comprising an anti-TNFα antibody, one or more drugs useful for treating psoriasis, and a pharmaceutically acceptable carrier. The instructions may describe how, e.g., subcutaneously, and when, e.g., at week 0, week 2, week 4, etc., the different doses of TNFα inhibitor and/or the additional therapeutic agent shall be administered to a subject for treatment.

The kit may contain instructions for dosing of the pharmaceutical compositions for the treatment of psoriasis. Additional description regarding articles of manufacture of the invention are described in subsection III.

The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

III. Methods and Compositions for Treating Skin Disorders Associated with Detrimental TNFα Activity Tumor necrosis factor has been implicated in the pathophysiology of certain skin disorders. In one embodiment, the methods of the invention can be used to treat a subject having a skin disorder in which TNFα activity is detrimental. The term "skin disorder" or "skin disease" as used interchangeably herein, refers to abnormalities, other than injury wounds, of the skin which have induced a state of inflammation. In one embodiment, the skin disorder of the invention is an inflammatory skin disorder, wherein the skin is characterized by capillary dilatation, leukocytic infiltration, redness, heat, and/or pain. Examples of skin disorders include, but are not limited to, psoriasis, pemphigus vulgaris, scleroderma, atopic dermatitis, sarcoidosis, erythema nodosum, hidradenitis suppurative, lichen planus, Sweet's syndrome, and vitiligo. As used herein, the term "skin disorder in which TNFα activity is detrimental" is intended to include skin disorders and other disorders in which the presence of TNFα in a subject suffering from the disorder has been shown to be or is suspected of being either responsible for the pathophysiology of the disorder or a factor that contributes to a worsening of the disorder, e.g., psoriasis. Accordingly, skin disorders in which TNFα activity is detrimental are disorders in which inhibition of TNFα activity is expected to alleviate the symptoms and/or progression of the disorder. The use of the antibodies, antibody portions, and other TNFα inhibitors of the invention in the treatment of specific skin disorders, e.g., psoriasis, is discussed further below.

Psoriasis

Tumor necrosis factor has been implicated in the pathophysiology of psoriasis (Takematsu et al. (1989) *Arch Dermatol Res.* 281:398; Victor and Gottlieb (2002) *J Drugs Dermatol.* 1(3):264). Psoriasis is described as a skin inflammation (irritation and redness) characterized by frequent episodes of redness, itching, and thick, dry, silvery scales on the skin. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the epidermis and polymorphonuclear leukocyte and lymphocyte infiltration into the epidermis layer resulting in an increase in the basal cell cycle. Psoriasis often involves the nails, which frequently exhibit pitting, separation of the nail, thickening, and discoloration. Psoriasis is often associated with other inflammatory disorders, for example arthritis, including rheumatoid arthritis, inflammatory bowel disease (IBD), and Crohn's disease.

Evidence of psoriasis is most commonly seen on the trunk, elbows, knees, scalp, skin folds, or fingernails, but it may affect any or all parts of the skin. Normally, it takes about a month for new skin cells to move up from the lower layers to the surface. In psoriasis, this process takes only a few days, resulting in a build-up of dead skin cells and formation of thick scales. Symptoms of psoriasis include: skin patches, that are dry or red, covered with silvery scales, raised patches of skin, accompanied by red borders, that may crack and become painful, and that are usually lovated on the elbows, knees, trunk, scalp, and hands; skin lesions, including pustules, cracking of the skin, and skin redness; joint pain or aching which may be associated with of arthritis, e.g., psoriatic arthritis.

Treatment for psoriasis often includes a topical corticosteroids, vitamin D analogs, and topical or oral retinoids, or combinations thereof. In one embodiment, the TNFα inhibitor of the invention is administered in combination with or the presence of one of these common treatments. Additional therapeutic agents which can also be combined with the TNFα inhibitor of the invention for treatment of psoriasis are described in more detail below.

The diagnosis of psoriasis is usually based on the appearance of the skin. Additionally a skin biopsy, or scraping and culture of skin patches may be needed to rule out other skin disorders. An x-ray may be used to check for psoriatic arthritis if joint pain is present and persistent.

Certain subtypes of psoriasis may be treated in accordance with the invention. In one embodiment, moderate to severe psoriasis is treated by administering a TNFα inhibitor, e.g., antibody, or antigen-binding portion thereof, to a subject. The invention also provides a method for treating certain subpopulations of psoriasis patients who may be especially difficult to treat. For example, the invention provides a method for treating patients who have a subtherapeutic response to a therapy, such as etanercept therapy.

In one embodiment of the invention, a TNFα inhibitor is used to treat psoriasis, including chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). In one embodiment, the methods of the invention are use to treat moderate to severe psoriasis. Specific types of psoriasis included in the treatment methods of the invention are described in detail below:

a. Chronic Plaque Psoriasis

Tumor necrosis factor has been implicated in the pathophysiology of chronic plaque psoriasis (Asadullah et al. (1999) *Br J Dermatol.* 141:94). Chronic plaque psoriasis (also referred to as psoriasis vulgaris) is the most common form of psoriasis. Chronic plaque psoriasis is characterized by raised reddened patches of skin, ranging from coin-sized to much larger. In chronic plaque psoriasis, the plaques may be single or multiple, they may vary in size from a few millimeters to several centimeters. The plaques are usually red with a scaly surface, and reflect light when gently scratched, creating a "silvery" effect. Lesions (which are often symmetrical) from chronic plaque psoriasis occur all over body, but with predilection for extensor surfaces, including the knees, elbows, lumbosacral regions, scalp, and nails. Occasionally chronic plaque psoriasis can occur on the penis, vulva and flexures, but scaling is usually absent. Diagnosis of patients with chronic plaque psoriasis is usually based on the clinical features described above. In particular, the distribution, color and typical silvery scaling of the lesion in chronic plaque psoriasis are characteristic of chronic plaque psoriasis.

b. Guttate Psoriasis

Guttate psoriasis refers to a form of psoriasis with characteristic water drop shaped scaly plaques. Flares of guttate psoriasis generally follow an infection, most notably a streptococcal throat infection. Diagnosis of guttate psoriasis is usually based on the appearance of the skin, and the fact that there is often a history of recent sore throat.

c. Inverse Psoriasis

Inverse psoriasis is a form of psoriasis in which the patient has smooth, usually moist areas of skin that are red and inflamed, which is unlike the scaling associated with plaque psoriasis. Inverse psoriasis is also referred to as intertiginous psoriasis or flexural psoriasis. Inverse psoriasis occurs mostly in the armpits, groin, under the breasts and in other skin folds around the genitals and buttocks, and, as a result of the locations of presentation, rubbing and sweating can irritate the affected areas.

d. Pustular Psoriasis

Pustular psoriasis is a form of psoriasis that causes pus-filled blisters that vary in size and location, but often occur on the hands and feet. The blisters may be localized, or spread over large areas of the body. Pustular psoriasis can be both tender and painful, can cause fevers.

e. Other Psoriasis Disorders

Other examples of psoriatic disorders which can be treated with the TNFα antibody of the invention include erythrodermic psoriasis, vulgaris, psoriasis associated with IBD, and psoriasis associated with arthritis, including rheumatoid arthritis.

Clinical Severity of Psoriasis

Severity of psoriasis may be determined according to standard clinical definitions. For example, the Psoriasis Area and Severity Index (PASI) is used by dermatologists to assess psoriasis disease intensity. This index is based on the quantitative assessment of three typical signs of psoriatic lesions: erythema, infiltration, and desquamation, combined with the skin surface area involvement. Since its development in 1978, this instrument has been used throughout the world by clinical investigators (Fredriksson T, Petersson U: Severe psoriasis—oral therapy with a new retinoid. Dermatologica 1978; 157: 238-41). PASI is indicated as PASI 50 (a 50 percent improvement in PASI from baseline), PASI 75 (a 75 percent improvement in PASI from baseline), PASI 90 (a 90 percent improvement in PASI from baseline), and PASI 100 (a 100 percent improvement in PASI from baseline). The efficacy of a TNFα inhibitor for treatment of psoriatic arthritis in a patient population who has psoriasis, may be evaluated by determining the percentage of the patient population in whom a PASI 50, PASI 75, PASI 90, or PASI 100 response has been achieved following administration of the TNFa inhibitor.

The Physicians Global Assessment (PGA) is used to assess psoriasis activity and follow clinical response to treatment. It is a six-point score that summarizes the overall quality (erythema, scaling and thickness) and extent of plaques relative to the baseline assessment. A patient's response is rated as worse, poor (0-24%), fair (25-49%), good (50-74%), excellent (75-99%), or cleared (100%) (van der Kerkhof P. The psoriasis area and severity index and alternative approaches for the assessment of severity: persisting areas of confusion. Br J Dermatol 1997; 137:661-662).

Another measure of improvement in the disease state of a subject having psoriasis includes clinical responses, such as the Dermatology Life Quality Index (DLQI). Characteristics of the DLQI include:

- ten items on an overall scoring range of 0-30; higher scores represent greater quality of life impairment and lower scores represent lower quality of life impairment;
- well-established properties of reliability and validity for the DLQI total score in a dermatology setting (see Badia et al. (1999) *Br J Dermatol* 141:698; Finlay et al. (1994) *Clin Exp Dermatol* 19:210; and Shikier et al. (2003) *Health and Quality of Life Outcomes* 1:53);
- six subcategories: symptoms and feelings; daily activities; leisure; work/school; personal relationships; and treatment;
- all data are observed values. Patients who discontinued before the time point were not included in this analysis.

Ranges of DLQI scores can be evaluated for their correspondence to categories of disease impact.

Other measures of improvements in the disease state of a subject having psoriasis include clinical responses, such as the Minimum Clinically Important Difference (MCID), described in more detail below in the Examples.

Methods of Treatment

In one aspect, the invention provides a method for treating patients having a skin disorder in which TNFa activity is detrimental, e.g., psoriasis, who may be especially difficult to treat. For example, the invention provides a method for treating patients who have a subtherapeutic response to a therapy (such as a biologic therapy), who have failed to respond to a therapy, or have lost responsiveness to a therapy. In certain embodiments, the invention provides a method for treating psoriasis patients who have a subtherapeutic response, who have failed to respond to or have lost responsiveness to a biologic therapy, including, but not limited to, a TNF fusion proteins (e.g., etanercept), a soluble TNF receptor Type I, a pegylated soluble TNF receptor Type I (e.g., PEGs TNF-R1), p55TNFR1gG, a recombinant TNF binding protein (r-TBP-I) (Serono) and a TNFα antibody.

In one embodiment, the patients who have a subtherapeutic response to a therapy, who have failed to respond to a therapy, or have lost responsiveness to a therapy are selected using the PASI score. In one embodiment, the patient has failed to achieve a PASI 50. In one embodiment, the patient has a PASI≥10. In one embodiment, the therapy is a biologic therapy, e.g., a TNFα inhibitor biologic therapy.

In one embodiment, the patients who have a subtherapeutic response to a therapy, who have failed to respond to a therapy, or have lost responsiveness to a therapy are selected measurement of DLQI. In one embodiment, the patient has a DLQI>10. In another embodiment, the patient has a PASI≥10 and a DLQI>10. In one embodiment, the therapy is a biologic therapy, e.g., a TNFa inhibitor biologic therapy.

In one embodiment, the biologic therapy is entanercept. In one embodiment, the invention provides a method for treating psoriasis patients who have a subtherapeutic response, who have failed to respond or have lost responsiveness to etanercept after prior failure of one or more conventional psoriasis therapies. Conventional psoriasis therapies include, but are not limited to, methotrexate, cyclosporine, psoralen, and PUVA (long-wave UV radiation) treatment.

In one embodiment, treatment of psoriasis is achieved by administering a TNFα inhibitor, e.g., a human TNFα antibody, or an antigen-binding portion thereof, to a subject having psoriasis, wherein the TNFα inhibitor, e.g., human TNFα antibody, or an antigen-binding portion thereof, is administered on a biweekly dosing regimen. Biweekly dosing regimens can be used to treat disorders in which TNFα activity is detrimental, and are further described in U.S. application Ser. No. 10/163,657 (US 20030235585), incorporated by reference herein. In one embodiment, biweekly dosing includes a dosing regimen wherein doses of a TNFα inhibitor are administered to a subject every other week beginning at week 1. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing is preferably administered parenterally, including subcutaneously. In one embodiment, the human TNFα antibody, or an antigen-binding portion thereof, is administered biweekly at a fixed dose of about 40 mg. In one embodiment, the human TNFα antibody, or an antigen-binding portion thereof, is adalimumab. Additional examples of dosing regimens within the scope of the invention are provided herein in the Examples.

In one embodiment, treatment of psoriasis is achieved using multiple variable dosing methods of treatment. Examples of such multiple variable dosing regimens are described in PCT appln. no. PCT/US05/12007, incorporated by reference herein. For example, a loading dose of about 80 mg of a TNFα inhibitor may first be administered to a subject having psoriasis, followed by a maintenance or treatment dose of about 40 mg.

In one embodiment, the invention provides a method of treating psoriasis in a subject comprising administering an initial loading dose of a TNFα inhibitor to the subject at week 0. In one embodiment, the initial dose is given in its entirety on one day or is divided over 2 days. In one embodiment, the initial dose is administered subcutaneously. Following administration of the initial loading dose, a second dose, i.e., maintenance or treatment dose, of the TNFα inhibitor may be administered to the subject, wherein the second dose is about half the dose amount of the initial loading dose. In one embodiment, the second dose is administered to the subject about one week after the first dose. In one embodiment, the second dose is administered subcutaneously. Subsequent doses may be administered following the second dose in order to achieve treatment of the subject.

In another embodiment, the initial dose of the human TNFα antibody, or antigen-binding portion thereof, comprises 80 mg and may be given at week 0, followed by at least one maintenance dose of the human TNFα antibody, or antigen-binding portion thereof, comprising 40 mg, administered on a biweekly dosing regimen.

In one embodiment of the invention, a human TNFα antibody, or antigen-binding portion thereof, is administered to a subject for the treatment of psoriasis, including but not limited to moderate to severe psoriasis, where the subject has failed prior treatment with etanercept. The human TNFα antibody, or antigen-binding portion thereof, is administered to the subject at an initial dose of 80 mg followed by 40 mg every other week starting one week after the initial dose. The human TNFα antibody, or antigen-binding portion thereof, is administered subcutaneously.

In another embodiment, the initial dose of human TNFα antibody, or antigen-binding portion thereof, comprises 80 mg and may be given at week 0, and a second dose of 80 mg at week one, followed by at least one maintenance dose comprising 40 mg of the human TNFα antibody, or antigen-binding portion thereof, administered on a biweekly dosing regimen.

In another embodiment, the initial dose of human TNFα antibody, or antigen-binding portion thereof, comprises 80 mg and may be given at week 0, and a second dose of 80 mg at week one, followed by at least one maintenance dose comprising 40 mg of the human TNFα antibody, or antigen-binding portion thereof, administered on a weekly dosing regimen for a given period of time, e.g., 12 weeks, followed by biweekly administration of a maintenance dose comprising 40 mg of the human TNFα antibody, or antigen-binding portion thereof.

Dosage regimens described herein may be adjusted to provide the optimum desired response, e.g., treating psoriasis, in consideration of the teachings herein. It is to be noted that dosage values may vary with the type and severity of psoriasis. It is to be further understood that for any particular subject, specific dosage regimens may be adjusted over time according to the teachings of the specification and the individual need and the professional judgment of the person administering or supervising the administration of the compositions, and that dosage amounts and ranges set forth herein are exemplary only and are not intended to limit the scope or practice of the claimed invention.

Methods of treatment described herein may include administration of a TNFα inhibitor, such as a human TNFa antibody, to a subject to achieve a therapeutic goal, using appropriate indices known in the art, e.g., treatment of psoriasis, increase in PASI response, maintenance of a level of PASI response, improvement in PASI score, and/or achievement of a PGA score of "clear" or "almost clear." Also included in the scope of the invention are uses of a TNFα inhibitor in the manufacture of a medicament to achieve a therapeutic goal, e.g., treatment, of psoriasis, increase in PASI response, maintenance of a level of PASI response, and/or improvement in PASI score, and/or achievement of a PGA score of "clear" or "almost clear."

The invention also provides methods for improving psoriasis in a subject based on indices used to measure the disease state. In one embodiment, the invention provides a method for improving the DLQI score of a subject. In one embodiment, the improvement in the DLQI score is determined by achieving a score correlating with a "no" or "small impact" of the disease state on the subject. In one embodiment, the improvement in the DLQI score is determined by achieving an improvement in the DLQI score of the subject. Examples of such improvements are provided in the examples described herein.

The invention also includes a method of decreasing a PGA score of a subject comprising administering a human TNFα antibody, or antigen-binding portion thereof, to the subject, such that partial remission of psoriasis is induced. In one embodiment, the invention provides an improvement of at least about 2 points in the PGA score of a subject having psoriasis. The invention also includes a method of improving the PASI score of a subject.

Subpopulations

The invention provides uses and methods for treating certain subpopulations of patients having a skin disorder in which TNFa activity is detrimental, e.g., psoriasis, with a TNFα inhibitor.

In one embodiment, the invention provides a method of treating moderate to severe psoriasis in a subject comprising administering to the subject a human TNFα antibody, such that moderate to severe psoriasis is treated. Subjects having moderate to severe psoriasis may be administered a TNFα inhibitor such that moderate to severe psoriasis is treated and advancement of the disease is prevented. The invention also provides use of a TNFα inhibitor in the manufacture of a medicament for the treatment of moderate to severe psoriasis in a subject who has moderate to severe psoriasis. In a preferred embodiment, a patient having moderate to severe psoriasis is defined as a patient having a PASI score greater than 10, indicating a disease state.

The invention also provides a method for treating a subpopulation of patients having a skin disorder in which TNFa activity is detrimental, such as psoriasis, who are intolerant to or have lost response to a previous biologic therapy, such as a first TNFα inhibitor therapy, e.g., infliximab or etanercept. While clinical trials have demonstrated the efficacy of infliximab, a chimeric monoclonal antibody to TNFa, for treatment of patients with moderate to severe psoriasis, infusions of infliximab, especially when given episodically, may result in the development of antibodies to infliximab, which in turn may lead to infusion reactions, loss of efficacy, and delayed hypersensitivity reactions (Baert et al. N Engl J Med 2003; 348:601-608; Cheifetz et al. Am J Gastroenterol 2003; 98:1315-1324; Farrell et al. Gastroenterology 2003; 124:917-924; Hanauer et al. Gastroenterology 1999; 116:A731; and Hanauer et al. Clin Gastroenterol Hepatol 2004; 2:542-553). In certain instances, some patients who are administered a TNFα inhibitor for the treatment of psoriasis and respond to said treatment, may eventually lose their response to the first TNFα inhibitor. In other patient populations, intolerance to a certain TNFα inhibitor may be marked from the initial administration of the TNFα inhibitor. In one embodiment, the invention provides use of a TNFα inhibitor in the manufacture of a medicament for treating psoriasis in a subject who has lost response to or is intolerant to a different TNFα inhibitor. In one embodiment, the TNFα inhibitor which the subject has lost response to or is intolerant to is infliximab or etanercept.

In one embodiment, the invention also provides methods and compositions for use in a subject who has not previously been administered a TNF inhibitor, such as infliximab or etanercept. Thus, in one embodiment, the methods and compositions of the invention are directed to a subpopulation of psoriasis patients who have not previously received infliximab or etanercept.

In one embodiment, the invention provides an article of manufacture comprising a human TNFα antibody, e.g., adalimumab and a package insert, wherein the package insert indicates that adalimumab may be used to treat psoriasis in patients who have had an inadequate response to conventional therapy and/or who have lost response to or are intolerant to infliximab or etanercept.

Articles of Manufacture

The invention also provides a packaged pharmaceutical composition wherein the TNFα inhibitor, e.g., human TNFα antibody, is packaged within a kit or an article of manufacture. The kit or article of manufacture of the invention contains materials useful for the treatment, including induction and/or remission, prevention and/or diagnosis of psoriasis. The kit or article of manufacture comprises a container and a label or package insert or printed material on or associated with the container which provides information regarding use of the TNFα inhibitor, e.g., a TNFα antibody, for the treatment of psoriasis.

A kit or an article of manufacture refers to a packaged product comprising components with which to administer a TNFα inhibitor for treatment of a psoriasis. The kit preferably comprises a box or container that holds the components of the kit. The box or container is affixed with a label or a Food and Drug Administration approved label, including a protocol for administering the TNFα inhibitor. The box or container holds components of the invention which are preferably contained within plastic, polyethylene, polypropylene, ethylene, or propylene vessels. The vessels can be capped-tubes or bottles. The kit can also include instructions for administering the TNFα antibody of the invention. In one embodiment the kit of the invention includes the formulation comprising the human antibody adalimumab (or D2E7), as described in PCT/IB03/04502 and U.S. application Ser. No. 10/222,140, incorporated by reference herein.

The term "package insert" is used to refer to instructions customarily included in commercial packages of therapeutic products, that contain information about the indications, usage, dosage, administration, contraindications and/or warnings concerning the use of such therapeutic products.

In one embodiment, the article of manufacture of the invention comprises (a) a first container with a composition contained therein, wherein the composition comprises a TNFα antibody; and (b) a package insert indicating that the TNFα antibody may be used for reducing signs and symptoms and inducing and maintaining remission of psoriasis.

In a preferred embodiment, the label or package insert indicates that the TNFα inhibitor, e.g., a TNFα antibody, is used for treating psoriasis.

Suitable containers for the TNFα inhibitor, e.g., a TNFα antibody, include, for example, bottles, vials, syringes, pens, etc. The containers may be formed from a variety of materials such as glass or plastic. The container holds a composition which is by itself or when combined with another composition effective for treating, preventing and/or diagnosing the condition and may have a sterile access port.

In one embodiment, the article of manufacture comprises a TNFα inhibitor, e.g., a human TNFα antibody, and a label or package insert which indicates to a subject who will be administering the TNFα inhibitor about using the TNFα inhibitor for the treatment of psoriasis. The label may be anywhere within or on the article of manufacture. In one embodiment, the article of manufacture comprises a container, such as a box, which comprises the TNFα inhibitor and a package insert or label providing information pertaining to use of the TNFα inhibitor for the treatment of psoriasis. In another embodiment, the information is printed on a label which is on the outside of the article of manufacture, in a position which is visible to prospective purchasers.

In one embodiment, the label or package insert of the invention informs a reader, including a subject, e.g., a purchaser, who will be administering the TNFα inhibitor for treatment, that the TNFα inhibitor, e.g., a TNFα antibody such as adalimumab, is an indicated treatment of psoriasis, including of moderately to severely active disease in adult patients.

In one embodiment, the label or package insert describes certain patient populations who may respond favorably to the TNFα inhibitor within the article of manufacture. For example, the label or package insert may indicate that the TNFα antibody, e.g., adalimumab, may be used to treat psoriasis in patients who have had an inadequate response to conventional therapy and/or who have lost response to or are intolerant to infliximab or etanercept.

In one embodiment, the package insert of the invention informs a reader, including a subject, e.g., a purchaser, who will be administering the TNFα inhibitor for treatment, that the TNFα inhibitor, e.g., a TNFα antibody such as adalimumab, is an indicated treatment of psoriasis, including of moderately to severely active disease in adult patients who have had an inadequate response to a previous biologic therapy and/or who have lost response to or are intolerant to entanercept.

In another embodiment, the label of the invention indicates that adalimumab is indicated for treatment of moderately to severely active psoriasis in adult patients who have had an inadequate response to a previous biologic therapy. In another embodiment, the label of the invention indicates that the TNFα inhibitor, e.g., a TNFα antibody such as adalimumab, is also indicated for treatment in adult patients with moderately to severely active psoriasis who have lost response to or are intolerant to entanercept.

In one embodiment, the label or package insert of the invention describes certain therapeutic benefits of the TNFα antibody, e.g., adalimumab, including specific symptoms of psoriasis which may be reduced by using the TNFα antibody, e.g., adalimumab. It should be noted that the package insert may also contain information pertaining to other disorders which are treatable using the TNFα antibody, e.g., adalimumab. Information described herein which is provided in a label or package insert and pertains to other disorders, i.e., diseases other than psoriasis, is also included within the scope of the invention. The package insert of the invention may indicate that extra TNFα in your body can attack normal healthy body tissues and cause inflammation especially in the tissues in your bones, cartilage, joints and digestive tract. The package insert of the invention may also indicate that adalimumab helps reduce the signs and symptoms of immune diseases, including rheumatoid and psoriatic arthritis (pain and swollen joints), ankylosing spondylitis (morning stiffness and back pain), and psoriasis (abdominal pain and diarrhea).

In another embodiment, the package insert of the invention describes the dose and administration of adalimumab, for the treatment of psoriasis. The label may indicate that the initiation of therapy includes a 80 mg dose at week 0 and 40 mg at week 1. The label may also indicate that the maintenance dosing for the treatment of psoriasis with adalimumab is 40 mg every other week. The label may also indicate that some patients with psoriasis may derive additional benefit by increasing frequency to 40 mg every week. In another embodiment, the label or package insert of the invention indicates that adalimumab is administered by subcutaneous injection.

In another embodiment, the label or the package insert of the invention may indicate that the recommended TNFα inhibitor, e.g., a TNFα antibody such as adalimumab, dose regimen for adult patients with psoriasis is 80 mg at week 0, followed by 40 mg every other week beginning at week 1. The label or package insert of the invention may also indicate that some patients may derive additional benefit from increasing the dosing frequency of the TNFα inhibitor, e.g., a TNFα antibody such as adalimumab from 40 mg every other week to 40 mg every week.

The label or the package insert of the invention may also provide information to subjects who will be receiving adalimumab regarding combination uses for both safety and efficacy purposes. In another embodiment, the label or the package insert of the invention indicates that aminosalicylates, corticosteroids, and/or immunomodulatory agents (e.g., 6-mercaptopurine and azathioprine) may be continued during treatment with the TNFα inhibitor, e.g., a TNFα antibody, including adalimumab. In one embodiment, the invention provides an article of manufacture comprising a packaging material; a TNFα antibody, or antigen-binding portion thereof; and a label or package insert contained within the packaging material indicating that aminosalicylates, corticosteroids, and/or immunomodulatory agent, e.g., 6-mercaptopurine and azathioprine, may be continued during treatment with the TNFα antibody, or antigen-binding portion thereof.

The label or the package insert of the invention may contain warnings and precautions regarding the use of the TNFα inhibitor, e.g., a TNFα antibody such as adalimumab. In one embodiment, the information provided in the label or the package insert describes malignancies.

The label or the package insert of the invention may contain information regarding the use of the TNFα inhibitor, e.g., a TNFα antibody such as adalimumab, in clinical studies for psoriasis. In one embodiment, the label of the invention describes the studies described herein as Examples 1 to 23, either as a whole or in portion. The label of the invention may also indicate that adalimumab has been studied in over 1400 patients with psoriasis in four placebo-controlled and two open-label extension studies. The label of the invention may also indicate that the safety profile for patients with psoriasis treated with HUMIRA® was similar to the safety profile seen in patients with rheumatoid arthritis.

The label of the invention may contain information regarding the pharmacodynamics of the TNFα inhibitor, e.g., a TNFα antibody such as adalimumab. In one embodiment, the label of the invention indicates that after treatment with adalimumab, a rapid decrease in levels of acute phase reactants of inflammation (C-reactive protein (CRP) and erythrocyte sedimentation rate (ESR) and serum cytokines (IL-6) was observed compared to baseline in patients with rheumatoid arthritis. In one embodiment, the label of the invention indicates that a rapid decrease in CRP levels was also observed in patients with psoriasis. The label may further indicate that serum levels of matrix metalloproteinases (MMP-1 and MMP-3) that produce tissue remodeling responsible for cartilage destruction were also decreased after adalimumab administration.

In one embodiment of the invention, the kit comprises a TNFα inhibitor, such as an antibody, an second pharmaceutical composition comprising an additional therapeutic agent, and instructions for administration of both agents for the treatment of psoriasis. The instructions may describe how, e.g., subcutaneously, and when, e.g., at week 0, week 2, and biweekly thereafter, doses of TNFα antibody and/or the additional therapeutic agent shall be administered to a subject for treatment.

Another aspect of the invention pertains to kits containing a pharmaceutical composition comprising an anti-TNFα antibody and a pharmaceutically acceptable carrier and one or more additional pharmaceutical compositions each comprising a drug useful for treating a TNFα related disorder and a pharmaceutically acceptable carrier. Alternatively, the kit comprises a single pharmaceutical composition comprising an anti-TNFα antibody, one or more drugs useful for treating a TNFα related disorder and a pharmaceutically acceptable carrier. The kits further contain instructions for dosing of the pharmaceutical compositions for the treatment of a TNFα related disorder.

The package or kit alternatively may contain the TNFα inhibitor and it may be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

Additional Therapeutic Agents

TNFα inhibitors, including TNFα antibodies, or antigen binding portions thereof, may be used in the methods, uses, and compositions of the invention either alone or in combination with an additional therapeutic agent. It should be understood that the TNFα inhibitors can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the TNFα inhibitors. The additional agent also can be an agent that imparts a beneficial attribute to the therapeutic composition, e.g., an agent which effects the viscosity of the composition.

It should further be understood that the combinations which are to be included within this invention are those combinations useful for their intended purpose. The agents set forth below are illustrative for purposes and not intended to be limited. The combinations, which are part of this invention, can be the TNFα inhibitors of the present invention and at least one additional agent selected from the lists below. The combination can also include more than one additional agent, e.g., two or three additional agents if the combination is such that the formed composition can perform its intended function.

Non-limiting examples of therapeutic agents for Psoriasis with which an antibody, or antibody portion, of the invention can be combined include the following: small molecule inhibitor of KDR (ABT-123), small molecule inhibitor of Tie-2, calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine.

TNFα inhibitors described herein may be used in combination with additional therapeutic agents such as a Disease Modifying Anti-Rheumatic Drug (DMARD) or a Nonsteroidal Antiinflammatory Drug (NSAID) or a steroid or any combination thereof. Preferred examples of a DMARD are hydroxychloroquine, leflunomide, methotrexate, parenteral gold, oral gold and sulfasalazine. Preferred examples of non-steroidal anti-inflammatory drug(s) also referred to as NSAIDS include drugs like ibuprofen. Other preferred combinations are corticosteroids including prednisolone; the well known side effects of steroid use can be reduced or even eliminated by tapering the steroid dose required when treating patients in combination with TNFα inhibitors of this invention.

Preferred combinations of therapeutic agents may interfere at different points in the autoimmune and subsequent inflammatory cascade; preferred examples include TNF antagonists such as soluble p55 or p75 TNF receptors, derivatives, thereof, (p75TNFR1gG (Enbrel™) or p55TNFR1gG (Lenercept), chimeric, humanized or human TNF antibodies, or a fragment thereof, including infliximab (Remicade®, Johnson and Johnson; described in U.S. Pat. No. 5,656,272, incorporated by reference herein), PSORIASIS P571 (a humanized monoclonal anti-TNF-alpha IgG4 antibody), PSORIASIS P 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451,983; and 6,448,380, each of which is incorporated by reference herein. Other combinations including TNFα converting enzyme (TACE) inhibitors; IL-1 inhibitors (Interleukin-1-converting enzyme inhibitors, IL-1RA etc.) may be effective for the same reason. Other preferred combinations include Interleukin 11. Yet another preferred combination are other key players of the autoimmune response which may act parallel to, dependent on or in concert with TNFα inhibitors function; especially preferred are IL-18 antagonists including IL-18 antibodies or soluble IL-18 receptors, or IL-18 binding proteins. Yet another preferred combination are non-depleting anti-PSORIASIS 4 inhibitors. Yet other preferred combinations include antagonists of the co-stimulatory pathway PSORIASIS 80 (B7.1) or PSORIASIS 86 (B7.2) including antibodies, soluble receptors or antagonistic ligands.

The TNFα inhibitors used in the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, PSORIASIS C-801, and Mesopram.

Non-limiting examples of therapeutic agents for psoriasis with which TNFα inhibitor of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6 (including Actemra (tocilizumab), IL-7, IL-8, IL-15, IL-16, IL-17, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

The antibodies of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TNFα converting enzyme inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ).

Additional examples of therapeutic agents for psoriasis in which a TNFα inhibitor can be combined include the following: combinations of TNF antagonists, for example, anti-TNF antibodies, D2E7 (PCT Publication No. WO 97/29131; HUMIRA®), CA2 (REMICADE), PSORIASIS P 571, TNFR-Ig constructs, (p75TNFRIgG (ENBREL) and p55TNFRIgG (LENERCEPT)) inhibitors and PDE4 inhibitors. TNFα inhibitors of the invention can be combined with corticosteroids, for example, budenoside and dexamethasone. TNFα inhibitors of the invention may also be combined with agents such as sulfasalazine, 5-aminosalicylic acid and olsalazine, and agents which interfere with synthesis or action of proinflammatory cytokines such as IL-1, for example, IL-1β converting enzyme inhibitors and IL-1ra. TNFα inhibitors may also be used with T cell signaling inhibitors, for example, tyrosine kinase inhibitors 6-mercaptopurines. TNFα inhibitors can be combined with IL-11. TNFα inhibitors can be combined with mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab and interferon-gamma The TNFα inhibitors may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists, and the humanized IL-6 antibody tocilizumab.

In yet another embodiment, the invention includes an article of manufacture or a method comprising the combination of a TNF inhibitor and an antibiotic or antiinfective agent. Antiinfective agents include those agents known in the art to treat viral, fungal, parasitic or bacterial infections. The term, "antibiotic," as used herein, refers to a chemical substance that inhibits the growth of, or kills, microorganisms. Encompassed by this term are antibiotic produced by a microorganism, as well as synthetic antibiotics (e.g., analogs) known in the art. Antibiotics include, but are not limited to, clarithromycin (Biaxin®), ciprofloxacin (Cipro®), and metronidazole (Flagyl®).

Any one of the above-mentioned therapeutic agents, alone or in combination therewith, can be administered to a subject suffering from a TNFα-related disorder in which TNFα is detrimental, in combination with the TNFα antibody using a multiple variable dose treatment regimen. In one embodiment, any one of the above-mentioned therapeutic agents, alone or in combination therewith, can be administered to a subject suffering from an intestinal disorder in addition to a TNFα antibody to treat another TNFα-related disorder, such as rheumatoid arthritis. It should be understood that the additional therapeutic agents can be used in combination therapy as described above, but also may be used in other indications described herein wherein a beneficial effect is desired.

The combination of agents used within the methods and pharmaceutical compositions described herein may have a therapeutic additive or synergistic effect on the condition(s) or disease(s) targeted for treatment. The combination of agents used within the methods or pharmaceutical compositions described herein also may reduce a detrimental effect associated with at least one of the agents when administered alone or without the other agent(s) of the particular pharmaceutical composition. For example, the toxicity of side effects of one agent may be attenuated by another agent of the composition, thus allowing a higher dosage, improving patient compliance, and improving therapeutic outcome. The additive or synergistic effects, benefits, and advantages of the compositions apply to classes of therapeutic agents, either structural or functional classes, or to individual compounds themselves.

IV. Efficacy of TNFα Inhibitor

The invention provides methods for determining whether a TNFα inhibitor is effective at treating a skin disorder associated with detrimental TNFα activity, such as psoriasis, in a subject who has a subtherapeutic response to a therapy, who has failed to respond to a therapy, or has lost responsiveness to a therapy. Such methods may be used to determine the efficacy of a TNFα inhibitor, including those which are unknown or unconfirmed to have such efficacy. Using the methods described herein, effective TNFα inhibitors may be determined or confirmed, and, subsequently, used in the method of treating psoriasis. Further methods for determining whether a TNFα inhibitor is effective at treating psoriasis in a subject are described in U.S. Provisional Application Nos. 60/832,370 (filed Jul. 20, 2006), 60/851,830 (filed Oct. 6, 2006), and 60/857,352 (filed Nov. 6, 2006), each of which are incorporated herein by reference.

Patient populations described in the methods of the invention are generally selected based on common characteristics In one non-limiting example, the patient population contains subjects diagnosed with psoriasis who are in remission as a result of being on a dosing regimen comprising a TNFα. Such a patient population would be appropriate for determining the efficacy of the TNFα inhibitor for maintaining remission in psoriasis in the given patient population. In another embodiment, the patient population contains subjects who have a subtherapeutic response to a biologic therapy, who have failed to respond to a biologic therapy, or have lost responsiveness to a biologic therapy, such as etanercept. In one embodiment, the patient population contains subjects who have failed to respond or lost responsiveness to a biologic TNFα inhibitor (e.g., entanercept). In a related embodiment, the patient population is an adult population, e.g., older than 17 years of age or older than 18 years of age.

In one embodiment, the article of manufacture of the invention comprises instructions regarding how to determine the efficacy of the TNF inhibitor for the treatment of psoriasis. In one embodiment, the article of manufacture of the invention comprises instructions regarding how to determine the efficacy of the TNF inhibitor for the treatment of psoriasis in patients who has a subtherapeutic response to a biologic therapy, who has failed to respond to a biologic therapy, or has lost responsiveness to a biologic therapy, such as entanercept.

The invention also provides methods for determining whether a TNFα inhibitor is effective at treating psoriasis in a subject. Such methods may be used to determine the efficacy of a TNFα inhibitor, including those which are unknown or unconfirmed to have such efficacy. Using the methods described herein, effective TNFα inhibitors may be determined or confirmed, and, subsequently, used in the method of treating psoriasis.

The PASI, PGA, and DLQI scores may be used as an index for measuring efficacy of a TNFα inhibitor in a subject or patient population having psoriasis, where attaining a certain percentage of patients within a population who were administered the TNFα inhibitor and who maintain clinical remission, i.e. PASI<50 or PASI<75, indicates that the TNFα inhibitor is effective for treating of psoriasis. In one embodiment, the invention provides a method for determining whether a human TNFα antibody is effective for treating psoriasis.

The efficacy of a TNFα inhibitor for treating psoriasis in a patient population, e.g., PASI 75 response (also referred to herein as a PASI/PASI75 score), may be evaluated by determining the percentage of the patient population in treatment of psoriasis has been effective following administration of the TNFα inhibitor.

In one embodiment, a PASI 50 response is achieved in at least about 57% of the patient population indicates that the human TNFα antibody is an effective human TNFα antibody for the treatment of psoriasis in a subject. In one embodiment, a PASI 50 response is achieved in at least about 65% of the patient population indicates that the human TNFα antibody is an effective human TNFα antibody for the treatment of psoriasis in a subject. In one embodiment, a PASI50 response is achieved in at least about 70% of the patient population indicates that the human TNFα antibody is an effective human TNFα antibody for the treatment of psoriasis in a subject. In one embodiment, a PASI 50 response is achieved in at least about 75% of the patient population indicates that the human TNFα antibody is an effective human TNFα antibody for the treatment of psoriasis in a subject. In one embodiment, a PASI 50 response is achieved in at least about 80% of the patient population indicates that the human TNFα antibody is an effective human TNFα antibody for the treatment of psoriasis in a subject. In one embodiment, a PASI 50 response is achieved in at least about 85% of the patient population indicates that the human TNFα antibody is an effective human TNFα antibody for the treatment of psoriasis in a subject. In one embodiment, a PASI 50 response is achieved in at least about 92% of the patient population indicates that the human TNFα antibody is an effective human TNFα antibody for the treatment of psoriasis in a subject.

Numbers intermediate to the above recited percentages, e.g., 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, as well as all other numbers recited herein, are also intended to be part of this invention. Ranges of values using a combination of any of the above recited values as upper and/or lower limits are intended to be included in the scope of the invention. For example, in one embodiment a PASI 50 response score of in at least between 59% and 90% of the patient population indicates that the TNFα inhibitor is an effective TNFα inhibitor for the treatment of psoriasis in a subject.

In one embodiment, the invention provides a method of determining the efficacy of a TNFα inhibitor for treating psoriasis in a subject comprising determining a Psoriasis Area Severity Index (PASI) score of a patient population having psoriasis and who was administered the TNFα inhibitor, wherein a PASI 75 response is achieved in at least about 77% of the patient population indicates that the TNFα inhibitor is an effective TNFα inhibitor for the treatment of psoriasis in a subject. In one embodiment, the method further comprises administering the effective TNFα inhibitor to a subject to treat psoriasis. The invention provides a method of treating psoriasis in a subject comprising administering an effective amount of a TNFα inhibitor to the subject such that treatment of psoriasis is maintained, wherein the effective human TNFα antibody was previously identified as achieving a PASI 75 response in at least about 62% of a patient population having psoriasis and a baseline PASI greater than 10.

In one embodiment, the invention provides a method of treating psoriasis in a subject comprising administering an effective amount of a human TNFα antibody to the subject such that psoriasis is treated, wherein the effective human TNFα antibody was previously identified as achieving a PASI 75 response in at least about 62% of a patient population having psoriasis and a baseline PASI greater than 10.

In one embodiment, a PASI 75 response is achieved in at least about 23% of the patient population indicates that the human TNFα antibody is an effective human TNFα antibody for the treatment of psoriasis in a subject. In one embodiment, a PASI 75 response is achieved in at least about 45% of the patient population indicates that the human TNFα antibody is an effective human TNFα antibody for the treatment of psoriasis in a subject. In one embodiment, a PASI 75 response is achieved in at least about 64% of the patient population indicates that the human TNFα antibody is an effective human TNFα antibody for the treatment of psoriasis in a subject. In one embodiment, a PASI 75 response is achieved in at least about 75% of the patient population indicates that the human TNFα antibody is an effective human TNFα antibody for the treatment of psoriasis in a subject. In one embodiment, a PASI 75 response is achieved in at least about 82% of the patient population indicates that the human TNFα antibody is an effective human TNFα antibody for the treatment of psoriasis in a subject. In one embodiment, the method further comprises administering the effective TNFα inhibitor to a subject to treat psoriasis.

Numbers intermediate to the above recited percentages, e.g., 20%, 21%, 22%, 23%, 24%, 25%, 26%, 27%, 28%, 29%, 30%, 31%, 32%, 33%, 34%. 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%. 81%, 82%, 83%, 84%, 85%, 86%, 87%, 88%, and 89%, as well as all other numbers recited herein, are also intended to be part of this invention. Ranges of values using a combination of any of the above recited values as upper and/or lower limits are intended to be included in the scope of the invention. For example, in one embodiment a PASI 75 response score of in at least between 35% and 81% of the patient population indicates that the TNFα inhibitor is an effective TNFα inhibitor for the treatment of psoriasis in a subject.

The invention provides a method of treating psoriasis in a subject comprising administering an effective amount of a TNFα inhibitor to the subject such that treatment of psoriasis is maintained, wherein the effective human TNFα antibody was previously identified as achieving a PASI 75 response in at least about 23% of a patient population having psoriasis.

In one embodiment the invention provides a method of determining the efficacy of a TNFα inhibitor for treating psoriasis in a subject comprising determining a PASI 90 response of a patient population having psoriasis who was administered the human TNFα antibody, wherein a PASI 90 response is achieved in at least about 27% of the patient population indicates that the human TNFα antibody is an effective human TNFα antibody for treating psoriasis in a subject.

In one embodiment, a PASI 90 response is achieved in at least about 27% of the patient population indicates that the human TNFα antibody is an effective human TNFα antibody for achieving a clinical response in psoriasis in a subject. In one embodiment, a PASI 90 response is achieved in at least about 39% of the patient population indicates that the human TNFα antibody is an effective human TNFα antibody for achieving a clinical response in psoriasis in a subject. In one embodiment, a PASI 90 response is achieved in at least about 48% of the patient population indicates that the human TNFα antibody is an effective human TNFα antibody for achieving a clinical response in psoriasis in a subject. In one embodiment, a PASI 90 response is achieved in at least about 52% of the patient population indicates that the human TNFα antibody is an effective human TNFα antibody for achieving a clinical response in psoriasis in a subject. In one embodiment, a PASI 90 response is achieved in at least about 58% of the patient population indicates that the human TNFα antibody is an effective human TNFα antibody for achieving a clinical response in psoriasis in a subject. In one embodiment, a PASI 90 response is achieved in at least about 62% of the patient population indicates that the human TNFα antibody is an effective human TNFα antibody for achieving a clinical response in psoriasis in a subject.

Numbers intermediate to the above recited percentages, e.g., 27%, 28%, 29%, 30%, 31%, 32%, 33%, 34%. 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, as well as all other numbers recited herein, are also intended to be part of this invention. Ranges of values using a combination of any of the above recited values as upper and/or lower limits are intended to be included in the scope of the invention. For example, in one embodiment a PASI 90 response score of in at least between 31% and 49% of the patient population indicates that the TNFα inhibitor is an effective TNFα inhibitor for the treatment of psoriasis in a subject.

In one embodiment the invention provides a method of determining the efficacy of a TNFα inhibitor for treating psoriasis in a subject comprising determining a PASI 100 response of a patient population having psoriasis who was administered the human TNFα antibody, wherein a PASI 100 response is achieved in at least about 11% of the patient population indicates that the human TNFα antibody is an effective human TNFα antibody for treating psoriasis in a subject.

In one embodiment, a PASI 100 response is achieved in at least about 11% of the patient population indicates that the human TNFα antibody is an effective human TNFα antibody for achieving a clinical response in psoriasis in a subject. In one embodiment, a PASI 100 response is achieved in at least about 14% of the patient population indicates that the human TNFα antibody is an effective human TNFα antibody for achieving a clinical response in psoriasis in a subject. In one embodiment, a PASI 100 response is achieved in at least about 20% of the patient population indicates that the human TNFα antibody is an effective human TNFα antibody for achieving a clinical response in psoriasis in a subject. In one embodiment, a PASI 100 response is achieved in at least about 22% of the patient population indicates that the human TNFα antibody is an effective human TNFα antibody for achieving a clinical response in psoriasis in a subject. In one embodiment, a PASI 100 response is achieved in at least about 32% of the patient population indicates that the human TNFα antibody is an effective human TNFα antibody for achieving a clinical response in psoriasis in a subject.

Numbers intermediate to the above recited percentages, e.g., 11%, 12%, 13%, 14%, 15%, 16%, 17%, 18%, 19%, 20%, 21%, 22%, 23%, 24%, 25%, 26%, 27%, 28%, 29%, 30%, 31%, 32%, as well as all other numbers recited herein, are also intended to be part of this invention. Ranges of values using a combination of any of the above recited values as upper and/or lower limits are intended to be included in the scope of the invention. For example, in one embodiment a PASI 100 response of between 11% and 19% of the patient population indicates that the TNFα inhibitor is an effective TNFα inhibitor for the treatment of psoriasis in a subject.

In one embodiment the invention provides a method of determining the efficacy of a TNFα inhibitor for achieving a clinical response in psoriasis in a subject comprising determining a Physician's Global Assessment (PGA) score of a patient population having psoriasis who was administered the human TNFα antibody, wherein a PGA score of "clear" or "almost clear" in at least about 27% of the patient population indicates that the human TNFα antibody is an effective human TNFα antibody for treating psoriasis in a subject.

In one embodiment, the invention provides a method of treating psoriasis in a subject comprising administering an effective amount of a human TNFα antibody to the subject, wherein the effective human TNFα antibody was previously identified as maintaining a PGA score of "clear" or "almost clear" in at least about 27% of a patient population having psoriasis.

In one embodiment, a PGA score of "clear" or "almost clear" in at least about 27% of a patient population having psoriasis indicates that the human TNFα antibody is an effective human TNFα antibody for treating psoriasis in a subject. In one embodiment, a PGA score of "clear" or "almost clear" in at least about 33% of a patient population having psoriasis indicates that the human TNFα antibody is an effective human TNFα antibody for treating psoriasis in a subject. In one embodiment, a PGA score of "clear" or "almost clear" in at least about 48% of a patient population having psoriasis indicates that the human TNFα antibody is an effective human TNFα antibody for treating psoriasis in a subject. In one embodiment, a PGA score of "clear" or "almost clear" in at least about 52% of a patient population having psoriasis indicates that the human TNFα antibody is an effective human TNFα antibody for treating psoriasis in a subject. In one embodiment, a PGA score of "clear" or "almost clear" in at least about 66% of a patient population having psoriasis indicates that the human TNFα antibody is an effective human TNFα antibody for treating psoriasis in a subject. In one embodiment, a PGA score of "clear" or "almost clear" in at least about 81% of a patient population having psoriasis indicates that the human TNFα antibody is an effective human TNFα antibody for treating psoriasis in a subject.

Numbers intermediate to the above recited percentages, e.g., 27%, 28%, 29%, 30%, 31%, 32%, 33%, 34%. 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%. 81%, as well as all other numbers recited herein, are also intended to be part of this invention. Ranges of values using a combination of any of the above recited values as upper and/or lower limits are intended to be included in the scope of the invention. For example, in one embodiment a PGA score of "clear" or "almost clear" in at least between 77% and 90% of the patient population indicates that the TNFα inhibitor is an effective TNFα inhibitor for the treatment of psoriasis in a subject.

In one embodiment the invention provides a method of determining the efficacy of a TNFα inhibitor for achieving a clinical response in psoriasis in a subject comprising determining a DLQI score of a patient population having psoriasis who was administered the human TNFα antibody, wherein a DLQI score of no or small impact in at least about 67% of the patient population indicates that the human TNFα antibody is an effective human TNFα antibody for treating psoriasis in a subject. In one embodiment, a DLQI score of no or small impact in at least about 85% of the patient population indicate efficacy. Numbers intermediate to the above recited percentages, e.g., 67%, 68%, 69%, 70%, 71%, 72%, 73%, 74%, 75%, 76%, 77%, 78%, 79%, 80%. 81%, 82%, 83%, 84%, and 85%, as well as all other numbers recited herein, are also intended to be part of this invention. Ranges of values using a combination of any of the above recited values as upper and/or lower limits are intended to be included in the scope of the invention. For example, in one embodiment a DLQI score of no or small impact in at least between 68% and 76% of the patient population indicates that the TNFα inhibitor is an effective TNFα inhibitor for the treatment of psoriasis in a subject.

It should be noted that the Examples provided herein represent different methods of determining the efficacy of a TNFα inhibitor, such as a human TNFα antibody, or antigen-binding portion thereof. As such, data and results described in the Examples section which shows efficacy of a TNFα inhibitor, e.g., ability to maintain remission of psoriasis, are included in the methods of determining efficacy of the invention.

Time points for determining efficacy will be understood by those of skill in the art to depend on the type of efficacy being determined, e.g., treatment of psoriasis. In one embodiment, measurements in scores, e.g., the PASI response or PGA score of a subject, may be measured against a subject's baseline score. Generally, a baseline refers to a measurement or score of a patient before treatment, i.e. week 0. Other time points may also be included as a starting point in determining efficacy, however.

Patient populations described in the methods of the invention are generally selected based on common characteristics, such as, but not limited to, subjects diagnosed with psoriasis, e.g., certain PASI score. Such a patient population would be appropriate for determining the efficacy of the TNFα inhibitor for treating psoriasis in the given patient population. In one embodiment, the patient population is an adult population, e.g., older than 17 years of age or older than 18 years of age.

In one embodiment, the methods of the invention for determining whether a TNFα inhibitor is an effective TNFα inhibitor, include determining changes, improvements, measurements, etc., in psoriasis using appropriate indices known in the art, e.g., PASI, PGA, DLQI, status of psoriasis related disorders, etc. from a patient population who has already been administered the TNFα inhibitor. Such a patient population may be pre-selected according to common characteristics, e.g., PASI score, and may have already been given the TNFα inhibitor. Administration of the TNFα inhibitor may or may not be performed by the same person of ordinary skill who is determining the efficacy of the TNFα inhibitor in accordance with the teachings of the specification.

In one embodiment, the methods of the invention comprise administering the TNFα inhibitor to the subjects of a patient population and determining the efficacy of the TNFα inhibitor by determining changes, improvements, measurements, etc., using psoriasis indices known in the art, in the patient population in comparison to the Examples set forth below. For example, in one embodiment the invention includes a method for determining efficacy of a TNFα inhibitor for the treatment of psoriasis comprising administering the TNFα inhibitor to a preselected patient population having psoriasis; and determining the effectiveness of the TNFα inhibitor by using a mean baseline Psoriasis Area Severity Index (PASI) response of the patient population and a mean PASI response following administration of the TNFα inhibitor, wherein a PASI 75 response achieved in at least about 45% of the patient population indicates that the TNFα inhibitor is effective for the treatment of psoriasis.

In addition, while the above methods are described in terms of patient populations, methods of efficacy described herein may also be applied to individual subjects. For example, a method for determining efficacy may comprise determining whether a subject who has psoriasis, and who is on a dosage regimen comprising a human TNFα antibody, is able to achieve a PASI 75 response to determining if the human TNFα antibody is an effective human TNFα antibody. In one embodiment, if the subject is able to achieve a PASI 75 response for at least about 24 weeks, then the human TNFα antibody is effective at treating psoriasis.

The Examples and discoveries described herein are representative of a TNFα inhibitor, i.e., adalimumab, which is effective for treating psoriasis. As such, the studies and results described in the Examples section herein may be used as a guideline for determining the efficacy of a TNFα inhibitor, i.e., whether a TNFα inhibitor is an effective TNFα inhibitor for the treatment of psoriasis. In one embodiment, methods of determining efficacy described herein may be used to determine whether a TNFα inhibitor is bioequivalent to another TNFα inhibitor.

Some of the Examples and discoveries described herein are representative of a TNFα inhibitor, i.e., adalimumab, which is effective for treating psoriasis, including inducing and maintaining remission of psoriasis in patients who has a subtherapeutic response to a biologic therapy, who has failed to respond to a biologic therapy, or has lost responsiveness to a biologic therapy, such as entanercept. As such, the studies and results described in the Examples section herein may be used as a guideline for determining the efficacy of a TNFα inhibitor, i.e., whether a TNFα inhibitor is an effective TNFα inhibitor for the treatment of psoriasis for subjects in this patient population.

The present invention is further illustrated by the following examples which should not be construed as limiting in any way.

EXAMPLES

Example 1

Rapid Improvement in Functional Limitations of Patients with Moderate to Severe Chronic Plaque Psoriasis Treated with Adalimumab Psoriasis affects approximately 1-3% of the worldwide population. Moderate to severe disease is associated with psoriatic lesions on ≥3% body surface area. Clinical manifestations of moderate to severe psoriasis can severely limit a patient's physical function.

Efficacy and safety of adalimumab was evaluated in a 48-week extension trial conducted at eighteen sites. The study was a randomized, double-blind, placebo-controlled, multi-center clinical trial, wherein patients were randomized to one of three treatment groups. The three treatment groups consisted of the following:
1. 80 mg adalimumab at baseline (week 0) and 40 mg at week 1 followed by 40 mg every other week (eow) starting at week 3 (referred to as ada 40 mg eow);
2. 80 mg adalimumab at baseline (week 0) and 80 mg at week 1 followed by 40 mg weekly starting at week 2 (referred to as ada 40 mg weekly); or
3. placebo administered weekly beginning at baseline (referred to as placebo).

Inclusion criteria included a diagnosis of moderate to severe chronic plaque psoriasis≥1 year prior to entry, a psoriasis-affected body surface area (BSA)>5%, and no previous use of TNF-antagonist therapy.

A total of 142 patients who completed the 12 week randomized trial enrolled in the extension trial. Patients initially randomized to active treatment continued on their assigned dose. Placebo patients were switched to receive adalimumab 80 mg the first week followed by adalimumab 40 mg eow. During the first 12 weeks of the extension trial, patients remained on blinded therapy.

The Dermatology Life Quality Index (DLQI) was used to evaluate the improvement in functional limitations of patients with moderate to severe chronic plaque psoriasis treated with adalimumab. The DLQI is a validated instrument used to measure disease impact on daily function. DLQI was specified as an endpoint in a 12-week, Phase II placebo-controlled trial of two different dose regimens of adalimumab in moderate to severe plaque psoriasis. The overall study design is shown in FIG. 1. The object of this study was to assess the effects of adalimumab on the impact of psoriasis in patients' lives.

The DLQI is a validated instrument used to assess dermatologic-related functional limitations, and was used as the patient related outcomes (PRO) measure. The DLQI consists of ten items and an overall scoring range of 0-30, where higher scores represent greater quality of life impairment and lower scores represent lower quality of life impairment. The DLQI also includes well-established properties of reliability and validity for the DLQI total score in a dermatology setting and measures six subcategories: symptoms and feelings, daily activities, leisure, work/school, personal relationships, and treatment.

Characteristics of the DLQI include:
  ten items on an overall scoring range of 0-30; higher scores represent greater quality of life impairment and lower scores represent lower quality of life impairment;
  well-established properties of reliability and validity for the DLQI total score in a dermatology setting (see Badia et al. (1999) *Br J Dermatol* 141:698; Finlay et al. (1994) *Clin Exp Dermatol* 19:210; and Shikier et al. (2003) *Health and Quality of Life Outcomes* 1:53);
  six subcategories: symptoms and feelings; daily activities; leisure; work/school; personal relationships; and treatment;
  all data are observed values. Patients who discontinued before the time point were not included in this analysis.

Ranges of DLQI scores were evaluated for their correspondence to categories of disease impact and are described below in Table 1.

TABLE 1

DLQI total score and disease impact on daily life (see Hongbo et al. (2004) *Br J Dermatol* 151 (suppl. 68)45; Hongbo et al. (2005) *Invest Dermatol*)

| DLQI Total Score | Disease Impact |
| --- | --- |
| 0-1 | None |
| 2-5 | Small |
| 6-10 | Moderate |
| 11-20 | Large |
| 21-30 | Extremely large |

The results were obtained from 147 patients, who were randomized and treated as described above. Patient demographics are provided below in Table 2:

TABLE 2

Baseline Demographics and Clinical Characteristics

|  | Placebo (n = 52) | Adalimumab 40 mg eow (n = 45) | Adalimumab 40 mg weekly (n = 50) |
| --- | --- | --- | --- |
| Age (yrs) | 43 | 46 | 44 |
| Range | (20-70) | (20-71) | (24-86) |
| Duration of Psoriasis (yrs) | 19.1 | 20.5 | 18.4 |
| Range | (1.0-39.8) | (1.3-57.9) | (1.7-47.7) |
| % Male | 65 | 71 | 66 |
| % Caucasian | 92 | 89 | 90 |
| Body Weight (kg) | 94 | 93 | 99 |
| Range | (50-147) | (63-159) | (42-149) |
| % BSA | 27.7 | 29.2 | 24.6 |
| Range | (7-75) | (6-58) | (5-83) |
| PASI Score | 16.0 | 16.7 | 14.5 |
| Range | (5.5-40.4) | (5.4-39.0) | (2.3-42.4) |
| % with Psoriatic Arthritis | 31 | 33 | 24 |

Mean values.

At baseline, 56% of patients reported a very large/extremely large disease effect as assessed by baseline DLQI scores, as shown below in Table 3:

TABLE 3

Disease impact at baseline by treatment group

| Disease Impact | Ada 40 mg eow | Ada 40 mg weekly | Placebo |
| --- | --- | --- | --- |
| Moderate | 27% | 24% | 39% |
| Large/Extremely Large | 60% | 60% | 50% |

By week 12, 85% of patients with large/extremely large disease impact at baseline who were randomized to adalimumab had no/small disease effect, compared with 1 (4%) placebo patient. More specifically, 85% of patients receiving ada 40 mg eow and 86% patients receiving ada 40 mg weekly had a change from large/extremely large impact at baseline to no/small impact at week 12. This level of improvement was maintained for up to 60 weeks of treatment with adalimumab as shown in Table 4.

TABLE 4

Percentages of patients with change from large/extremely large impact at baseline to no/small impact at weeks 24, 36, and 60

| Weeks | Ada 40 mg eow | Ada 40 mg weekly |
| --- | --- | --- |
| 24 | 85% | 88% |
| 36 | 83% | 91% |
| 60 | 83% | 100% |

Of placebo patients with large/extremely large impact at baseline, 67% had improved to no/small effect by week 24 after switching to adalimumab at week 12. More specifically, the percentage of patients with a change from large/extremely large impact at baseline to no/small impact at week 24 was 67%; at week 36 was 79%; and at week 60 was 71%.

In conclusion, rapid reduction in disease impact was seen with adalimumab treatment of moderate to severe plaque psoriasis. Patients initially treated with placebo experienced a similar level of improvement after 12 weeks of treatment with adalimumab. Resolution of disease impact was maintained in most patients through 60 weeks of adalimumab treatment.

Example 2

Efficacy and Safety of Adalimumab Treatment of Chronic Plaque Psoriasis in Patients Who Meet Some Criteria for Biological Interventions in Accordance with British Association of Dermatologists Guidelines The British Association of Dermatologists (BAD) has published guidelines for the treatment of psoriasis with approved biologic interventions such as infliximab, etanercept, and efalizumab. This subanalysis study measured the efficacy of adalimumab in patients from the above study who qualified for biologic treatment under these guidelines.

The efficacy and safety of adalimumab in patients eligible for biologic therapy under selected BAD guidelines was evaluated. The selected BAD guidelines included a PASI≥10 and a DLQI>10. The efficacy outcome measures were PASI, PGA, and DLQI. FIG. 1 shows the study design.

The following analytic methods were employed in this subanalysis: modified intention to treat analyses were preformed on all randomized patients receiving at least one dose of adalimumab; missing data were imputed using non-responder imputation (NRI) for PASI and PAG and observed data for DLQI; and a post-hoc analysis was conducted to examine key efficacy and safety outcomes for patients who were eligible for treatment with a biological agent as specified in the current BAD guidelines (PASI≥10 and a DLQI>10).

For the patients who met the selected BAD criteria, the baseline demographics and disease severity characteristics were similar across treatment groups. These characteristics were consistent with those of the overall patient population. Table 5 shows the overall baseline demographics and clinical characteristics of the patients enrolled in the overall study (not just specific to BAD).

TABLE 5

|  | Placebo (N = 52) | Adalimumab 40 mg eow (N = 45) | Adalimumab 40 mg weekly (N = 50) |
| --- | --- | --- | --- |
| Age, years (range) | 43 (20-70) | 46 (20-71) | 44 (24-86) |
| Duration of Ps, years (range) | 19 (1-40) | 21 (1-58) | 18 (2-48) |
| % Male | 65 | 71 | 66 |
| % Caucasian | 92 | 89 | 90 |
| Body Weight, kg (range) | 94 (50-147) | 93 (63-159) | 99 (42-149) |
| % BSA (range) | 28 (7-75) | 29 (6-58) | 25 (5-83) |
| PASI Score (range) | 16 (6-40) | 17 (5-39) | 15 (2-42) |
| DLQI Score | 12 | 13 | 14 |

Table 6 shows the overall baseline demographics and clinical characteristics for patients included in this subanalysis (those who met the above described selected BAD guidelines).

TABLE 6

|  | Placebo (N = 18) | Adalimumab 40 mg eow (N = 26) | Adalimumab 40 mg weekly (N = 23) |
| --- | --- | --- | --- |
| Age, years (range) | 44 (20-70) | 45 (20-71) | 42 (24-86) |
| Duration of Ps, years (range) | 19 (5-40) | 19 (1-58) | 19 (2-48) |
| % Male | 61 | 65 | 61 |
| % Caucasian | 89 | 85 | 91 |
| Body Weight, kg (range) | 89 (57-146) | 92 (70-159) | 104 (42-149) |
| % BSA (range) | 37 (10-75) | 31 (8-56) | 35 (10-83) |
| PASI Score (range) | 20 (11-34) | 19 (11-39) | 19 (11-42) |
| DLQI Score | 18 | 18 | 18 |

TABLE 7

Overall PASI 75 Response Rates Up To Week 60

| Treatment | | % of Patients |
| --- | --- | --- |
| Week 12 n = 147 | Placebo | 4 |
| | Placebo/Adalimumab 40 mg eow | — |
| | Adalimumab 40 mg eow | 53* |
| | Adalimumab 40 mg weekly | 80* |
| Week 24 n = 142 | Placebo | — |
| | Placebo/Adalimumab 40 mg eow | 55 |
| | Adalimumab 40 mg eow | 64 |
| | Adalimumab 40 mg weekly | 72 |

TABLE 7-continued

Overall PASI 75 Response Rates Up To Week 60

| Treatment | | % of Patients |
| --- | --- | --- |
| Week 36 n = 142 | Placebo | — |
| | Placebo/Adalimumab 40 mg eow | 62 |
| | Adalimumab 40 mg eow | 64 |
| | Adalimumab 40 mg weekly | 68 |
| Week 60 n = 142 | Placebo | — |
| | Placebo/Adalimumab 40 mg eow | 45 |
| | Adalimumab 40 mg eow | 58 |
| | Adalimumab 40 mg weekly | 64 |

At Week 12, placebo patients received 80-mg loading dose, then 40 mg eow.
Modified ITT, NRI.
*p < 0.001 vs. placebo/adalimumab 40 eow group.
Patients with <PASI 50 response on or after Week 24 were eligible to receive OL weekly adalimumab rescue therapy.
Patients receiving rescue therapy were considered non-responders in this analysis.

As can be seen in Table 7, a substantial portion of all patients achieved and sustained a PASI 75 response up to Week 60 of adalimumab treatment. Also seen in Table 6, placebo patients who started adalimumab at Week 12 achieved rapid improvements in their PASI scores, as indicated by PASI 75 response rates at Week 24.

TABLE 8

Overall DLQI Scores Up To Week 60

| Treatment | | % of Patients |
| --- | --- | --- |
| Week 12 n = 140 | Placebo | 11 |
| | Placebo/Adalimumab 40 mg eow | — |
| | Adalimumab 40 mg eow | 4 |
| | Adalimumab 40 mg weekly | 3 |
| Week 24 n = 131 | Placebo | — |
| | Placebo/Adalimumab 40 mg eow | 3 |
| | Adalimumab 40 mg eow | 5 |
| | Adalimumab 40 mg weekly | 3 |
| Week 36 n = 118 | Placebo | — |
| | Placebo/Adalimumab 40 mg eow | 2 |
| | Adalimumab 40 mg eow | 3 |
| | Adalimumab 40 mg weekly | 2 |
| Week 60 n = 106 | Placebo | — |
| | Placebo/Adalimumab 40 mg eow | 2 |
| | Adalimumab 40 mg eow | 4 |
| | Adalimumab 40 mg weekly | 1 |

At Week 12, placebo patients received 80-mg loading dose, then 40 mg eow.
Modified ITT, observed.
Patients with <PASI 50 response on or after Week 24 were eligible to receive OL weekly adalimumab rescue therapy.
Patients receiving rescue therapy were considered non-responders in this analysis.

Table 8 shows the overall DLQI scores up to Week 60 for patients included in the subanalysis study. As can be seen in this figure, all patients demonstrated a significant improvement in DLQI scores up to Week 60 of adalimumab treatment. Also, placebo patients who started adalimumab at Week 12 achieved rapid improvements in DLQI scores.

Overall, substantial percentages of patients who met the selected BAD criteria achieved PASI 75 responses, comparable to PASI 75 response rates in the overall patient population (see Table 9). PASI improvements were largely sustained out to Week 60 (Table 9).

TABLE 9

PASI 75 Response Rates Up To Week 60 in Patients With Baseline PASI ≥10 and DLQI >10

|  | n | Treatment | % of Patients |
|---|---|---|---|
| Week 12 | 18 | Placebo | 0 |
|  | 26 | Placebo/Adalimumab 40 mg eow | — |
|  | 23 | Adalimumab 40 mg eow | 69 |
|  | — | Adalimumab 40 mg weekly | 74 |
| Week 24 | — | Placebo | — |
|  | 15 | Placebo/Adalimumab 40 mg eow | 50 |
|  | 26 | Adalimumab 40 mg eow | 77 |
|  | 23 | Adalimumab 40 mg weekly | 78 |
| Week 36 | — | Placebo | — |
|  | 15 | Placebo/Adalimumab 40 mg eow | 50 |
|  | 26 | Adalimumab 40 mg eow | 73 |
|  | 23 | Adalimumab 40 mg weekly | 74 |
| Week 60 | — | Placebo | — |
|  | 15 | Placebo/Adalimumab 40 mg eow | 44 |
|  | 26 | Adalimumab 40 mg eow | 65 |
|  | 23 | Adalimumab 40 mg weekly | 65 |

At Week 12, placebo patients received 80-mg loading dose, then 40 mg eow.
Modified ITT, NRI.
Patients with <PASI 50 response on or after Week 24 were eligible to receive OL weekly adalimumab rescue therapy.
Patients receiving rescue therapy were considered non-responders in this analysis.

Also, in the subset of patients who met the selected BAD criteria for biologic treatment, patients achieved and largely sustained clinical improvements as demonstrated by PASI 90 responses to Week 60 (Table 10). As can be seen in Table 11, there were significant percentages of patients who achieved a PGA score of "Clear" or "Almost Clear" and sustained these responses until Week 60.

TABLE 10

PASI 90 Response Rates Up To Week 60 in Patients With Baseline PASI ≥10 and DLQI >10

|  | n | Treatment | % of Patients |
|---|---|---|---|
| Week 12 | 18 | Placebo | 0 |
|  | 26 | Placebo/Adalimumab 40 mg eow | — |
|  | 23 | Adalimumab 40 mg eow | 39 |
|  | — | Adalimumab 40 mg weekly | 61 |
| Week 24 | — | Placebo | — |
|  | 15 | Placebo/Adalimumab 40 mg eow | 28 |
|  | 26 | Adalimumab 40 mg eow | 54 |
|  | 23 | Adalimumab 40 mg weekly | 70 |
| Week 36 | — | Placebo | — |
|  | 15 | Placebo/Adalimumab 40 mg eow | 50 |
|  | 26 | Adalimumab 40 mg eow | 58 |
|  | 23 | Adalimumab 40 mg weekly | 65 |
| Week 60 | — | Placebo | — |
|  | 15 | Placebo/Adalimumab 40 mg eow | 39 |
|  | 26 | Adalimumab 40 mg eow | 42 |
|  | 23 | Adalimumab 40 mg weekly | 48 |

At Week 12, placebo patients received 80-mg loading dose, then 40 mg eow.
Modified ITT, NRI.
Patients with <PASI 50 response on or after Week 24 were eligible to receive OL weekly adalimumab rescue therapy.
Patients receiving rescue therapy were considered non-responders in this analysis.

TABLE 11

PGA "Clear" or "Almost Clear" Up To Week 60 in Patients With Baseline PASI ≥10 and DLQI >10

|  | n | Treatment | % of Patients |
|---|---|---|---|
| Week 12 | 18 | Placebo | 0 |
|  | 26 | Placebo/Adalimumab 40 mg eow | — |
|  | 23 | Adalimumab 40 mg eow | 62 |
|  | — | Adalimumab 40 mg weekly | 70 |
| Week 24 | — | Placebo | — |
|  | 15 | Placebo/Adalimumab 40 mg eow | 33 |
|  | 26 | Adalimumab 40 mg eow | 69 |
|  | 23 | Adalimumab 40 mg weekly | 74 |
| Week 36 | — | Placebo | — |
|  | 15 | Placebo/Adalimumab 40 mg eow | 44 |
|  | 26 | Adalimumab 40 mg eow | 65 |
|  | 23 | Adalimumab 40 mg weekly | 65 |
| Week 60 | — | Placebo | — |
|  | 15 | Placebo/Adalimumab 40 mg eow | 39 |
|  | 26 | Adalimumab 40 mg eow | 54 |
|  | 23 | Adalimumab 40 mg weekly | 52 |

At Week 12, placebo patients received 80-mg loading dose, then 40 mg eow.
Modified ITT, NRI.
Patients with <PASI 50 response on or after Week 24 were eligible to receive OL weekly adalimumab rescue therapy.
Patients receiving rescue therapy were considered non-responders in this analysis..

Adalimumab-treated patients showed rapid and sustained improvement in their DLQI scores (Table 12), with mean scores of 3.0 and 0.7 at Week 60 in the adalimumab every other week and adalimumab weekly groups respectively.

TABLE 12

Change in DLQI Scores Up To Week 60 in Patients With Baseline PASI ≥10 and DLQI >10

|  | n | Treatment | Mean change from baseline |
|---|---|---|---|
| Week 12 | 15 | Placebo | −2 |
|  | 26 | Placebo/Adalimumab 40 mg eow | — |
|  | 22 | Adalimumab 40 mg eow | −15 |
|  | — | Adalimumab 40 mg weekly | −16 |
| Week 24 | — | Placebo | — |
|  | 15 | Placebo/Adalimumab 40 mg eow | −12 |
|  | 25 | Adalimumab 40 mg eow | −14 |
|  | 20 | Adalimumab 40 mg weekly | −17 |
| Week 36 | — | Placebo | — |
|  | 13 | Placebo/Adalimumab 40 mg eow | −14 |
|  | 22 | Adalimumab 40 mg eow | −15 |
|  | 18 | Adalimumab 40 mg weekly | −18 |
| Week 60 | — | Placebo | — |
|  | 12 | Placebo/Adalimumab 40 mg eow | −12 |
|  | 22 | Adalimumab 40 mg eow | −15 |
|  | 15 | Adalimumab 40 mg weekly | −17 |

At Week 12, placebo patients received 80-mg loading dose, then 40 mg eow.
Modified ITT, observed.
Patients with <PASI 50 response on or after Week 24 were eligible to receive OL weekly adalimumab rescue therapy.
Patients receiving rescue therapy were considered non-responders in this analysis.

As can be seen in Table 13, withdrawal rates due to adverse events in this post-hoc analysis were comparable for patients treated with adalimumab every other week and adalimumab weekly.

TABLE 13

| Event, n (%) | Weeks 0-12 | | | Weeks 12-60 | |
|---|---|---|---|---|---|
| | Placebo (N = 18) | Adalimumab 40 mg eow (N = 26) | Adalimumab 40 mg weekly (N = 23) | Placebo/ Adalimumab 40 mg eow + Adalimumab 40 mg eow (N = 41) | Adalimumab 40 mg weekly (N = 23) |
| Any AE | 13 (72) | 16 (62) | 19 (83) | 23 (56) | 11 (48) |
| Serious AEs | 0 (0) | 0 (0) | 2 (9) | 1 (2) | 0 (0) |
| Any Infectious Serious AEs | 0 (0) | 0 (0) | 0 (0) | 0 (0) | 0 (0) |
| AEs leading to withdrawal | 1 (6) | 0 (0) | 1 (4) | 2 (5) | 0 (0) |

Overall, patients with moderate to sever plaque psoriasis achieved sustained efficacy up to Week 60 of treatment with adalimumab. Adalimumab treatment significantly reduced the signs and symptoms and improved the quality of life in patients with psoriasis who meet some of the necessary criteria of the BAD guidelines for biologic treatment. The adverse events observed in this study were similar to those previously reported in adalimumab rheumatoid arthritis and psoriatic arthritis trials.

Example 3

Recent History of Systemic or Biologic Therapy does not Adversely Affect Adalimumab Efficacy and Safety in Patients with Moderate to Severe Chronic Plaque Psoriasis Psoriasis is a chronic, inflammatory proliferative disease of the skin that affects 1-3% of the general population (Greaves and Weinstein (1995) N Engl J Med 332: 581). Treatment of moderate to severe psoriasis with systemic therapy such as methotrexate or cyclosporine or biologic therapy such as efalizumab can be limited by lack of efficacy or precluded by side effects. Ultraviolet light therapy is often inconvenient.

Previous studies demonstrated adalimumab is effective in treating moderate to severe plaque psoriasis (Ps), with an acceptable safety profile. Some study patients had a recent (within past 12 months) history of exposure systemic or biologic (except TNF antagonists) therapy, but could enroll if systemic therapy stopped at least 4 wks prior to study (at least 12 wks for biologics). The impact of prior treatment with these agents on the safety and efficacy of patients receiving adalimumab is a practical concern to physicians and patients and was investigated in this subanalysis. Thus, the following study describes an analysis of the efficacy and safety of adalimumab treatment in psoriasis patients with or without recent exposure to systemic or biologic agents.

The objective of the study was to investigate the impact of prior treatment with systemic non-biologic or biologic therapies on the safety and efficacy of adalimumab in patients with psoriasis The efficacy and safety of adalimumab was evaluated in a 12-week, double-blind, placebo-controlled trial, followed by a 48-week extension, conducted at 18 sites two different countries. Inclusion criteria for the study included the following parameters: ≥18 years of age; moderate to severe chronic plaque psoriasis≥1 year; and affected BSA≥5%. Exclusion criteria for the study included prior TNF-antagonist therapy and discontinuation of other systemic psoriasis therapies Impact of prior biologics, other than TNF antagonists, on the safety and efficacy of adalimumab for psoriasis was measured in this subanalysis study. Efficacy outcome measures included PASI and PGA. Analytical methods included the following:

Modified intent-to-treat analyses were performed on all randomized patients receiving at least one dose of adalimumab Missing data were imputed using non-responder imputation Subanalyses were conducted on the outcomes of patients who were and were not exposed to systemic therapy within 12 months of study entry A diagram of the study design is shown in FIG. 1.

Out of 148 patients enrolled in a double-blind, placebo (pbo)-controlled study, 147 patients received at least one dose of study medication in 1 of 3 randomized treatment arms: 1) pbo (n=52); 2) adalimumab 80 mg subcutaneous (sc) at Wk 0, then 40 mg sc every other wk (eow) starting at Wk 1 (n=45); and 3) adalimumab 80 mg sc at Wks 0 and 1, then 40 mg sc wkly (qw) starting at Wk 2 (n=50). Placebo patients were eligible at Week 12 to receive adalimumab 40 mg eow (placebo/adalimumab eow).

Baseline data were similar among randomization groups. Baseline demographics, disease severity characteristics, and recent history of systemic therapies were similar across the treatment groups. Table 2 shows the baseline demographics and clinical characteristics.

Systemic non-biologic therapies taken by more than 2% of patients included methotrexate (16%), oral tazarotene (11%), cyclosporine (9%), and acitretin (4%). The only systemic biologic therapy taken by more than 2% of patients was efalizumab (15%) (prior use of TNF-antagonist therapy was an exclusion criterion for study entry). Table 14 shows clinical characteristics of the patients involved in the study, including recent past history of systemic therapy.

TABLE 14

Clinical Characteristics: Recent Past History of Systemic Therapy*

| | Placebo (N = 52) | Adalimumab 40 mg eow (N = 45) | Adalimumab 40 mg weekly (N = 50) |
|---|---|---|---|
| No Recent History of Systemic Therapy, n (%) | 28 (54) | 23 (51) | 25 (50) |
| Recent History of Systemic Non-biologic Therapy, n (%) | 19 (37) | 19 (42) | 22 (44) |

TABLE 14-continued

Clinical Characteristics: Recent Past History of Systemic Therapy*

|  | Placebo (N = 52) | Adalimumab 40 mg eow (N = 45) | Adalimumab 40 mg weekly (N = 50) |
|---|---|---|---|
| Recent History of Systemic Biologic Therapy, n (%) | 8 (15) | 8 (18) | 9 (18) |

*Within 12 months of study entry.

Percentages in each column do not sum to 100 because some patients had recent history of systemic non-biologic and biologic therapy. The numbers of patients exposed to multiple types of systemic therapy were too small to permit meaningful analysis of their outcomes.

The results show that substantial percentages of all patients achieved and sustained PASI 75 responses up to Week 60 of adalimumab treatment. In addition, placebo patients who started adalimumab at Week 12 attained clinically significant improvement in their PASI 75 response rates by Week 24. These results are described in Table 6.

Patients with and without a recent history of systemic non-biologic or biologic therapy had similar percentages of PASI 75 responses at Week 24, which were largely sustained out to Week 60. Tables 15 and 16 shows PASI 75 response rates in patients stratified by recent history of systemic therapy at week 24 (Table 15) and week 60 (Table 16).

TABLE 15

PASI 75 Response Rates at Week 24 in Patients Stratified by Recent History of Systemic Therapy

|  | n | Treatment | % Patients |
|---|---|---|---|
| Prior Systemic Use | 17 | Placebo/Adalimumab 40 mg eow | 47 |
|  | 19 | Adalimumab 40 mg eow | 68 |
|  | 22 | Adalimumab 40 mg weekly | 73 |
| Prior Biological Use | 8 | Placebo/Adalimumab 40 mg eow | 63 |
|  | 8 | Adalimumab 40 mg eow | 50 |
|  | 9 | Adalimumab 40 mg weekly | 67 |
| No Prior Use | 25 | Placebo/Adalimumab 40 mg eow | 56 |
|  | 23 | Adalimumab 40 mg eow | 65 |
|  | 25 | Adalimumab 40 mg weekly | 76 |

Modified ITT, NRI.

TABLE 16

PASI 75 Response Rates at Week 60 in Patients Stratified by Recent History of Systemic Therapy

|  | n | Treatment | % Patients |
|---|---|---|---|
| Prior Systemic Use | 17 | Placebo/Adalimumab 40 mg eow | 41 |
|  | 19 | Adalimumab 40 mg eow | 68 |
|  | 22 | Adalimumab 40 mg weekly | 64 |
| Prior Biological Use | 8 | Placebo/Adalimumab 40 mg eow | 63 |
|  | 8 | Adalimumab 40 mg eow | 63 |
|  | 9 | Adalimumab 40 mg weekly | 78 |
| No Prior Use | 25 | Placebo/Adalimumab 40 mg eow | 40 |
|  | 23 | Adalimumab 40 mg eow | 48 |
|  | 25 | Adalimumab 40 mg weekly | 64 |

Modified ITT, NRI.

Patients with and without a recent history of systemic non-biologic or biologic therapy who received adalimumab 40 mg eow dosing achieved and largely sustained clinical improvement to Week 60, as measured by a variety of secondary efficacy variables. Table 17 shows secondary efficacy outcomes after 60 weeks of adalimumab 40 mg eow.

TABLE 17

|  | PASI 50 (%) | PASI 90 (%) | PASI 100 (%) | % PGA "Clear"/ "Almost Clear" |
|---|---|---|---|---|
| No Prior Use | 65 | 30 | 17 | 44 |
| Prior Systemic Use | 68 | 37 | 11 | 47 |
| Prior Biologic Use | 63 | 38 | 13 | 38 |

Table 18 show PASI responses up to week 60. Overall, percent of PASI 75 responders in the (placebo/adalimumab eow)/adalimumab eow/adalimumab weekly arms were 55/64/72 at Wk 24 and 45/58/64 at Wk 60, respectively. For patients with prior biologic therapy (n=25), the rates were 63/50/67 at Week 24 and 63/63/78 at Week 60. For patients in neither of these groups (n=73), the rates were 56/65/76 at Week 24 and 40/48/64 at Week 60.

TABLE 18

Percentages of PASI 75 responders for each subgroup at Wks 24 and 60

|  | Wk 24 Pbo/Adalimumab eow/ Adalimumab qw | Wk 60 Adalimumab eow (formerly Pbo)/ Adalimumab eow/ Adalimumab qw |
|---|---|---|
| Systemic, n = 58 (%) | 47/68/73 | 41/68/64 |
| Biologic, n = 25 (%) | 63/50/67 | 63/63/78 |
| Other, n = 73 (%) | 56/65/76 | 40/48/64 |

Withdrawal rates due to adverse events were similarly low for patients treated with adalimumab eow and adalimumab weekly. All patients treated with adalimumab in the double-blind portion of the trial continued into the open-label extension. The percentage of patients who withdrew due to adverse events between Weeks 12 and 60 ranged from 3.3% to 10.0%

Serious adverse events (SAEs) were detected in 7 prior-systemic patients, 4 prior-biologic patients, and 5 patients without recent prior systemic or biologic therapy during the 60-week trial. Most SAEs did not appear to be related to adalimumab use. Table 19 shows adverse events by treatment period, while Tables 20 and 21 shows adverse events by subgroup (Table 20: weeks 0-12; Table 21: Weeks 12-60).

TABLE 19

Adverse Events by Treatment Period

| | Weeks 0-12 | | | Weeks 12-60 | |
| --- | --- | --- | --- | --- | --- |
| Event, n (%) | Placebo (N = 52) | Adalimumab 40 mg eow (N = 45) | Adalimumab 40 mg weekly (N = 50) | Placebo/ Adalimumab 40 mg eow + Adalimumab 40 mg eow (N = 92) | Adalimumab 40 mg weekly |
| Any AE | 35 (67) | 28 (62) | 39 (78) | 72 (78) | 39 (78) |
| Serious AEs | 0 (0) | 1 (2) | 4 (8) | 2 (2) | 7 (14) |
| AEs leading to withdrawal | 1 (1) | 2 (4) | 3 (6) | 3 (3) | 5 (10) |

TABLE 20

Adverse Events by Subgroup: Weeks 0-12 - Results for Patients Stratified by Recent Past History

| | Placebo | | | Adalimumab 40 mg eow | | | Adalimumab 40 mg weekly | | |
| --- | --- | --- | --- | --- | --- | --- | --- | --- | --- |
| | No Prior Use (n = 28) | Prior Systemic Use (n = 19) | Prior Biologic Use (n = 8) | No Prior Use (n = 23) | Prior Systemic Use (n = 19) | Prior Biologic Use (n = 8) | No Prior Use (n = 25) | Prior Systemic Use (n = 22) | Prior Biologic Use (n = 9) |
| Any AE, n (%) | 18 (64) | 15 (79) | 5 (63) | 16 (70) | 11 (58) | 2 (25) | 20 (80) | 17 (77) | 6 (67) |
| Serious AE, n (%) | 0 (0) | 0 (0) | 0 (0) | 0 (0) | 1 (5) | 0 (0) | 1 (4) | 2 (9) | 2 (22) |
| AE's→Withdrawal, n (%) | 0 (0) | 1 (5) | 0 (0) | 1 (4) | 1 (5) | 0 (0) | 1 (4) | 1 (5) | 2 (22) |

TABLE 21

Adverse Events by Subgroup: Weeks 12-60 - Results for Patients Stratified by Recent Past History

| | Placebo/Adalimumab 40 mg eow + Adalimumab 40 mg eow | | | Adalimumab 40 mg weekly | | |
| --- | --- | --- | --- | --- | --- | --- |
| | No Prior Use (n = 47) | Prior Systemic Use (n = 35) | Prior Biologic Use (n = 16) | No Prior Use (n = 24) | Prior Systemic Use (n = 21) | Prior Biologic Use (n = 7) |
| Any AE (%) | 37 (79) | 28 (80) | 12 (75) | 19 (79) | 17 (81) | 6 (86) |
| Serious AE (%) | 0 (0) | 2 (6) | 2 (13) | 4 (17) | 2 (10) | 0 (0) |
| AE's→Withdrawal (%) | 1 (2) | 2 (6) | 1 (6) | 2 (8) | 3 (14) | 0 (0) |

The most frequent adverse events, between weeks 12 and 60 are described in Table 22.

In conclusion, patients with moderate to severe psoriasis achieved sustained efficacy up to week 60 of treatment with adalimumab. Prior biologic or non-biologic therapy did not appear to adversely affect adalimumab efficacy or safety in patients with moderate to severe psoriasis. Finally, the types and rates of adverse events in this study were similar to those previously reported in adalimumab RA and PsA trials. In sum, this post-hoc analysis suggests that recent treatment with systemic or biologic therapy does not adversely affect adalimumab efficacy or safety in moderate to severe psoriasis patients.

TABLE 22

Most frequent adverse events, between weeks 12 and 60

| Event | Placebo/Adalimumab 40 mg eow + Adalimumab 40 mg eow (N = 92) | Adalimumab 40 mg weekly (N = 50) |
| --- | --- | --- |
| Nasopharyngitis | 13 (14.1) | 6 (12.0) |
| URI, NOS | 9 (9.8) | 7 (14.0) |
| URI, viral NOS | 4 (4.3) | 3 (6.0) |
| Muscle strain | 1 (1.1) | 4 (8.0) |
| Blood CPK increased | 5 (5.4) | 2 (4.0) |
| Blood TG increased | 7 (7.6) | 2 (4.0) |
| Back pain | 4 (4.3) | 4 (8.0) |
| Skin papilloma | 3 (3.3) | 5 (10.0) |

TABLE 22-continued

Most frequent adverse events, between weeks 12 and 60

| Event | Placebo/Adalimumab 40 mg eow + Adalimumab 40 mg eow (N = 92) | Adalimumab 40 mg weekly (N = 50) |
|---|---|---|
| Headache | 3 (3.3) | 6 (12.0) |
| Urticari | 0 (0.0) | 3 (6.0) |

URI = upper respiratory infection; NOS = not otherwise specified; CPK = Creatine phosphokinase; TG = Triglycerides.

Example 4

Improvements in DLQI in Moderate to Severe Plaque Psoriasis Patients Treated with Adalimumab The following example provides additional details regarding Dermatology Life Quality Index (DLQI) changes in a Phase II clinical study, as described in Examples 1, 3, 5, 6, and 8. The study showed that changes in functional ability as measured by DLQI were consistent with clinical response in moderate to severe plaque psoriasis patients treated with adalimumab. The following example also describes the Minimum Clinically Important Difference (MCID) in DLQI in moderate to severe plaque psoriasis patients treated with adalimumab.

Because psoriasis exerts substantial deleterious effects on physical function and quality of life (HRQOL) (see de Arruda et al. (2001) Br J Dermatol 144 (Suppl 58):33; Finlay (1998) Seminars Cutan Med Surgery 17:291; Rapp et al. (2001) Br J Dermatol 145:610; and Wahl et al. (2000) J Am Acad Dermatol 43:803), patient-reported outcomes (PROs) help evaluate the beneficial effects of treatment, in addition to clinical endpoints.

The minimum clinically important difference (MCID) is defined as "the smallest difference in score that patients perceive as beneficial" (see Juniper et al. (1994) J Clin Epidemiol 47:81). While clinical trials of biologics in the treatment of psoriasis have included PROs—particularly the Dermatology Life Quality Index (DLQI) (see Feldman et al. (2004)) Br J Dermatol 150:317; Finlay et al. (2003) Dermatology 206:307; Gordon et al. (2003) JAMA 290:3073; Gottlieb et al. (2003) Arch Dermatol 139:1627; Leonardi et al. (2003) N Engl J Med 349:2014; and Menter et al. (2004) J Drugs Dermatol 3:27)—the clinical relevance and MCID for this instrument have not been established in moderate to severe plaque psoriasis.

The following describes a study which examined the DLQI as a secondary efficacy endpoint in a 12-week study (placebo-controlled trial) of two different dose regimens of adalimumab in moderate to severe plaque psoriasis. Thus, one of the objectives of the study was to estimate the sensitivity of DLQI to clinical changes associated with moderate to severe plaque psoriasis. An additional objective was to determine the MCID for use in future studies and treatments.

Patients were randomized into one of the following treatment groups: 80 mg adalimumab at baseline (week 0) and 40 mg at week 1 followed by 40 mg every other week (eow) starting at week 3 (referred to as ada 40 mg eow); 80 mg adalimumab at baseline (week 0) and 80 mg at week 1 followed by 40 mg weekly starting at week 2 (referred to as ada 40 mg weekly); or placebo administered weekly beginning at baseline (referred to as placebo). Inclusion criteria included a diagnosis of moderate to severe chronic plaque psoriasis≥1 year prior to entry, a psoriasis-affected body surface area (BSA)>5%, and no previous TNF-antagonist therapy.

The two primary clinical outcome measures used in this study were the psoriasis area and severity index (PASI) and the physician's global assessment (PGA). PASI improvement of greater than or equal to 75% (used as an endpoint in psoriasis clinical trials) at week 12 was the primary efficacy outcome measure for this study. PASI is a composite index indicating severity for three main signs of psoriatic plaques (erythema, scaling, and thickness), weighted by the amount of coverage of these plaques in four main body areas, i.e., head, trunk, upper extremities, and lower extremities. PASI scores, which range from 0-72, with higher scores indicating greater severity, were assessed at screening, baseline, week 1, week 2, week 4, week 8, week 12/early termination, and follow-up.

PROs were assessed using the DLQI. The DLQI is a validated instrument used to assess dermatologic-related functional limitations. Characteristics of the DLQI include: ten items on an overall scoring range of 0-30; higher scores represent greater quality of life impairment and lower scores represent lower quality of life impairment; well-established properties of reliability and validity for the DLQI total score in a dermatology setting (see Badia et al. (1999) Br J Dermatol 141:698; Finlay et al. (1994) Clin Exp Dermatol 19:210; and Shikier et al. (2003) Health and Quality of Life Outcomes 1:53); and six subcategories: symptoms and feelings; daily activities; leisure; work/school; personal relationships; and treatment.

The Physician's Global Assessment (PGA), which was used as a clinical endpoint in the trial, was used to determine the MCID for DLQI. The PGA is a seven point scale used to measure disease severity from a physician's evaluation. Scoring under the PGA ranges from 1 (Clear) to 7 (Severe). Categories for the 7-point scale include the following:

Severe: very marked plaque elevation, scaling and/or erythema;
Moderate to severe: marked plaque elevation, scaling and/or erythema;
Moderate: moderate plaque elevation, scaling and/or erythema;
Mild to moderate: intermediate between moderate and mild;
Mild: slight plaque elevation, scaling and/or erythema;
Almost clear: intermediate between mild and clear; and
Clear: no signs of psoriasis (post-inflammatory hypopigmentation or hyperpigmentation could be present).

Scoring regions were from 1 (clear) to 7 (severe). PGA was assessed at screening; baseline; week 1; week 2; week 4; week 8; and week 12/early termination; and follow up. The same investigator performed the assessment for each patient throughout the study. Statistical methods were performed according to the following summary. Analyses were performed on blinded data, combining results from all three groups. Changes in the PGA from baseline to week 12 were correlated with changes in DLQI total score.

Mean changes in DLQI total score were calculated and compared for two sets of patients: those whose PGA scores improved by 1 or 2 points ("minimal responders") and those whose PGA scores stayed the same of declined or declines by 1 point "non-responders"). It should be noted that there is no universally accepted method to calculate MCID. One method to estimate the MCID is to calculate the difference between the mean DLQI changes for patients classified as "minimal responders" and the changes for patients classified as "non-responders." Other methods to calculate MCID are based on mean DLQI change corresponding to PASI improvement 25%-49%. MCID for DLQI was also calculated based on mean DLQI change corresponding to PASI improvement 50%-74% and based on three distributional methods: standard error of the mean (SEM) change in DLQI; upper limit of the 95% confidence interval of the SEM; and half of the standard deviation (SD) of the DLQI mean change. MCID was applied to demonstrated changes in DLQI total score from baseline to week 12 in the three randomized groups of this trial. All data were observed values, and patients who discontinued before the time point were not included in the analysis.

Changes in the clinical measures from baseline to week 12 were also correlated with changes in DLQI total score. Mean changes in DLQI total score were calculated and compared by level of PASI response (PASI Improvement<25%; PASI Improvement 25-49%; PASI Improvement 50-74%, and PASI Improvement>75%). MCID for DLQI was determined based on mean DLQI change corresponding to PASI Improvement 25-49% (the study did not afford independent verification of the correspondence of this level of improvement with a level patients would indicate represents noticeable but minimum improvement. Nonetheless, these patients were characterized as "near responders," as patients with psoriasis who achieve PASI Improvement of 50-75% are sometimes termed "partial-responders"). MCID determination was also based on three standard distributional methods: 1) standard error of the mean (SEM) change in DLQI; 2) upper limit of the 95% confidence interval of the SEM; and 3) half of the standard deviation (SD) of the DLQI mean change. MCID was applied to demonstrated changes in DLQI total score from baseline to week 12 in the three randomized groups of this Phase II trial.

147 patients from 18 different sites enrolled in the study and received at least one dose of study medication. Demographic characteristics are provided below in Table 23:

TABLE 23

Demographic Characteristics

| Characteristic | (N = 147) |
|---|---|
| Age | |
| Mean (SD) | 44.2 (12.7) |
| Gender | |
| Female n (%) | 48 (32.7%) |
| Male n (%) | 99 (67.3%) |
| Race | |
| White n (%) | 133 (90.5%) |
| Black n (%) | 4 (2.7%) |

TABLE 23-continued

Demographic Characteristics

| Characteristic | (N = 147) |
|---|---|
| Asian n (%) | 5 (3.4%) |
| Other n (%) | 5 (3.4%) |

Data were available for 140 of the 147 patients at the end of the trial. Mean values for DLQI and PGA at baseline and week 12 are shown below in Table 24:

TABLE 24

Mean (SD) of DLQI and PGA at Baseline and Week 12

| | Baseline (N = 147) | Week 12 (N = 140) | Change[2] (N = 140) |
|---|---|---|---|
| DLQI Total Score | 12.7 (7.2) | 5.3 (6.5) | −7.5 (7.8) |
| Physician's Global Assessment[1] (PGA) | 5.5 (0.8) | 3.4 (1.7) | −2.1 (1.9) |
| Psoriasis and Severity Index (PASI) | 16.7 (7.3) | 6.8 (7.8) | −8.9 (8.4) |

[1]Scored such that 1 = "Clear" to 7 = "Severe"
[2]Calculated only for patients with both baseline and week-12 scores (Numbers in parentheses are standard deviations (SD)).

Correlation PASI

The correlation coefficient for DLQI total score and PASI was 0.69 ($p<0.001$), and for DLQI total score and PGA was 0.71 ($p<0.001$) (see Table 25). In addition, the results show that DLQI was highly correlated with clinical endpoints (see Table 26).

TABLE 25

Correlations* Between Changes in DLQI and Psoriasis Area and Severity Index (PASI) and Physician's Global Assessment (PGA)

| | PASI | PGA |
|---|---|---|
| DLQI Total Score | 0.69 | 0.71 |
| PASI | 1.00 | 0.75 |

*All correlations are significant at $p < 0.001$.

TABLE 26

Correlations between DLQI and Clinical Endpoints

| | Baseline | | Week 12 | |
|---|---|---|---|---|
| | PASI | PGA | PASI | PGA |
| DLQI | 0.31 | 0.29 | 0.67 | 0.65 |
| PASI | 1.00 | 0.5 | 1.00 | 0.83 |

$p < 0.001$ for all correlations.
PASI = Psoriasis Area and Severity Index.
PGA = Physician's Global Assessment.

Corresponding mean (SD) DLQI change scores improved with increases in PASI response ($p<0.001$), as shown in Table 27.

TABLE 27

Mean (SD) DLQI Change Score Corresponding to Levels of PASI Improvement

| | PASI Improvement | | | | |
|---|---|---|---|---|---|
| | <25% (N = 31) | 25%-49% (N = 22) | 50%-74% (N = 21) | ≥75% (N = 66) | Overall F-Value |
| DLQI Total Score | −0.16 (5.41) | −4.05 (4.95) | −6.95 (5.71) | −12.17 (6.78) | 30.4* |

Negative change scores indicate improvement; p-values are:
*<0.001.
Post-hoc tests indicate that the PASI >75% differed significantly from each of the three other groups. In addition, the PASI <25% group differed significantly from the PASI 50-74% group. Numbers in parentheses are standard deviations (SD).

It is believed that these data support an MCID in the range of 2.3-4.0, which is consistent with estimates derived from a prior analysis of data from two psoriasis clinical trials. The mean change in DLQI total score from baseline in both adalimumab treatment arms was much greater than an MCID range of 2.3-4.0. The placebo group did not achieve the MCID, as shown in Table 28.

TABLE 28

Mean Change in DLQI at Week 12

| | Placebo | Adalimumab 40 mg eow | Adalimumab 40 mg weekly |
|---|---|---|---|
| Mean change | −1.3 | −10.8* | −11.5* |

*p < 0.001 vs. placebo
MCID 2.3-4.0

Table 29 below shows the DLQI improvement corresponding to a PASI improvement of 25-49%, as well as the three "distributional" estimates of the MCID.

TABLE 29

Estimates of MCID for the DLQI

| | Change in Scale/Subscale | | | |
|---|---|---|---|---|
| | MCID 1: PASI Improvement 25%-49% | MCID 2: SEM | MCID 3: 1.96 SEM | MCID 4: 0.5 SD |
| DLQI Total Score | −4.05 (4.95) | 2.33 | 4.57 | 3.59 |

Numbers in parentheses are standard deviations (SD).
MCID = minimum clinically important difference; SEM = standard error of measurement.

PGA Correlation

Mean improvements in DLQI between "minimal responders" and "non-responders" based on PGA was significantly different (p<0.0001), as shown in Table 30.

TABLE 30

Mean (SD) DLQI Change Score by PGA Response

| | PGA Minimal Responder | PGA Non-Responder | Difference in Mean DLQI Total Score* |
|---|---|---|---|
| DLQI Total Score | −5.7 (5.7) | 0.0 (4.7) | 5.7 |

*p < 0.0001
Note:
Negative numbers indicate improvement, positive numbers indicate worsening in dermatologic-related functional limitations as measured by DLQI.

Based on the above MCID calculations with PASI (2.3-4) and these MCID calculations with PGA (5.7) in the same study population, the MCID for DLQI was estimated to range between 2.3 and 5.7, with the most conservative estimate of MCID derived from analysis of the mean change in DLQI for PGA "minimal responders." Table 31 shows DLQI improvement at 12 weeks in each of the three arms of the study.

TABLE 31

DLQI improvement at 12 weeks in each of the three arms of the study

| Treatment | Mean Change |
|---|---|
| Placebo | −1.3 |
| Adalimumab 40 mg eow | −10.8 |
| Adalimumab 40 mg weekly | −11.5* |

*p < 0.001 vs. Placebo

In conclusion, through a variety of methods, the MCID for the DLQI was estimated to range between 2.3 and 5.7. Given that adalimumab-treated patients demonstrated mean change in DLQI of ≥10 points, which is well above the most conservative estimate of MCID for DLQI, treatment with adalimumab is associated with clinically important improvements in dermatologic-related functional limitations.

Example 5

Enhanced Adalimumab Efficacy Following Dosage Escalation in Psoriasis Patients with Subtherapeutic Response to Every-Other-Week Adalimumab Adalimumab is a fully human, monoclonal $IgG_1$ antibody against TNF. A 60-week, Phase II study demonstrated that adalimumab is effective in moderate to severe plaque psoriasis patients, with an acceptable safety profile (see FIG. 1 for study design). Patients with a subtherapeutic (<PASI 50) response to adalimumab at Week 24 could increase their dosages from every other week (eow) to every week (qw). The objective of this study was to assess efficacy and safety of adalimumab weekly dosing in those psoriasis patients who had a subtherapeutic response to every-other-week adalimumab dosage Thus, the present subanalysis evaluated adalimumab efficacy and safety in those patients who increased their dosages.

The efficacy and safety of adalimumab was evaluated in a 48-week extension trial conducted at 18 sites in the US and Canada. Prior to this open label study, patients were enrolled in a 12-week, double-blind, placebo-controlled trial. Inclusion criteria included patients being 18 years of age; having moderate to severe chronic plaque psoriasis≥1 year; and affected BSA≥5%. Exclusion criteria included prior TNF-antagonist therapy and discontinuation of other systemic psoriasis therapies. Efficacy outcome measures which were used included PASI, PGA, DLQI. The study design is shown in FIG. 1. Baseline demographics and clinical characteristics are described in Table 2 above. In addition, the percentage of patients with PsA was 31% placebo, 33% adalimumab 40 mg eow, and 24% adalimumab 40 mg weekly.

Randomized treatment arms included: 1) placebo (n=52); 2) adalimumab 80 mg subcutaneously (sc) at Week 0, then 40 mg sc eow starting at Week 1 (n=45); and 3) adalimumab 80 mg sc at Weeks 0 and 1, then 40 mg sc qw starting at Week 2 (n=50). At Week 12, placebo patients were switched to adalimumab 40 mg eow (placebo/eow). At Week 24 and thereafter, adalimumab eow patients with <PASI 50 improvement from baseline started adalimumab 40 mg qw. Skin and safety outcomes were assessed up to Week 60.

Of 148 patients enrolled in the double-blind, placebo-controlled study, 147 received at least one dose of study medication. At Week 24, PASI 50 responses were 77/73/80 and PASI 75 responses were 55/64/72 for the (placebo/eow)/eow/weekly arms, respectively.

On or after Week 24, 18 of the 47 patients in the placebo/adalimumab eow group and 12 of the 45 patients in the adalimumab eow group achieved a PASI<50 response, which qualified them for dosage escalation to adalimumab weekly (Table 32)

TABLE 32

Number of Patients Who Qualified for Dosage Escalation at Each Timepoint

|  | Placebo/Adalimumab 40 mg eow (n = 18) | Adalimumab 40 mg eow (n = 12) |
| --- | --- | --- |
| Week 24 | 10 | 9 |
| Week 28 | 2 | 1 |
| Week 32 | 2 | 0 |
| Week 44 | 1 | 1 |
| Week 52 | 3 | 0 |
| Week 60 | 0 | 1 |

Patients whose dosages were increased to weekly dosing had baseline demographics and clinical characteristics similar to the overall patient population (Table 33).

TABLE 33

Baseline Demographics and Clinical Characteristics for the Dosage Escalation Group*

| Characteristics | Dosage Escalation Group (n = 30) |
| --- | --- |
| Age, years | 46.5 ± 12.0 |
| Duration of Ps, years | 19.2 ± 12.8 |
| % Male | 63 |
| % Caucasian | 97 |
| Body Weight, kg | 97.4 ± 24.2 |
| % BSA ± SD | 23 ± 13.8 |
| PASI Score | 14.1 ± 6.1 |
| % with PsA | 37 |

*Mean values ± SD except percentages

After qualifying for dosage escalation, nearly 20% of patients achieved a PASI 75 response in their psoriasis at Week 60 (Table 34)

TABLE 34

Efficacy Results at Week 60 for Dosage Escalation Group

|  | Dosage Escalation Group (n = 30) |
| --- | --- |
| PASI 50 Response Rate (%) | 40 |
| PASI 75 Response Rate (%) | 17 |
| PASI 90 Response Rate (%) | 0 |
| PGA ("Clear" or "Almost Clear") (%) | 20 |

ITT for patients qualifying for dosage escalation.
Patients with missing PASI or PGA evaluations were considered non-responders.

Figure 2:
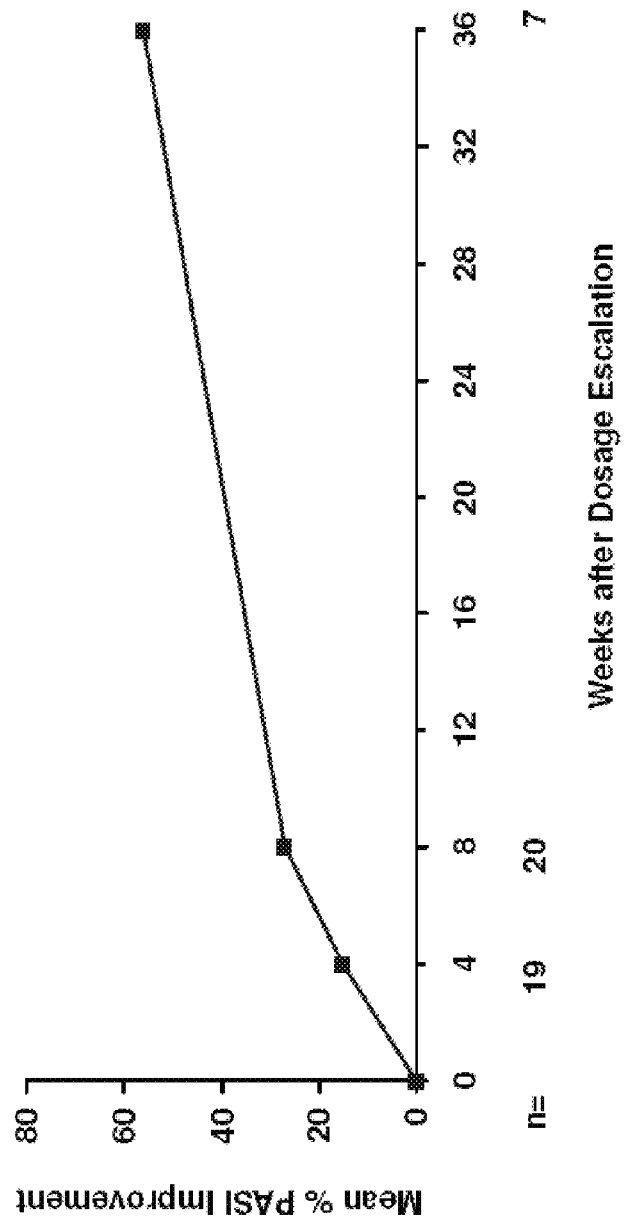
FIG. 2 shows the PASI improvement in patients after dosage escalation.

FIG. 2 shows the PASI improvement in patients after dosage escalation.

DLQI was evaluated at the time of dosage escalation and at Week 60 for 18 of the 30 patients who switched to weekly dosing. Mean improvement in DLQI for these patients was 2.1. One patient in the dosage escalation group experienced a serious adverse event, and two others withdrew from the study due to adverse events In conclusion, the majority of psoriasis patients treated with adalimumab eow dosing had a sufficiently satisfactory clinical response and did not require dosage escalation. Adalimumab 40 mg eow dosing provided sustained, clinically significant improvement in ~80% of psoriasis patients. Among patients whose dosages increased to 40 mg weekly, 40% achieved PASI 50, and no serious adverse events were observed. After qualifying for dosage escalation, nearly 20% of patients achieved at least 75% improvement in their psoriasis at Week 60. Adalimumab's safety profile in the population of patients who qualified for dosage escalation was consistent with the safety profile of adalimumab in rheumatoid arthritis clinical trials Example 6

Achievement of PASI 100 is Associated with Better Dermatology-Specific Patient Reported Outcomes Compared to Achievement of PASI 75-99

Adalimumab is a fully human anti-TNF monoclonal antibody efficacious in the treatment of psoriasis, based on results from a Phase II clinical study. The present subanalysis was performed to assess if there was additional benefit to patients who achieved PASI 100 as compared with the benefit experienced by patients who achieved PASI 75-99.

The efficacy and safety of adalimumab was evaluated in a 48-week extension trial conducted at 18 sites in the US and Canada. Prior to this open-label study, patients were enrolled in a 12-week, double-blind, placebo-controlled trial. Inclusion criteria included:
  ≥18 years of age
  Moderate to severe chronic plaque psoriasis 1 year
  Affected BSA≥5%
Exclusion criteria included:
  Prior TNF-antagonist therapy
  Discontinuation of other systemic psoriasis therapies
Efficacy outcome was measured using PASI and DLQI responses/scores.
  Analytical methods included the following:
    Analyses of clinical data were performed on a modified intention-to-treat population (ITT). Missing data were analyzed by non-responder imputation (NRI) for PASI scores. Patients whose dosages were increased on or after Week 24 were considered non-responders;

Patients with similar percentage PASI improvement across treatment arms were pooled into four strata: PASI<50, PASI 50-74, PASI 75-99, and PASI 100; and Week-60 distribution of DLQI scores, mean DLQI scores, and mean change in DLQI from Week 0-60 were calculated within each stratum.

The study design is shown in FIG. 1, and the baseline demographics and clinical characteristics are shown in Table 2.

Randomized treatment arms included: 1) placebo (n=52); 2) adalimumab 80 mg subcutaneously (sc) at Week 0, then 40 mg sc every other week (eow) starting at Week 1 (n=45); and 3) adalimumab 80 mg sc at Weeks 0 and 1, then 40 mg sc weekly starting at Week 2 (n=50). At Week 12, placebo patients were switched to adalimumab 40 mg eow (placebo→eow). Skin and patient reported outcomes were assessed up to Week 60.

TABLE 35

PASI Response Rates at Week 60

| | Treatment | % Patients |
|---|---|---|
| PASI 50 | Placebo/Adalimumab 40 mg eow | 57 |
| | Adalimumab 40 mg eow | 64 |
| | Adalimumab 40 mg weekly | 66 |
| PASI 75 | Placebo/Adalimumab 40 mg eow | 45 |
| | Adalimumab 40 mg eow | 56 |
| | Adalimumab 40 mg weekly | 64 |
| PASI 90 | Placebo/Adalimumab 40 mg eow | 40 |
| | Adalimumab 40 mg eow | 33 |
| | Adalimumab 40 mg weekly | 48 |
| PASI 100 | Placebo/Adalimumab 40 mg eow | 19 |
| | Adalimumab 40 mg eow | 16 |
| | Adalimumab 40 mg weekly | 26 |

At Week 12, placebo patients started adalimumab 40 mg eow, after an initial 80-mg dose.
Modified ITT, NRI.
Patients with PASI <50 response on or after Week 24 received open-label adalimumab weekly rescue therapy.
Patients receiving rescue therapy were considered non-responders in this analysis.

As shown in Table 35, 16-26% of patients who received at least one dose of adalimumab at baseline reported a PASI 100 response at Week 60. There were no marked differences in the baseline characteristics between patients with DLQI=0 and DLQI>0 within each PASI stratum, with the exception that a higher percentage of patients with concomitant psoriatic arthritis reported DLQI=0 (Table 36)

TABLE 36

Baseline Characteristics by DLQI Score Among Key PASI Strata

| | PASI 100 | | PASI 75-99 | |
|---|---|---|---|---|
| | DLQI = 0 (n = 23) | DLQI > 0 (n = 6) | DLQI = 0 (n = 20) | DLQI > 0 (n = 34) |
| Age (years) | 43.9 | 44.2 | 43.5 | 44.6 |
| % Male | 74 | 83 | 95 | 85 |
| Body Weight (kg) | 94.2 | 98.2 | 97.6 | 100.4 |
| Psoriasis Duration (years) | 17.1 | 23.4 | 19.9 | 20.1 |
| % PsA | 22 | 0 | 35 | 18 |
| PASI Score at Baseline | 13.3 | 13.6 | 17.2 | 19.3 |
| % BSA at Baseline | 23 | 23 | 29 | 36 |

Mean values except percentages

At week 60, PASI 75-99/100 response rates were 38/17 for the (placebo→eow+eow) group and 38/26 for the weekly group (observed analysis). Pooling patients with similar % PASI improvement across treatment arms, the distribution of DLQI scores (lower score indicates better health status) at week 60 for patients with PASI<50, 50-74, 75-99,100 are shown below in Table 37. Pooling across treatment arms, 48 of the total 106 patients receiving adalimumab at Week 60 achieved DLQI=0. A majority of patients (79%) with PASI 100 achieved a DLQI=0 at Week 60 compared with 37% in patients with PASI 75-99 and 28% in patients with 50-74.

TABLE 37

Number and Percentage of Patients with DLQI Scores of 0, 1, 2, ≥3 by PASI Improvement at Week 60 (DLQI Scores By PASI Strata at Week 60)

| PASI Improvement Group | DLQI = 0 n (%) | DLQI = 1 n (%) | DLQI = 2 n (%) | DLQI ≥ 3 n (%) |
|---|---|---|---|---|
| <50 (n = 5) | 0 (0) | 1 (20.0) | 2 (40) | 2 (40) |
| 50-74 (n = 18) | 5 (28) | 3 (17) | 3 (17) | 7 (39) |
| 75-99 (n = 54) | 20 (37) | 19 (35) | 4 (7) | 11 (20) |
| 100 (n = 29) | 23 (79) | 3 (10) | 3 (10) | 0 (0) |

Across all PASI strata, DLQI mean scores were substantially lower at Week 60 (Table 38). At Week 60, patients with PASI<50, 50-74, 75-99, and 100 had mean DLQI scores of 3.0, 3.3, 1.8, and 0.3, respectively with mean changes in DLQI from baseline of −6, −8, −11.5, and −11.1, respectively.

TABLE 38

Mean Change in DLQI by PASI Response Rates at Week 60

| PASI Response | Mean DLQI at Week 60 | Mean ΔDLQI |
|---|---|---|
| PASI <50 | −6.0 | 3.0 |
| PASI 50-74 | −8.8 | 3.3 |
| PASI 75-99 | −11.5 | 1.8 |
| PASI 100 | −11.1 | 0.3 |

Observed values.
MID[1,2] (Minimum important difference) = −5
[1]Shikiar R, et al. Health Qual Life Outcomes 2006, in press.
[2]Khilji F A, et al. Br J Dermatol 2002, 147: 50 (abstract).

Among those PASI 75-99 responders who had DLQI>0 at Week 60, approximately 50% experienced persistent symptoms of itching, soreness, pain, or stinging of the skin and approximately 20% experienced embarrassment/self-consciousness because of their skin condition.

Withdrawal rates due to adverse events were similarly low in all treatment groups. All patients treated with adalimumab in the placebo-controlled study continued into the extension study (Tables 22 and 39). The percentage of patients who withdrew due to adverse events from Weeks 12-60 ranged from 3-10% (Tables 22 and 39). A higher percentage of patients with PASI 100 and DLQI=0 had adverse events than did patients with PASI 100 and DLQI>0 (91% vs. 50%), but a lower percentage of patients with PASI 75-99 and DLQI=0 had adverse events than did patients with PASI 75-99 and DLQI>0 (80% vs. 91%).

TABLE 39

Adverse Events by Treatment Period

| | Weeks 0-12 | | | Weeks 12-60 | |
|---|---|---|---|---|---|
| Event | Placebo (n = 52) n (%) | Adalimumab 40 mg eow (n = 45) n (%) | Adalimumab 40 mg weekly (n = 50) n (%) | Placebo/Adalimumab 40 mg eow + Adalimumab 40 mg eow (n = 92) n (%) | Adalimumab 40 mg weekly (n = 50) n (%) |
| Any AE | 35 (67.3) | 28 (62.2) | 39 (78.0) | 72 (87.3) | 39 (78) |
| Serious AE | 0 (0) | 1 (2.2) | 4 (8.0) | 2 (2.2) | 7 (14) |
| AEs leading to withdrawl | 1 (1.9) | 2 (4.4) | 3 (6.0) | 3 (3.3) | 5 (10.0) |

Gordon K B et al., J. Am. Acad. Dermatol., Published online. DOI: 10.1016/j.jaad.2006.05.027

In sum, approximately 45% of patients receiving adalimumab at Week 60 achieved DLQI=0. In this post-hoc subanalysis of a Phase II study, patients who achieved PASI 100 responses averaged lower DLQI scores than patients who achieved PASI 75-99 responses at Week 60. Long-term adalimumab treatment of psoriasis patients provided sustained, clinically significant improvement. Patients who achieved PASI 100 typically had superior dermatology-specific patient reported outcomes compared with patients who achieved PASI 75-99. The types and rates of adverse events in this study were similar to those previously reported in adalimumab rheumatoid arthritis and psoriatic arthritis trials.

Example 7

Use of TNF Inhibitor in Patients with Hepatitis B Virus

Use of TNF blockers, including Humira, has been associated with reactivation of hepatitis B virus (HBV) in patients who are chronic carriers of this virus. In some instances, HBV reactivation occurring in conjunction with TNF blocker therapy has been fatal. The majority of these reports have occurred in patients concomitantly receiving other medications that suppress the immune system, which may also contribute to HBV reactivation. Patients at risk for HBV infection should be evaluated for prior evidence of HBV infection before initiating TNF blocker therapy. Prescribers should exercise caution in prescribing TNF blockers for patients identified as carriers of HBV. Adequate data are not available on the safety or efficacy of treating patients who are carriers of HBV with anti-viral therapy in conjunction with TNF blocker therapy to prevent HBV reactivation. Patients who are carriers of HBV and require treatment with TNF blockers should be closely monitored for clinical and laboratory signs of active HBV infection throughout therapy and for several months following termination of therapy. In patients who develop HBV reactivation, HUMIRA should be stopped and effective anti-viral therapy with appropriate supportive treatment should be initiated. The safety of resuming TNF blocker therapy after HBV reactivation is controlled is not known. Therefore, prescribers should exercise caution when considering resumption of HUMIRA therapy in this situation and monitor patients closely.

Example 8

The Validity and Responsiveness of Three Quality of Life Measures in the Assessment of Psoriasis Patients: Results of a Phase II Study Moderate to severe plaque psoriasis has been demonstrated to have substantial impact on function limitations and psychosocial factors of patients with the disease [1-5]. Moreover, successful treatment of moderate to severe psoriasis—as assessed by improved physical functioning and reduction of signs and symptoms—has been shown to have a positive impact on social and psychological aspects of psoriasis [6-11].

Given the functional and psychosocial impact of the disease, studies of moderate to severe psoriasis patients often include both physician-assessed clinical endpoints and dermatology-specific patient-reported outcomes (PROs) to obtain a holistic view of the disease and treatment effects in patients [12]. Such practices are bolstered by the assertion of the Medical Advisory Board of the National Psoriasis Foundation (NPF) that, even more so than physical signs, such as the percentage of body surface area (BSA) affected by psoriasis, the severity of psoriasis is "first and foremost a quality-of-life (QOL) issue" [13]. The same values for percentage BSA involvement can result in very different degrees of impact for different patients, depending on the location of psoriatic plaques, the pain associated with the lesions and plaques, the extent of bleeding associated with the psoriatic lesions, and resulting functional limitations. The NPF Advisory Board suggests an alternative basis for defining mild, moderate, or severe psoriasis, predicated on QOL impacts of the disease. Similarly, the guidelines recently promulgated by the British Association of Dermatologists [14] for the use of biologics in psoriasis indicate that eligible patients must have a Psoriasis Area and Severity Index (PASI) score of at least 10 and a score on the Dermatology Life Quality Index (DLQI) [15]—a dermatology-specific validated PRO measure—of greater than 10.

A Phase II clinical trial of two dosages of adalimumab and placebo in the treatment of moderate to severe psoriasis provided an opportunity to further explore the psychometric characteristics—including responsiveness and minimum important differences—of the three PROs used in the trial: the DLQI; the general health-related QOL measure MOS Short Form 36 (SF-36) Health Survey [16]; and the general health status measure EuroQOL 5D (EQ-5D) [17,18]. Establishing the reliability, validity, and responsiveness of PRO measures is necessary for their use in support of labeling claims, according to an FDA draft guide to industry [19]. Reliability refers to the accuracy of a measure, while validity refers to the extent the measure actually is measuring what it purports to measure. Responsiveness is a component of validity and represents the PRO's capability to detect changes related to changes in the clinical status of patients or other relevant outcomes measures Minimum important difference (MID) is related to responsiveness and provides guidance to those reviewing clinical trial results as to whether the statistically significant group differences or changes are clinically meaningful and important. Jaeschke and colleagues [20] define a minimal clinically important difference (MCID) (MID is used here instead of MCID to avoid confusion) as "the smallest difference in score . . . which patients perceive as beneficial and which would mandate, in the absence of troublesome side-effects and excessive cost, a change in the patient's management." Estimation of the MID—using several different approaches—is also emphasized in the FDA guidance and is consistent with recently published recommendations of health outcomes researchers [21,22].

The objective of the study was to examine the relationships among the Dermatology Life Quality Index (DLQI), the Short Form 36 (SF-36), and the EuroQOL 5D (EQ-5D) and to assess their validity, responsiveness, and estimates of minimum important differences.

Methods

Overview

A Phase II, randomized, double-blind, parallel group, placebo-controlled, multi-center clinical trial assessed the clinical efficacy and safety of two doses of subcutaneously administered adalimumab vs. placebo for 12 weeks in the treatment of patients with moderate to severe plaque psoriasis. This study provided the opportunity to evaluate the validity and responsiveness to change in clinical status of PROs instruments. Patients completed the DLQI, SF-36, and EQ-5D questionnaires at baseline and at 12 weeks. Blinded investigators assessed the Psoriasis Area and Severity Index (PASI) scores and the Physician's Global Assessment (PGA) scores of enrolled patients. The responsiveness of the measures to changes in the clinical endpoints from baseline to Week 12 was assessed. Estimates of minimum important differences (MID) were derived. All analyses were performed with blinded data; findings and conclusions were not biased based on treatment condition.

The objectives of the Phase II, randomized, double-blind, parallel group, placebo-controlled, multi-center clinical trial were to assess the clinical efficacy and safety of subcutaneously administered adalimumab vs. placebo using two dosage regimens for 12 weeks in the treatment of patients with moderate to severe plaque psoriasis. The study included a screening period, a blinded 12-week treatment period, and a 30-day follow-up visit for patients not completing 12 weeks of active treatment or not entering an extension study. Time between screening and baseline visits was not to exceed 28 days. The trial found that adalimumab was both safe and efficacious vs. placebo in the treatment of moderate to severe, chronic plaque psoriasis [23].

Patients and Inclusion Criteria

Patients with a diagnosis of moderate to severe plaque psoriasis and an affected BSA of ≥5% for at least 1 year were eligible for the study. In addition to other inclusion criteria (e.g., age≥18 years, willingness to give informed consent), patients had to be able to self-inject medication or have a designee or nurse who could inject the randomized assignment. Patients signed informed consent forms, and the study complied with FDA Good Clinical Practices, Health Protection Branch guidelines, and all other applicable ethical, legal, and regulatory requirements [23].

Clinical Measures

For purposes of the analyses reported here, there were two primary clinical outcomes:

Psoriasis Area and Severity Index

Frequently used as an endpoint in psoriasis clinical trials [24], the PASI [25] was the primary efficacy outcome in this trial. PASI is a composite index indicating the severity of the three main signs of psoriatic plaques (i.e., erythema, scaling, and thickness) and is weighted by the amount of coverage of these plaques in the four main body areas (head, trunk, upper extremities, and lower extremities). PASI scores range from 0-72, with higher scores indicating greater disease severity. PASI was assessed at screening and baseline, at Weeks 1, 2, 4, 8, and 12/Early Termination, and at the final follow-up visit.

Physician's Global Assessment

The PGA is a seven-point scale used to measure the severity of disease at the time of the physician's evaluation. The seven disease categories are:

Severe: very marked plaque elevation, scaling, and/or erythema

Moderate to Severe: marked plaque elevation, scaling, and/or erythema

Moderate: moderate plaque elevation, scaling, and/or erythema

Mild to moderate: intermediate between moderate and mild

Mild: slight plaque elevation, scaling, and/or erythema

Almost Clear: intermediate between mild and clear

Clear: no signs of psoriasis (post-inflammatory hypopigmentation or hyperpigmentation could be present).

The PGA scale is scored from 1 (Clear) to 7 (Severe). The PGA was assessed by the investigator at screening, baseline, and Weeks 1, 2, 4, 8, 12/Early Termination, and the follow-up visit. Each study site was to make every attempt to have the same investigator perform these assessments throughout the study for each patient.

Patient-Reported Outcome Measures

Three PROs measures were used in the study and are the subject of the analyses reported here. All PROs measures were assessed at baseline and at Week 12 (or early termination, if applicable).

Dermatology Life Quality Index

The DLQI was developed as a simple, compact, and practical questionnaire for use in dermatology clinical settings to assess limitations related to the impact of skin disease [15]. The instrument contains 10 items dealing with skin (e.g., Item 1: "Over the last week, how itchy sore, painful, or stinging has your skin been?"). The DLQI score ranges from 0-30, with "30" corresponding to the worst quality of life, and "0" corresponding to the best score. The DLQI has well-established properties of reliability and validity in the dermatology setting [15,26-28].

Short Form 36 Health Survey

The SF-36 is a 36-item general health status instrument often used in clinical trials and health services research [16]. It consists of eight domains: Physical Function, Role Limitations—Physical, Vitality, General Health Perceptions, Bodily Pain, Social Function, Role Limitations—Emotional, and Mental Health. Two overall summary scores can be obtained—a Physical Component Summary (PCS) score and a Mental Component Summary (MCS) score [29]. The PCS and MCS scores range from 0-100, with higher scores indicating better health. The SF-36 has been used in a wide variety of studies involving psoriasis, including descriptive studies [30] and clinical research studies [6,7], and has demonstrated good reliability and validity. Internal consistency for most SF-36 domains is greater than 0.70. The SF-36 has been shown to discriminate between known groups in a variety of diseases, is reproducible, and is responsive to longitudinal clinical changes.

EuroQOL 5D

The EQ-5D [17,18] is a six-item, preference-based instrument designed to measure general health status. The EQ-5D has two sections: The first consists of five items to assess degree of physical functioning (mobility, self-care, usual activities, pain/discomfort, and anxiety/depression). Items are rated on a three-point scale ranging from "No Problem" to "Extreme Problem" or "Unable to Do." Each pattern of scores for the five items is linked to an index score that has a value ranging from 0-1, indicating the health utility of that person's health status. The specific linkage can differ from country to country, reflecting differences in cultures to the item responses. The second section is the sixth item on the EQ-5D, which is a visual analog scale with endpoints of "100" or "Best Imaginable Health," and "0" or "Worst Imaginable Health." It offers a simple method for the respondents to indicate how good or bad their health statuses are "today." The score is taken directly from the patients' responses.

Statistical Methods

Validity of the PRO measures was assessed in several ways. First, an assessment was made of the concurrent validity of scales and subscales (i.e., the extent to which PRO measures are correlated with one another). As a disease-specific PRO measure, the DLQI was expected to correlate moderately to extremely well with general PRO measures. Another important aspect of validity in this study was to assess the extent to which the PRO measures correlated with the clinical endpoints—PASI and PGA—both at baseline and at Week 12.

Responsiveness of PRO measures was assessed via two approaches. First, changes in these measures from baseline to Week 12 were correlated with changes in the PASI or PGA over the 12-week course of treatment within the trial. Concurrent improvement in both clinical measures and PRO measures was expected to result in positive correlations. The second approach to assessing responsiveness involved categorizing patients into responder groups based on the changes in their PASI scores from baseline to Week 12. This was done in two ways. First, a responder was defined as a patient with >75% improvement in PASI (consistent with the definition of success with the primary efficacy variable), and a non-responder was defined as a patient with a PASI improvement<50% (consistent with the definition of failure for a secondary efficacy variable). Tests of mean differences in improvement on the PRO measures were completed between the two groups. Secondly, in support of the estimation of the MID, discussed below, patients were further categorized by degree of PASI response, and assessed differences among these four groups: PASI improvement<25%; PASI improvement 25-49%; PASI improvement 50-74%; and PASI improvement≥75%. Analyses of variance tests were performed among these four groups for changes in PRO measures.

In accordance with the FDA draft guidance [19] and consistent with recent recommendations from PRO researchers [21,22], five methods were used to estimate MIDs of the PROs. The PRO change score corresponding to PASI 25-PASI 49 was the first estimate of MID, called MID-1. This was based on the assumption that patients would perceive a PASI improvement of 25% as beneficial. The trial did not provide data to test this assumption (e.g., there was no rating by patients of their overall improvements). A second estimate, MID-2, was based on the PRO change score corresponding to a PASI improvement between 50-74%. The PASI 50 is seen as clinically relevant, and, as such, this degree of improvement served as a secondary efficacy endpoint in this trial. A third method for estimating MID relied on the association of changes in the PRO measure with changes in the PGA. A non-responder was defined as a patient with a PGA change score of either "0" (no change) or "1" (slight increase in severity of disease) from baseline to Week 12. A minimal responder was defined as a patient whose PGA improved by either 1 or 2 points from baseline to Week 12. The third estimate of MID, MID-3, was the difference in the PRO score between non-responders and minimal responders.

In addition, two distributional methods were used to support the anchor-based MID estimates for the PROs [21,22]. Based on evidence by Wyrwich and associates [31,32], the standard error of measurement (SEM) can be used to approximate the MID. The SEM, which describes the error associated with the measure, was estimated by the standard deviation of the measure multiplied by the square root of 1 minus its reliability coefficient. Finally, there has been discussion [33] concerning a number of studies demonstrating that one-half of the standard deviation of a measure represents the upper limit of the MID [22]. In estimating the SEM for the SF-36 and the EQ-5D, reliability estimates from the literature were used. The SEM for the DLQI incorporated the reliability estimated from the trial data, which was consistent with what has been found in the literature for this instrument [27].

Finally, it is important to note that all analyses were performed with blinded data (i.e., the statuses of patients with respect to their assigned treatment groups were not known).

Results

Overview

The dermatology-specific DLQI was highly correlated to clinical endpoints at baseline and at Week 12, and was the most responsive PRO to changes in endpoints. Compared with the SF-36, the EQ-5D index score and VAS scores were generally more highly correlated with clinical endpoints, but displayed about the same degree of responsiveness. The most responsive SF-36 scales were the Bodily Pain and Social Functioning scales. Estimates of the MID for the DLQI ranged from 2.3-5.7 and for the SF-36 Physical Component Summary (PCS) score ranged from 2.5-3.9.

Patient Demographics and Clinical Characteristics

A total of 147 patients enrolled and received at least one dose of study medication at 18 sites in the United States and Canada. Blinded data were available for the PROs for 147 patients at baseline and 140 patients at Week 12. Since the focus of these analyses were on the psychometric properties of the PROs rather than with efficacy, observed cases were employed rather than last observation carried forward or other methods for treating missing observations at the end of trial. The mean age of the patients enrolled in the trial was 44.2 years, two-thirds were male, and the preponderance were white (Table 40).

TABLE 40

| Baseline Demographic Characteristics | |
|---|---|
| Characteristic | (N = 147) |
| Age | |
| Mean (SD) | 44.2 (12.7) |
| Gender | |
| Female n (%) | 48 (32.7%) |
| Male n (%) | 99 (67.3%) |

TABLE 40-continued

Baseline Demographic Characteristics

| Characteristic | (N = 147) |
|---|---|
| Race | |
| White n (%) | 133 (90.5%) |
| Black n (%) | 4 (2.7%) |
| Asian n (%) | 5 (3.4%) |
| Other n (%) | 5 (3.4%) |

Clinical Endpoints

The results for the PASI and the PGA at baseline and Week 12, as well as the change from baseline to Week 12, are displayed in Table 41. The mean PASI at baseline was 15.7, which decreased by 8.9 points (improvement) to 6.8 by Week 12. The mean PGA at baseline was 5.5 (i.e., midway between "Moderate" and "Moderate to Severe"), and decreased (improved) by 2.1 points to 3.4 by Week 12 (i.e., between "Mild" and "Mild to Moderate"). In evaluating the improvement in the two clinical endpoints, it is important to keep in mind that these analyses included pooled placebo and active treatment groups.

TABLE 41

Mean (Standard Deviation) of PASI and PGA at Baseline and Week 12, and Change from Baseline to Week 12

| Measure | Baseline | Week 12 | Change[2] |
|---|---|---|---|
| PASI | 15.69 (7.34) | 6.84 (7.77) | −8.87 (8.41) |
| PGA[1] | 5.48 (0.81) | 3.36 (1.74) | −2.14 (1.87) |

[1]Scored such that 1 = "Clear" to 7 = "Severe."
[2]Change scores are computed only for the 140 patients with scores at baseline and Week 12; sample size at baseline = 147.

Patient-Reported Outcome Measures

The results for the DLQI, SF-36, and EQ-5D at baseline and Week 12, and the change from baseline are shown in Table 42. Based on blinded data, mean PRO measures improved during the course of the trial (a decrease in DLQI scores indicates an improvement; an increase in the SF-36 and EQ-5D indicates improvement). The greatest improvement in a DLQI item occurred for the first item, assessing how "itchy, sore, painful, or stinging" the person's skin felt. Similarly, as shown in Table 19, the greatest improvement among the SF-36 scales was for Bodily Pain, although there were improvements in each of the SF-26 scales using adalimumab treatment for psoriasis. The largest improvement among the five EQ-5D dimensions occurred for the Pain/Discomfort dimension. Given these findings, it appears that improvement in pain and discomfort is the most pronounced among all PRO measures assessed.

TABLE 42

Mean (Standard Deviation) of PROs at Baseline and Week 12, and Change from Baseline to Week 12

| Measure | Baseline | Week 12 | Change[1] |
|---|---|---|---|
| DLQI Total Score | 12.71 (7.18) | 5.28 (6.49) | −7.45 (7.78) |
| SF-36 | | | |
| Physical Functioning | 79.26 (24.95) | 84.43 (22.62) | 5.63 (22.25) |
| Role-Physical | 72.45 (37.56) | 82.50 (34.67) | 9.64 (40.30) |
| Bodily Pain | 59.58 (25.37) | 75.87 (24.89) | 16.59 (26.90) |
| General Health | 66.7 (20.6) | 72.69 (20.79) | 6.10 (16.25) |
| Vitality | 53.89 (22.81) | 61.04 (23.18) | 7.60 (20.88) |
| Social Functioning | 74.49 (27.56) | 85.98 (23.63) | 11.16 (27.80) |
| Role- Emotional | 76.03 (35.39) | 85.48 (30.77) | 8.39 (37.02) |
| Mental Health | 69.39 (19.30) | 77.43 (17.73) | 8.14 (18.57) |
| Physical Summary Score (PCS) | 47.93 (10.23) | 51.24 (9.51) | 3.47 (9.30) |
| Mental Summary Score (MCS) | 47.30 (11.23) | 51.36 (10.08) | 3.94 (11.04) |
| EQ-5D | | | |
| Index Score | 0.66 (0.28) | 0.82 (0.23) | 0.16 (0.29) |
| VAS Overall Health | 72.25 (20.67) | 81.22 (17.26) | 9.35 (20.71) |

[1]Change scores are computed only for patients with scores at baseline and Week 12; this number varied between 138 and 140, depending on the specific measure, as compared with the 147 patients at baseline.

The reliability of the DLQI, as assessed by coefficient alpha, was 0.89 at baseline and 0.92 at Week 12, indicating that this is a highly reliable measure, and in line with previous findings [27, 28].

Relationships Among Patient-Reported Outcome Measures

Table 43 displays the correlations among PRO measures at baseline and at Week 12, as well as the correlations among changes in these measures from baseline to Week 12. There were a few trends evident form this data. First, all measures were statistically significantly inter-correlated. Second, with respect to the relationship between the DLQI and the SF-36, the DLQI correlated the greatest with the Bodily Pain and Social Functioning domains, both at baseline and at Week 12, and, for changes in these scores over the course of the trial. Third, the DLQI correlated highly with the EQ-5D index score, and these correlations were consistently higher than the correlations with the EQ-5D visual analog scale (VAS) scores. Fourth, the EQ-5D index score tended to correlate greatest with the Bodily Pain domain of the SF-36. Finally, the scores tended to be more highly correlated at the end of the trial than at baseline, consistent with previous findings [28].

TABLE 43

Correlations[1] among PROs at Baseline and Week 12, and Change from Baseline to Week 12

| | Baseline | | | Week 12 | | | Change | | |
|---|---|---|---|---|---|---|---|---|---|
| Measure | DLQI Total | EQ-5D Index | EQ-5D VAS | DLQI Total | EQ-5D Index | EQ-5D VAS | DLQI Total | EQ-5D Index | EQ-5D VAS |
| DLQI Total Score | 1.00 | −0.51 | −0.35 | 1.00 | −0.71 | −0.58 | 1.00 | −0.53 | −0.46 |
| SF-36 | | | | | | | | | |
| Physical Functioning | −0.44 | 0.58 | 0.35 | −0.41 | 0.61 | 0.49 | −0.29 | 0.47 | 0.32 |
| Role-Physical | −0.45 | 0.64 | 0.38 | −0.57 | 0.67 | 0.50 | −0.47 | 0.51 | 0.45 |

TABLE 43-continued

Correlations[1] among PROs at Baseline and Week 12, and Change from Baseline to Week 12

| Measure | Baseline | | | Week 12 | | | Change | | |
|---|---|---|---|---|---|---|---|---|---|
| | DLQI Total | EQ-5D Index | EQ-5D VAS | DLQI Total | EQ-5D Index | EQ-5D VAS | DLQI Total | EQ-5D Index | EQ-5D VAS |
| Bodily Pain | −0.55 | 0.73 | 0.45 | −0.61 | 0.76 | 0.56 | −0.66 | 0.64 | 0.53 |
| General Health | −0.24** | 0.39 | 0.47 | −0.38 | 0.59 | 0.69 | −0.33 | 0.46 | 0.46 |
| Vitality | −0.31 | 0.43 | 0.48 | −0.43 | 0.62 | 0.60 | −0.46 | 0.37 | 0.48 |
| Social Functioning | −0.69 | 0.52 | 0.46 | −0.68 | 0.74 | 0.60 | −0.68 | 0.50 | 0.56 |
| Role-Emotional | −0.41 | 0.45 | 0.42 | −0.56 | 0.67 | 0.53 | −0.50 | 0.41 | 0.48 |
| Mental Health | −0.44 | 0.46 | 0.50 | −0.56 | 0.66 | 0.67 | −0.52 | 0.49 | 0.56 |
| Physical Summary Score (PCS) | −0.41 | 0.64 | 0.36 | −0.46 | 0.65 | 0.52 | −0.41 | 0.56 | 0.39 |
| Mental Summary Score (MCS) | −0.45 | 0.39 | 0.49 | −0.58 | 0.66 | 0.63 | −0.59 | 0.42 | 0.57 |
| EQ-5D | | | | | | | | | |
| Index Score | −0.51 | 1.00 | 0.39 | −0.71 | 1.00 | 0.63 | −0.53 | 1.00 | 0.39 |
| VAS-General Health | −0.35 | 0.39 | 1.00 | −0.58 | 0.63 | 1.00 | −0.46 | 0.39 | 1.00 |

[1]All correlations were significant at p < 0.001, unless otherwise noted.
*p ≤ 0.05,
**p ≤ 0.01,
ns = no n-significant.

Correlations with Clinical Endpoints

Table 44 displays correlations of PRO measures with the two clinical assessments—PASI score and PGA—at baseline (first two columns of data) and at Week 12 (second two columns) In addition to almost uniformly greater correlations at Week 12 vs. at baseline—consistent with previous findings [28]—one can also note that both the DLQI and EQ-5D index score tended to be more highly correlated with the two clinical endpoints than any of the SF-36 domains. The SF-36 scales with the strongest association with clinical endpoints are Social Functioning and Bodily Pain.

TABLE 44

Correlations[1] between PROs and Clinical Endpoints at Baseline and Week 12, and Change from Baseline to Week 12

| Measure | Baseline | | Week 12 | | Change | |
|---|---|---|---|---|---|---|
| | PASI | PGA | PASI | PGA | PASI | PGA |
| DLQI Total Score | 0.31 | 0.29 | 0.67 | 0.65 | 0.69 | 0.71 |
| SF-36 | | | | | | |
| Physical Functioning | −0.32 | −0.14 ns | −0.28 | −0.25** | −0.38 | −0.14 ns |
| Role-Physical | −0.22** | −0.14 ns | −0.41 | −0.37 | −0.42 | −0.31 |
| Bodily Pain | −0.36 | −0.19* | −0.47 | −0.42 | −0.60 | −0.44 |
| General Health | −0.08 ns | 0.05 ns | −0.34 | −0.33 | −0.34 | −0.24** |
| Vitality | −0.15 ns | −0.06 ns | −0.37 | −0.37 | −0.38 | −0.31 |
| Social Functioning | −0.23** | −0.21** | −0.46 | −0.38 | −0.44 | −0.43 |
| Role-Emotional | −0.16 ns | −0.06 ns | −0.37 | −0.29 | −0.39 | −0.36 |
| Mental Health | −0.17* | −0.09 ns | −0.46 | −0.38 | −0.43 | −0.36 |
| Physical Summary | −0.28 | −0.13 ns | −0.35 | −0.33 | −0.45 | −0.25** |
| Mental Summary | −0.12 ns | −0.08 ns | −0.44 | −0.36 | −0.40 | −0.42 |
| EQ-5D | | | | | | |
| Index Score | −0.40 | −0.31 | −0.60 | −0.51 | −0.57 | −0.44 |
| VAS-General Health | −0.24** | −0.09 ns | −0.52 | −0.43 | −0.43 | −0.38 |
| PASI | 1.00 | 0.59 | 1.00 | 0.83 | 1.00 | 0.75 |

[1]All correlations were significant at p < 0.001, unless otherwise noted.
*p ≤ 0.05,
**p ≤ 0.01,
ns = non-significant.

Responsiveness of the Patient-Reported Outcome Measures

An important attribute for a PRO measure is responsiveness to change in the clinical status of a patient (i.e., as a patient's disease improves, the PRO measures also improve). The last two columns of Table 44 display the correlations between changes in PRO measures used in the trial and changes in PASI scores and the PGA from baseline to Week 12. These data demonstrate that the DLQI is the most responsive of the PRO measures. The correlations between changes over the course of the trial in the DLQI total score and changes in the PASI score (r=0.69, p<0.001) and PGA (r=0.71, p<0.001) approach the correlation between changes in the two clinical measures themselves (r=0.75, p<0.001). In addition, the DLQI is the only one of the PRO measures to demonstrate equal responsiveness to PGA and PASI scores. The correlation between changes in the EQ-5D index score and the two clinical assessments was r=−0.57 (p<0.001) for changes in the PASI to r=−0.44 for changes in the PGA (p<0.001). Similarly, the correlations between changes in all but one of the SF-36 scores and changes in the PGA were smaller than correlations between changes in the SF-36 and the PASI.

A second way to assess responsiveness was to contrast patients who were defined as clinical responders with those characterized as non-responders. Given that the primary endpoint in the trial was defined as the percentage of patients achieving a PASI 75 response (i.e., ≥75% improvement in PASI from baseline) by Week 12, a responder was defined as a patient with a PASI75 response. A non-responder was a patient with <PASI 50, since some of the secondary endpoints in the trial used this cut-off. The results of these analyses are displayed in Table 45. DLQI total scores for responders improved by 12.17 points, while scores of non-responders improved by 1.77 points. This difference was statistically significant (t=9.0; p<0.0001). All the PRO measures except for the SF-36 Physical Functioning domain were responsive, as defined by a statistically significant difference between responders and non-responders. The DLQI was the most responsive of the PRO measures, as evidenced by the size of the t-statistic and the effect size. The responsiveness of the EQ-5D index and VAS scores were generally the same as several of the SF-36 domain scores.

TABLE 45

Change in PRO Measures among Responder[1] Groups

| Change in Measure | Mean Change Score for Responders (n = 66) | Mean Change Score for Non-Responders (n = 53) | Difference | t-value | P Value | Effect Size |
|---|---|---|---|---|---|---|
| DLQI Total Score | −12.17 (6.78) | −1.77 (5.52) | −10.39 | 9.0 | <.0001 | 0.40 |
| SF-36 | | | | | | |
| Physical Functioning | 9.12 (23.50) | 3.52 (20.19) | 5.59 | 1.4 | 0.1724 | 0.01 |
| Role-Physical | 20.08 (35.69) | −5.19 (44.76) | 25.26 | 3.4 | 0.0008 | 0.08 |
| Bodily Pain | 26.47 (27.40) | 4.21 (22.74) | 22.26 | 4.7 | <.0001 | 0.15 |
| General Health | 8.87 (15.62) | 1.47 (17.77) | 7.39 | 2.4 | 0.0178 | 0.04 |
| Vitality | 13.01 (22.58) | 1.13 (18.20) | 11.87 | 3.1 | 0.0024 | 0.07 |
| Social Functioning | 21.59 (28.13) | −2.59 (25.04) | 24.19 | 4.9 | <.0001 | 0.16 |
| Role-Emotional | 19.70 (32.54) | −9.62 (36.95) | 29.31 | 4.6 | <.0001 | 0.14 |
| Mental Health | 14.55 (17.77) | −0.38 (18.15) | 14.92 | 4.5 | <.0001 | 0.14 |
| Physical Summary Score (PCS) | 5.35 (9.67) | 1.47 (9.08) | 3.88 | 2.2 | 0.0287 | 0.03 |
| Mental Summary Score (MCS) | 8.03 (10.59) | −2.03 (10.42) | 10.06 | 5.1 | <.0001 | 0.17 |
| EQ-5D | | | | | | |
| Index Score | 0.25 (0.30) | 0.04 (0.26) | 0.22 | 4.2 | <.0001 | 0.12 |
| VAS General Health | 15.69 (18.96) | 1.92 (23.24) | 13.77 | 3.5 | 0.0006 | 0.09 |

[1]Responder is defined as PASI improvement ≥75%; non-responder is defined as PASI improvement <50

While the estimates of responsiveness displayed in the last two columns of Table 44 take into account the full range of PASI change scores and their relationship to PRO change scores, the responsiveness analysis in Table 45 places patients in two categories—responders and non-responders. Table 46 defines four categories of responders: responders, defined as those with PASI improvements≥75%; "partial responders," those with PASI improvement 50-74%, inclusively; "near responders," those with PASI improvement 25-49%, inclusively; and non-responders, with <PASI25. One-way analyses of variance were performed among these groups for each of the PRO measures. As can be seen by the size of the f-statistics, the DLQI was the most responsive of the PRO measures. In fact, only the DLQI was able to demonstrate statistically significant differences between responders and partial responders based on post-hoc significance tests among the four responder groups. These results for the DLQI total score with respect to differences among responder groups were similar to those reported previously in the literature, except that the improvement in DLQI total scores displayed in Table 40 was larger for each of the responder groups than for the equivalent responder groups described by Shikiar and colleagues in a study of efalizumab [28]. As was the case for the data displayed in Table 45, the responsiveness of the EQ-5D index and VAS scores were generally the same as for most of the SF-36 scores. Finally, both the SF-36 MCS and PCS scores were responsive, but the MCS was more responsive, indicating that the impact of the disease was both physical and mental, with the latter perhaps being more prominent for this study population.

TABLE 46

PRO Change Scores Corresponding to Levels of PASI Improvement

| Change in Measure | PASI Improvement <25% (n = 31) | PASI Improvement 25-49% (n = 22) | PASI Improvement 50-74% (n = 21) | PASI Improvement >75% (n = 66) | Overall F Value | p Values[1] |
|---|---|---|---|---|---|---|
| DLQI Total Score | −0.16 (5.41) | −4.05 (4.95) | −6.95 (5.71) | −12.17 (6.78) | 30.4*** | 2**, 3*** 5***, 6* |
| SF-36 | | | | | | |
| Physical Functioning | 2.15 (17.67) | 5.45 (23.60) | 0.02 (22.36) | 9.12 (23.50) | 1.2 | |
| Role-Physical | −11.29 (39.18) | 3.41 (51.35) | 14.29 (31.20) | 20.08 (35.69) | 4.9** | 3** |
| Bodily Pain | −1.03 (21.42) | 11.59 (22.96) | 16.76 (22.74) | 26.47 (27.40) | 9.0*** | 3*** |
| General Health | −0.61 (17.33) | 4.41 (18.37) | 9.19 (11.29) | 8.87 (15.62) | 2.8* | |
| Vitality | −1.45 (16.29) | 4.77 (20.44) | 6.90 (17.43) | 13.01 (22.58) | 3.8* | 3* |
| Social Functioning | −3.23 (23.71) | −1.70 (27.36) | 13.10 (17.44) | 21.59 (28.13) | 8.7*** | 3***, 5** |
| Role-Emotional | −11.11 (36.44) | −7.58 (38.40) | 17.46 (34.35) | 19.70 (32.54) | 7.6*** | 2*, 3**, 5* |
| Mental Health | −0.77 (18.08) | 0.18 (18.66) | 9.52 (13.53) | 14.55 (17.77) | 7.2*** | 3**, 5* |
| Physical Summary | −0.31 (7.18) | 3.91 (10.88) | 2.57 (7.78) | 5.35 (9.67) | 2.7* | |
| Mental Summary | −2.19 (9.86) | −1.82 (11.38) | 6.05 (6.90) | 8.03 (10.59) | 9.9*** | 2*, 3***, 5** |
| EQ-5D | | | | | | |
| Index Score | −0.01 (0.26) | 0.10 (0.24) | 0.20 (0.21) | 0.25 (0.30) | 7.1*** | 3*** |
| VAS General Health | 0.58 (24.31) | 3.82 (22.07) | 8.43 (11.24) | 15.69 (18.96) | 4.8** | 3** |
| Mean PASI Improvement | 0.94 (4.07) | −6.24 (2.99) | −8.94 (3.47) | −14.33 (7.65) | | |

[1]Pairwise comparisons between means were performed using Scheffe's test adjusting for multiple comparisons. 1 = improvement <25% vs. improvement 25-49%, 2 = improvement <25% vs. improvement 50-74%, 3 = improvement <25% vs. improvement ≥75%, 4 = improvement 25-49% vs. improvement 50-74%, 5 = improve 25-49% vs. improvement ≥75%, and 6 = improvement 50-74% vs. improvement ≥75%.

*p < 0.05,

**p < 0.01,

***p < 0.001.

[2]Negative change scores indicate improvement

Estimates of Minimum Important Differences

There is no one best way to estimate the MID for a PRO measure [21,34]. Table 47 contains three different anchor-based methods for estimating the MID based on data from this study. MID-1 contains the estimate obtained from the scores from the "near-responders," shown as the PASI 25-PASI 49 group in Table 46; MID-2 contains the estimate corresponding to "partial responders" in the same table 40. MID-3 corresponds to the difference between non-responders for the PGA (defined as patients who had no change in score or a decrease in score by one point on this 7-point scale) and minimal responders for this same measure (defined as patients who improved by 1 or 2 points). The distribution-based estimates, the SEM and one-half the standard deviation of baseline scores are also reported in Table 47.

TABLE 47

Estimates of MCID for PRO Measures

| Change in Measure | MID-1: PASI Improvement 25-49% | MID-2: PASI Improvement 50-74% | MID-3: Difference Between Non-Responders (n = 34) and Minimal Responders (n = 41) on PGA | SEM | 0.5 SD |
|---|---|---|---|---|---|
| DLQI Total Score | −4.05 (4.95) | −6.95 (5.71) | −5.69 | 2.33 | 3.59 |
| SF-36 | | | | | |
| Physical Functioning[1] | N/A | N/A | N/A | N/A | N/A |
| Role-Physical | 3.41 (51.35) | 14.29 (31.20) | 10.51 | 15.02 | 18.78 |
| Bodily Pain | 11.59 (22.96) | 16.76 (22.74) | 9.05 | 10.76 | 12.69 |
| General Health | 4.41 (18.37) | 9.19 (11.29) | 4.97 | 9.67 | 10.31 |
| Vitality | 4.77 (20.44) | 6.90 (17.43) | 6.54 | 8.22 | 11.40 |
| Social Functioning | −1.70 (27.36) | 13.10 (17.44) | 13.62 | 10.67 | 13.78 |
| Role-Emotional | −7.58 (38.40) | 17.46 (34.35) | 24.71 | 14.59 | 17.70 |
| Mental Health | 0.18 (18.66) | 9.52 (13.53) | 4.90 | 6.10 | 9.65 |
| Physical Summary Score (PCS) | 3.91 (10.88) | 2.57 (7.78) | 0.51 | 2.71 | 5.12 |
| Mental Summary Score (MCS) | −1.82 (11.38) | 6.05 (6.90) | 6.61 | 3.89 | 5.61 |
| EQ-5D | | | | | |
| Index Score | 0.10 (0.24) | 0.20 (0.21) | 0.09 | 0.22 | 0.14 |
| VAS-General Health | 3.82 (22.07) | 8.43 (11.24) | 4.59 | N/A | 10.34 |

Note:
MID-1 corresponds to the score for the PASI 25-49 group; MID-2 corresponds to the score for the PASI50-74; for MID-3 and MID-4, reliability estimates for computing SEM were obtained from the data in this study for the DLQI and from estimates found in the literature for the SF-36 and EQ-5D.
[1]MID estimates are not provided for the SF-36 Physical Function domain since there were not significant differences among responder groups.

Estimates for the DLQI MID ranged from 4.05 (for MID-1) to 6.95 (for MID-2), while the SEM was 2.33 and one-half standard deviation was 3.59. The MID results for the SF-36 PCS ranged from 0.51 (for MID-3) to 3.91 (for MID-1), with the SEM estimated as 2.71 and one-half standard deviation estimates as 5.12. For the MCS, the MID estimates included a decrease of 1.82 points based on a PASI improvement of 25-49%, but the other two MIDs were 6.05 and 6.61, respectively. The SEM for the MCS was 3.89 and one-half standard deviation was 5.61. Consistent with the MCS findings, decreases were observed for the Role-Emotional and Social Functioning domains for the MID-1 definition. The differences between non-responders and minimal responders ranged from 4.90 for Mental Health to 24.71 for Social Functioning (Table 47). The results for the EQ-5D index score demonstrated an MID ranging from 0.09 (for MID-3) to 0.20 (for MID-2). For the EQ-5D VAS, the available estimates ranged from 3.82 (MID-1) to 8.43 (MID-3).

Discussion

A Phase II randomized clinical trial of adalimumab in moderate to severe plaque psoriasis provided the opportunity to evaluate the validity and responsiveness to clinical change of three PRO assessment instruments—one dermatology-specific instrument and two general health status instruments—all used as endpoints in the study. All analyses were performed on a blinded basis, since the main focus of these secondary analyses was on the psychometric qualities of the PRO instruments.

The present study further establishes the reliability and validity of the DLQI and its responsiveness to change in the clinical status of patients over the course of a 12-week clinical trial, confirming previous findings [28]. Changes in the DLQI total score demonstrated significant and sizeable correlations with independently obtained physician-assessed changes in the clinical statuses of patients. This indicates that the alleviation of psoriatic signs, as determined by clinical assessments, results in significant and marked improvement in dermatologic-related functional limitations and quality of life in patients with moderate to severe plaque psoriasis. Based on this study, the DLQI is a psychometrically sound and responsive measure of psoriasis-specific outcomes that captures more comprehensively the impact of clinical signs and symptoms on patient well-being.

We used both the PASI and the PGA, as well as two distributional approaches to derive estimates of the MID of the DLQI. These estimates ranged from 2.33-6.95, although the PASI 50 was too conservative for estimating the minimum change that patients will find beneficial. Therefore, we the estimate based on PASI improvement of 25-49% or between non-responders and minimal responders provided a better estimate of MID for this study. Therefore, the results indicate that the MID is in the range of approximately 2.3-5.7, which is slightly higher than the range of estimates derived from Shikiar et al. [28] in an analysis of two clinical trials involving another psoriasis therapy. The distributional approaches resulted in the lowest estimates of MID for the DLQI, but it should be noted that the distributional approach to estimating the MID is considered supportive of the anchor-based methods [22,35]. For example, the one-half standard deviation estimate is certainly clinically meaningful, but is likely not a minimum magnitude of change. Finally, the range of estimates incorporates another previous estimate of the MID of the DLQI of 5.0 [36].

Two general PRO measures were used in this study. In general, the EQ-5D index and VAS scores demonstrated higher correlations than the SF-36 scale scores with the clinical endpoints (Table 42). However, the responsiveness of these two EQ-5D scores were generally the same as the responsiveness of most of the SF-36 scores. Although most of the SF-36 scores showed improvements associated with clinical outcomes, the MCS, Social Functioning, and Role-Emotional domain scores demonstrated decreases in the PASI 25-49% group. These findings may have been driven by several outliers and the relatively small sample size for this group. Alternatively, given that Bodily Pain and other physical domains may be more related to the signs and symptoms of psoriasis than Role-Limitations and Social Functioning, small improvements in PASI scores may not be directly associated with changes in these PRO domains. That is, larger changes in clinical outcomes may be needed to significantly impact the areas of physical function and well-being. This idea seems to be supported by the observed changes in the PASI 50-74% and other analyses. However, the SF-36 domain and summary scores demonstrated consistently reasonable validity and were correlated with clinical endpoints and DLQI scores.

The SF-36 PCS and MCS scores demonstrated good evidence of validity and responsiveness in this sample of patients with moderate to severe plaque psoriasis. There were demonstrable associations between changes in PASI score categories and changes in PCS scores, with the largest improvements seen in the PASI75 responder groups. The MID estimates for the PCS were in the range of 0.51-3.91, with the best estimate at approximately 2.5 points. The SEM estimate (2.71) also supports this range of MID values for the PCS. The MID findings for the MCS were somewhat weaker, but there is evidence that a change of 4-6 points is certainly clinically meaningful. The MID for the EQ-5D index score was in the range of 0.09-0.22.

Given the impact of psoriasis on the functional ability of patients the importance attached to assessing physical function in psoriasis patients, the results of the present study provide positive support for the use of a dermatology-specific health-related PRO measure, the DLQI, in the assessment of psoriasis and responses to treatment. In addition, the correlation of SF-36 and DLQI indicates that disease-related changes in the SF-36 are largely dependent on two specific domains, Bodily Pain and Social Functioning. It appears that the DLQI total score, as a single index score, adequately captures the functional and psychosocial impact of moderate to severe plaque psoriasis. Further, the DLQI does so in a way that is more responsive than the general health-related quality of life measures used to assess changes in patients' underlying clinical statuses.

In conclusion, the findings of this study highlight the importance of capturing PRO measures in clinical trials of moderate to severe plaque psoriasis. This analysis provides additional evidence supporting the psychometric qualities and responsiveness of the DLQI as a disease-specific measure of PROs in psoriasis. The DLQI MID was determined as ranging from 2.3-5.7 points. The study further shows that adalimumab was effective at improving DLQI, SF-36, and EQ-5D scores in patients with psoriasis.

REFERENCES 1. de Arruda L H, De Moraes A P: The impact of psoriasis on quality of life. *Br J Dermatol* 2001, 144:33-36.
2. Finlay A Y: Quality of life assessments in dermatology. *Semin Cutan Med Surg* 1998, 17:291-296.
3. Rapp S R, Cottrell C A, Leary M R: Social coping strategies associated with quality of life decrements among psoriasis patients. *Br J Dermatol* 2001, 145:610-616.
4. Wahl A: The impact of psoriasis on psychosocial life domains. A review. *Scand J Caring Sci* 1997, 11:243-249.
5. Weiss S C, Kimball A B, Liewehr D J, Blauvelt A, Turner M L, Emanuel E J: Quantifying the harmful effect of psoriasis on health-related quality of life. *J Am Acad Dermatol* 2002, 47:512-518.
6. Feldman S R, Menter A, Koo J Y: Improved health-related quality of life following a randomized controlled trial of alefacept treatment in patients with chronic plaque psoriasis. *Br J Dermatol* 2004, 150:317-326.
7. Finlay A Y, Salek M S, Haney J: Intramuscular alefacept improves health-related quality of life in patients with chronic plaque psoriasis. *Dermatology* 2003, 206:307-315.
8. Gordon K B, Papp K A, Hamilton T K, Walicke P A, Dummer W, Li N, Bresnahan B W, Menter A: Efalizumab for patients with moderate to severe plaque psoriasis: a randomized controlled trial. *JAMA* 2003, 290:3073-3080.
9. Gottlieb A B, Matheson R T, Lowe N, Krueger G G, Kang S, Goffe B S, Gaspari A A, Ling M, Weinstein G D, Nayak A, Gordon K B, Zitnik R: A randomized trial of etanercept as monotherapy for psoriasis. *Arch Dermatol* 2003, 139:1627-1632; discussion 1632.
10. Leonardi C L, Powers J L, Matheson R T, Goffe B S, Zitnik R, Wang A, Gottlieb A B: Etanercept as monotherapy in patients with psoriasis. *N Engl J Med* 2003, 349:2014-2022.
11. Menter A, Kosinski M, Bresnahan B W, Papp K A, Ware J E, Jr.: Impact of efalizumab on psoriasis-specific patient-reported outcomes. Results from three randomized, placebo-controlled clinical trials of moderate to severe plaque psoriasis. *Drugs Dermatol* 2004, 3:27-38.
12. Kirby B, Richards H L, Woo P, Hindle E, Main C J, Griffiths C E: Physical and psychologic measures are necessary to assess overall psoriasis severity. *J Am Acad Dermatol* 2001, 45:72-76.
13. Krueger G G, Feldman S R, Camisa C, Duvic M, Elder J T, Gottlieb A B, Koo J, Krueger J G, Lebwohl M, Lowe N, Menter A, Morison W L, Prystowsky J H, Shupack J L, Taylor J R, Weinstein G D, Barton T L, Rolstad T, Day R M: Two considerations for patients with psoriasis and their clinicians: what defines mild, moderate, and severe psoriasis? What constitutes a clinically significant improvement when treating psoriasis? *J Am Acad Dermatol* 2000, 43:281-285.

14. Smith C H, Anstey A V, Barker J N, Burden A D, Chalmers R J, Chandler D, Finlay A Y, Grifitths C E, Jackson K, McHugh N J, McKenna K E, Reynolds N J, Ormerod A D: British Association of Dermatologists guidelines for use of biological interventions in psoriasis 2005. *Br J Dermatol* 2005, 153:486-497.

15. Finlay A Y, Khan G K: Dermatology Life Quality Index (DLQI)—a simple practical measure for routine clinical use. *Clin Exp Dermatol* 1994, 19:210-216.

16. Ware J E, Snow K K, Kosinski M K, Gandek B: *SF-36 Health Survey: Manual and Interpretation Guide*. Boston: The Health Institute, New England Medical Center; 1993.

17. EuroQol Group: EuroQol—a new facility for the measurement of health-related quality of life. *Health Policy* 1990, 16:199-208.

18. Kind P: The EuroQol Instrument: An index of health-related quality of life. In *Quality of Life and Pharmacoeconomics in Clinical Trials*. 2nd edition. Edited by Spilker B. Philadelphia: Lippincott-Raven Publishers; 1996: 191-201

19. Food and Drug Administration: Guidance for industry. Patient-reported outcome measures: use in medical product development to support labeling claims. Draft. February 2006.

20. Jaeschke R, Singer J, Guyatt G H. Measurement of health status. Ascertaining the minimal clinically important difference. *Control Clin Trials*. 1989; 10:407-415.

21. Wyrwich K W, Bullinger M, Aaronson N, Hays R D, Patrick D L, Symonds T, Sloan J A. Estimating clinically significant differences in quality of life outcomes. *Qual Life Res* 2005; 14: 285-295.

22. Sloan J A, Dueck A, Erickson P A, Guess H, Revicki D A, Santanello N C. Analysis and interpretation of patient reported outcome results. Presented at the FDA Guidance on Patient Reported Outcomes: Discussion, Dissemination and Operationalization, Chantilly, Virgina, February 2006.

23. Gordon K B, Langley R G, Leonardi C, Toth D, Menter M A, Kang S, Heffernan M, Miller B, Hamlin R, Lim L, Zhong J, Hoffman R, Okun M M: Clinical response to adalimumab treatment in patients with moderate to severe psoriasis patients: Double-blind, randomized controlled trial and open-label extension study. *J Am Acad Dermatol*, in progress.

24. Ashcroft D M, Wan Po A L, Williams H C, Griffiths C E: Clinical measures of disease severity and outcome in psoriasis: a critical appraisal of their quality. *Br J Dermatol* 1999, 141:185-191.

25. Fredriksson T, Pettersson U: Severe psoriasis—oral therapy with a new retinoid. *Dermatologica* 1978, 157: 238-244.

26. Badia X, Mascaro J M, Lozano R: Measuring health-related quality of life in patients with mild to moderate eczema and psoriasis: clinical validity, reliability and sensitivity to change of the DLQI. The Cavide Research Group. *Br J Dermatol* 1999, 141:698-702.

27. Lewis V, Finlay A Y: 10 years experience of the Dermatology Life Quality Index (DLQI). *J Investig Dermatol Symp Proc* 2004, 9:169-180.

28. Shikiar R, Bresnahan B W, Stone S P, Thompson C, Koo J, Revicki D A: Validity and reliability of patient reported outcomes used in Psoriasis: results from two randomized clinical trials. *Health Qual Life Outcomes* 2003, 1:53.

29. Ware J E, Kosinski M K, Keller S D: *SF-36 Physical and Mental Health Summary Scales: A User's Manual*. Boston: The Health Institute, New England Medical Center; 1994.

30. Wahl A, Loge J H, Wiklund I, Hanestad B R: The burden of psoriasis: a study concerning health-related quality of life among Norwegian adult patients with psoriasis compared with general population norms. *J Am Acad Dermatol* 2000, 43:803-808.

31. Wyrwich K W, Nienaber N A, Tierney W M, Wolinsky F D: Linking clinical relevance and statistical significance in evaluating intra-individual changes in health-related quality of life. *Med Care* 1999, 37:469-478.

32. Wyrwich K W, Tierney W M, Wolinsky F D: Further evidence supporting an SEM-based criterion for identifying meaningful intra-individual changes in health-related quality of life. *J Clin Epidemiol* 1999, 52:861-873.

33. Norman G R, Sloan J A, Wyrwich K W: Interpretation of changes in health-related quality of life: the remarkable universality of half a standard deviation. *Med Care* 2003, 41:582-592.

34. Beaton D E, Boers M, Wells G A: Many faces of the minimal clinically important difference (MCID): a literature review and directions for future research. *Curr Opin Rheumatol* 2002, 14:109-114.

35. Hays R D, Farivar S S, Liu H: Approaches and recommendations for estimating minimally important differences for health-related quality of life measures. *Journal of Chronic Obstructive Pulmonary Disease* 2005, 2:63-67.

36. Khilji F A, Gonzalez M, Finlay A Y: Clinical meaning of change in Dermatology Life Quality Index. *Br J Dermatol* 2002, 147:50 (abstract).

37. Kosinski M, Zhao S Z, Dedhiya S, Osterhaus J T, Ware J E, Jr.: Determining minimally important changes in generic and disease-specific health-related quality of life questionnaires in clinical trials of rheumatoid arthritis. *Arthritis & Rheumatism* 2000, 43:1478-1487.

38. Chren M M, Lasek R J, Quinn L M, Mostow E N, Zyzanski S J: Skindex, a quality-of-life measure for patients with skin disease: reliability, validity, and responsiveness. *J Invest Dermatol* 1996, 107:707-713.

39. McKenna S P, Lebwohl M, Kahler K N: Development of the US PSORIQoL: a psoriasis-specific measure of quality of life. *Int J Dermatol* 2005, 44:462-469.

Example 9

Adalimumab Efficacy and Safety Compared with Methotrexate and Placebo in Patients with Moderate to Severe Psoriasis The following study was the first to directly compare the clinical efficacy, safety, and tolerability of a biologic (adalimumab) vs. a traditional systemic agent (methotrexate or MTX) in the treatment of moderate to severe chronic plaque psoriasis. A published international consensus statement recommends that for patients with moderate to severe psoriasis, "equal consideration" should be given to traditional systemic therapy (e.g., MTX, phototherapy, or biologics) (Sterry et al. Brit J. Dermatol. 2004; 151(Suppl 69):3-17). Resistance to using biologics as first-line therapy has rested in part on the absence of data demonstrating superiority of a biologic to a traditional systemic agent in a direct, head-to-head study.

Figure 3:
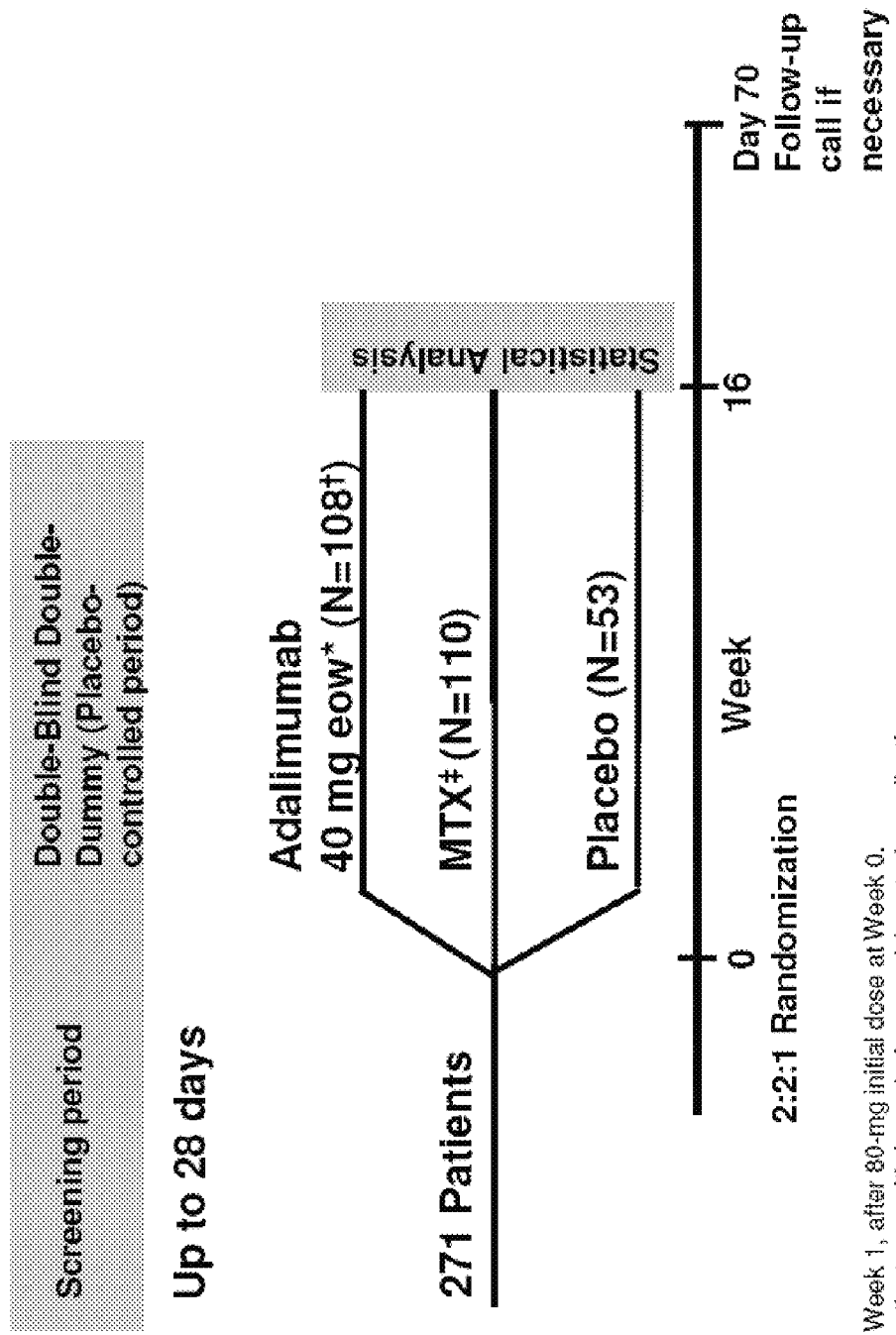
FIG. 3 shows the study design for the Phase III trial described in Example 9.

The objective of this study was to compare the clinical efficacy, safety, and tolerability of adalimumab vs. MTX and vs. placebo in the treatment of moderate to severe chronic plaque psoriasis The study was a multi-center, 16-week, randomized controlled Phase III trial. The study design is shown in FIG. 3. The main inclusion criteria included:

Clinical diagnosis of psoriasis for ≥1 year

Affected body surface area (BSA)≥10%

Psoriasis Area and Severity Index (PASI)≥10

The main exclusion criteria was previous use of MTX or systemic anti-TNF therapy. The study required a washout period, including the following:

2 weeks for topical and phototherapy 4 weeks for non-biologic systemic therapies 12 weeks for biologic therapies Efficacy was measured according to the following:

PASI, PGA (Physician's Global Assessment)

Primary endpoint was PASI 75 response rate at Week 16

Safety measures was examined using adverse events and laboratory parameters

The adalimumab dosage regimen (subcutaneous) included an 80 mg (two 40 mg injections) at Week 0 (baseline), followed by 40 mg every other week (eow) from Week 1 until Week 15. The MTX dosage regimen included the following:

- 7.5 mg at Weeks 0 and 1 (weekly MTX dose adjusted to ALT, AST, WBC count, platelet count and serum creatinine from Week 2 until Week 15, and reduced or withheld if deemed appropriate by the safety assessor);
- 10 mg at Weeks 2 and 3 (weekly MTX dose adjusted to ALT, AST, WBC count, platelet count and serum creatinine from Week 2 until Week 15, and reduced or withheld if deemed appropriate by the safety assessor);
- 15 mg from Weeks 4-15 (Weekly MTX dose increased to 20 mg at Week 8, 25 mg at Week 12 if PASI<50 and there were no safety concerns).

Analytical methods included the following:

Intention-to-treat analyses were performed for all randomized patients

Missing data were analyzed using non-responder imputation (NRI)

PASI 75 at Week 16 (primary endpoint) was analyzed using adjusted Cochran-Mantel-Haenszel test.

Baseline characteristics were similar across treatment groups and consistent with expectations for patients with moderate to severe chronic plaque psoriasis (Table 48)

TABLE 48

Baseline Demographics and Clinical Characteristics

| | Placebo (N = 53) | MTX (N = 110) | Adalimumab (N = 108†) |
|---|---|---|---|
| Age (yrs) | 40.7 ± 11.43 | 41.6 ± 11.98 | 42.9 ± 12.57 |
| Duration of Psoriasis (mos) | 225.3 ± 104.2 | 226.5 ± 122.1 | 214.8 ± 121.1 |
| % Male | 66.0 | 66.4 | 64.8 |
| Body Weight (kg) | 82.6 ± 19.91 | 83.1 ± 17.50 | 81.7 ± 19.98 |
| % BSA | 28.4 ± 16.09 | 32.4 ± 20.60 | 33.6 ± 19.88 |
| PASI score | 19.2 ± 6.89 | 19.4 ± 7.39 | 20.2 ± 7.53 |
| % with Psoriatic Arthritis | 20.8 | 17.3 | 21.3 |

*Mean values ± SD except % Male and % with Psoriatic Arthritis.
†One patient was withdrawn before receiving any study medication.

PASI 75 response rate for adalimumab-treated patients was significantly superior to PASI 75 response rates for MTX-treated and placebo-treated patients at Week 16 (primary endpoint) (Table 49).

TABLE 49

PASI 75 Response Rates

| | n | Treatment | % Patients |
|---|---|---|---|
| Week 4 | 53 | Placebo | 4 |
| | 110 | Methotrexate | 3 |
| | 108 | Adalimumab | 23*† |
| Week 8 | 53 | Placebo | 13 |
| | 110 | Methotrexate | 9 |
| | 108 | Adalimumab | 62‡ |
| Week 12 | 53 | Placebo | 15 |
| | 110 | Methotrexate | 25 |
| | 108 | Adalimumab | 77‡ |
| Week 16 | 53 | Placebo | 19 |
| | 110 | Methotrexate | 36 |
| | 108 | Adalimumab | 80‡ |

*p = 0.001,
†p < 0.001, both vs. placebo;
‡p < 0.001 vs. MTX.
ITT, patients with missing PASI scores were considered non-responders

TABLE 50

PASI 90 Response Rates

| | n | Treatment | % Patients |
|---|---|---|---|
| Week 4 | 53 | Placebo | 0 |
| | 110 | Methotrexate | 1 |
| | 108 | Adalimumab | 7* |
| Week 8 | 53 | Placebo | 4 |
| | 110 | Methotrexate | 3 |
| | 108 | Adalimumab | 27†‡ |
| Week 12 | 53 | Placebo | 8 |
| | 110 | Methotrexate | 9 |
| | 108 | Adalimumab | 48†‡ |
| Week 16 | 53 | Placebo | 11 |
| | 110 | Methotrexate | 14 |
| | 108 | Adalimumab | 52†‡ |

*p < 0.05 vs. MTX;
†p < 0.001 vs. placebo;
‡p < 0.001 vs. MTX.
ITT, patients with missing PASI scores were considered non-responders.

Figure 4:
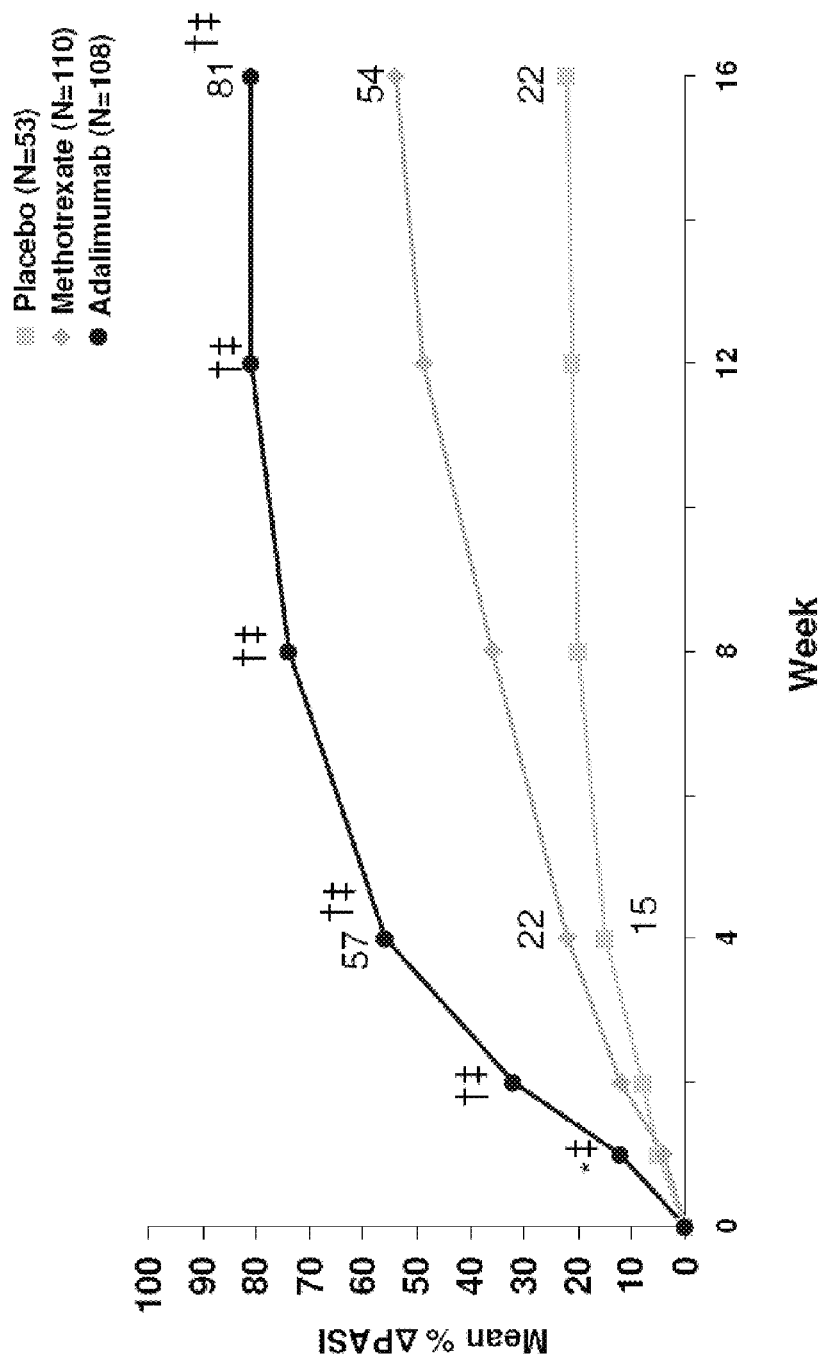
FIG. 4 shows a graph describing mean percentage PASI improvement

Adalimumab-treated patients achieved a significantly superior PASI 90 response rate vs. MTX-treated and placebo-treated patients at Week 16 (Table 50). Mean percentage PASI improvement for adalimumab-treated patients was rapid, with a mean percentage PASI improvement of 57% achieved at Week 4 (FIG. 4). The percentage of adalimumab-treated patients who achieved PGA "Clear" or "Minimal" was similar to the percentage of adalimumab-treated patients who achieved PASI 75 or greater improvement (Table 51).

TABLE 51

PGA "Clear" or "Minimal" Responses

|  | n | Treatment | % Patients |
|---|---|---|---|
| Week 4 | 53 | Placebo | 0 |
|  | 110 | Methotrexate | 1 |
|  | 108 | Adalimumab | 7*† |
| Week 8 | 53 | Placebo | 4 |
|  | 110 | Methotrexate | 3 |
|  | 108 | Adalimumab | 27‡§ |
| Week 12 | 53 | Placebo | 8 |
|  | 110 | Methotrexate | 9 |
|  | 108 | Adalimumab | 48‡§ |
| Week 16 | 53 | Placebo | 11 |
|  | 110 | Methotrexate | 14 |
|  | 108 | Adalimumab | 52‡§ |

*p < 0.01 vs. placebo;
†p < 0.01 vs. MTX;
‡p < 0.001 vs. placebo;
§p < 0.001 vs. MTX.
ITT, patients missing PGA scores were counted as not achieving PGA "Clear" or "Minimal".

There were no significant differences in the incidences of adverse events reported for adalimumab-treated vs. MTX-treated and vs. placebo-treated patients (Tables 52 and 53). The most frequent adverse events were nasopharyngitis (21-28%) and headache (9-13%) (Table 53)

TABLE 52

Adverse Events

| Event, n (%) | Placebo (N = 53) | MTX (N = 110) | Adalimumab (N = 107*) |
|---|---|---|---|
| Any AE | 42 (79) | 89 (81) | 79 (74) |
| Any SAE | 1 (2) | 1 (1) | 2 (2) |
| Any AE leading to discontinuation | 1 (2) | 6 (6) | 1 (1) |
| Any infectious AE | 23 (43) | 46 (42) | 51 (48) |
| Any infectious SAE | 0 (0) | 0 (0) | 0 (0) |

*Does not include patient who was withdrawn from study before receiving any study medication.
AE = adverse events. SAE = serious adverse events.
SAE were a calculus of right uretero-pelvic junction in one placebo patient, hepatitis secondary to methotrexate in one MTX patient, pancreatitis in one adalimumab patient, and an increase in a benign ovarian cyst in one adalimumab patient.

TABLE 53

Common Adverse Events in ≥5% of Patient Population in Study

| Event, n (%) | Placebo (N = 53) | MTX (N = 110) | Adalimumab (N = 107*) |
|---|---|---|---|
| Nausea | 4 (8) | 8 (7) | 4 (4) |
| Nasopharyngitis | 11 (21) | 26 (24) | 30 (28) |
| Rhinitis | 4 (8) | 4 (4) | 3 (3) |
| Viral Infection | 1 (2) | 6 (6) | 0 (0) |
| Gamma-Glutamyltransferase Increased | 3 (6) | 0 (0) | 2 (2) |
| Arthralgia | 1 (2) | 5 (5) | 6 (6) |
| Headache | 5 (9) | 12 (11) | 14 (13) |
| Rhinorrhea | 3 (6) | 0 (0) | 3 (3) |
| Pruritus | 6 (11) | 2 (2) | 4 (4) |

*One patient was withdrawn from study before receiving any study medication.

In conclusion, adalimumab demonstrated significantly superior efficacy in the treatment of moderate to severe psoriasis vs. MTX and vs. placebo—PASI 75 at Week 16: 80% for adalimumab vs. 36% for MTX and vs. 19% for placebo. Furthermore, response to adalimumab was rapid. Adalimumab was well-tolerated, with a safety profile in this psoriasis trial comparable to its profile in RA clinical trials.

The results of CHAMPION suggest a paradigm shift in the treatment of moderate to severe psoriasis, from "equal consideration" to "first-line consideration" for biologics

Example 10

Efficacy and Safety of a 120-Week Open-Label Extension Study in Patients with Moderate to Severe Chronic Plaque Psoriasis Psoriasis is a chronic, inflammatory proliferative disease of the skin that affects 1-3% of general population (Greaves and Weinstein N Engl J Med 1995; 332:581-8). Treatment of moderate to severe psoriasis with systemic agents such as methotrexate or cyclosporine can be limited by lack of efficacy or precluded by dose dependent side effects, and ultraviolet light therapy is often inconvenient The objective of the following study was to determine the long-term (120 weeks) efficacy and safety of adalimumab in patients with moderate to severe plaque psoriasis.

The study includes a Phase III open-label extension (OLE) study of adalimumab in which patients with moderate to severe chronic plaque psoriasis (PASI≥12, PGA of at least moderate, BSA≥10%) who completed the lead-in 60-week Phase II adalimumab clinical trials could enroll (described in Examples 1-6, 8, 13 and 14). This example summarizes results in patients treated with adalimumab eow for up to 120 weeks (up to 60 weeks in the preceding Phase II studies and for up to 72 weeks in the Phase III extension trial). The 120-week efficacy and safety of adalimumab 40 mg every other week (eow) was evaluated in an open-label extension trial (III) that followed a 48-week extension trial (II.B), which was conducted at 18 sites. Prior to the II.B study, patients were enrolled in a 12-week, double-blind, placebo-controlled trial (II.A). Inclusion criteria included: moderate to severe chronic plaque psoriasis: ≥1 year and affected BSA: ≥5%. Exclusion criteria included prior TNF-antagonist therapy. As observed analysis was conducted to assess efficacy and safety over the 120-week treatment period.

Patients who had completed the lead-in studies could enroll in the open-label extension (OLE) trial, during which they received adalimumab 40 mg every other week (eow). After 24 weeks of OL therapy, patients with an inadequate response (<PASI 50 relative to baseline of II.A—see Study Design of FIG. 5) could increase to adalimumab 40 mg weekly. PASI responses and PGA scores were analyzed as observed. Patients who underwent dose escalation, and patients randomized at Week 0 to adalimumab 40 mg weekly are not included in this analysis. Thus, patients whose dosages increased were counted as non-responders from the time of dosage escalation. Adverse events were collected throughout the 120-week period.

A total of 92 patients were enrolled in Study 1.1 (see FIG. 5) and received at least one dose of adalimumab 40 mg eow during the 120-week observation period. Baseline demographics and clinical characteristics for patients randomized to placebo or to adalimumab 40 mg eow in Study 1.1 were typical for patients with moderate to severe chronic plaque psoriasis (Table 54)

TABLE 54

Baseline Demographics and Clinical Characteristics

| | Adalimumab 40 mg eow (n = 92) |
|---|---|
| Age (years) | 45.1 |
| Duration of Ps (years) | 19.7 |
| % Male | 70.7 |
| % Caucasian | 90.2 |
| Body Weight (kg) | 94.7 |
| % BSA | 28.6 |
| PASI Score | 16.3 |
| % with PsA | 29.3 |

Mean values except % Male, % Caucasian, and % with Ps.

Fifty-three percent (49/92) of patients were evaluable for efficacy and safety after more than 2 years of continuous adalimumab 40 mg eow dosing (Table 55). Week 0 corresponds to the beginning of adalimumab therapy

TABLE 55

Number of Evaluable Patients Over 120 Weeks

| Time | No. of Evaluable Patients |
|---|---|
| Week 0 | 92 |
| Week 4 | 92 |
| Week 8 | 91 |
| Week 12 | 89 |
| Week 16 | 79 |
| Week 24 | 75 |
| Week 36 | 64 |
| Week 48 | 60 |
| Week 60 | 57 |
| Week 72 | 52 |
| Week 84 | 52 |
| Week 96 | 53 |
| Week 108 | 50 |
| Week 120 | 49 |

Figure 6:
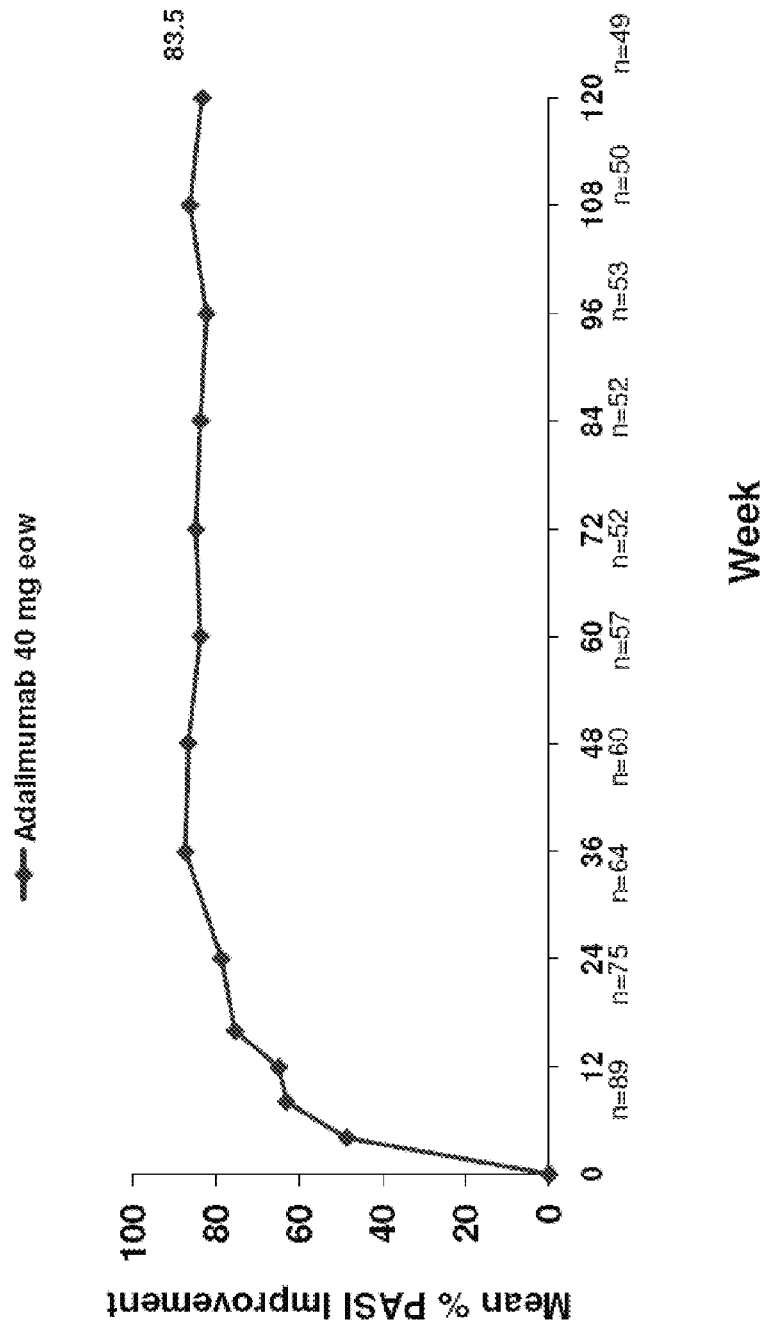
FIG. 6 graphically depicts the mean percentage PASI improvement through week 60.

Among patients who continued to receive adalimumab 40 mg eow, PASI responses peaked at Week 48 and were generally maintained up to Week 120 of adalimumab therapy (Table 56). Among patients who continued to receive adalimumab 40 mg eow, mean percentage PASI improvement peaked at Week 36 and was generally maintained to Week 120 (FIG. 6)

TABLE 56

PASI Response Rates Up To Week 120

| | PASI response | % Patients |
|---|---|---|
| Week 12 | PASI 50 | 78.7 |
| | PASI 75 | 56.2 |
| | PASI 90 | 29.2 |
| | PASI 100 | 11.2 |
| Week 24 | PASI 50 | 86.7 |
| | PASI 75 | 74.7 |
| | PASI 90 | 52 |
| | PASI 100 | 20 |
| Week 48 | PASI 50 | 96.7 |
| | PASI 75 | 81.7 |
| | PASI 90 | 61.7 |
| | PASI 100 | 31.7 |
| Week 72 | PASI 50 | 96.2 |
| | PASI 75 | 73.1 |
| | PASI 90 | 53.8 |
| | PASI 100 | 25 |
| Week 96 | PASI 50 | 92.5 |
| | PASI 75 | 75.5 |
| | PASI 90 | 52.8 |
| | PASI 100 | 24.5 |
| Week 120 | PASI 50 | 93.9 |
| | PASI 75 | 77.6 |
| | PASI 90 | 53.1 |
| | PASI 100 | 28.6 |

Patients who received OL weekly adalimumab rescue therapy and are not included in the as observed analysis.

The percentage of patients who reported malignant, serious, and serious infectious adverse events were low and stable over the surveillance period (Table 57). The malignant adverse event reported was a squamous cell carcinoma of the neck in an ex-smoker who had been noted to have lymphadenopathy at screening. The serious adverse events reported were squamous cell carcinoma (case described above), fall, and dyspepsia. No cases of tuberculosis, demyelinating disorder, lupus-like syndrome, lymphoma, or congestive heart failure were noted. The percentage of patients who reported malignant, serious, and serious infectious adverse events were low and stable over the surveillance period. The malignant adverse event reported was a squamous cell carcinoma of the neck in an ex-smoker who had been noted to have lymphadenopathy at screening. The serious adverse events reported were squamous cell carcinoma (case described above), fall, and dyspepsia. No cases of tuberculosis, demyelinating disorder, lupus-like syndrome, lymphoma, or congestive heart failure were noted.

TABLE 57

Patients Experiencing Adverse Events over 120 Weeks

| | Week 0-24 n = 92 n (%) | Week 25-48 n = 78 n (%) | Week 49-72 n = 62 n (%) | Week 73-96 n = 55 n (%) | Week 97-120 n = 53 n (%) |
|---|---|---|---|---|---|
| Any AE | 69 (75.0) | 33 (42.3) | 28 (45.2) | 27 (49.1) | 25 (47.2) |
| Serious AEs | 2 (2.2) | 0 (0.0) | 0 (0.0) | 0 (0.0) | 1 (1.9) |
| Infectious AEs | 28 (30.4) | 22 (28.2) | 17 (27.4) | 15 (27.3) | 7 (13.2) |
| Serious Infectious AEs | 0 (0.0) | 0 (0.0) | 0 (0.0) | 0 (0.0) | 0 (0.0) |
| Malignant AEs | 1 (1.1) | 0 (0.0) | 0 (0.0) | 0 (0.0) | 0 (0.0) |
| AEs leading to withdrawal | 4 (4.3) | 0 (0.0) | 0 (0.0) | 0 (0.0) | 0 (0.0) |

Adverse event profile of adalimumab was stable over the 120-week treatment period (Table 58). Blood tests were performed under non-fasting conditions

TABLE 58

Common Adverse Events >5% in Any 24-Week Period

| Adverse Events | Week 0-24<br>n = 92<br>n (%) | Week 25-48<br>n = 78<br>n (%) | Week 49-72<br>n = 62<br>n (%) | Week 73-96<br>n = 55<br>n (%) | Week 97-120<br>n = 53<br>n (%) |
|---|---|---|---|---|---|
| Nasopharyngitis | 9 (9.8) | 5 (6.4) | 1 (1.6) | 3 (5.5) | 2 (3.8) |
| Increased triglycerides | 7 (7.6) | 1 (1.3) | 1 (1.6) | 1 (1.8) | 0 (0.0) |
| Headache | 7 (7.6) | 0 (0.0) | 0 (0.0) | 0 (0.0) | 0 (0.0) |
| Upper respiratory tract infection | 6 (6.5) | 3 (3.8) | 2 (3.2) | 2 (3.6) | 0 (0.0) |
| Diarrhea | 5 (5.4) | 1 (1.3) | 1 (1.6) | 0 (0.0) | 3 (5.7) |
| Hypercholesterolemia | 4 (4.3) | 0 (0.0) | 1 (1.6) | 3 (5.5) | 1 (1.9) |
| Sinusitis | 1 (1.1) | 1 (1.3) | 1 (1.6) | 3 (5.5) | 1 (1-9) |

In conclusion, patients with moderate to severe psoriasis achieved sustained efficacy up to Week 120 of treatment with adalimumab. The types of adverse events in this study were similar to those previously reported in adalimumab rheumatoid arthritis and psoriatic arthritis trials. The percentage of patients diagnosed with adverse events appeared stable over the 120-week observation period Example 11

Short- and Long-Term Efficacy and Safety of Adalimumab in a Pivotal Phase III Study in Adult Patients with Moderate to Severe Chronic Plaque Psoriasis Psoriasis is a chronic, immune-mediated, inflammatory skin disease that affects 1-3% of general population (Greaves and Weinstein, N Engl J Med. 1995; 332:581-8). Treatment of moderate to severe psoriasis with systemic agents such as cyclosporine or methotrexate can be limited by lack of efficacy or precluded by dose-dependent adverse events. In addition, ultraviolet light therapy is often inconvenient.

This example describes a Phase III trial of adalimumab conducted at 81 sites, in adult patients with moderate to severe chronic plaque psoriasis. The objective of the study was to compare the efficacy and safety of adalimumab with placebo during an initial placebo-controlled, double-blind trial period, and to determine if improvement with adalimumab is sustained during open-label treatment. This study also sought to determine whether discontinuation of adalimumab therapy is associated with a loss of adequate clinical response, and to determine the adverse event (AE) profile of adalimumab-treated patients over a 52-week period.

The main inclusion criteria for this study included a clinical diagnosis of psoriasis for ≥6 months and affected body surface area (BSA)≥10% and PASI≥12. The main exclusion criteria included prior use of systemic or biologic anti-TNF therapy. The washout period included two weeks for topical agents and UVB, 4 weeks for PUVA and non-biologic systemic therapies, and 12 weeks for all biologic therapies. The two co-primary endpoints were:
  Percentage of patients achieving PASI≥75 at Week 16
  Percentage of patients, among Week 33 PASI≥75 responders, losing an adequate response after Week 33, characterized by:
    PASI<50 (relative to baseline) and
    At least a 6 point increase in PASI Safety measures included the following:
  AEs and laboratory parameters
  Percentages of patients and rates (events/patient-year) of AEs for adalimumab in Period A were compared with those of placebo in period A, and with those of adalimumab-treated patients over the entire 52-week study period As described in the study design of FIG. 7, there were three treatment periods, Periods A, B, and C.

Figure 7:
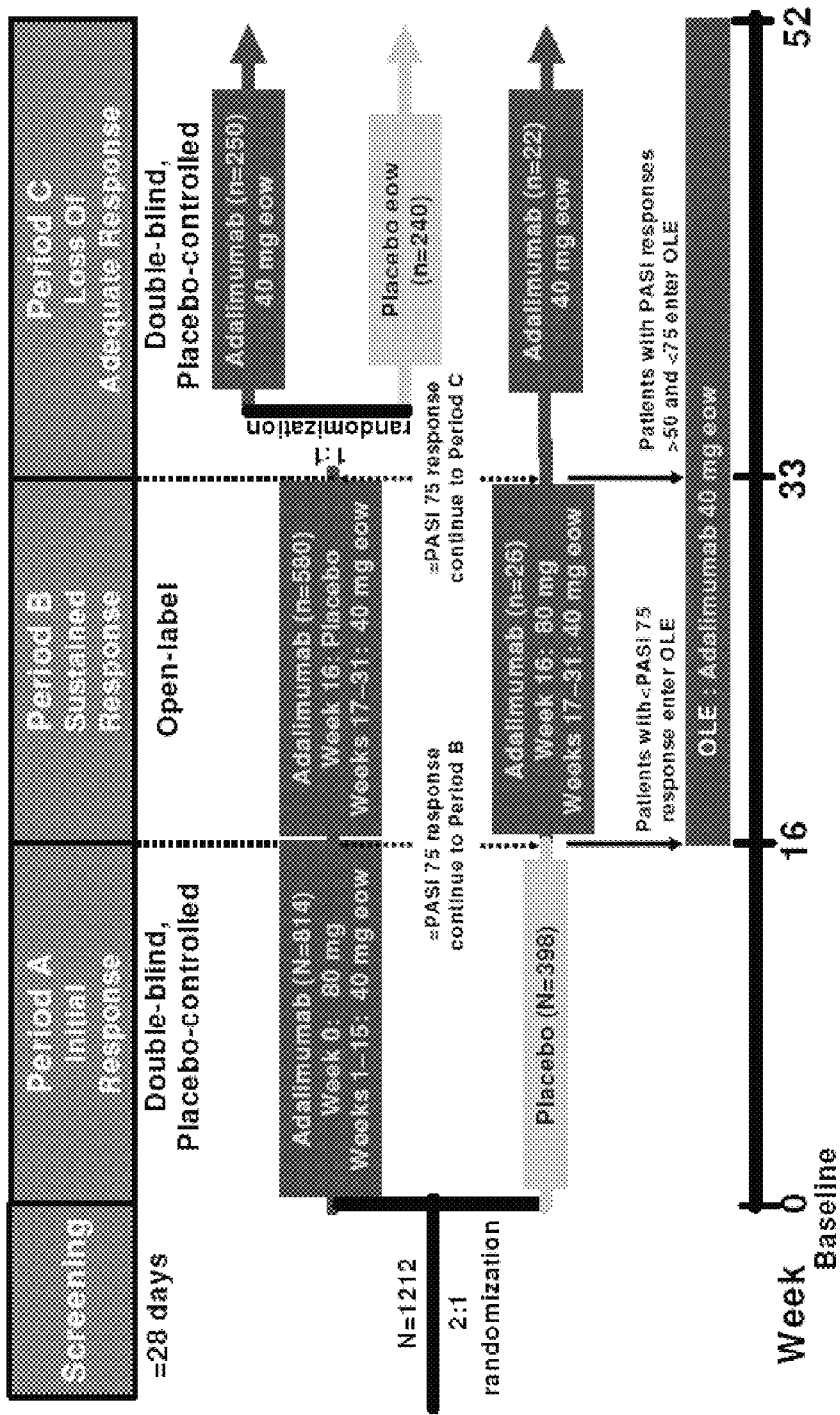
FIG. 7 describes the study design of the Phase III study described in Example 11.

Period A was double-blind, placebo-controlled, and lasted from weeks 0-16. During Period A, patients were randomized 2:1 to adalimumab or placebo. Patients in the adalimumab arm received: Week 0: 80 mg subcutaneously (sc) and Weeks 1-15: 40 mg every other week (eow). At Week 16 patients who achieved ≥PASI 75 improvement continued into Period B, while those patients having <PASI 75 improvement entered the open label extension (OLE) study (FIG. 7).

Period B was open-label and lasted from Weeks 17-33. Adalimumab was administered at 40 mg every other week (eow) subcutaneously (sc). Patients who achieved ≥PASI 75 response at Week 33 entered Period C. Those who had a PASI 50-<75 response at the end of Period B entered the OLE, while those with a <PASI 50 response discontinued the study.

Period C was a double-blind, placebo-controlled which was held from weeks 34-52. Patients randomized to adalimumab treatment in Period A and who achieved ≥PASI 75 at Week 33 were re-randomized 1:1 to either continue adalimumab 40 mg eow or receive placebo treatment. Patients randomized to placebo treatment in Period A and who received adalimumab in Period B, continued adalimumab treatment in Period C if they achieved a ≥PASI 75 in Period B Various analytical methods were used in the study. Intention-to-treat (ITT) analyses were performed for all randomized patients in Periods A and C. Binary variables were analyzed with non-responder imputation (NRI) in Period A. In order to assess efficacy beyond Week 16, efficacy outcomes for all patients who had been randomized to adalimumab at Week 0 were assessed in Period B and in the OLE. Week 24 results from NRI analysis include pooled efficacy outcomes from OLE and Period B. After Week 24, non-overlapping OLE and Period B study visits prevent complete pooling of efficacy outcomes. Continuous variables were analyzed as observed during Period B Baseline characteristics were similar across treatment groups and consistent with expectations for patients with moderate to severe chronic plaque psoriasis (Table 59)

TABLE 59

Baseline Demographics and Clinical Characteristics

|  | Placebo (N = 398) | Adalimumab (N = 814) |
|---|---|---|
| Age (years) | 45.4 ± 13.4 | 44.1 ± 13.2 |
| % Male | 64.6 | 67.1 |
| % Caucasian | 90.2 | 91.2 |
| Duration of Ps (years) | 18.4 ± 11.94 | 18.1 ± 11.91 |
| Body Weight (kg) | 94.1 ± 23.1 | 92.3 ± 22.9 |
| BSA (%) | 25.6 ± 14.76 | 25.8 ± 15.51 |
| PASI Score | 18.8 ± 7.09 | 19.0 ± 7.08 |
| % with PsA | 28.4 | 27.5 |

Mean values ± SD except % Male, % Caucasian and % with psoriatic arthritis.

Adalimumab-treated patients achieved rapid, and significantly superior, PASI 75 response rates vs. placebo-treated patients from Week 4, the first time point evaluated, and every visit through Week 16 (Table 60). PASI 75 response rates were sustained through open-label treatment to Week 24. Week 24 results include both Period B and OLE efficacy outcomes. Pooling of efficacy outcomes after this time point was not possible because of disparate Period B and OLE study visit schedules (Table 60).

TABLE 60

PASI 75 Response Rates at Weeks 0-24

|  | n | Treatment | % Patients |
|---|---|---|---|
| Week 4 | 398 | Placebo | 1.3 |
|  | 814 | Adalimumab | 18.9* |
| Week 8 | 398 | Placebo | 3.0 |
|  | 814 | Adalimumab | 54.1* |
| Week 12 | 398 | Placebo | 4.8 |
|  | 814 | Adalimumab | 67.7* |
| Week 16 | 398 | Placebo | 6.5 |
|  | 814 | Adalimumab | 71.0* |
| Week 24 | 398 | Placebo | — |
|  | 814 | Adalimumab | 71.0* |

*$p < 0.001$, adalimumab vs. placebo.
ITT; Patients with missing PASI scores were considered non-responders.
Week 24 results represent pooling of efficacy outcomes from Period B and OLE.
Weeks 4 to 16 were double-blind, placebo-controlled. Week 24 was open-label.

TABLE 61

PASI 100 Response Rates at Weeks 0-24

|  | n | Treatment | % Patients |
|---|---|---|---|
| Week 4 | 398 | Placebo | 0.3 |
|  | 814 | Adalimumab | 0.9 |
| Week 8 | 398 | Placebo | 0.3 |
|  | 814 | Adalimumab | 7.1* |
| Week 12 | 398 | Placebo | 0.3 |
|  | 814 | Adalimumab | 14.4* |
| Week 16 | 398 | Placebo | 0.8 |
|  | 814 | Adalimumab | 20* |
| Week 24 | 398 | Placebo | — |
|  | 814 | Adalimumab | 22.5* |

*$p < 0.001$, adalimumab vs. placebo.
ITT; Patients with missing PASI scores were considered non-responders.
Week 24 results represent pooling of efficacy outcomes from Period B and OLE.
Weeks 4 to 16 were double-blind, placebo-controlled. Week 24 was open-label.

PASI 100 responses were sustained from Week 16 to Week 24 during open-label adalimumab treatment (Table 61).

Only patients who achieved ≥PASI 75 responses entered Period B. For patients who entered Period B, mean percentage PASI improvement achieved at Week 16 was maintained throughout Period B (Table 62).

TABLE 62

Mean Percentage PASI Improvement During Period B in Adalimumab-Treated Patients*

|  | n | % PASI improvement |
|---|---|---|
| Week 16 | 574 | 91.9 |
| Week 24 | 577 | 91.2 |
| Week 33 | 551 | 89.3 |

*Relative to baseline for patients who were randomized to adalimumab at Week 0 and entered Period B.
As observed.

Clinical characteristics were similar between patients re-randomized to adalimumab and placebo in Period C. The proportion of patients losing an adequate response during Period C was significantly lower for patients re-randomized to continue adalimumab therapy (Table 63).

TABLE 63

Loss of Adequate Response by Week 52

| Treatment | n | % Patients |
|---|---|---|
| Placebo in period C | 240 | 28.4 |
| Adalimumab in period C | 250 | 4.9* |

*$p < 0.001$, adalimumab vs. placebo.
Primary endpoint: Proportion of patients experiencing an event (loss of adequate response) on or before Week 52. An event was defined as the more stringent of
a) a PASI <50 (relative to baseline) or
b) a ≥6 point increase in PASI from weeks 34 to 52 relative to week 33
ITT; Missing Week 52 PASI assessment imputed as an event because of lack of efficacy or study drug toxicity.

Adalimumab Treatment Group comprised all patients who received at least one dose of adalimumab, with adverse event rate for this group calculated for the entire 52 week study period (See Table 64). Percentages of patients and rates of AEs and of infectious AEs were higher among adalimumab- vs. placebo-treated patients. The percentage of patients with serious AEs was comparable among placebo- and adalimumab-treated patients in Period A (1.8%). The rates of serious AEs in the adalimumab-treated patients of Period A were consistent with serious AE rates throughout the study. The vast majority of Infectious AEs in Period A were not severe. Severe infectious AE rates were comparable between patients receiving adalimumab and those receiving placebo. Percentages of patients and rates of AEs leading to withdrawal were lower for adalimumab-treated patients vs. placebo treated patients

TABLE 65

Safety Results

| | Percentage of AEs During Period A | | Rates of AEs during Period A and for the Adalimumab Treatment Group | | |
|---|---|---|---|---|---|
| | Period A* Placebo (N = 398) (%) | Period A* Adalimumab (N = 814) (%) | Period A* Placebo (120.7 PYs) (Event/PY) | Period A* Adalimumab (250.2 PYs) (Event/PY) | Adalimumab Treatment Group† (540.5 PYs) (Event/PY) |
| Any AE | 55.5 | 62.2‡ | 4.127 | 4.616 | 3.991 |
| Serious AEs | 1.8 | 1.8 | 0.058 | 0.068 | 0.061 |
| Serious Infectious AEs | 1.0 | 0.6 | 0.033 | 0.028 | 0.022 |
| Infectious AEs | 22.4 | 28.9‡ | 0.878 | 1.259 | 1.203 |
| Severe Infectious AEs | 0.8 | 0.7 | 0.025 | 0.036 | 0.030 |
| AEs leading to withdrawal | 2.0 | 1.7 | 0.124 | 0.072 | 0.078 |

*Includes safety data up to 70 days after last dose for patients not continuing into Period B.
†Includes safety data up to 70 days after last dose of adalimumab for all patients who received at least one dose of adalimumab in REVEAL. Adverse events experienced by patients re-randomized to placebo in Period C (within 70 days after last dose of adalimumab in Period B) are included in this group.
‡p < 0.05, adalimumab vs. placebo.

From Table 65 it can be seen that no lymphomas were diagnosed in this study. The percentages of patients with non-melanoma skin cancers and the percentages of patients with all other types of malignancies (excluding non-melanoma skin cancers and lymphomas) were comparable among placebo- and adalimumab-treated patients in Period A, and for Period A vs. the entire 52-week study. One case of oral candidiasis (opportunistic infection) was diagnosed, and one case of presumptive tuberculosis (−ve AFB and −ve culture, with clinical course suggestive of tuberculosis) was diagnosed in a patient who was PPD+ve at baseline and who was non-compliant with INH prophylaxis. No cases of rebound were noted among patients re-randomized to placebo in Period C.

TABLE 65

Adverse Events of Interest

| | Percentage of AEs during Period A | | Rates of AEs during Period A and for the Adalimumab Treatment Group | | |
|---|---|---|---|---|---|
| | Period A* Placebo (N = 398) % | Period A* Adalimumab (N = 814) % | Period A* Placebo (120.7 PY) Event/PY | Period A* Adalimumab (250.2 PY) Event/PY | Adalimumab Treatment Group† (540.5 PY) Event/PY |
| Tuberculosis (TB) | 0 | 0 | 0 | 0 | 0.002 |
| Opportunistic Infections, excluding TB | 0 | 0 | 0 | 0 | 0.002 |
| Congestive Heart Failure | 0 | 1 | 0 | 0.004 | 0.002 |
| Allergic Reaction | 0 | 1 | 0 | 0.004 | 0.002 |
| Injection Site Reaction | 5.3 | 6.9 | 0.215 | 0.276 | 0.017 |
| Malignancies, excluding NMSC + lymphoma | 0.3 | 0.2 | 0.008 | 0.008 | 0.004 |
| Non-melanoma skin cancers | 0.3 | 0.5 | 0.008 | 0.016 | 0.013 |
| Lymphoma | 0 | 0 | 0 | 0 | 0 |
| Lupus-like Syndrome | 0 | 0 | 0 | 0 | 0 |
| Demyelinating Disorder | 0 | 0 | 0 | 0 | 0 |

*Includes safety data up to 70 days after last dose for patients not continuing into Period B.
†Includes safety data up to 70 days after last dose of adalimumab for all patients who received at least one dose of adalimumab in REVEAL. Adverse events experienced by patients re-randomized to placebo in Period C (within 70 days after last dose of adalimumab in Period B) are included in this group.

From Table 66 it can be seen that during Period A, infectious AEs experienced by more than 2% of adalimumab-treated patient were upper respiratory tract infections (7.2%), nasopharyngitis (5.3%), and sinusitis (2.7%). The most common adverse events reported in the Adalimumab Treatment Group were upper respiratory tract infections, nasopharyngitis, and headache.

TABLE 67

Common Adverse Events ≥5%: Period A

|  | Placebo (N = 398) n (%) | Adalimumab (N = 814) n (%) |
|---|---|---|
| Upper Respiratory Tract Infection | 14 (3.5) | 59 (7.2) |
| Nasopharyngitis | 26 (6.5) | 45 (5.3) |

Includes safety data up to 70 days after last dose for patients not continuing into period B.

In conclusion, treatment with adalimumab 40 mg eow is efficacious for patients with moderate to severe psoriasis. Efficacy is sustained during open-label adalimumab treatment. Discontinuation of adalimumab is associated with loss of adequate response Percentages of serious AEs, serious infectious AEs, and malignancies were comparable between placebo- and adalimumab-treated patients during Period A.

achieved a Psoriasis Area and Severity Index (PASI) response of at least 50% after 12 weeks of open-label 40-mg weekly therapy.

Figure 8:
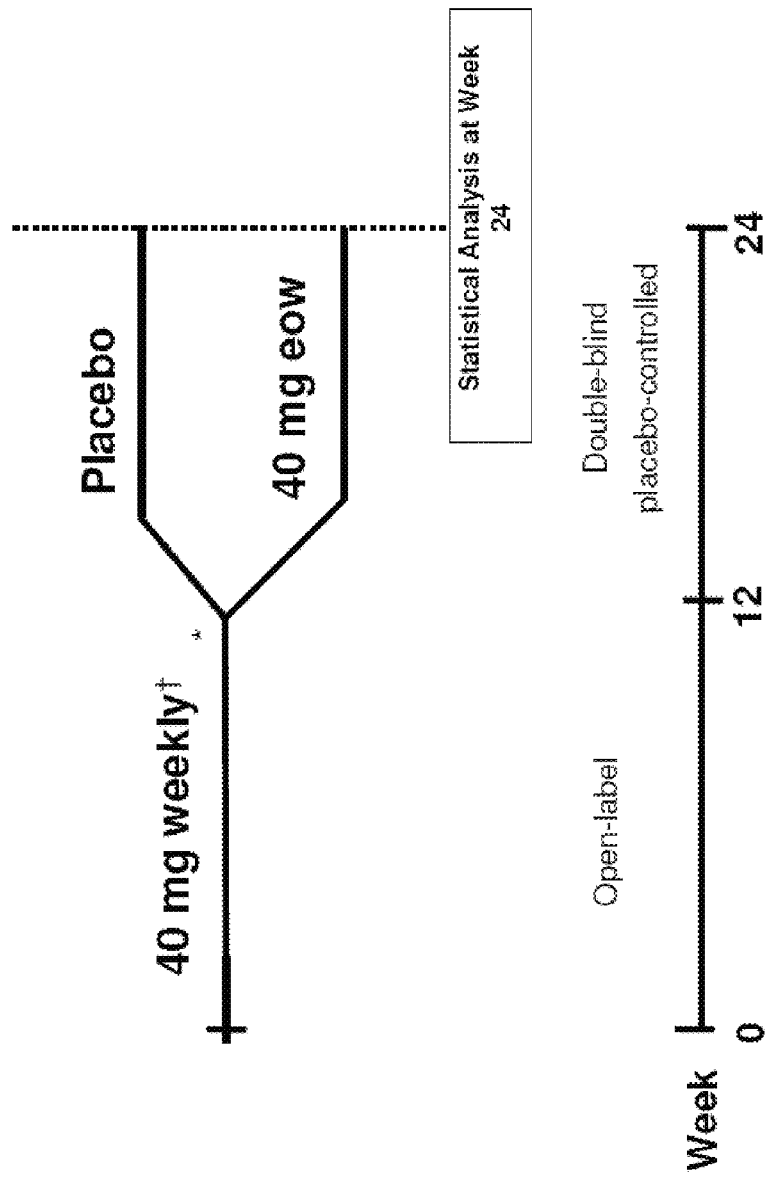
FIG. 8 describes the study design of Example 12.
Figure 9:
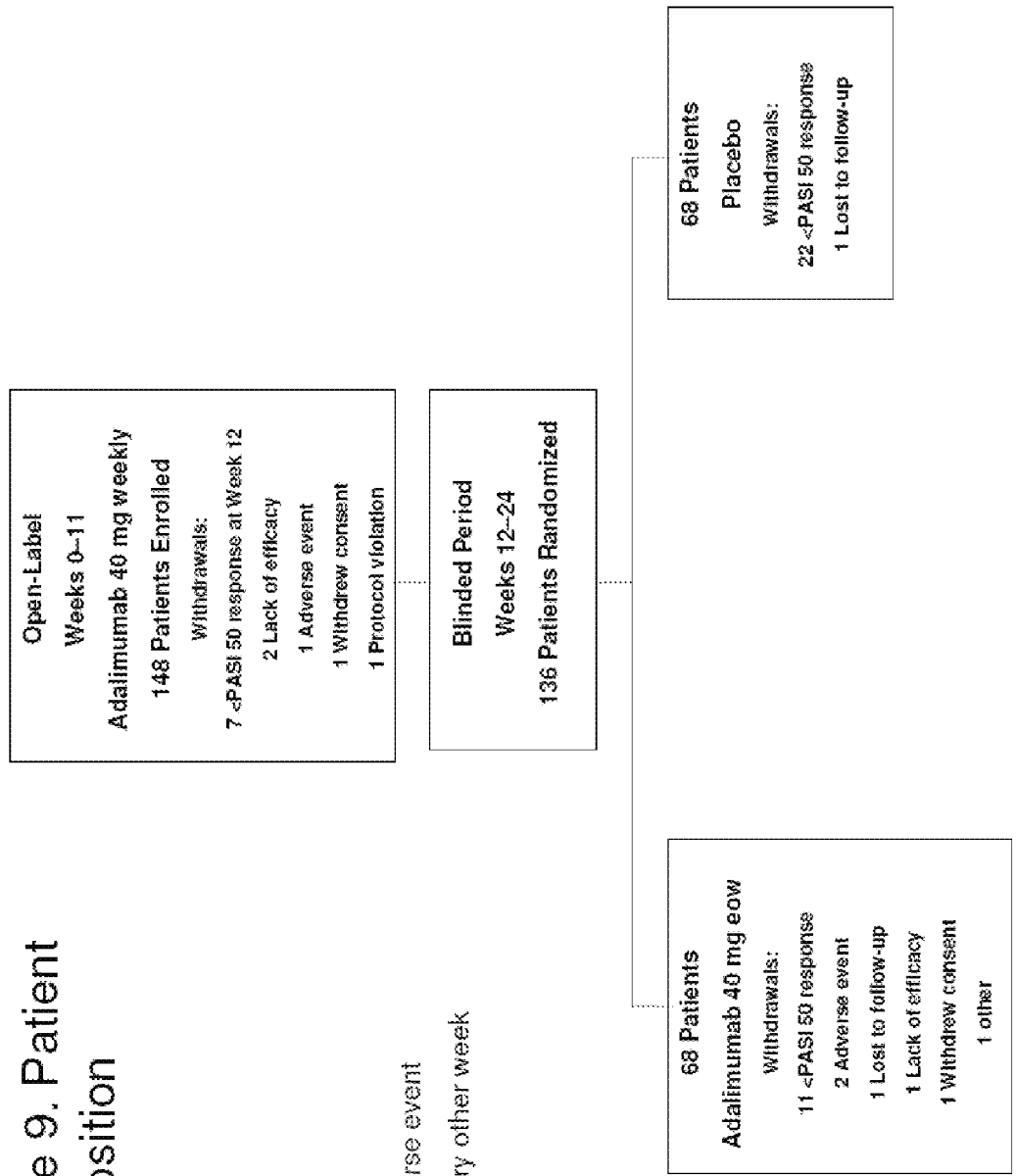
FIG. 9 describes patient disposition for Example 12.

In this multicenter, randomized, double-blind, placebo-controlled study, patients with moderate to severe plaque psoriasis received 12-week, open-label therapy with subcutaneous adalimumab, consisting of 80 mg of adalimumab at Weeks 0 and 1, followed by 40 mg weekly Weeks 2-11. At Week 12, patients who had an improvement in Psoriasis Area and Severity Index (PASI) score of ≥50% were randomized to blinded therapy and received either adalimumab 40 mg every other week (eow) or placebo for an additional 12 weeks. A diagram of the study design is shown in FIG. 8. During the double-blind period, 33.8% (23/68) of placebo patients discontinued early, vs. 25% (17/68) of adalimumab 40 mg eow patients (FIG. 9). This trial also featured a 52-week, follow-up period, during which no patients received injections in order to collect additional information regarding treatment-free relapse.

Baseline data were similar among randomization groups. Baseline demographics, disease severity characteristics, and recent history of systemic therapies were similar across the treatment groups. Table 68 shows the baseline demographics and clinical characteristics.

TABLE 68

Baseline Demographics and Clinical Characteristics

|  | All patients | Randomized patients (Week 12) | |
|---|---|---|---|
| Characteristic | (baseline) (N = 148) | Placebo (N = 68) | Adalimumab 40 mg eow (N = 68) |
| Age, years | 44 (18-69) | 45 (19-69) | 43 (18-64) |
| Male, % | 63 | 66 | 56 |
| Caucasian, % | 94 | 96 | 91 |
| Body weight, kg | 92 (47-155) | 90 (55-155) | 90 (47-150) |
| Duration of psoriasis, years | 20 (2-52) | 20 (2-45) | 21 (2-52) |
| BSA affected, % | 25 (5-99) | 25 (5-91) | 25 (5-99) |
| PASI score | 16.4 (8-46) | 16.3 (8-39) | 16.4 (8-46) |
| History of psoriatic arthritis, % | 29.0% | 26.5% | 35.3% |
| PGA, % |  |  |  |
| Severe psoriasis | 13 | 16 | 10 |
| Moderate to severe psoriasis | 40 | 41 | 38 |

Values represent means and ranges unless otherwise specified.
BSA = body surface area; PASI = Psoriasis Area and Severity Index; PGA = Physician's Global Assessment; eow = every other week.

Rates of serious AEs, serious infectious AEs, and malignancies were low over the 52-week duration of the study.

Example 12

Efficacy and Safety of Adalimumab Treatment in Patients with Moderate to Severe Psoriasis Patients: a Double-Blind, Randomized Clinical Trial It is necessary to assess the efficacy and safety of adalimumab therapy for patients with moderate to severe plaque psoriasis and evaluate the duration of treatment response after withdrawal from or dosage reduction of adalimumab therapy. Accordingly, the objective of this clinical trial was to investigate the time to relapse after either withdrawal of adalimumab or continued adalimumab therapy (but at a dosage lower [40 mg eow] than initially used) in patients with moderate to severe chronic plaque psoriasis who had During open-label treatment with adalimumab 40 mg weekly, most patients experienced clinically significant improvements in their psoriasis (Table 69. Clinical response was rapid, with a PASI 50 response rate of 28% at Week 2 of therapy. Ultimately, a PASI 50 response rate was observed in the vast majority of patients, with 92% (136/148) reaching PASI 50 at Week 12. In addition, PASI 75 and PASI 90 responses were achieved by 76.4% (113/148) and 47.3% (70/148) of patients, respectively. The percentage of patients who achieved a PGA "Clear" or "Minimal" was 66% (98/148) at Week 12. Patients with a recent history of treatment with biologic agents (within the past year), including TNF antagonists, had PASI 50 response rates similar to those of biologic-naïve patients. To this point, 12/14 patients exposed to etanercept, 4/4 patients exposed to infliximab, 6/6 exposed to alefacept, and 14/15 exposed to efalizumab achieved ≥PASI 50 responses and were randomized to placebo or adalimumab eow at Week 12.

TABLE 69

PASI Response During Open-Label Therapy, Weeks 0-12*

| | Week | Patients (%) |
|---|---|---|
| PASI50 | 4 | 59 |
| | 8 | 84 |
| | 12 | 92 |
| PASI75 | 4 | 26 |
| | 8 | 55 |
| | 12 | 30 |
| PASI90 | 4 | 9 |
| | 8 | 30 |
| | 12 | 47 |

*Patients with missing scores swere considered non-responders.

During the double-blind, placebo-controlled period (Weeks 12-24), the majority of patients in both groups sustained >PASI 50 scores vs. baseline. The point estimate of the hazard ratio of the risk of relapse for patients continuing on adalimumab was 0.7 (95% CI of 0.37-1.34), with a hazard ratio below 1 signifying lower risk of relapse than would be observed in the overall psoriasis population.

At Week 24, greater percentages of patients who had been randomized to adalimumab 40 mg eow sustained efficacy response, as assessed by several efficacy measures, compared with patients who had been randomized to adalimumab withdrawal (Table 70). A greater percentage of patients randomized to adalimumab 40 mg eow (54.4% 137/681) achieved PGA "Clear" or "Minimal" at Week 24 vs. patients who were withdrawn from adalimumab (39.7% 127/681) (p=0.069). For patients who achieved ≥PASI 75 at Week 12, the relapse rate (loss of PASI 50 response relative to baseline) at Week 24 was 17.2% for patients randomized to adalimumab eow and 23.6% for patients randomized to placebo.

TABLE 70

Percentages of patients achieving at least 75% and 90% Improvements in PASI at Week 24*

| | | Patients (%) |
|---|---|---|
| Placebo | PASI50 | 66 |
| | PASI75 | 49 |
| | PASI90 | 28 |
| Adalimumab | PASI50 | 78 |
| 40 mg eow | PASI75 | 68** |
| | PASI90 | 47** |

*Patients with missing scores were considered non-responders.
**p < 0.05 vs. placebo Adalimumab therapy was generally well-tolerated (Table 71). Of the 148 patients who received at least one dose of adalimumab, three withdrew because of an adverse event. The most frequently reported adverse events were nasopharyngitis and upper respiratory infection. The incidences of specific adverse events during Weeks 12-24 were similar between the placebo and adalimumab eow groups, with the exception of reports of arthralgias in the adalimumab group (7.4%), which were characterized as mild to moderate. Across the open-label and placebo-controlled periods of the trial, adverse events were most often mild or moderate and typically deemed unrelated or probably unrelated to treatment by the investigators.

TABLE 71

Adverse events by treatment group during the open-label (Weeks 0-11) and double-blind (Weeks 12-24) treatment periods

| | Open-label period | Double-blind period | |
|---|---|---|---|
| Event, n (%) | 40 mg weekly (N = 148) | Placebo (N = 68) | 40 mg eow (N = 68) |
| Any AE | 105 (70.9) | 36 (52.9) | 46 (67.6) |
| Any SAE | 2 (1.4) | 0 | 2 (2.9) |
| Any infectious SAE | 1 (0.7) | 0 | 2 (2.9) |
| Any AEs leading to discontinuation | 1 (0.7) | 0 | 2 (2.9) |
| Adverse Events* | | | |
| Upper respiratory tract infection | 9 (6.1) | 6 (8.8) | 10 (14.7) |
| Injection site reaction | 17 (11.5) | 1 (1.5) | 4 (5.9) |
| Nasopharyngitis | 11 (7.4) | 7 (10.3) | 3 (4.4) |
| Headache | 11 (7.4) | 0 | 1 (1.5) |
| Arthralgia | 4 (2.7) | 0 | 5 (7.4) |

All data are for the types of adverse events that occurred in ≥5% of patients in any group.
AE = adverse event; eow = every other week; SAE = serious adverse event; eow = every other week.

Four patients experienced serious adverse events during the 24-week trial. The two serious adverse events in the open-label period were cellulitis due to insect bite and limb pain, which were attributed by the investigator to fissures in the psoriatic plaques of the lower extremities. The two serious adverse events in the placebo-controlled period were diverticulitis and post-operative wound infection after Mohs' surgery for a basal cell carcinoma of the left hand with flap repair (both events in the adalimumab 40 eow group).

Three patients discontinued prematurely primarily because of an adverse event: one during the open-label period and two after randomization to adalimumab 40 mg eow. During the initial open-label period, one patient who experienced cellulitis subsequently developed acute renal failure, which the investigator ascribed to antibiotic treatment and deemed not related to study drug. Another patient in the open-label period developed pneumonia. This event was deemed possibly related to study drug. However, the patient's primary reason for discontinuation was withdrawal of consent. During the second, blinded period of the trial, a patient experienced a post-operative wound infection and subsequently developed a basal cell carcinoma and squamous cell carcinoma of the skin. Both of these events were deemed mild and considered possibly related to study drug by the investigator.

No patients developed tuberculosis or other opportunistic infections, lymphoma, melanoma, malignancies other than non-melanoma skin cancers, demyelinating disorders, lupus-like syndromes, or congestive heart failure. One patient in the adalimumab weekly/placebo group developed a herpes simplex infection, which was deemed a flare of a pre-existing herpes infection and was considered probably not related to study medication by the investigator. The patient who developed three non-melanoma skin cancers during the study previously had a keratoacanthoma excised 2 years earlier.

Three patients were classified by investigators as "rebounders." One patient had a baseline PASI score of 19.5, which increased to 27.3 by Week 4 of the open-label period. However, the patient did not discontinue, and, upon continued therapy, achieved a PASI score of 6.9 at Week 12. Another patient had a baseline PASI score of 17.1 and was assessed as having a treatment-emergent AE of "psoriasis aggravated" during the treatment-free follow-up period, at which time the patient's PASI score was 1.6. A third patient had a baseline PASI of 31.8 and was assessed as having a treatment-emergent AE of "worsening of psoriasis" during the treatment-free follow-up period, at which time this patient's PASI score was 15.5. None of the three patients met the study's pre-specified definition of rebound (ie, PASI score≥125% of Week-0 PASI score or new generalized pustular or erythrodermic psoriasis any time after Week 12 and within 90 days of last dose of study drug).

The majority of patients had no clinically significant laboratory abnormalities or changes from baseline during the 24-week period. No patients discontinued because of laboratory abnormalities. No patients had alanine aminotransferase (ALT) elevations greater than 2.5 times the upper limit of normal at Week 12. One patient in the adalimumab eow group had an ALT elevation greater than 2.5 times the upper limit of normal (212.0 U/ml) at Week 24. At the 30-day follow-up visit, the patient's ALT value was 125.0 U/ml. The patient was a self-reported moderate drinker.

In conclusion, weekly adalimumab therapy rapidly improved psoriasis during an initial 12-week period Improvement was sustained in most, but not all patients, despite dosage reduction to every other week. No patients randomized to adalimumab withdrawal (placebo at Week 12) experienced rebound, and most maintained >PASI50 improvement, relative to baseline, during the 3 months following adalimumab discontinuation. Overall, greater efficacy rates were observed for patients randomized to adalimumab 40 mg eow than for patients randomized to adalimumab withdrawal.

Example 13

A Comparison of Quality of Life Improvement as Measured by EQ-SD with Clinical Response in Moderate to Severe Plaque Psoriasis Patients Treated with Adalimumab The objective of this analysis was to assess the relationship between clinical efficacy and EQ-5D in moderate to severe plaque psoriasis patients treated with adalimumab for 12 weeks. Because moderate to severe psoriasis impairs patient function, patient-reported outcomes (PROs) that measure this effect are important in determining effectiveness of treatment. Clinical trials of biologics in patients with psoriasis have demonstrated significant improvements in PROs, as well as in clinical endpoints. However, the sensitivity of EQ-5D to clinical change has not been established. Several PRO measures, including the EuroQoL 5D (EQ-5D), were included as secondary efficacy endpoints in a 12-week, Phase II, placebo-controlled trial of adalimumab for the treatment of moderate to severe plaque psoriasis. The EQ-5D is a validated measure of general health status.

In this randomized, double-blind, multi-center clinical trial (FIG. 1), patients were randomized to one of three treatment groups: 80 mg adalimumab at baseline (Week 0) and 40 mg at Week 1 followed by 40 mg every other week (eow) starting at Week 3; 80 mg adalimumab at baseline (Week 0) and 80 mg at Week 1 followed by 40 mg weekly starting at Week 2; or placebo administered weekly starting at baseline. Inclusion criteria included a diagnosis of moderate to severe chronic plaque psoriasis≥1 year prior to entry, a psoriasis-affected body surface area (BSA)>5%, and no previous use of TNF-antagonist therapy. The relationship between mean change in EQ-5D and clinical responses was evaluated from baseline to Week 12. Table 72 shows the baseline demographics of the patients included in the study.

TABLE 72

Baseline Demographics

| Characteristic | (n = 147) |
| --- | --- |
| Age | |
| Mean (SD) | 44.2 (12.7) |
| Gender | |
| Female n (%) | 48 (32.7%) |
| Male n (%) | 99 (67.3%) |
| Race | |
| White n (%) | 133 (90.5%) |
| Black n (%) | 4 (2.7%) |
| Asian n (%) | 5 (3.4%) |
| Other n (%) | 5 (3.4%) |

PROs included the EQ-5D. The EQ-5D is a 6-item instrument validated to measure general health status. The EQ-5D consists of two measures: the EQ-5D Index, which consists of five items to assess level of function (mobility, self-care, usual activities, pain/discomfort, and anxiety/depression), each rated on a 3-point scale ranging from "no problem" to "extreme problem" to "unable to do"; and the EQ-5D VAS, which is a visual analog scale scored from 0-100, with 100 representing "best imaginable health" and 0 representing "worst imaginable health."

There were two primary clinical outcome measures in this clinical trial of adalimumab: Psoriasis Area and Severity Index (PASI), and Physician's Global Assessment (PGA). PASI improvement is frequently used as an endpoint in psoriasis clinical trials. PASI improvement≥75% at Week 12 was the primary efficacy outcome measure for this trial. PASI is a composite index indicating severity for three main signs of psoriatic plaques (erythema, scaling, and thickness), weighted by the amount of coverage of these plaques in four main body areas (i.e., head, trunk, upper extremities, and lower extremities). PASI scores range from 0-72, with higher scores indicating greater severity. PASI scores were assessed at screening; baseline; Week 1, Week 2, Week 4, Week 8, and Week 12/early termination; and follow-up.

The PGA is a 7-point scale used to measure disease severity from a physician's evaluation. The categories for the 7-point scale include: Severe: very marked plaque elevation, scaling, and/or erythema; Moderate to severe: marked plaque elevation, scaling, and/or erythema; Moderate: moderate plaque elevation, scaling, and/or erythema; Mild to moderate: intermediate between moderate and mild; Mild: slight plaque elevation, scaling, and/or erythema; Almost clear: intermediate between mild and clear; and Clear: no signs of psoriasis (post-inflammatory hypopigmentation or hyperpigmentation could be present). The scoring ranges are from 1 (Clear) to 7 (Severe). PGA was assessed at screening, baseline, Week 1, Week 2, Week 4, Week 8, Week 12/early termination, and follow-up. The same investigator performed this assessment for each patient throughout the study.

Data were available at the end of trial for 140 of the 147 patients enrolled. Mean values at baseline and mean values/change in mean values after 12 weeks for the EQ-5D index score and VAS score, as well as for PASI and PGA, are shown in Table 73. EQ-5D demonstrated significant responsiveness to changes in clinical efficacy. The correlation coefficient between EQ-5D and PASI response was 0.57 (p<0.001), and between EQ-5D and PGA was 0.44 (p<0.001). Mean change in EQ-5D was 15.69 in patients with >PASI 75 response vs. 1.92 points in non-responders (<PASI 50 response) (p<0.0001). Table 74 below shows the correlations between changes in EQ-5D with PASI and PGA. All correlations in Table 74 are significant (p<0.001).

TABLE 73

Mean (SD) EQ-5D and Clinical Measures at Baseline and Week 12

|  | Baseline (N = 147) | Week 12 (N = 140) | Change[2] (N = 140) |
|---|---|---|---|
| EQ-5D: VAS-Overall Health | 72.25 (20.67) | 81.22 (17.26) | 9.35 (20.71) |
| EQ-5D: Total Index Score | 0.66 (0.28) | 0.82 (0.23) | 0.16 (0.29) |
| Psoriasis Area and Severity Index (PASI) | 15.7 (7.3) | 6.8 (7.8) | −8.9 (8.4) |
| Physician's Global Assessment[1] (PGA) | 5.5 (0.8) | 3.4 (1.7) | −2.1 (1.9) |

[1]Scored such that 1 = "Clear" to 7 = "Severe."
[2]Calculated only for patients with both baseline and Week-12 scores.
Numbers in parentheses are standard deviations (SD).

TABLE 74

Correlation Between Changes in EQ-5D with PASI and PGA

|  | PASI | PGA |
|---|---|---|
| EQ-5D: VAS Overall Health | −0.43 | −0.38 |
| EQ-5D: Total Index Score | −0.57 | −0.44 |
| PASI | 1.00 | 0.75 |

The mean change in EQ-5D index scores was 0.25 (0.30) for patients with >PASI 75 response versus 0.04 (0.29) for non-responders (<PASI 50 response) (p=0.0006), as shown in Table 75.

TABLE 75

Mean (SD) EQ-5D Change Score Corresponding to Levels of PASI Improvement
PASI Improvement

| Change in EQ-5D | <25% (n = 31) | 25%-49% (n = 22) | 50%-74% (n = 21) | ≥75% (n = 66) | Overall F-Value |
|---|---|---|---|---|---|
| Index Score | −0.01 (0.26) | 0.10 (0.24) | 0.20 (0.21) | 0.25 (0.30) | 7.1** |
| VAS-General Health | 0.58 (24.31) | 3.82 (22.07) | 8.43 (11.24) | 15.69 (18.69) | 4.8* |

Negative change scores indicate improvement; p-values are:
*<0.01 and
**<0.001.
Post-hoc tests indicate that the PASI <25% group differed significantly from the PASI >75% group.
Numbers in parentheses are standard deviations (SD).

Patients in both adalimumab treatment arms demonstrated statistically significant improvement versus placebo in EQ-5D, in PASI 75 response rate, and in percentage of patients with PGA "clear" or "almost clear" from baseline to Week 12 (see Table 76 through Table 79).

TABLE 76

Mean Change in EQ-5D Index at Week 12

|  | Placebo | Adalimumab 40 mg eow | Adalimumab 40 mg weekly |
|---|---|---|---|
| Change from Baseline | 0.014 | 0.212 | 0.198 |

TABLE 77

Mean Change in EQ-5D VAS at Week 12

|  | Placebo | Adalimumab 40 mg eow | Adalimumab 40 mg weekly |
|---|---|---|---|
| Change from Baseline | 0.6 | 18 | 10.9 |

TABLE 78

Percentages of Patients with PGA "Clear" or "Almost Clear" at Week 12

|  | Placebo | Adalimumab 40 mg eow | Adalimumab 40 mg weekly |
|---|---|---|---|
| % of Patients | 2 | 51 | 81 |

TABLE 79

Percentages of Patients with > PASI 75 Response at Week 12

|  | Placebo | Adalimumab 40 mg eow | Adalimumab 40 mg weekly |
|---|---|---|---|
| % of Patients | 4 | 53 | 80 |

Overall, the EQ-5D VAS and index scores were highly responsive to clinical improvement in patients with moderate to severe plaque psoriasis who received adalimumab. The level of agreement shown suggests that adalimumab may be highly efficacious in improving both health status and clinical efficacy in patients with moderate to severe plaque psoriasis.

Example 14

Long-Term Safety and Efficacy of Adalimumab in the Treatment of Moderate to Severe Chronic Plaque Psoriasis Psoriasis is a chronic inflammatory proliferative disease of the skin that affects 1-3% of the general population. Conventional treatments of psoriasis such as NSAIDs and DMARDs fail to achieve adequate efficacy. Newer biologics have been developed that focus on the immunopathogenic pathway of the disease.

Figure 5:
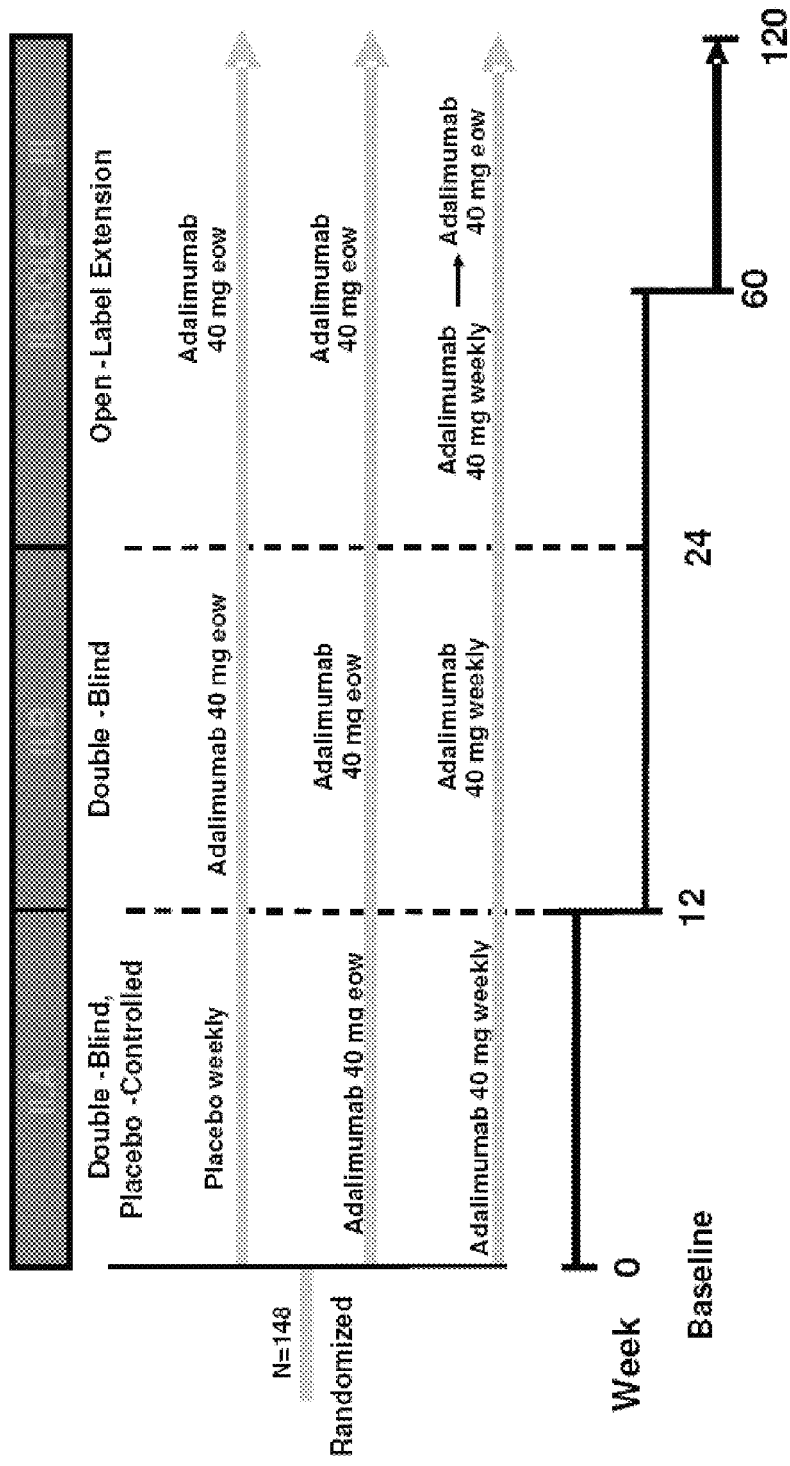
FIG. 5 describes the study design described in Example 10, which is a Phase III study off of a Phase II study.

A 12 week, double-blind placebo controlled trial, with a 48 week extension, was performed to evaluate the long-term safety and efficacy of adalimumab in the treatment of moderate to severe chronic plaque psoriasis. The criteria for inclusion in this study were as follows: patients were at least 18 years of age; patients had moderate to severe chronic plaque psoriasis for at least one year; and patients had a BSA of at least 5%. Patients were excluded if they had prior TNF-antagonist therapy, and/or if they had discontinued other systemic psoriasis therapies. The study design is shown in FIGS. 1 and 5

The baseline demographics and clinical characteristics of the patient population included in this study are shown below in Table 2.

TABLE 80

Baseline Demographics and Clinical Characteristics*

|  | Placebo (n = 52) | Adalimumab 40 mg eow (n = 45) | Adalimumab 40 mg weekly (n = 50) |
|---|---|---|---|
| Age, years (range) | 43 (20-70) | 46 (20-71) | 44 (24-86) |
| Duration of Ps, years (range) | 19.1 (1.0-39.8) | 20.5 (1.3-57.9) | 18.4 (1.7-47.7) |
| % Male | 65 | 71 | 66 |
| % Caucasian | 92 | 89 | 90 |
| Body weight, kg (range) | 94 (50-147) | 93 (63-159) | 99 (42-149) |
| % BSA (range) | 27.7 (7-75) | 29.2 (6-58) | 24.6 (5-83) |
| Psoriasis Area and Severity Index (PASI) Score (range) | 16.0 (5.5-40.4) | 16.7 (5.4-39.0) | 14.5 (2.3-42.4) |
| % with PsA | 31 | 33 | 24 |

*Mean values except percentages
Langely, R., et al., *J. Am. Acad. Dermatol* 2005; 52(3 Suppl): 2.

Overall, patients with moderate to severe psoriasis treated with adalimumab achieved sustained efficacy through 60 weeks of treatment (see Table 80). At week 12, placebo patients received an 80-mg loading dose, then 40 mg every other week. Patients with missing PASI scores were considered non-responders. Patients with less than PASI 50 response on or after week 24 received OL weekly adalimumab rescue therapy. Patients who receive the rescue therapy were considered non-responders in this analysis.

TABLE 80

Psoriasis Efficacy is Sustained Through 60 Weeks of Adalimumab Therapy

|  | Week 12 | Week 24 | Week 36 | Week 60 |
|---|---|---|---|---|
| Percentage of patients treated with placebo/adalimumab 40 mg eow who achieved PASI 100 | 0 | 11 | 19 | 19 |
| Percentage of patients treated with adalimumab 40 mg eow who achieved PASI 100 | 11* | 13 | 22 | 16 |
| Percentage of patients treated with adalimumab 40 mg weekly who achieved PASI 100 | 26* | 24 | 36 | 26 |

*$p < 0.001$ versus placebo.
N = 148 (modified ITT, N = 147) at week 12. N = 142 at weeks 12 through 60.

The PASI 90 results through week 60 are shown below in Table 18. At week 12, placebo patients received an 80-mg loading dose and then a 40 mg dose every other week. Patients with less than PASI 50 response on or after week 24 received OL weekly adalimumab rescue therapy. Patients receiving rescue therapy were considered non-responders in this analysis.

TABLE 81

PASI 90 Results through Week 60

|  | Week 12 N = 147 | Week 24 N = 142 | Week 36 N = 142 | Week 60 N = 142 |
|---|---|---|---|---|
| Percentage of patients treated with placebo/adalimumab 40 mg eow who achieved PASI 90 | 0 | 32 | 43 | 40 |
| Percentage of patients treated with adalimumab 40 mg eow who achieved PASI 90 | 24* | 42 | 49 | 33 |
| Percentage of patients treated with | 48* | 62 | 58 | 48 |

TABLE 81-continued

PASI 90 Results through Week 60

| | Week 12 N = 147 | Week 24 N = 142 | Week 36 N = 142 | Week 60 N = 142 |
|---|---|---|---|---|
| adalimumab 40 mg weekly who achieved PASI 90 | | | | |

*p < 0.001 versus placebo.
Modified ITT, NRI

In the adalimumab 40 mg every other week treatment group, 58% of patients achieved a PASI 75 response at week 60 (see Table 82 below). At week 12, placebo patients received an 80-mg loading dose and then a 40 mg dose every other week. Patients with less than PASI 50 response on or after week 24 received OL weekly adalimumab rescue therapy. Patients receiving rescue therapy were considered non-responders in this analysis.

TABLE 82

PASI 75 Results through Week 60

| | Week 12 N = 147 | Week 24 N = 142 | Week 36 N = 142 | Week 60 N = 142 |
|---|---|---|---|---|
| Percentage of patients treated with placebo/adalimumab 40 mg eow who achieved PASI 75 | 4 | 55 | 62 | 45 |
| Percentage of patients treated with adalimumab 40 mg eow who achieved PASI 75 | 53* | 64 | 64 | 58 |
| Percentage of patients treated with adalimumab 40 mg weekly who achieved PASI 75 | 80* | 72 | 68 | 64 |

*p < 0.001 versus placebo/adalimumab 40 mg eow group
Modified ITT, NRI

The PASI 50/75/90 results at weeks 12 and 60 are shown in Table 83. At week 12, the group of patients receiving placebo began an 80 mg loading dose, followed by 40 mg every other week. Patients for whom adalimumab dosages were escalated were considered non-responders from time of dose escalation forward.

TABLE 83

PASI 50/75/90 at Weeks 12 and 60

| | Week 12 (n = 147) | | | Week 60 (n = 142) | | |
|---|---|---|---|---|---|---|
| | PASI 50 (% patients) | PASI 75 (% patients) | PASI 90 (% patients) | PASI 50 (% patients) | PASI 75 (% patients) | PASI 90 (% patients) |
| placebo/ adalimumab 40 mg eow | 17 | 4 | 0 | 64 | 45 | 40 |
| adalimumab 40 mg eow | 76 | 53 | 24 | 67 | 58 | 33 |
| adalimumab 40 mg weekly | 88 | 80 | 48 | 66 | 64 | 48 |

Modified ITT, NRI

The percentage of patients included in this study who achieved a PGA of "clear" or "almost clear" is shown below in Table 84. At week 12, placebo patients received an 80 mg loading dose, and then received 40 mg every other week. Patients with less than a PASI 50 response on or after week 24 received OL weekly adalimumab rescue therapy. Patients receiving rescue therapy were considered non-responders in this analysis.

TABLE 84

Percentage of Patients Achieving PGA "Clear" or "Almost Clear"

| | Week 12 N = 147 | Week 24 N = 142 | Week 36 N = 142 | Week 60 N = 142 |
|---|---|---|---|---|
| placebo/adalimumab 40 mg eow (% patients) | 2 | 45 | 51 | 45 |
| adalimumab 40 mg eow (% patients) | 49* | 64 | 60 | 44 |
| adalimumab 40 mg weekly (% patients) | 76* | 72 | 68 | 52 |

*p < 0.001 versus placebo/adalimumab 40 mg eow group
Modified ITT, NRI

Figure 10:
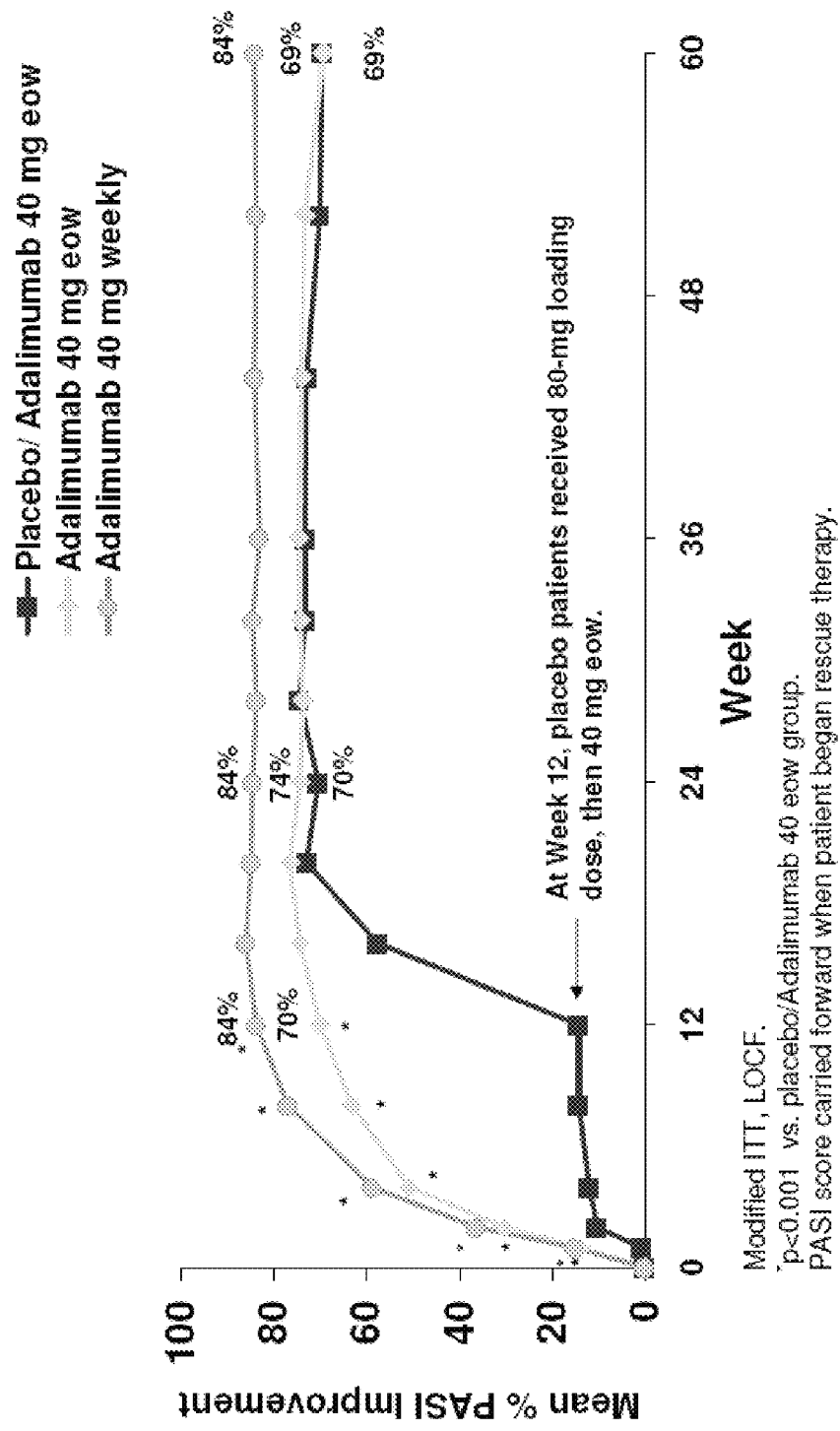
FIG. 10 describes the mean percentage PASI improvement through week 60 of the Phase II trial.

The mean percentage PASI improvement through week 60 is shown in FIG. 10. At week 12, placebo patients received an 80-mg loading dose of adalimumab, and then a 40 mg dose every other week. The PASI score was carried forward when the patient began rescue therapy. As can be seen in FIG. 10, at week 60, there was an 84% overall PSAI improvement in patients receiving a 40 mg weekly dose of adalimumab, and a 69% PASI improvement in patients receiving either a 40 mg every other week dosage of placebo/adalimumab, or 40 mg of adalimumab alone, on a weekly basis. The PASI response after dose escalation from every other week to weekly dosing is shown in Table 85.

TABLE 85

PASI Response After Dose Escalation

| Efficacy at Weeks 24-60 (n = 22) | | | Efficacy at Week 60 (n = 22) | | |
|---|---|---|---|---|---|
| PASI 50 (% patients) | PASI 75 (% patients) | PASI 90 (% patients) | PASI 50 (% patients) | PASI 75 (% patients) | PASI 90 (% patients) |
| 55 | 23 | 5 | 36 | 18 | 0 |

The study described herein also indicated that a dose escalation improves the outcome in a subset of patients. For example, 15% (two out of thirteen patients in the treatment arm that received a dose escalation) of patients in the original placebo/adalimumab 40 mg every other week treatment arm had a PASI≥75 at week 60. In the original adalimumab 40 mg every other week treatment arm, 22% (two out of nine patients) of patients receiving a dose escalation had a PASI≥75 at week 60. However, few patients needed dose escalation to achieve PASI 75 at week 60 (see Table 86 below).

TABLE 86

Patients Eligible for Dose Escalation

| Patients Eligible for Dose Escalation | Placebo/Adalimumab 40 mg eow (n = 13) | Adalimumab 40 mg eow (n = 9) |
|---|---|---|
| Week 24 | 5 | 5 |
| Week 28 | 2 | 1 |
| Week 32 | 2 | 0 |
| Week 44 | 1 | 1 |
| Week 52 | 3 | 0 |
| Week 60 | 0 | 2 |
| PASI 75 Response at Week 60 | 15% (2/13) | 22% (2/9) |

The types and rates of adverse events recorded in this study were similar to those previously reported in adalimumab rheumatoid arthritis and psoriatic arthritis trials. Table 87 shows the number of patients who withdrew from the study, and the reasons for the withdrawal. The number of adverse events by treatment period is shown in Table 88.

TABLE 87

Patient Disposition

| | Placebo-Controlled Period Week 0-12 | | | Integrated Data Set Week 0-60 | | |
|---|---|---|---|---|---|---|
| | | | | Placebo/ | | |
| | Placebo (N = 52) | Adalimumab 40 mg eow (N = 45) | Adalimumab 40 mg weekly (N = 50) | Adalimumab 40 mg eow (N = 52) | Adalimumab 40 mg eow (N = 45) | Adalimumab 40 mg weekly (N = 50) |
| Withdrawals | 2 | 2 | 3 | 14 | 10 | 17 |
| Adverse events | 1 | 2 | 2 | 2 | 4 | 8 |
| Lack of Efficacy | 1 | 0 | 0 | 6 | 6 | 4 |
| Withdrew Consent | 0 | 0 | 0 | 2 | 0 | 1 |
| Abnormal lab value | 0 | 0 | 1 | 0 | 0 | 1 |
| Other | 0 | 0 | 0 | 1 | 0 | 3 |
| Did not Enter Study 1.2 | N/A | N/A | N/A | 3 | 0 | 0 |

TABLE 88

Adverse Events by Treatment Period

| | Weeks 0-12 | | | Weeks 12-60 Placebo/Adalimumab | |
|---|---|---|---|---|---|
| Event, n (%) | Placebo (n = 52) | Adalimumab 40 mg eow (n = 45) | Adalimumab 40 mg weekly (n = 50) | 40 mg eow + Adalimumab 40 mg eow (n = 92) | Adalimumab 40 mg weekly (n = 50) |
| Any Adverse Event | 35 (67.3) | 28 (62.2) | 39 (78.0) | 72 (78.3) | 39 (78.0) |
| Serious Adverse Events | 0 (0.0) | 1 (2.2) | 4 (8.0) | 2 (2.2) | 7 (14.0) |
| Adverse Events Leading to Withdrawal | 1 (1.9) | 2 (4.4) | 3 (6.0) | 3 (3.3) | 5 (10.0) |

Table 89 shows the most common adverse events that occurred in patients between weeks 12 and 60.

TABLE 89

Common Adverse Events, Week 12-60

| Event, n (%) | Placebo/Adalimumab 40 mg eow + Adalimumab 40 mg eow (n = 92) | Adalimumab 40 mg weekly (n = 50) |
|---|---|---|
| Nasopharyngitis | 13 (14.1) | 6 (12.0) |
| Upper Respiratory Infection, Not otherwise specified | 9 (9.8) | 7 (14.0) |
| Upper Respiratory Infection, Viral not otherwise specified | 4 (4.3) | 3 (6.0) |
| Muscle strain | 1 (1.1) | 4 (8.0) |
| Blood creatine phosphokinase increased | 5 (5.4) | 2 (4.0) |
| Blood triglycerides increased | 7 (7.6) | 2 (4.0) |
| Back pain | 4 (4.3) | 4 (8.0) |
| Skin papilloma | 3 (3.3) | 5 (10.0) |
| Headache | 3 (3.3) | 6 (12.0) |
| Urticaria | 0 (0.0) | 3 (6.0) |

Some serious adverse events that occurred during weeks 0-12 included: squamous cell carcinoma of the neck (in an ex-smoker, prior to study entry); breast cancer on routine mammogram (5 weeks after entry); migraine; cerebrovascular accident reported by patient after last dose; and bronchitis. Some of the serious adverse events that occurred through weeks 12-60 included: malignant melanoma (discovered under plaque that cleared with adalimumab treatment); accidental fall with soft tissue injury; osteoarthritis; kidney stones; stomach adenocarcinoma (history of peptic ulcer disease); palpitations; coronary artery disease; malignant melanoma; and cerebrovascular accident.

Example 15

Psoriasis Patients Treated Continuously with Adalimumab: Efficacy and Safety Results from Month 12 to 18

Objective:

Adalimumab is a fully human, $IgG_1$ monoclonal antibody specific for tumor necrosis factor, a pivotal cytokine in the pathogenesis of psoriasis. This analysis was designed to determine the long-term (up to 18 months) efficacy and safety of adalimumab in patients with moderate to severe psoriasis.

Methods:

REVEAL (Randomized Controlled EValuation of Adalimumab Every Other Week Dosing in Moderate to Severe Psoriasis TriAL) was a 52 week, randomized, double-blind, placebo-controlled, Phase III clinical trial of adalimumab in 1,212 patients for the treatment of moderate to severe chronic plaque psoriasis. Patients who completed REVEAL could subsequently enroll in an open-label extension (OLE), during which continuous adalimumab therapy was administered. The experience during the first 6 months of OLE for the subset of patients who had received continuous adalimumab for 12 months in REVEAL was summarized based on interim analyses conducted in May 2007. PASI responses were analyzed relative to the baseline of REVEAL for the intention-to-treat population, defined as patients who received continuous adalimumab dosing in the 52-week REVEAL, completed REVEAL, and received ≥1 dose of adalimumab in OLE.

Main inclusion criteria for REVEAL were: clinical diagnosis of psoriasis for ≥6 months; affected body surface area (BSA)≥10%; PASI≥12; and a Physician's Global Assessment (PGA) of at least "Moderate". Main exclusion criteria was the previous use of systemic anti-TNF therapy. The study measured PASI 75, 90 and 100 response rates at weeks 0, 12, and 24 of the OLE period. PGA scores were assessed at weeks 0, 12 and 24 of the OLE period. Laboratory parameters and adverse events were also recorded.

The REVEAL study had two independent primary endpoints. The first endpoint was the proportion of patients achieving 75 percent improvement in skin clearance after 16 weeks. The second endpoint was the proportion of patients who lost adequate response through week 52 after stopping treatment with HUMIRA at week 33. Signs of psoriasis were evaluated using the Psoriasis Area and Severity Index (PASI), among other measures. Patients receiving adalimumab who achieved at least a PASI 75 response at week 16 continued to receive adalimumab on an open-label basis. At week 33, the 490 patients who maintained PASI 75 were randomized to receive placebo or continue receiving adalimumab. At week 52, the start of the OLE period, patients randomized at week 33, as well as patients originally in the placebo group at week 0, were able to enter the OLE period. Patients in the OLE period received 40 mg adalimumab EOW.

Results:

PASI 75 response scores were measures at the end of weeks 4, 8, 12, 16 and 24 during the double-blind phase of the study. PASI 75, 90 and 100 response rates were also measured at weeks 0, 12 and 24 of the OLE (weeks 52, 64 and 76 after the start of REVEAL). PGA scores were assessed at the same timepoints during OLE. Results are shown below in Tables 90-92.

TABLE 90

PASI 75 Response: Week 0 to 24

| | Placebo † | Adalimumab ‡ |
|---|---|---|
| Week 4 | 1.3% | 18.9% * |
| Week 8 | 3.0% | 54.1% * |
| Week 12 | 4.8% | 67.7% * |
| Week 16 | 6.5% | 71.0% * |
| Week 24 | | 70.3% ** |

* $p < 0.001$ adalimumab vs placebo;
† n = 398;
‡ n = 814
** Pooling of efficacy outcomes from Period B (wks. 16 to 33) and OLE
ITT: NRI

TABLE 91

PASI Response Rates During the First 24 Weeks of OLE

| | PASI 75 | PASI 90 | PASI 100 |
|---|---|---|---|
| Week 0 | 85% | 84% | 87% |
| Week 12 | 59% | 60% | 63% |
| Week 24 | 35% | 33% | 34% | n = 233; ITT: Last observation carried forward (LOCF).

TABLE 92

PGA Scores of "Clear" or "Minimal"
During the First 24 Weeks of the OLE

| | PGA "Clear" or "Minimal" |
|---|---|
| Week 0 | 70% |
| Week 12 | 71% |
| Week 24 | 74% | n = 233; ITT: LOCF

TABLE 93

Adverse Events During the First 24 Weeks of OLE

| Adverse Events (AEs) | Patients (%) |
|---|---|
| Any AE | 47 |
| AEs leading to withdrawal | 1 |
| Infectious AEs | 18 |
| Serious AE* | 3 |
| Serious infectious AE | 1 |
| Malignancy† | 1 |
| Lymphoma | 0 |
| Non-melanoma skin cancer | 0 |
| AEs occurring ≥5% of patients | |
| Nasopharyngitis | 5 |

*Serious AEs included a bile duct stone, coronary artery disease in a patient with a history of coronary artery bypass graft, myocardial infarction (MI) in a patient with a history of 2 previous MIs, renal cell carcinoma, gastroenteritis, and staphylococcal infection.
†Renal cell carcinoma and prostate cancer.

A total of 233 patients were included in the intention-to-treat population. Their PASI 75/90/100 response rates were 85%/59%/35% after 12 months of continuous adalimumab dosing, and 87%/63%/34% after 18 months. Six patients (2.6%) experienced serious adverse events, and 2 patients (0.9%) reported serious infections (between Months 12-18).

PGA scores of "clear" or "minimal were reported for 74% of patients.

Conclusion:

Patients who had received adalimumab for 12 months experienced sustained improvement when continued through 18 months. Adalimumab was safe and well-tolerated for up to 18 months of treatment. Long-term adalimumab treatment of patients with moderate to severe psoriasis was associated with sustained and substantial degrees of improvement and a low risk of serious infections, which suggests a favorable benefit/risk balance.

Example 16

Methotrexate-treated Psoriasis Patients Transitioning to Adalimumab: Efficacy and Safety Outcomes Objective:

Adalimumab is a fully human, $IgG_1$ monoclonal antibody that inhibits TNF, a pivotal cytokine in the pathogenesis of psoriasis. This analysis was conducted to determine the efficacy and safety of transitioning methotrexate-treated psoriasis patients to adalimumab.

Methods:

CHAMPION was a 16-week, Phase III, active- and placebo-controlled trial in which patients with moderate to severe chronic plaque psoriasis were randomized to receive placebo, methotrexate, or adalimumab. Patients who completed CHAMPION could subsequently enroll in an open-label extension (OLE) study, during which patients received adalimumab 40 mg every other week. Patient experience associated with transitioning from methotrexate to adalimumab was summarized based on interim analyses conducted in May 2007. PASI responses were analyzed relative to baseline of CHAMPION for the intention-to-treat population, defined as patients who were randomized to methotrexate in the 16-week CHAMPION, completed CHAMPION, and received ≥1 dose of adalimumab in the OLE.

Results:

At week 16 of CHAMPION, PASI response rates were evaluated from placebo, methotrexate and adalimumab patients. Results are shown in Table 94.

TABLE 94

PASI Response Rates at Week 16 of CHAMPION

| | Placebo (N = 53) | MTX (N = 110) | ADA (N = 108) |
|---|---|---|---|
| PASI 50 | 30.2% | 61.8% | 88.0% * † |
| PASI 75 | 18.9% | 35.5% | 79.6% * † |
| PASI 90 | 11.3% | 13.6% | 51.9% * † |
| PASI 100 | 1.9% | 7.3% | 16.7% ‡ § |

* $p < 0.001$ vs. placebo;
† $p < 0.001$ vs. MTX;
‡ $p < 0.01$ vs. placebo;
§ $p < 0.05$ vs. MTX.
Analysis: ITT, nonresponder imputation (NRI).
ITT population defined as population randomized in CHAMPION.
Saurat J H, et al. Br J Dermatol. 2007; DOI: 10.1111/j.1365-2133.2007.08315.x.a.

The intention-to-treat population comprised 95 patients. These patients received a mean methotrexate dose of 19.1 mg in the penultimate week of CHAMPION. Their PASI 75/90/100 response rates were 28%/14%/5% prior to starting adalimumab, 75%/47%/18% after 12 weeks of adalimumab therapy and 73%/53%/32% after 24 weeks of adalimumab therapy. No cases of rebound were observed, and no patients experienced serious infections during the first 24 weeks of the OLE. Adverse events are presented in Table 95.

TABLE 95

Adverse Events through Week 24 of the OLE (N = 95)

| Adverse Events (AE) | Percentage of Patients |
|---|---|
| Any AE | 47 |
| AEs leading to withdrawal | 1 |
| Infectious AEs | 15 |
| Serious AE* | 5 |
| Serious infectious AE | 0 |
| Rebound psoriasis | 0 |
| Any malignancy | 0 |
| AEs occurring ≥5% of patients | |
| Nasopharyngitis | 6 |
| Injection-site reaction | 5 |

*Serious AEs during the OLE included pneumothorax, neuralgia, avascular necrosis of hip, spontaneous abortion, and motorbike accident.

Conclusion:

The transition of patients with psoriasis from methotrexate to adalimumab was safe and well-tolerated (no rebound psoriasis observed when adalimumab was started 1 week after MTX was discontinued), with low risk of serious infections. Adalimumab therapy led to substantial skin improvements in these transitioning patients and was found to be more efficacious than MTX for treatment of moderate to severe chronic plaque psoriasis.

Example 17

Health-Related Quality of Life (HRQOL) and Work Productivity Outcomes for Psoriasis Patients in Europe Background:

Psoriasis (Ps) dramatically affects patients' HRQOL and daily functioning. Ps often leads to work impairment in 2 forms: absenteeism and presenteeism (reduced productivity while at work).

Objectives:

With data on patient-reported outcomes, this study investigated the extent to which Ps impairs patients' HRQOL, or leads to absence from work, reduced productivity while at work, and decreases in daily activities.

Methods:

The study consisted of respondents to a 2007 EU National Health and Wellness Survey (NHWS), an annual cross-sectional survey of representative samples of adults (≥18 years) from 5 countries (France, Germany, Italy, Spain, UK). The Internet survey was completed by 53,524 respondents in June 2007. We assumed self-reports of a diagnosis of Ps were bona fide. All respondents completed a self-administered questionnaire, which included the Short Form 12 (SF-12) and Work Productivity and Activity Impairment (WPAI) questionnaire. Results were stratified by disease severity based on BSA affected (mild, <2% BSA; moderate, 2-10%; severe, ≥10%) and compared with the non-Ps population. Bivariate analyses compared subgroups. Statistical testing employed Z-test in Quantum for percentages and t-tests for means.

Results:

2,288 respondents reported being diagnosed with Ps by a physician. Of these, 598 reported moderate (n=484) or severe (n=114) disease. SF-12 results demonstrated poor quality of life, via both the Physical and Mental Component Summary scores, especially for patients with moderate and severe Ps. Overall, moderate and severe Ps patients reported significantly lower mental and physical health status than mild and non-Ps sufferers (PCS: 48.51, 46.62, 45.18, and 43.09; MCS: 46.86, 45.43, 42.74, and 41.12, for non-Ps, mild, moderate and severe Ps, respectively, $p<0.05$). For employed patients with severe Ps, a mean 4-hour absence from work per week was reported, vs. 2 hours per week for mild and non-Ps sufferers ($p<0.05$). For patients with moderate Ps, a mean of 3 hours' absence from work per week was reported, which was greater than the absence of non-Ps sufferers ($p<0.05$). If those with absenteeism alone (19%) were considered, mean hours missed were 16/week and 18/week for moderate and severe Ps patients, respectively. Moderate and severe Ps sufferers had greater work productivity and activity impairment vs. mild or non-Ps sufferers ($p<0.05$). Severe Ps sufferers had 29% impairment in work productivity and 28% impairment in daily activities, while moderate Ps patients had 24% and 25% impairments respectively. By comparison, mild Ps patients/non-Ps sufferer reported lower reductions in work impairment (20%/17%) and daily activities (19%/17%).

Conclusions:

Psoriasis has both physical and mental impacts, which increase with severity. Associated loss in work productivity and daily activities has considerable costs to society. Therapies that help patients achieve mild disease or remission improve HRQOL and work productivity outcomes.

Example 18

Effect of Adalimumab Treatment on C-Reactive Protein in Patients with Moderate to Severe Psoriasis Background:

C-reactive protein (CRP), a biomarker of systemic inflammation, is elevated in patients with psoriasis (Ps) and is a predictor of future cardiovascular risk. Recent studies have demonstrated that patients with moderate to severe Ps are at increased risk for cardiovascular disease.

Objectives:

To evaluate CRP concentrations in patients with moderate to severe Ps before and after treatment with adalimumab.

Methods:

REVEAL (Randomized Controlled Evaluation of Adalimumab Every Other Week Dosing in Moderate to Severe Psoriasis Trial) was a 52-week (wk), double-blind, randomized, placebo-controlled, Phase III trial of adalimumab in patients with moderate to severe chronic plaque Ps conducted in the United States and Canada. During the first 16 weeks (Period A), patients were treated with adalimumab (80 mg at Wk 0, 40 mg every other wk from Wk 1-15) or placebo. This post-hoc analysis of REVEAL evaluated CRP concentrations in Ps patients at baseline and after 16 wks of treatment with adalimumab or placebo. Changes in CRP concentrations were also evaluated in subgroups with or without self-reported psoriatic arthritis (PsA) and with or without obesity (by body mass index [BMI]). The CRP assay had an upper limit of normal of 9.0 mg/L. The lower limit of detection was 4.0 mg/L; results ≤4.0 were recorded as 4.0 mg/L.

Results:

Of 1,212 patients in REVEAL, 814 were randomized to adalimumab and 398 were randomized to placebo. At baseline, 28% of patients had PsA, and the mean BMI was 31 kg/m$^2$ (obese). For patients in the Ps group (i.e., without self-reported PsA), the mean CRP concentrations at baseline were 6.5 mg/L (range 4.0-70.8) for adalimumab-treated patients and 6.4 mg/L (range 4.0-61.3) for placebo-treated patients; the mean changes from baseline in CRP were −1.3 vs. 0.3 ($p≤0.01$). Of those patients in the Ps group with an elevated CRP at baseline, 64.6% of adalimumab patients (53 of 82) vs. 33.3% of PBO patients (13 of 39) had a normal CRP at Wk 16 ($p=0.0017$). For patients in the PsA group, the mean CRP concentrations at baseline were 11.6 mg/L (range 4.0-206.0) for adalimumab-treated patients and 9.7 mg/L (range 4.0-106.0) for PBO-treated patients; the mean changes from baseline in CRP were −6.3 vs. −1.9 ($p<0.01$). Of those patients in the PsA group with an elevated CRP at baseline, 71.9% of adalimumab patients (41 of 57) vs. 42.9% of placebo patients (12 of 28) had a normal CRP at Week 16 ($p=0.017$). Of patients who were obese, 64.1% of adalimumab patients (59 of 92) and 36% of placebo patients (18 of 50) changed from an elevated CRP concentration at baseline to a normal CRP at Week 16 ($p=0.0016$).

Conclusions:

Among patients with moderate to severe Ps, CRP concentrations were greater for those with PsA than with those with Ps alone. Adalimumab treatment led to significant reductions in CRP concentrations, regardless of the presence of PsA or obesity.

Example 19

Efficacy Outcomes for Patients with Psoriasis Who Interrupt Adalimumab Therapy Background:

Adalimumab is a fully human, IgG[1] monoclonal antibody specific for tumor necrosis factor (TNF), a potent inflammatory cytokine.

Objective:

The purpose of this analysis was to determine whether interruption of adalimumab therapy affected efficacy outcomes in patients with psoriasis.

Methods:

Patients with moderate to severe psoriasis (Psoriasis Area and Severity Index [PASI] score≥12) who previously failed topical therapy and were anti-TNF therapy-naïve were enrolled in REVEAL (Randomized Controlled Evaluation of Adalimumab Every Other Week Dosing in Moderate to Severe Psoriasis Trial), a 52-week (wk) study in which patients received adalimumab 40 mg every other wk. At Wk 33 of REVEAL, patients who had initially been randomized to adalimumab and who had achieved a PASI 75 response vs. baseline were re-randomized in a double-blind manner to either continued adalimumab or placebo. Upon loss of adequate response (defined as <PASI 50 relative to baseline and at least a 6-point increase in PASI score relative to Wk 33), patients were eligible to receive adalimumab in an open-label extension (OLE). All patients who completed Wk 52 of REVEAL were eligible to receive adalimumab in the OLE. This analysis compared PASI 75 response rates between patients re-randomized at Wk 33 of REVEAL to placebo or adalimumab, for patients who lost or did not lose adequate response during REVEAL, using data from Wk 24 of the OLE relative to baseline.

Results:

The percentage of patients who lost adequate response was significantly greater among those re-randomized to placebo (28%, 68/240) compared with those re-randomized to adalimumab (5%, 12/250) (p<0.001). Among patients re-randomized to the placebo group, PASI 75 response rates were 55% for patients who lost adequate response vs. 84% for patients who did not lose adequate response. Among patients re-randomized to adalimumab, PASI 75 response rates after 24 weeks of re-treatment in OLE were 55% for patients who lost adequate response vs. 83% for patients who did not lose adequate response.

Conclusions:

Interruption of adalimumab was significantly associated with loss of adequate response. Patients who lost adequate response were less likely to achieve their previous efficacy upon re-treatment compared with patients who resumed treatment without prior loss of adequate response. These results suggest that adalimumab therapy should be used continuously in psoriasis treatment.

Example 20

Benefits of Loading Dose in an Adalimumab Therapeutic Regimen for Moderate to Severe Psoriasis Aims:

The primary goal of adalimumab treatment for moderate to severe chronic plaque psoriasis is to induce and maintain clinical response. In addition, improving patients' quality of life with an early clinical response may increase treatment compliance. This analysis employed Phase II clinical results and a modeling and simulation approach to evaluate time to achieving efficacious steady-state drug concentration with a single 80-mg loading dose of adalimumab.

Methods:

In a Phase II, 12-week, placebo-controlled trial, patients with moderate to severe chronic plaque psoriasis were randomized to one of three arms: placebo (n=52); adalimumab 80 mg at Week 0, followed by 40 mg every other week (eow) beginning at Week 1 (n=45); or adalimumab 80 mg at Weeks 0 and 1, followed by 40 mg weekly beginning at Week 2 (n=50).[1] Adalimumab serum concentrations were measured by ELISA at baseline and Weeks 1, 2, 4, 8, 11, and 12.[1] A regimen of adalimumab 40 mg eow without a loading dose was not studied in this trial. Therefore, a population pharmacokinetic (PK) model was developed using the concentration data from the Phase II trial and clinical trial simulations were then conducted to predict and compare adalimumab concentration time profiles for two dosing regimens of interest: 40 mg eow vs. an 80-mg loading dose followed one week later by 40 mg eow.

Results:

For patients in the Phase II trial, who were treated with adalimumab doses of 80 mg at Week 0 and 40 mg at Week 1, the mean adalimumab serum concentrations were 6.0 μg/mL and 8.8 μg/mL at Weeks 1 and 2, respectively. By comparison, the steady-state concentrations during 40 mg eow dosing were 6.0 μg/mL and 6.9 μg/mL at Weeks 11 and 12. With the PK model, a total of 2,500 patients were simulated for each regimen (with and without an 80-mg loading dose one week before the start of a 40-mg eow dosing regimen). Clinical trial simulations demonstrated that a single 80-mg loading dose of adalimumab resulted in steady-state concentrations as early as Week 1, which was consistent with Phase II study results. The simulations also indicated that patients who do not receive loading doses may need approximately 12 weeks to reach therapeutic steady-state concentrations.

Conclusions:

Clinical trial simulations demonstrated that a single 80-mg loading dose of adalimumab may help psoriasis patients achieve therapeutic steady-state drug concentrations substantially earlier (1 vs. 12 weeks) than without the loading dose.

REFERENCES

[1]Gordon K B, et al. *J Am Acad Dermatol.* 2006; 55:598-606.

Example 21

Adalimumab is Efficacious in Patients with Moderate to Severe Psoriasis Regardless of Prior Exposure or Lack of Response to Systemic Therapies Aims:

Adalimumab is a fully human monoclonal antibody specific for tumor necrosis factor. This post-hoc subanalysis assessed response to adalimumab in patients with prior exposure to systemic therapies (biologics, non-biologics, and/or oral PUVA), and in patients who failed to respond to these therapies.

Methods:

Data were pooled from three double-blind, placebo-controlled, efficacy and safety studies of adalimumab for the treatment of moderate to severe psoriasis: one 12-week, Phase II study of 147 patients (M02-528), and two 16-week, Phase III studies of 271 (CHAMPION) and 1,212 (REVEAL) patients. For the Phase III studies, study investigators collected patient histories of use of systemic psoriasis treatments over lifetime and response to systemic treatments administered within 12 months of study entry (patient recall of response to treatments administered more than 12 months before enrollment was not collected). For the Phase II study, patient histories of use of systemic treatments for psoriasis administered within 12 months of study entry and response to treatment within 12 months were collected. PASI response rates were assessed through Week 12 for the Phase II study and through Week 16 for the Phase III studies. Intention-to-treat analyses were conducted, with patients with missing PASI responses considered non-responders.

Results:

The overall Week-4/Week-16 PASI 75 response rates were 19.4% (n=966)/72.1% (n=921) for adalimumab-treated patients, and 1.4% (n=503)/8.0% (n=451) for placebo-treated patients. PASI 75 response rates at Week 4/Week 16 for patients who had received systemic therapies were 21.7% (n=511)/72.7% (n=491) for adalimumab-treated patients, and 1.5% (n=269)/8.5% (n=247) for placebo-treated patients. PASI-75 response rates at Week 4/Week 16 for patients who had failed to respond to systemic therapy were 15.6% (n=160)/70.4% (n=152) for adalimumab-treated patients, and 0% (n=69)/8.1% (n=62) for placebo-treated patients. All results were statistically significantly greater for adalimumab vs. placebo (p<0.001). Additional results are provided in Tables 96 and 97 below.

TABLE 96

PASI 75 Response: Overall

|  | Placebo | Adalimumab * |
| --- | --- | --- |
| Week 4 | 1.4% | 19.4% |
| Week 8 | 3.8% | 54% |
| Week 12 | 5.8% | 68.1% |
| Week 16 | 8.0% | 72.1% |

* p < 0.001 adalimumab vs placebo.
ITT: patients with missing PASI scores considered nonresponders.

TABLE 97

PASI 75 Response: Week 16

|  | Placebo | Adalimumab |
| --- | --- | --- |
| Overall | 8.0% (N = 451) | 72.1% * (N = 921) |
| Lack of Response: MTX | 0.0% (N = 17) | 65.6% * (N = 32) |
| Lack of Response: Cyclosporine | 20.0% (N = 5) | 71.4% (N = 7) |
| Lack of Response: Oral PUVA | 50% (N = 4) | 83.3% (N = 6) |

* p < 0.001 adalimumab vs placebo.
ITT: patients with missing PASI scores considered nonresponders Conclusions:

Adalimumab is efficacious for the treatment of moderate-to-severe psoriasis. Adalimumab-treated patients who had received or had failed systemic therapies had similar responses compared with the overall population.

Example 22

Treatment of Etanercept Non-Responders with Human TNFa Antibody

Objectives:

To assess the efficacy and safety of adalimumab (40 mg weekly) in psoriasis patients who were non-responders to high-dosage etanercept (50 mg twice weekly).

Methods:

All patients attending a tertiary referral service for severe psoriasis who were non-responders to high-dosage etanercept (i.e., failed to achieve at least a 50% improvement in the Psoriasis Area and Severity Index [PASI 50] after treatment for at least 12 weeks) were considered for open-label adalimumab therapy for 12 weeks. Details on clinical course and adverse events were recorded, along with measurements of PASI and Dermatology Life Quality Index (DLQI) at baseline and Weeks 2, 4, 8, and 12.

Results:

Four of 5 patients treated in this study with adalimumab had reached at least PASI 50 by Week 12. Of these, 2 achieved a 75% improvement in PASI (PASI 75). No serious adverse events were reported.

Conclusions:

Initial data from this open-label prospective evaluation suggested that weekly adalimumab therapy was an effective and well-tolerated treatment for patients with severe psoriasis who had failed to respond to at least 3 months of high-dosage etanercept.

Introduction

Psoriasis is an immune-mediated chronic inflammatory disease affecting 2-3% of the world's population.[1,2] Moreover, 20-30% of those patients have moderate to severe disease, which has a substantial impact of on quality of life, and imposes an economic burden to health services.[3] Cytokines, especially tumour necrosis factor (TNF) and chemokines contribute to the initiation and maintenance of psoriasis.[4] Two types of TNF antagonists are approved the treatment of moderate to severe psoriasis—soluble TNF receptors (etanercept) and monoclonal antibodies (adalimumab and infliximab). Etanercept is a recombinant fusion protein that consists of the soluble TNF receptor (p75) linked to the Fc portion of human $IgG_1$ (TNFR:Fc)[5] and is effective in treating psoriasis and psoriatic arthritis.[6,7] Etanercept has been recommended by NICE in the United Kingdom as first-line biologic therapy for patients with moderate to severe psoriasis at a dosage of 25 mg twice weekly.

To be eligible for etanercept therapy, patients must have disease severity defined by a total Psoriasis Area and Severity Index (PASI) score≥10 and a Dermatology Life Quality Index (DLQI)>10. The patient must have failed to respond to standard systemic therapies including ciclosporin, methotrexate, psoralen, and long-wave ultraviolet radiation (PUVA); or have been intolerant to or had contraindications for these treatments. Most patients with moderate to severe psoriasis will achieve disease control (i.e., reach a PASI 50) within 12 weeks. Although not approved by NICE, high-dosage etanercept (50 mg twice weekly) is licensed and can result in efficacy for some patients.[8] However, many patients do not respond to even high-dosage etanercept,[9,10] and there are no data available on the role of other TNF blockers for psoriasis patients who fail etanercept. Adalimumab is a fully human, anti-TNF monoclonal antibody and effective and well-tolerated in the treatment of psoriasis and psoriatic arthritis.[11,12,13] In Europe, adalimumab is indicated for the treatment of moderate to severe chronic plaque psoriasis in adult patients who failed to respond to or who have a contraindication to, or are intolerant to other systemic therapy including cyclosporine, methotrexate or PUVA.[14] In the United States, adalimumab is approved the treatment of adult patients with moderate to severe chronic plaque psoriasis who are candidates for systemic therapy or phototherapy, and when other systemic therapies are medically less appropriate.[15] In the present study, we assessed the efficacy and safety of adalimumab for patients with moderate to severe psoriasis who were non-responders to high-dosage etanercept.

Materials and Methods

Study Design and Treatment Regimens

This was an open-label prospective evaluation of adalimumab (HUMIRA®, Abbott Laboratories, Abbott Park, Ill., USA). Patients who were non-responders to etanercept were recruited from the Severe Psoriasis Clinic at St John's Institute of Dermatology in London. Non-responders were defined as patients who had failed to achieve at least 50% improvement in PASI (PASI 50) after treatment with etanercept 50 mg twice weekly for 12 weeks. Inclusion criteria included male and female patients more than 18 years of age with plaque psoriasis (Table 98). The study was approved by St Thomas' Research Ethics Committee, and informed consent was obtained from all participants.

Figure 11:
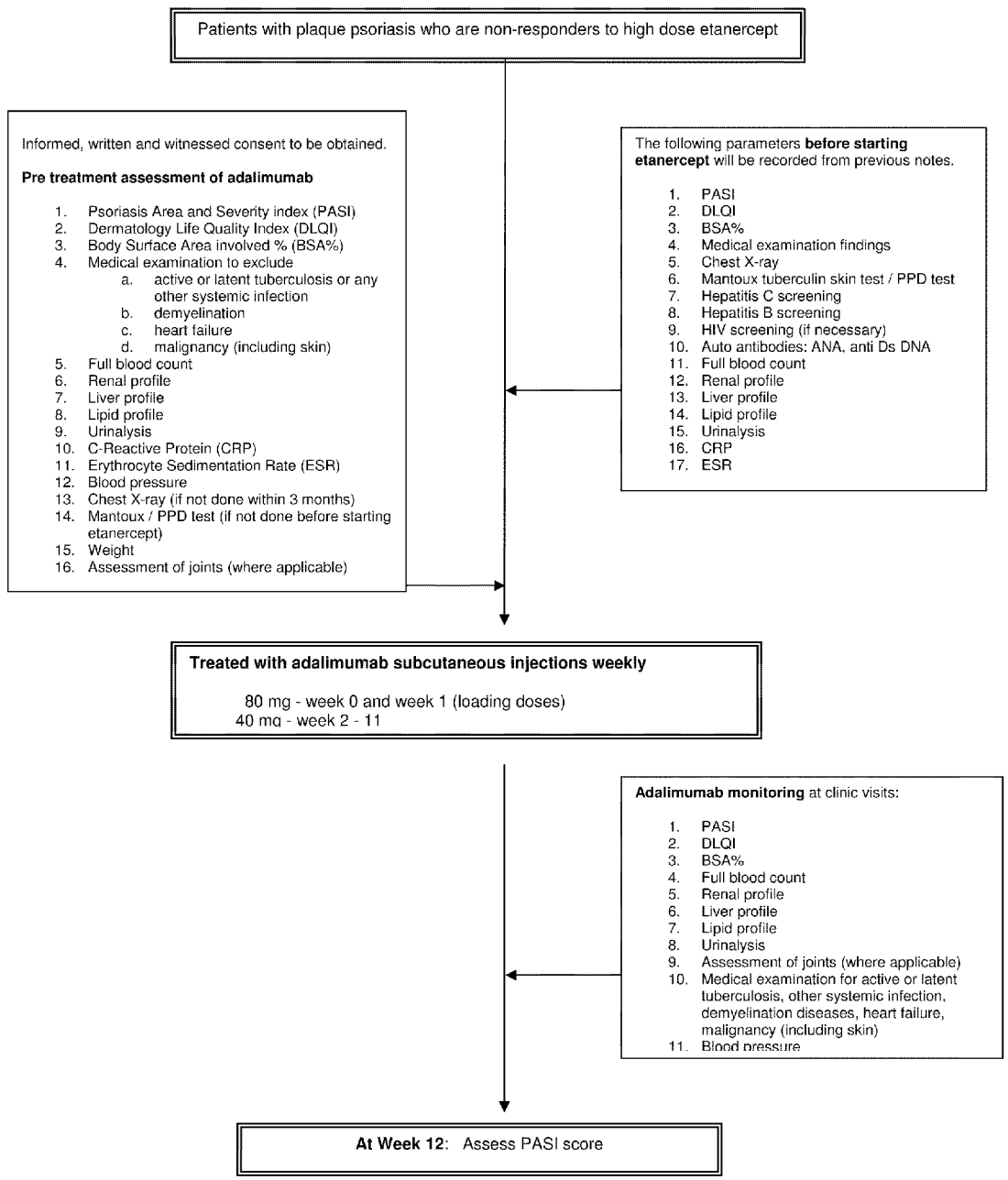
FIG. 11 is a flow chart depicting the disposition and assessment of patients with plaque psoriasis who were non-responders to high dose entanercept.

Drug Information Leaflet." They were observed at Weeks 0, 2, 4, 8, and 12. At each clinical visit PASI, DLQI, and percentage body surface area (% BSA) affected were assessed and recorded. In addition, patients received medical assessments together with monitoring laboratory investigations (FIG. 11).

Efficacy Assessments

The primary efficacy endpoint of the study was PASI 50 response rate at Week 12 of adalimumab therapy. The secondary efficacy endpoint was PASI 75 response rate at Week 12.

Results

Patients

Five patients completed the 12-week trial (Table 1). Each patient had severe psoriasis as defined by a PASI≥10 and DLQI>10 and had failed to achieve at least a PASI 50 after treatment with etanercept 50 mg twice weekly for 12 weeks. All five patients had a diagnosis of chronic plaque psoriasis.

Primary Efficacy

Figure 12:
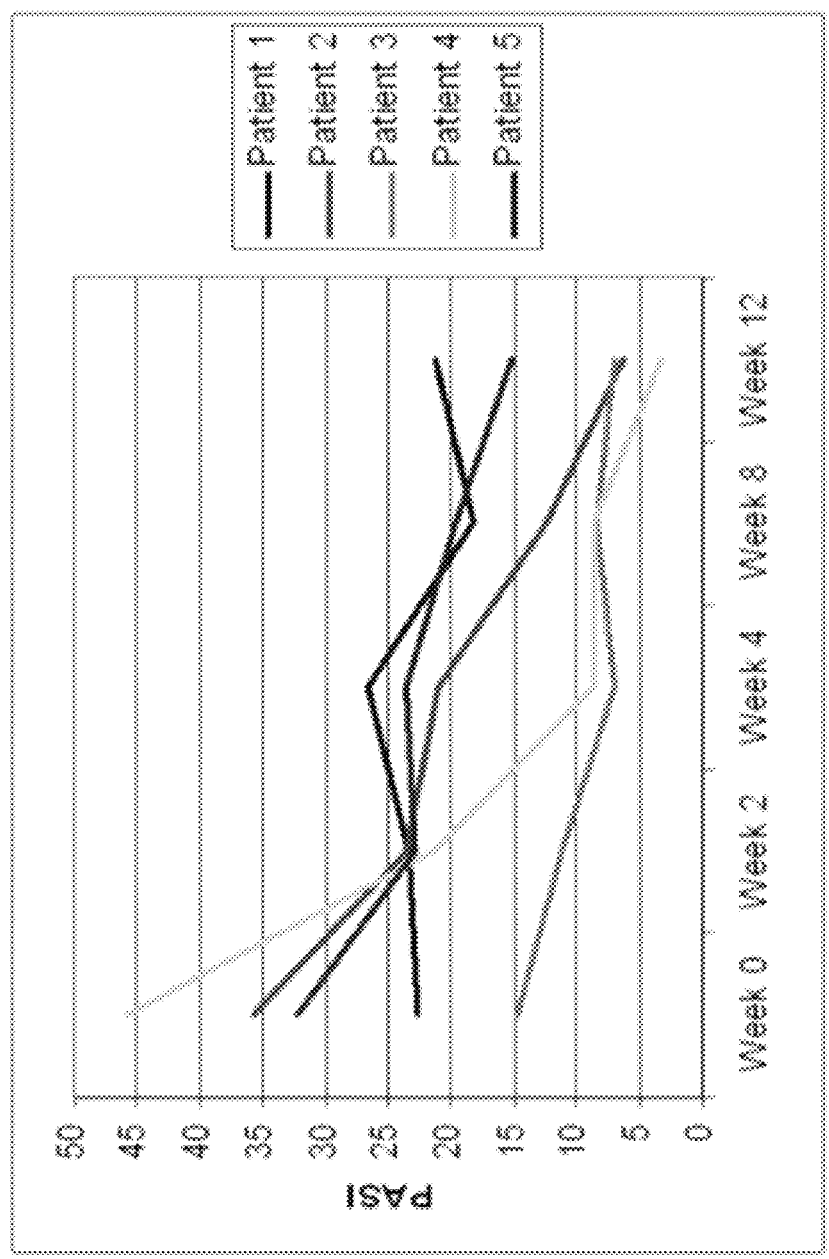
FIG. 12 is a graph depicting the Psoriasis Area and Severity Index scores (PASI) for patients treated with adalimumab.

The primary efficacy parameter (PASI 50 at Week 12) was achieved by 4 of 5 patients. Patient 2 achieved PASI 50 by Week 8; Patient 3 by Week 4; Patient 4 by Week 2; and Patient 5 by Week 12. Patient 1 was a non-responder to high-dosage adalimumab (FIG. 12)

TABLE 98

Summary of Efficacy Results with 12 Weeks of Adalimumab Therapy for Psoriasis

| Patient Number | 1 | 2 | 3 | 4 | 5 |
| --- | --- | --- | --- | --- | --- |
| Sex | Female | Male | Male | Male | Male |
| Age (yrs) | 54 | 51 | 42 | 45 | 42 |
| Weight (kg) | 96.5 | 85.4 | 105.35 | 111.0 | 67.35 |
| Duration of psoriasis (yrs) | 4 | 21 | 22 | 30 | 28 |
| Psoriatic arthritis | Yes | No | Yes | No | No |
| PASI/DLQI Week 0 | 22.6/19 | 35.8/11 | 45.9/30 | 14.7/11 | 32.2/14 |
| PASI/DLQI Week 2 | 23.4/17 | 23.6/10 | 21.6/30 | 11.2/9 | 22.9/5 |
| PASI/DLQI Week 4 | 26.7/16 | 20.1/5 | 8.70/28 | 7.00/4 | 23.6/7 |
| PASI/DLQI Week 8 | 18.2/15 | 12.3/3 | Not recorded | 8.40/0 | 19.6/9 |
| PASI/DLQI Week 12 | 21.2/6 | 6.30/1 | 3.3/26 | 7.10/2 | 15.2/6 |
| % Improvement in PASI/DLQI from baseline to Week 12 | 6/68 | 82/91 | 93/13 | 52/82 | 53/57 |
| ESR (mm/hr)/CRP (mg/L) Week 0 | 36/20 | 34/<5 | 20/10 | 44/6 | 2/<5 |
| ESR (mm/hr)/CRP (mg/L) Week 12 | 13/7 | 12/<5 | Not recorded/<5 | 12/<5 | 2/<5 |

PASI, psoriasis area severity index; DLQI, Dermatology Life Quality Index; ESR, erythrocyte sedimentation rate; CRP, C-reactive protein.

Prior to inclusion into the trial, all patients underwent a full clinical history, physical examination, and investigations according to British Association of Dermatologists (BAD) guidelines[8] as shown in FIG. 11. All patients fulfilled the inclusion criteria.

Intervention

Adalimumab 80-mg loading doses were administered to the first 5 patients who enrolled in this investigator-initiated study at Weeks 0 and 1, followed by adalimumab 40 mg weekly from Weeks 2-11. The study period was 12 weeks. Adalimumab was initiated between 4 and 38 weeks (mean 12.8 weeks) following cessation of etanercept. Patients were able to withdraw from the study at any stage. They were permitted to continue topical treatments at stable dosages throughout the study, but could not use concomitant systemic therapy for psoriasis.

Patients were provided an information pack that included a "HUMIRA Treatment Guide," as well as a "HUMIRA Secondary Efficacy The secondary efficacy parameter (PASI 75 at Week 12) was achieved by two patients. Patient 2 reached a PASI 75 at Week 12, and Patient 4 did so at Week 4.

Patient-Reported Outcomes

Figure 13:
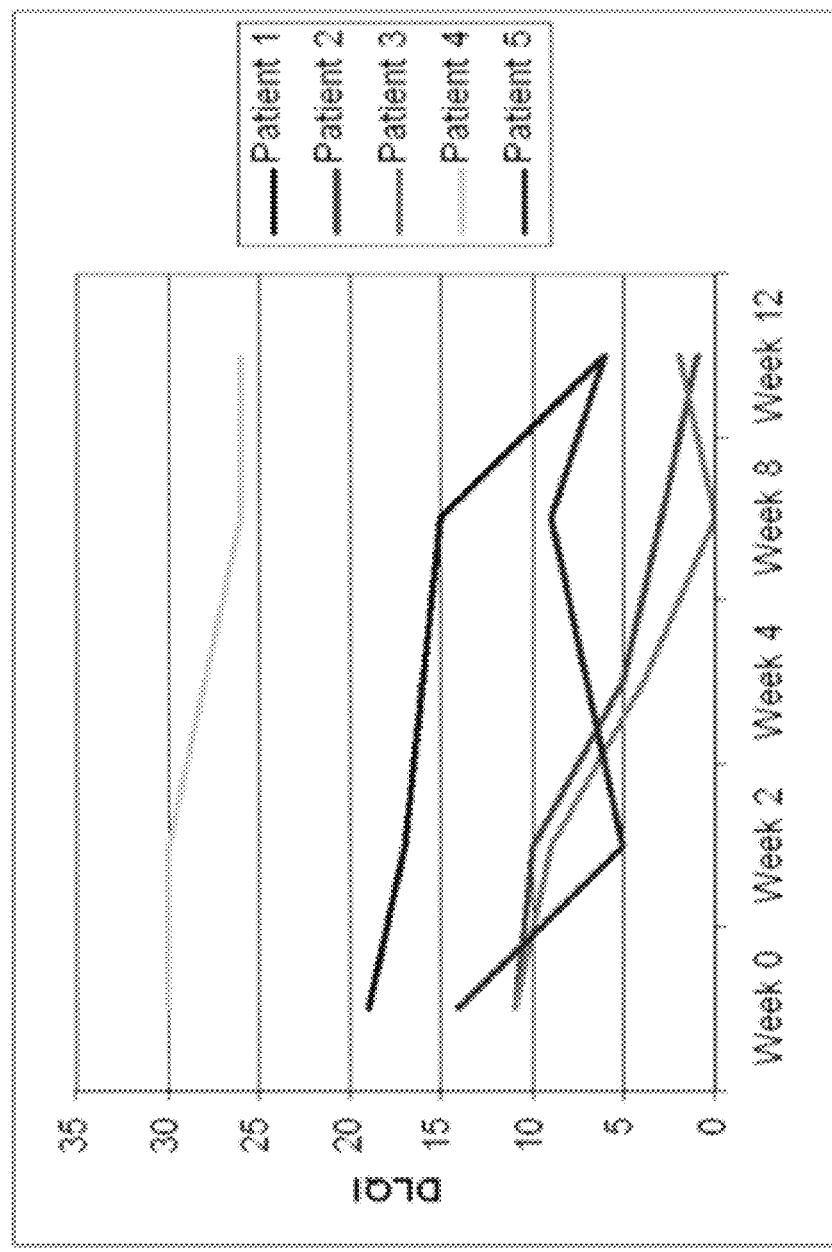
FIG. 13 is a graph depicting the Dermatology Life Quality Index (DLQI) for patients treated with adalimumab.

All five patients achieved a reduction in their DLQI scores, with a mean decrease of 8.8 at Week 12 (FIG. 13).

Adverse Events

No serious adverse events were reported.

Discussion

This is the first prospective study of patients with moderate to severe psoriasis who had failed high-dosage etanercept. At Week 12, 80% had achieved at least PASI 50, and of these, two had achieved PASI 75, with one patient achieving almost complete clearance. Previous studies support the theory that patients who have failed previous biological therapies can benefit from adalimumab.[16,17] Adalimumab has recently received NICE approval as a recommended treatment option for adults with plaque psoriasis for whom anti-TNF treatment is being considered. The recommended dosage is an initial loading dose of 80 mg (subcutaneously, followed by 40 mg every other week starting 1 week after initial dose. In this study, we used high-dosage adalimumab (40 mg weekly) following the loading dose.

Since our group of patients were "high-need" patients who had failed high-dosage etanercept, we decided to use adalimumab 40 mg weekly. Following our 12-week study, the dosage of adalimumab was reduced to 40 mg every other week. This preliminary study indicates that adalimumab, at a dosage greater than the currently recommended schedule, is an effective treatment for patients with severe psoriasis who had failed to respond to at least 12 weeks of high-dosage etanercept.

This study adds treatment options for patients with unmet medical need who pose a clinical challenge. Sequential biological therapy has been reported to be successful,[18] and our study supports this. Failure or loss of efficacy to one biologic therapy does not imply that alternative biologics, even ones, from the same class, will be ineffective as well.

REFERENCES

1. Smith C H, Barker J N. Psoriasis and its management. BMJ. 2006; 19:380-4.
2. Griffiths C E, Barker J N. Pathogenesis and clinical features of psoriasis. Lancet 2007; 370:263-71.
3. Griffiths C E, Clark C M, Chalmers R J, et al. A systematic review of treatments for severe psoriasis. Health Technol Asses 2000; 4:1-125.
4. Nickoloff B J, Xin H, Nestle F O, Qin J-Z. The cytokine and chemokine network in psoriasis. Clinic in Dermatol 2007; 25:568-73.
5. Moreland L W, Baumgartner S W, Schiff M H, et al. Treatment of rheumatoid arthritis with a recombinant human tumor necrosis factor receptor (p75)-Fc fusion protein. N Engl J Med 1997; 337:141-7.
6. Iyer S, Yamauchi P, Lowe N J. Etanercept for severe psoriasis and psoriatic arthritis: observations on combination therapy. Br J Dermatol 2002; 146:118-21.
7. Simpson D, Scott L J. Adalimumab in psoriatic arthritis. Drugs 2006; 66:1487-96.
8. Smith C H, et al. British association of Dermatologists guidelines for the use of biological interventions in psoriasis 2005. Br J Dermatol 2005; 153:486-97.
9. de Groot M, Appelman M, Spuls P I, de Rie M A, Bos J D. Initial experience with routine administration of etanercept in psoriasis. Br J Dermatol 2006; 155:808-14.
10. Ahmad K, Rogers S. Two years of experience with etanercept in recalcitrant psoriasis. Br J. Dermatol. 2007; 156:1010-4.
11. Sladden M J, Mortimer N J, Hutchinson P E. Extensive plaque psoriasis successfully treated with adalimumab. Br J Dermatol 2005; 152:1091-2.
12. Pitarch G, Sanchez-Carazo J L, Mahiques L, et al. Treatment of psoriasis with adalimumab. Clin Exp Dermatol 2006; 1:1-5.
13. Gladman D D, Ritchlin C T, Mease P J, et al. Adalimumab for the treatment of patients with moderately to severely active psoriatic arthritis. Arthritis Rheum 2005; 52:3279-89.
14. HUMIRA® (adalimumab) Summary of Product Characteristics. Available at www.emea.europa.eu/humandocs/Humans/EPAR/humira/humira.htm. Accessed Dec. 19, 2008.
15. HUMIRA® (adalimumab) prescribing information. Abbott Park, Ill. Abbott Laboratories, 2008. Available at www.rxabbott.com/pdf/humira.pdf. Accessed Dec. 19, 2008.
16. Pitarch J L, Sanchez-Carazo J L, Mahiques L, Perez-Ferriols Ma, Fortea J M. Treatment of psoriasis with adalimumab. Clin Exp Dermatol 2007; 32:18-22.
17. Van L, Modi S V, Yang D J, Hsu S. Sustained efficacy and safety of adalimumab in psoriasis treatment: a retrospective study of 49 patients with and without a history of TNF-alpha antagonist treatment. Arch Dermatol 2008; 144; 804-6.
18. Barde C, Thielen A M, Kuenzli S, Saurat J-H. Treatment of plaque psoriasis by sequential therapy with two "biologics": the "hit and run" approach, a report of two cases. Br J Dermatol 2006; 155:211-13.

Example 23

Efficacy of Human TNFa Antibody for Treating Skin Disorder in Patients Having Suboptimal Response to Systemic Therapy or Phototherapy Objective:

The purpose of this trial was to study the efficacy and safety of adalimumab in psoriasis patients with suboptimal response to systemic therapy (etanercept [ETN] or methotrexate [MTX]) or phototherapy.

Methods:

This 16-week, multicenter, open-label, Phase IIIb trial enrolled patients with chronic plaque psoriasis who were having a suboptimal response to ETN (Physician's Global Assessment [PGA]≥mild with months of therapy, or ≥3 months of therapy and deterioration of efficacy), MTX (PGA≥mild with ≥4 months of therapy), or narrow-band ultraviolet B (NB-UVB) phototherapy (PGA moderate with months of therapy). Per protocol, patients discontinued therapy 2 weeks (ETN) or 1 week (MTX, NB-UVB) before initiating adalimumab at the approved dose (80 mg at Week 0, then 40 mg every other week from Week 1). The primary endpoint was the proportion of patients who achieved PGA of clear or minimal at week 16. A secondary endpoint was the proportion achieving ≥1 grade of PGA improvement. Safety was assessed throughout the study. Efficacy analyses were intention to treat, with nonresponder imputation used for missing data. Efficacy and safety results were analyzed overall and for each prior-treatment group.

Results:

A total of 152 patients enrolled in the study (ETN, N=82; MTX, N=41; NB-UVB, N=29). The distribution of PGA scores at baseline was: very severe 0.7%, severe 15.8%, moderate 65.1%, mild 17.1%, minimal 1.3%, clear 0%. At week 16, PGA of clear or minimal was achieved in 52.0% (95% CI 43.7, 60.1) of all patients and 48.8% (37.6, 60.1), 61.0% (44.5, 75.8), and 48.3% (29.4, 67.5) of patients in the ETN, MTX, and NB-UVB groups, respectively. At week 16, ≥1 grade improvement in PGA was achieved by 75.0% (67.3, 81.7) of all patients and 72.0% (60.9, 81.3), 78.0% (62.4, 89.4), and 79.3% (60.3, 92.0) in the ETN, MTX, and NB-UVB groups, respectively. Four patients (2.6%; 2 MTX, 2 ETN) experienced >25% worsening in Psoriasis Area and Severity Index scores. One subject (NB-UVB) had a serious infection (cellulitis); no malignancies were reported.

Conclusions:

Approximately half of patients with suboptimal response to ETN, MTX, or NB-UVB achieved a clinically relevant improvement in psoriasis 16 weeks after transitioning to adalimumab. Patients had acceptable safety outcomes and a low risk of flare, despite immediate discontinuation of prior therapy and a short washout.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

The invention claimed is:

1. A method for treating psoriasis in a subject who has failed to respond to or has lost responsiveness to etanercept and infliximab, the method comprising administering 80 mg of adalimumab subcutaneously to the subject, and administering 40 mg of adalimumab subcutaneously to the subject every other week starting one week following administration of the 80 mg of adalimumab to the subject.

2. The method of claim 1, wherein the subject failed to achieve a PASI 50 response after receiving etanercept and infliximab.

3. The method of claim 1, wherein the subject has a Psoriasis Area and Severity Index (PAST) of ≥10 and/or a Dermatology Life Quality Index (DLQI)>10.

4. The method of claim 1, wherein said 40 mg of adalimumab is comprised in a pre-filled syringe for subcutaneous injection.

5. The method of claim 1, wherein said 40 mg of adalimumab is formulated at a concentration of 50 mg/ml.

6. A method for treating psoriasis in a subject who has failed to respond to or has lost responsiveness to etanercept and infliximab, the method comprising administering 80 mg of adalimumab subcutaneously to the subject, and administering 40 mg of adalimumab subcutaneously to the subject weekly starting one week following administration of the 80 mg of adalimumab to the subject.

7. The method of claim 6, wherein the subject failed to achieve a PASI 50 response after receiving etanercept and infliximab.

8. The method of claim 6, wherein the subject has a Psoriasis Area and Severity Index (PASI) of ≥10 and/or a Dermatology Life Quality Index (DLQI)>10.

9. The method of claim 6, wherein said 40 mg of adalimumab is comprised in a pre-filled syringe for subcutaneous injection.

10. The method of claim 6, wherein said 40 mg of adalimumab is formulated at a concentration of 50 mg/ml.

11. The method of claim 1, wherein the subject has lost response to infliximab.

12. The method of claim 6, wherein the subject has lost response to infliximab.

* * * * *